United States Patent
Ishikawa et al.

(10) Patent No.: US 11,730,856 B2
(45) Date of Patent: Aug. 22, 2023

(54) METHOD OF PRODUCING PRODUCT INORGANIC COMPOUND AND PRODUCT INORGANIC COMPOUND

(71) Applicant: KYUSHU UNIVERSITY, NATIONAL UNIVERSITY CORPORATION, Fukuoka (JP)

(72) Inventors: Kunio Ishikawa, Kasuya-gun (JP); Maho Ishikawa, Ube (JP); Yasuharu Nakashima, Fukuoka (JP)

(73) Assignee: KYUSHU UNIVERSITY NATIONAL UNIVERSITY CORPORATION, Fukuoka (JP)

( * ) Notice: Subject to any disclaimer, the term of this patent is extended or adjusted under 35 U.S.C. 154(b) by 0 days.

(21) Appl. No.: 16/745,615

(22) Filed: Jan. 17, 2020

(65) Prior Publication Data
US 2020/0147260 A1 May 14, 2020

Related U.S. Application Data

(63) Continuation of application No. 15/506,311, filed as application No. PCT/JP2015/074690 on Aug. 31, 2015, now abandoned.

(30) Foreign Application Priority Data

| Sep. 1, 2014 | (JP) | 2014-177564 |
| Sep. 1, 2014 | (JP) | 2014-177565 |
| Sep. 1, 2014 | (JP) | 2014-177566 |

(51) Int. Cl.
*A61L 27/02* (2006.01)
*A61L 27/12* (2006.01)
(Continued)

(52) U.S. Cl.
CPC .............. *A61L 27/02* (2013.01); *A61L 27/12* (2013.01); *C01B 25/32* (2013.01); *C01B 25/327* (2013.01);
(Continued)

(58) Field of Classification Search
None
See application file for complete search history.

(56) References Cited

U.S. PATENT DOCUMENTS 3,409,394 A   11/1968  Sprigg
3,929,971 A   12/1975  Roy
(Continued)

FOREIGN PATENT DOCUMENTS

CN   101843920 A   9/2010
JP   S63-107807 A   5/1988
(Continued)

OTHER PUBLICATIONS

Cazalbou et al. Ion exchanges in apatites for biomedical applications. J. Material Science: Materials in medicine, 2005, 405-409 (Year: 2005).*

(Continued)

*Primary Examiner* — Lakshmi S Channavajjala
(74) *Attorney, Agent, or Firm* — Oliff PLC

(57) ABSTRACT

A method of producing a product inorganic compound including: immersing a raw material inorganic compound having a volume of $10^{-13}$ m$^3$ or more in an electrolyte aqueous solution or an electrolyte suspension; exchanging anions in the raw material inorganic compound with anions in the electrolyte aqueous solution or the electrolyte suspension; cations in the raw material inorganic compound are exchanged with cations in the electrolyte aqueous solution or the electrolyte suspension; or including a component (that excludes water, hydrogen, and oxygen) in the electrolyte (Continued)

aqueous solution or the electrolyte suspension not included in the raw material inorganic compound in the raw material inorganic compound; and obtaining a product inorganic compound having a volume of $10^{-13}$ m$^3$ or more from the raw material inorganic compound.

11 Claims, 77 Drawing Sheets

(51) Int. Cl.
| | |
|---|---|
| C01F 11/46 | (2006.01) |
| C01B 25/32 | (2006.01) |
| C01F 11/18 | (2006.01) |
| C01F 11/22 | (2006.01) |
| C01F 11/02 | (2006.01) |

(52) U.S. Cl.
CPC .............. *C01F 11/02* (2013.01); *C01F 11/18* (2013.01); *C01F 11/185* (2013.01); *C01F 11/22* (2013.01); *C01F 11/46* (2013.01); *A61L 2430/02* (2013.01); *C01P 2002/72* (2013.01); *C01P 2002/84* (2013.01); *C01P 2002/85* (2013.01); *C01P 2004/02* (2013.01); *C01P 2004/03* (2013.01); *C01P 2004/84* (2013.01); *C01P 2006/16* (2013.01)

(56) References Cited

U.S. PATENT DOCUMENTS

| | | | |
|---|---|---|---|
| 4,612,059 A | 9/1986 | Mori et al. | |
| 4,938,938 A | 7/1990 | Ewers et al. | |
| 5,900,254 A * | 5/1999 | Constantz | A61L 27/58 606/76 |
| 6,129,928 A | 10/2000 | Sarangapani et al. | |
| 8,012,218 B2 | 9/2011 | Ishikawa et al. | |
| 8,546,356 B2 * | 10/2013 | Soula | A61K 9/0019 514/59 |
| 9,492,585 B2 * | 11/2016 | Gibson | C01B 25/322 |
| 10,723,625 B2 * | 7/2020 | Sugiura | C01B 25/322 |
| 2006/0225619 A1 | 10/2006 | Ishikawa et al. | |
| 2009/0215616 A1 | 8/2009 | Misumi et al. | |
| 2011/0282463 A1 * | 11/2011 | Ishikawa | A61L 27/306 623/23.53 |
| 2012/0288446 A1 * | 11/2012 | Garigapati | A61L 24/04 424/9.1 |

FOREIGN PATENT DOCUMENTS

| | | | | |
|---|---|---|---|---|
| JP | H07-002691 A | 1/1995 | | |
| JP | 07-118011 A * | 5/1995 | ............. | C01F 11/18 |
| JP | H07-118011 A | 5/1995 | | |
| JP | H07-171211 A | 7/1995 | | |
| JP | H07-246235 A | 9/1995 | | |
| JP | H11-099199 A | 4/1999 | | |
| JP | H11180705 A * | 6/1999 | ............. | C01B 25/32 |
| JP | H11-180705 A | 7/1999 | | |
| JP | 2001-000947 A | 1/2001 | | |
| JP | 2001-137328 A | 5/2001 | | |
| JP | 2001-252347 A | 9/2001 | | |
| JP | 2001-259016 A | 9/2001 | | |
| JP | 2002-011199 A | 1/2002 | | |
| JP | 2003-292321 A | 10/2003 | | |
| JP | 2003-320017 A | 11/2003 | | |
| JP | 2003-321281 A | 11/2003 | | |
| JP | 2004-222992 A | 8/2004 | | |
| JP | 2005-289763 A | 10/2005 | | |
| JP | 2007-151680 A | 6/2007 | | |
| JP | 2007-534449 A | 11/2007 | | |
| JP | 2008-137863 A | 6/2008 | | |
| JP | 2009-291304 A | 12/2009 | | |
| JP | 2010-508071 A | 3/2010 | | |
| JP | 4854300 B2 | 1/2012 | | |
| JP | 2014-014579 A | 1/2014 | | |
| WO | WO-0128920 A1 * | 4/2001 | ............. | A61L 24/02 |
| WO | 2004/112856 A1 | 12/2004 | | |
| WO | 2005/105170 A1 | 11/2005 | | |
| WO | 2008/054794 A2 | 5/2008 | | |
| WO | 2009/111307 A2 | 9/2009 | | |
| WO | 2012/093939 A1 | 7/2012 | | |

OTHER PUBLICATIONS

Patel et al., "A comparative study on the in vivo behavior of hydroxyapatite and silicon substituted hydroxyapatite granules". Journal of Materials Science: Materials in Medicine, vol. 13, pp. 1199-1206, 2002.

Hockin et al., "Strong and macroporous calcium phosphate cement: Effects of porosity and fiber reinforcement on mechanical properties". Journal Biomed Materials Research, vol. 57, pp. 457-466, 2001.

Takagi et al., "Formation of macropores in calcium phosphate cement implants". Journal of Materials Science: Materials in Medicine, vol. 12, pp. 135-139, 2001.

Almirall et al., "Fabrication of low temperature macroporous hydroxyapatite scaffolds by foaming and hydrolysis of an a-TCP paste". Biomaterials, vol. 25, pp. 3671-3680, 2004.

Cook et al., "Optimum Pore Size for Bone Cement Fixation". Clinical Orthopaedics and Related Research, vol. 223, pp. 296-302, 1987.

Schliephake et al., "Influence of pore dimensions on bone ingrowth into porous hydroxylapatite blocks used as bone graft substitutes". Department of Oral and Maxillofacial Surgery, vol. 20, pp. 53-58, 1991.

Holmes, Ralph. "Bone Regeneration Within a Coralline Hydroxyapatite Implant". Bone Regeneration, vol. 63, No. 5 pp. 626-633, 1979.

Hulbert et al., "Tissue Reaction to Three Ceramics of Porous and Non-Porous Structures". Journal of Biomedical Materials Research, vol. 6, pp. 347-374, 1972.

Lemaitre et al., "Calcium Phosphate Cements for Medical Use: State of the Art and Perspectives of Development". Silicates Industriels, vol. 52, pp. 141-146, 1987.

Monma et al., "The Hydration of a-Tricalcium Phosphate". Department of Industrial Chemistry, Faculty of Technology, Tokyo Metropolitan University, vol. 84, No. 4, pp. 209-213, 1976.

Daculsi G et al., "Current state of the art of biphasic calcium phosphate bioceramics". Journal of Materials in Medicine, vol. 14, pp. 195-200, 2003.

Karashima et al., "Fabrication of low-crystallinity hydroxyapatite foam based on the setting reaction of a-tricalcium phosphate foam". Journal of Biomedical Materials Research, vol. 88A, pp. 628-633, 2009.

Nov. 24, 2015 International Search Report issued International Patent Application No. PCT/JP2015/074690.

Monma H et al; "Preparation of Hydroxyapatite by the Hydrolysis of Brushite;" Journal of Materials Science, Kluwer Academic Publishers; Dordrecht; vol. 22, No. 12; Dec. 1, 1987; pp. 4247-4250; XP001161107.

May 17, 2018 Search Report issued in European Patent Application No. 15837907.3.

Ecologix, Mesh to Micron Conversion Table.3 pages (Year: 2018).

Jun. 18, 2019 Office Action issued in Japanese Patent Application No. 2016-546635.

* cited by examiner

METHOD OF PRODUCING PRODUCT INORGANIC COMPOUND AND PRODUCT INORGANIC COMPOUND

CROSS REFERENCE TO RELATED APPLICATIONS

This is a Continuation of application Ser. No. 15/506,311 filed on Apr. 5, 2017, which in turn is a 371 of PCT/JP2015/074690 filed on Aug. 31, 2015, which claims priority to JP 2014-177564, JP 2014-177565, and JP 2014-177566 each filed on Sep. 1, 2014. The disclosure of the prior applications is hereby incorporated by reference herein in its entirety.

TECHNICAL FIELD

The present invention relates to a method of producing a product inorganic compound and a product inorganic compound, and more specifically, to a method of producing a product inorganic compound which is obtained from a raw material inorganic compound having a volume of $10^{-13}$ m$^3$ or more and a solubility of 5 or less with respect to distilled water or electrolyte aqueous solution without substantially changing a macro form of the raw material inorganic compound, and in which at least one component in the raw material inorganic compound is included, and which has a composition that is different from a composition of the raw material inorganic compound, and a product inorganic compound to be produced.

BACKGROUND ART

Forms of a product inorganic compound in the present invention are granules or a block having a volume of a certain value or more. In general, inorganic compounds in the form of granules or a block having a volume of a certain value or more are produced from powders using a sintering or curing reaction.

Sintering is a process in which inorganic compound powder is pressed and molded to impart a shape and is sometimes called calcination, and when a powder compacted body is heated at a lower temperature than a melting point, inorganic compound elements diffuse through grain boundaries between particles and the powder solidifies. As a result of sintering, sinterable grain boundaries are formed between particles.

However, the sintering process is not applicable in some inorganic compounds because thermal decomposition occurs at a much lower temperature than a melting point. In addition, the sintering process is a mass energy consumption type production process which requires a high temperature of about 1000° C. or more. A low energy consumption type production process is desired in consideration of reducing an environmental load. Further, the obtained inorganic compound sintered body may have low functionality because a surface area of a material decreases and a crystallite size increases during sintering.

A curing reaction is a reaction in which a powder is cured and is known for gypsum, zinc phosphate cement, apatite cement, calcium hydrogen phosphate cement and the like. When calcium sulfate hemihydrate powder is mixed with water, gypsum is cured and is compositionally converted into calcium sulfate dihydrate. When zinc oxide powder is mixed in phosphoric acid, zinc phosphate cement is cured to zinc phosphate. Apatite cement is, for example, a powder in which calcium hydrogen phosphate and tetracalcium phosphate, is cured to apatite when mixed with water. Calcium hydrogen phosphate cement is, for example, a powder in which n-type tricalcium phosphate and calcium dihydrogen phosphate, is cured to calcium hydrogen phosphate when mixed with water or phosphoric acid.

Inorganic compounds are also used for medical treatment. For example, there are many cases in which bone defect emerged due to pathological causes or external injuries need to be reconstructed. In reconstruction therapy of bone defects, it is preferable to densely fill the bone defect with an artificial bone reconstruction material represented by an apatite or β-type tricalcium phosphate having excellent tissue compatibility and osteoconductivity. Artificial bone reconstruction materials in the form of a block or granules are currently being clinically applied, but such artificial bone reconstruction materials are generally produced through sintering. Also, since the bone is hard tissue, bone reconstruction materials are sometimes called hard tissue reconstruction materials and hard tissue reconstruction materials are sometimes called bone prosthetic materials because they fill and reconstruct bone defects, but they have basically the same meaning.

Calcium carbonate may be used as a bone reconstruction material in addition to an apatite and n-type tricalcium phosphate. Calcium carbonate is a skeletal tissue composition of an invertebrate animal and is produced from corals, shells, marble and the like. Corals are clinically applied as bone prosthetic materials also due to the presence of interconnected porous structure. However, the harvest of corals causes damage to the environment and problems such as a cost in finding appropriate corals, a cost for collection, a cleaning cost, impurity problems, and uniformity problems are unavoidable in order to use corals as materials for medical treatment. Therefore, artificial production is preferable.

As can be seen in plaster, calcium carbonate can be produced when calcium hydroxide is exposed to carbon dioxide for curing. However, there is a problem of the likelihood of there being remaining calcium hydroxide. In addition, it is necessary to prepare a mold for molding.

An apatite and tricalcium phosphate which are bone reconstruction materials are produced by sintering an apatite powder (Patent Literature 1 and Patent Literature 2). Recently, it has been found that, when a calcium compound such as a calcium carbonate block is immersed in a phosphoric acid aqueous solution, an apatite block can be produced without sintering (Patent Literature 3).

In addition, as a recycling method for gypsum board, it is known that potassium hydroxide and calcium sulfate dihydrate react in water and calcium hydroxide having an average particle size of 0.5 to 5 μm is produced (Patent Literature 4).

Similarly, as a recycling method for gypsum board and the like, it is known that, when gypsum is immersed in ammonia water or a sodium hydroxide aqueous solution and carbon dioxide gas is introduced, calcium carbonate is produced (Patent Literatures 5 and 6).

CITATION LIST

Patent Literature

[Patent Literature 1]
Japanese Unexamined Patent Application, First Publication No. 2004-222992
[Patent Literature 2]
Japanese Unexamined Patent Application, First Publication No. 2001-252347

[Patent Literature 3]
Japanese Patent No. 4854300
[Patent Literature 4]
Japanese Unexamined Patent Application, First Publication No. 2008-137863
[Patent Literature 5]
Japanese Unexamined Patent Application, First Publication No. 2001-947
[Patent Literature 6]
Japanese Unexamined Patent Application, First Publication No. 2003-292321

SUMMARY OF INVENTION

Problems to be Solved by the Invention

A product inorganic compound in the form of a block is generally produced in a sintering process or a curing reaction in which an inorganic compound powder is heated at a high temperature. In addition, a product inorganic compound in the form of granules is produced by pulverizing a product inorganic compound in the form of a block.

However, the sintering process has a large environmental load. In addition, this process cannot be applied for an inorganic compound that is easily thermally decomposed. Further, the sintering process may decrease functionality of an inorganic compound.

When a curing reaction is performed for production, problems of an environmental load, and thermal decomposition, and a problem of functional deterioration due to heat hardly arise, but there are not many inorganic compound blocks that can be produced by a curing reaction.

Accordingly, an object of the present invention is to provide a production method through which it is possible to produce a product inorganic compound in the form of a block or granules without sintering causing high energy consumption and a product inorganic compound.

Solution to Problem

The inventors conducted various studies and found a method that can achieve the above object, as a result, completed the present invention to be described below.

(1) A method of producing a product inorganic compound including:

a step A in which a raw material inorganic compound having a volume of $10^{-13}$ m$^3$ or more is immersed in an electrolyte aqueous solution or an electrolyte suspension;

a step B1 in which anions in the raw material inorganic compound are exchanged with anions in the electrolyte aqueous solution or the electrolyte suspension;

a step B2 in which cations in the raw material inorganic compound are exchanged with cations in the electrolyte aqueous solution or the electrolyte suspension; or a step B3 in which a component (provided that it excludes water, hydrogen, and oxygen) in the electrolyte aqueous solution or the electrolyte suspension that is not included in the raw material inorganic compound is made to be included in the raw material inorganic compound; and a step C in which a product inorganic compound having a volume of $10^{-13}$ m$^3$ or more is obtained from the raw material inorganic compound, wherein the raw material inorganic compound has a solubility that is greater than 0 and 5 or less with respect to distilled water at or the electrolyte aqueous solution 20° C., and wherein, in the electrolyte aqueous solution or the electrolyte suspension in which the raw material inorganic compound is immersed, at least, elements other than hydrogen and oxygen, which are included in the product inorganic compound but not included in the raw material inorganic compound are included (provided that it excludes a production method in which an apatite without pores with a diameter of 20 μm or more and an aspect ratio of 2 or more is produced from at least one selected from the group consisting of calcium sulfate dihydrate, an α-type tricalcium phosphate, and calcium carbonate, a production method in which calcium sulfate is immersed in an ammonia or alkali metal hydroxide-containing aqueous solution, carbon dioxide is introduced into the aqueous solution, and calcium carbonate without pores with a diameter of 20 μm or more and an aspect ratio of 2 or more is produced, and a production method in which a product inorganic compound is calcium hydrogen phosphate without pores with a diameter of 20 or more and an aspect ratio of 2 or more).

(2) The method of producing a product inorganic compound according to (1), wherein a porosity of the raw material inorganic compound is less than 30%.

(3) The method of producing a product inorganic compound according to (1), wherein the raw material inorganic compound is a porous body having a porosity of 30% or more.

(4) The method of producing a product inorganic compound according to any one of (1) to (3), wherein the raw material inorganic compound is an interconnected porous body.

(5) The method of producing a product inorganic compound according to any one of (1) to (4), wherein, in the step C, a product inorganic compound which is a porous body with pores having an aspect ratio of at least 2 or more is obtained.

(6) The method of producing a product inorganic compound according to any one of (1) to (5), wherein the raw material inorganic compound comprises a compositing material component selected from the group including an organic substance, a metal and an inorganic compound other than the raw material inorganic compound.

(7) The method of producing a product inorganic compound according to any one of (1) to (6), wherein the raw material inorganic compound comprises an alkaline earth metal.

(8) The method of producing a product inorganic compound according to any one of (1) to (7), wherein the raw material inorganic compound comprises at least one selected from the group consisting of calcium sulfate, calcium carbonate, calcium phosphate, a calcium-containing glass, and a bone.

(9) The method of producing a product inorganic compound according to any one of (1) to (8), wherein the raw material inorganic compound comprises calcium sulfate anhydrate.

(10) The method of producing a product inorganic compound according to any one of (1) to (9), wherein the raw material inorganic compound is an artificial material.

(11) The method of producing a product inorganic compound according to any one of (1) to (9), wherein the raw material inorganic compound is a natural material or a material of biological origin.

(12) The method of producing a product inorganic compound according to any one of (1) to (11),
wherein the electrolyte aqueous solution or the electrolyte suspension in which the raw material inorganic compound is immersed comprises an alkaline earth metal, an alkali metal, or an ammonia compound.

(13) The method of producing a product inorganic compound according to any one of (1) to (12),
wherein the electrolyte aqueous solution or the electrolyte suspension in which the raw material inorganic compound is immersed comprises at least one selected from the group consisting of carbonate ions, bicarbonate ions, sulfate ions, hydrogen sulfate ions, hydrogen phosphate ions, hydroxide ions, and fluoride ions.

(14) The method of producing a product inorganic compound according to any one of (1) to (13),
wherein a pH of the electrolyte aqueous solution or the electrolyte suspension in which the raw material inorganic compound is immersed is less than 7.

(15) The method of producing a product inorganic compound according to any one of (1) to (13),
wherein a pH of the electrolyte aqueous solution or the electrolyte suspension in which the raw material inorganic compound is immersed is 7 or more.

(16) The method of producing a product inorganic compound according to any one of (1) to (15),
wherein a temperature at which the raw material inorganic compound is immersed in the electrolyte aqueous solution or the electrolyte suspension is less than 100° C.

(17) The method of producing a product inorganic compound according to any one of (1) to (16),
wherein a temperature at which the raw material inorganic compound is immersed in the electrolyte aqueous solution or the electrolyte suspension is 10° C. or less.

(18) The method of producing a product inorganic compound according to any one of (1) to (15),
wherein a temperature at which the raw material inorganic compound is immersed in the electrolyte aqueous solution or the electrolyte suspension is a temperature exceeding 100° C.

(19) The method of producing a product inorganic compound according to any one of (1) to (18),
wherein, in the step B1 or step B2, a molar number of an ion component of an exchange target included in the electrolyte aqueous solution or the electrolyte suspension is equal to or greater than a molar number of an ion component of an exchange target in the raw material inorganic compound.

(20) The method of producing a product inorganic compound according to any one of (1) to (18),
wherein, in the step B1 or step B2, a molar number of an ion component of an exchange target included in the electrolyte aqueous solution or the electrolyte suspension is less than a molar number of an ion component of an exchange target in the raw material inorganic compound.

(21) The method of producing a product inorganic compound according to any one of (1) to (20),
wherein the step A includes a step al in which an ion component that is included in the raw material inorganic compound but not included in the product inorganic compound is removed from the electrolyte aqueous solution or the electrolyte suspension.

(22) The method of producing a product inorganic compound according to (21),
wherein the step al is a step in which at least one method selected from the group consisting of a method in which a part of all of the electrolyte aqueous solution or the electrolyte suspension is exchanged with a new electrolyte aqueous solution or electrolyte suspension, an ion exchange method, an adsorption method, an electrodialysis method, a diffusion dialysis method, and an electrolysis method is used.

(23) The method of producing a product inorganic compound according to any one of (1) to (22),
wherein, in the step C, a precipitated inorganic compound layer formed in the steps B1 to B3 forms a porous body according to a curing reaction in which the plurality of raw material inorganic compounds are bridged.

(24) A produced product inorganic compound produced by any one of production methods according to (1) to (23).

(25) A product inorganic compound which is a product inorganic compound that has a volume of at least $10^{-13}$ m$^3$ or more, comprises at least grain boundaries other than sinterable grain boundaries, preserves a form without disintegrating even if it is immersed in water for 24 hours, and has substantially the same composition from a surface to the inside (provided that it excludes a case in which gypsum, calcium hydrogen phosphate, zinc phosphate, calcium silicate, calcite, or an apatite, without pores with a diameter of 20 μm or more and an aspect ratio of 2 or more is used as the inorganic compound).

(26) The product inorganic compound according to (24) or (25),
comprising pores with a diameter of 20 μm to 3000 μm and a length twice or more of the diameter.

(27) The product inorganic compound according to any one of (24) to (26),
wherein the product inorganic compound comprises a composition having at least one selected from the group consisting of a carbonate apatite, vaterite-containing calcium carbonate, aragonite-containing calcium carbonate, calcium hydroxide, calcium fluoride, magnesium hydroxide, and whitlockite (provided that it excludes an apatite without pores with a diameter of 20 μm or more and an aspect ratio of 2 or more).

(28) A product inorganic compound which is a product inorganic compound that has a volume of $10^{-13}$ m$^3$ or more, comprising:
at least a core portion and a surface layer portion that covers the core portion,
wherein the core portion and the surface layer portion have different compositions,
wherein an inorganic compound of the surface layer portion comprises at least grain boundaries other than sinterable grain boundaries and preserves a form without disintegrating even if it is immersed in water for 24 hours, and
wherein an inorganic compound of the surface layer portion comprises at least one element included in a composition of the core portion (provided that it excludes a product inorganic compound that comprises a core portion formed of calcium carbonate that is not an artificial material and a surface layer portion formed of an apatite).

(29) A product inorganic compound which is a product inorganic compound that comprises at least a core portion and a surface layer portion that covers the core portion,
wherein the product inorganic compound has a volume of $10^{-13}$ m$^3$ or more,
wherein the core portion and the surface layer portion have different compositions,
wherein the core portion has a component the same as that of a raw material inorganic compound and the surface layer portion comprises at least grain boundaries other than sinterable grain boundaries and preserves a form without disintegrating even if it is immersed in water for 24 hours, and wherein the product inorganic compound comprises a component in which anions of the inorganic compound are exchanged with anions of an electrolyte aqueous solution or an electrolyte suspension, a component in which cations of the inorganic compound are exchanged with cations of an electrolyte aqueous solution or an electrolyte suspension, or a component derived from the electrolyte aqueous solution or the electrolyte suspension that is not included in a raw material inorganic compound (provided that it excludes a product inorganic compound that comprises a core portion formed of calcium carbonate that is not an artificial material and a surface layer portion formed of an apatite).

(30) The product inorganic compound according to (28) or (29), wherein an inorganic compound included at least in the core portion comprises at least grain boundaries other than sinterable grain boundaries.

(31) The product inorganic compound according to any one of (28) or (30), wherein an inorganic compound of either or both of the surface layer portion and the core portion is a calcium compound.

(32) The product inorganic compound according to any one of (28) or (31), wherein an inorganic compound of either or both of the surface layer portion and the core portion has a solubility that is 0.0001 or more and 5 or less at 20° C. with respect to distilled water.

(33) The product inorganic compound according to any one of (28) or (32), wherein a solubility of the inorganic compound of the surface layer portion with respect to distilled water at 20° C. is greater than a solubility of the inorganic compound of the core portion with respect to distilled water at 20° C.

(34) The product inorganic compound according to any one of (28) or (32), wherein a solubility of the inorganic compound of the surface layer portion with respect to distilled water at 20° C. is smaller than a solubility of the inorganic compound of the core portion with respect to distilled water at 20° C.

(35) The product inorganic compound according to any one of (28) or (34), wherein the inorganic compound of the surface layer portion comprises at least one selected from the group consisting of vaterite-containing calcium carbonate, aragonite-containing calcium carbonate, whitlockite, calcium hydrogen phosphate, calcium sulfate, calcium carbonate, calcium hydrogen phosphate, calcium hydroxide, and apatite.

(36) The product inorganic compound according to any one of (28) or (35), wherein the inorganic compound of the core portion comprises at least one selected from the group consisting of calcium phosphate, calcium carbonate, calcium sulfate, an apatite, a calcium-containing glass, a coral, and a bone.

(37) The product inorganic compound according to any one of (28) or (36), wherein an average conversion thickness of the surface layer portion is 1 µm or more.

(38) The product inorganic compound according to any one of (28) or (37), wherein a mass ratio between the core portion and the surface layer portion (core portion:surface layer portion) is 97:3 to 50:50.

(39) The product inorganic compound according to any one of (28) or (38), wherein the surface layer portion comprises at least calcium sulfate hemihydrate and has curability.

(40) The product inorganic compound according to any one of (28) or (39), wherein the surface layer portion comprises granules containing at least calcium sulfate hemihydrate, and has curability when an aqueous solution containing at least one of sodium ions and sulfate ions is used as a mixing solution.

(41) The product inorganic compound according to any one of (28) or (40), wherein the core portion is a porous body.

(42) The product inorganic compound according to any one of (28) or (41), wherein a support is included in the core portion.

(43) The product inorganic compound according to (42), wherein the support comprises at least one selected from the group consisting of a metal, a polymer, and a ceramic.

(44) The product inorganic compound according to (43), wherein the metal is at least one selected from the group consisting of titanium, a titanium alloy, stainless steel, and a cobalt chromium alloy, wherein the polymer is at least one selected from the group consisting of an aromatic polyether ketone, a polyimide, and a polysulfone, and wherein the ceramic is either or both of an alumina and a zirconia.

(45) The product inorganic compound according to any one of (42) or (44), wherein the support is a porous body.

(46) The product inorganic compound according to any one of (28) or (41), wherein the core portion does not comprise a support.

(47) A curable composition including:

a plurality of raw material inorganic compounds with a volume of $10^{-13}$ m$^3$ or more; and an electrolyte aqueous solution, wherein the curable composition includes a component in which the raw material inorganic compound and the electrolyte aqueous solution react and anions of the inorganic compound are exchanged with anions of the electrolyte aqueous solution or the electrolyte suspension or cations of the inorganic compound are exchanged with cations of the electrolyte aqueous solution or the electrolyte suspension or a component that is not included in the raw material inorganic compound and is derived from the electrolyte aqueous solution or the electrolyte suspension is to be formed on a surface of the raw material inorganic compound and a formed substance bridges the raw material inorganic compounds to form a porous body.

(48) The curable composition according to (47), wherein the formed porous body is an interconnected porous body.

(49) The curable composition according to (47) or (48), wherein the raw material inorganic compound is at least one selected from the group consisting of calcium phosphate, calcium carbonate, calcium sulfate, calcium hydroxide, calcium fluoride, calcium silicate, a calcium-containing glass, a coral, a shell, and a bone.

(50) The curable composition according to any one of (47) to (49), wherein the electrolyte aqueous solution includes at least one selected from the group consisting of hydrogen phosphate ions, sulfate ions, and carbonate ions.

(51) The curable composition according to any one of (47) to (50),
wherein the formed substance comprises at least one selected from the group consisting of calcium hydrogen phosphate, calcium sulfate, and calcium carbonate.
(52) The curable composition according to any one of (47) to (51),
wherein the curable composition is a material for medical treatment.
(53) The curable composition according to any one of (47) to (52),
wherein the curable composition is a hard tissue reconstruction material.
(54) A hard tissue reconstruction material for medical treatment characterized in that it comprises at least a core portion and a surface layer portion that covers the core portion, in which the core portion and the surface layer portion have different compositions, the core portion comprises a calcium component other than calcium hydrogen phosphate, and the surface layer portion comprises calcium hydrogen phosphate.
(55) The hard tissue reconstruction material for medical treatment according to (54),
wherein the calcium component is at least one selected from the group consisting of calcium phosphate, calcium carbonate, calcium sulfate, an apatite, a calcium-containing glass, a coral and a bone.
(56) The hard tissue reconstruction material for medical treatment according to (54) or (55),
wherein the calcium component is at least one selected from the group consisting of artificially produced calcium phosphate, calcium carbonate, calcium sulfate and a calcium-containing glass.
(57) The hard tissue reconstruction material for medical treatment according to any one of (54) or (56),
wherein the calcium component is at least one selected from the group consisting of a β-type tricalcium phosphate, an α-type tricalcium phosphate, a hydroxyapatite and a carbonate apatite.
(58) The hard tissue reconstruction material for medical treatment according to any one of (54) or (57),
wherein the core portion is a porous body.
(59) The hard tissue reconstruction material for medical treatment according to any one of (54) or (58),
wherein an average conversion thickness of the surface layer portion is 1 μm or more.
(60) The hard tissue reconstruction material for medical treatment according to any one of (54) or (59),
wherein a support is included in the core portion.
(61) The hard tissue reconstruction material for medical treatment according to (60),
wherein the support comprises at least one selected from the group consisting of a metal, a polymer and a ceramic.
(62) The hard tissue reconstruction material for medical treatment according to (61),
wherein the metal is at least one selected from the group consisting of titanium, a titanium alloy, stainless steel and a cobalt chromium alloy, the polymer is at least one selected from the group consisting of an aromatic polyether ketone, a polyimide and a polysulfone, and the ceramic is either or both of an alumina and a zirconia.
(63) The hard tissue reconstruction material for medical treatment according to any one of (60) or (62),
wherein the support is a porous body.
(64) The hard tissue reconstruction material for medical treatment according to any one of (54) or (59),
wherein no support is included.
(65) The hard tissue reconstruction material for medical treatment according to (64),
wherein it is a bone prosthetic material.
(66) The hard tissue reconstruction material for medical treatment according to (64) or (65),
wherein an average volume is $10^{-13}$ m$^3$ or more.
(67) A method of producing the hard tissue reconstruction material for medical treatment according to any one of (54) to (66), comprising
a covering step in which a core portion is brought into contact with an acidic aqueous solution to form a surface layer portion,
wherein the core portion comprises a calcium component other than calcium hydrogen phosphate and a pH of the acidic aqueous solution is 5 or less and the acidic aqueous solution comprises a phosphate component when the core portion does not include a phosphate component, and
wherein the surface layer portion comprising calcium hydrogen phosphate is formed according to the covering step.
(68) The method of producing a hard tissue reconstruction material for medical treatment according to (67),
wherein the acidic aqueous solution comprises a phosphate component and a calcium component.
(69) The method of producing a hard tissue reconstruction material for medical treatment according to (67) or (68),
wherein a pH of the acidic aqueous solution is 3 or less.
(70) The method of producing a hard tissue reconstruction material for medical treatment according to any one of (67) or (69), further including a surface layer portion adjusting step in which a part of the calcium hydrogen phosphate included in the formed surface layer portion is dissolved in a solvent to adjust a thickness or a form of the surface layer portion.
(71) A curable composition for forming a calcium hydrogen phosphate-containing porous body which is a curable composition comprising granules comprising a calcium component (provided that it excludes calcium dihydrogen phosphate) and in which 70 mass % or more of the granules have a particle size of 100 μm or more and 10 mm or less.
(72) The curable composition according to (71),
wherein 70 mass % or more of the granules have a particle size of 100 or more and 3 mm or less.
(73) The curable composition according to (71),
wherein 90 mass % or more of the granules have a particle size of 100 μm or more and 10 mm or less.
(74) The curable composition according to any one of (71) to (73),
wherein the calcium component is at least one selected from the group comprising calcium phosphate, calcium carbonate, calcium sulfate, calcium hydroxide, calcium fluoride, calcium silicate, a calcium-containing glass, a coral, a shell and a bone.
(75) The curable composition according to any one of (71) to (74),
wherein the granules include calcium dihydrogen phosphate as a phosphate component.
(76) A porous body comprising calcium hydrogen phosphate produced from any one of the curable compositions according to (71) to (75).
(77) A method of producing a porous body which is a method of producing the porous body according to (76) and which comprises a step in which the curable composition according to any one of (71) to (75) is reacted with water to form calcium hydrogen phosphate, and either or both of the granules and the water contains a phosphate component.

(78) The method of producing a porous body according to (77),
wherein the water is an aqueous solution having a pH of 4 or less.

(79) The method of producing a porous body according to (77) or (78),
wherein the phosphate component is included in the granules.

(80) The method of producing a porous body according to (79),
wherein the phosphate component is included in surfaces of the granules.

(81) The method of producing a porous body according to (79) or (80),
wherein the phosphate component is calcium dihydrogen phosphate.

(82) The method of producing a porous body according to any one of (77) to (79),
wherein the phosphate component is not included in the granules but is included in the water.

(83) The method of producing a porous body according to any one of (77) to (82),
wherein the water includes a calcium component.

(84) A surface apatitized porous body which is a surface apatitized porous body produced from the porous body according to (76) and in which at least a part of calcium hydrogen phosphate of a surface is apatitized.

(85) The method of producing a porous body according to (84),
wherein the apatitization is carbonate apatitization.

(86) A method of producing a surface apatitized porous body which is a method of producing the surface apatitized porous body according to (84) and which comprises a step in which the porous body according to (76) is immersed in an aqueous solution having a pH of 8 or more and at least a part of calcium hydrogen phosphate included in a surface of the porous body is apatitized.

(87) The method of producing a porous body according to (86),
wherein the aqueous solution includes a carbonate component.

(88) A calcined porous body which is a calcined porous body produced from the porous body according to (76) and obtained by calcining the porous body.

(89) A method of producing a calcined porous body which is a method of producing the calcined porous body according to (88) and which includes a step in which the porous body according to (76) is calcined at 700° C. or higher.

(90) A surface apatitized and calcined porous body which is a surface apatitized and calcined porous body produced from the surface apatitized porous body according to (84) and obtained by calcining the surface apatitized porous body.

(91) A method of producing a surface apatitized and calcined porous body which is a method of producing the surface apatitized and calcined porous body according to (90) and which comprises a step in which the surface apatitized porous body according to (84) is calcined at 700° C. or higher.

(92) A bone prosthetic material which comprises a core portion and a surface layer portion that covers the core portion and in which the surface layer portion comprises an apatite, the core portion is an artificial material including either or both of calcium phosphate, and calcium carbonate and which have a volume of $10^{-13}$ m$^3$ or more.

(93) The bone prosthetic material according to (92),
wherein the surface layer portion is formed of an apatite.

(94) The bone prosthetic material according to (92) or (93),
wherein the apatite is a carbonate apatite.

(95) The bone prosthetic material according to any one of (92) or (94),
wherein the core portion is an artificial material comprising at least one selected from the group consisting of α-type tricalcium phosphate, β-type tricalcium phosphate, an artificial apatite whose composition is different from the apatite included in the surface layer portion, and calcium carbonate.

(96) The bone prosthetic material according to any one of (92) or (95),
wherein the core portion is an artificial material that comprises calcium carbonate obtained by carbonating calcium oxide, calcium hydroxide or a mixture thereof.

(97) The bone prosthetic material according to any one of (92) or (94),
wherein the core portion is an artificial material that comprises either or both of calcium phosphate and calcium carbonate.

(98) The bone prosthetic material according to any one of (92) or (97),
wherein a volume ratio between the core portion and the surface layer portion (core portion:surface layer portion) is 90:10 to 70:30.

(99) The bone prosthetic material according to any one of (92) or (98),
wherein the surface layer portion further includes calcium hydrogen phosphate.

(100) A method of producing a bone prosthetic material which is a method of producing the bone prosthetic material according to any one of (92) to (98), and which comprises an apatite forming step in which an artificial material that comprises either or both of calcium phosphate and calcium carbonate and has a volume of $10^{-13}$ m$^3$ or more is immersed in water having a pH of 7 or more to form an apatite on a surface layer portion, and in which either or both of the artificial material and the water comprises a phosphate component.

(101) The method of producing a bone prosthetic material according to (100),
wherein the water comprises a carbonate component.

(102) A method of producing a bone prosthetic material which is a method of producing the bone prosthetic material according to (99), which comprises a pretreatment step in which an artificial material comprising either or both of calcium phosphate and calcium carbonate and having a volume of $10^{-13}$ m$^3$ or more is brought into contact with an aqueous solution having a pH of 5 or less to obtain a preprocessed artificial material in which calcium hydrogen phosphate is formed on at least a part of a surface layer portion of the artificial material, and an apatite forming step in which the preprocessed artificial material is immersed in water having a pH of 7 or more to form an apatite on at least a part of the surface layer portion, and in which either or both of the artificial material and the aqueous solution comprise a phosphate component.

(103) The method of producing a bone prosthetic material according to (102),
wherein the aqueous solution comprises a phosphate component and a calcium component.

Effects of the Invention

According to the present invention, it is possible to produce product inorganic compounds in the form of a block and granules without sintering causing high energy consumption. In addition, it is possible to produce highly active product inorganic compounds in the form of a block and granules.

In particular, when calcium sulfate is used as a raw material inorganic compound having a solubility of 5 or less, formation is easy since calcium sulfate has a characteristic form exhibiting self-curability. In addition, since calcium sulfate has a melting point of 1460° C., it is possible to easily produce a porous body inorganic substance using a method of introducing and incinerating an organic substance.

and produced calcium hydrogen phosphate covered calcium-containing glass granules (lower portion) under a scanning electron microscope.

Figure 40:
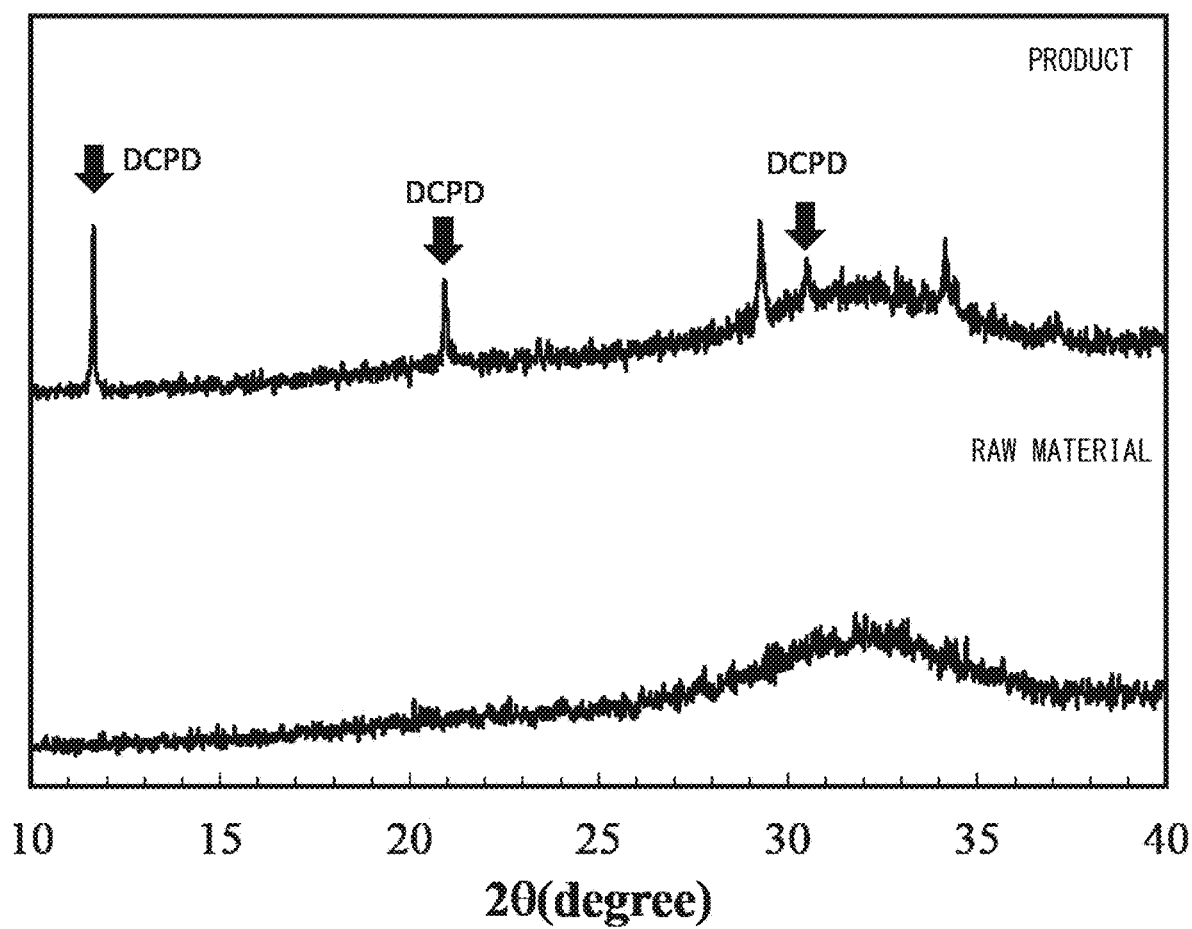

FIG. 40 shows X-ray diffraction patterns of calcium hydrogen phosphate covered calcium-containing glass granules produced in Example 39 (upper portion) and calcium-containing glass granules used as a raw material (lower portion).

Figure 41:
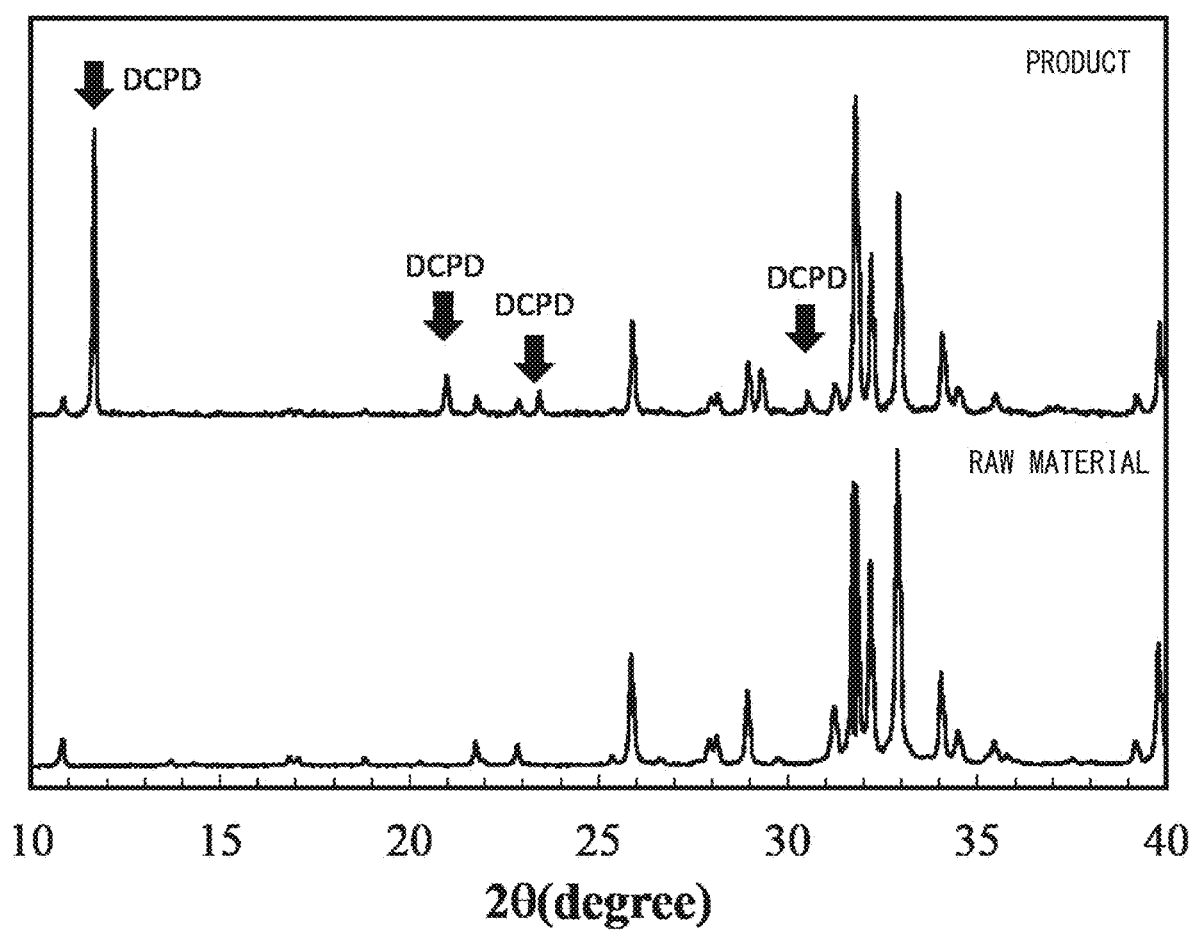

FIG. 41 shows X-ray diffraction patterns of calcium hydrogen phosphate covered calcined bone produced in Example 40 (upper portion) and a calcined bone used as a raw material (lower portion).

Figure 42:
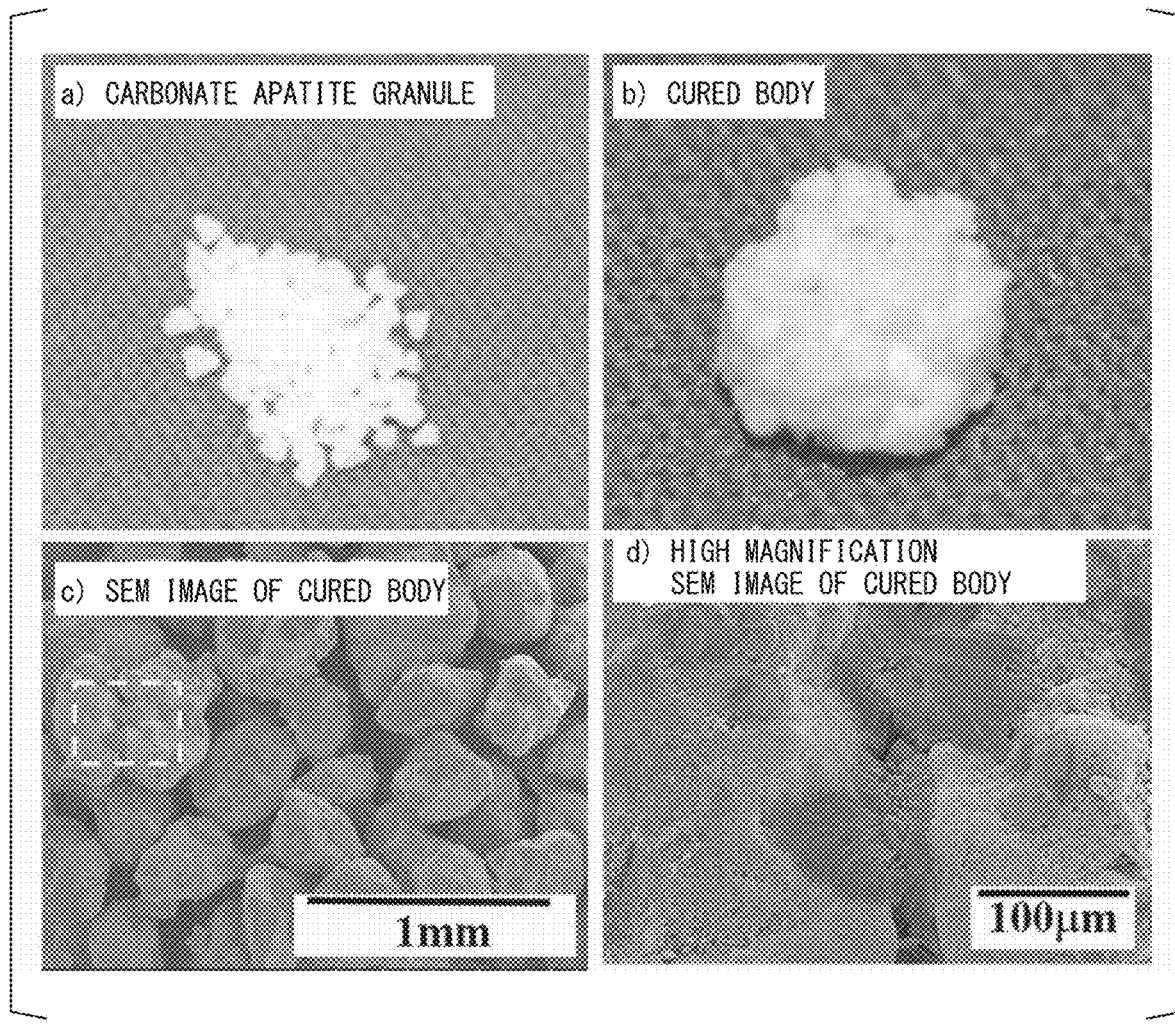

FIG. 42 shows a picture (a) of carbonate apatite granules used for production, a picture (b) of produced cured bodies and scanning electron microscope images (c and d) in Example 42.

Figure 43:
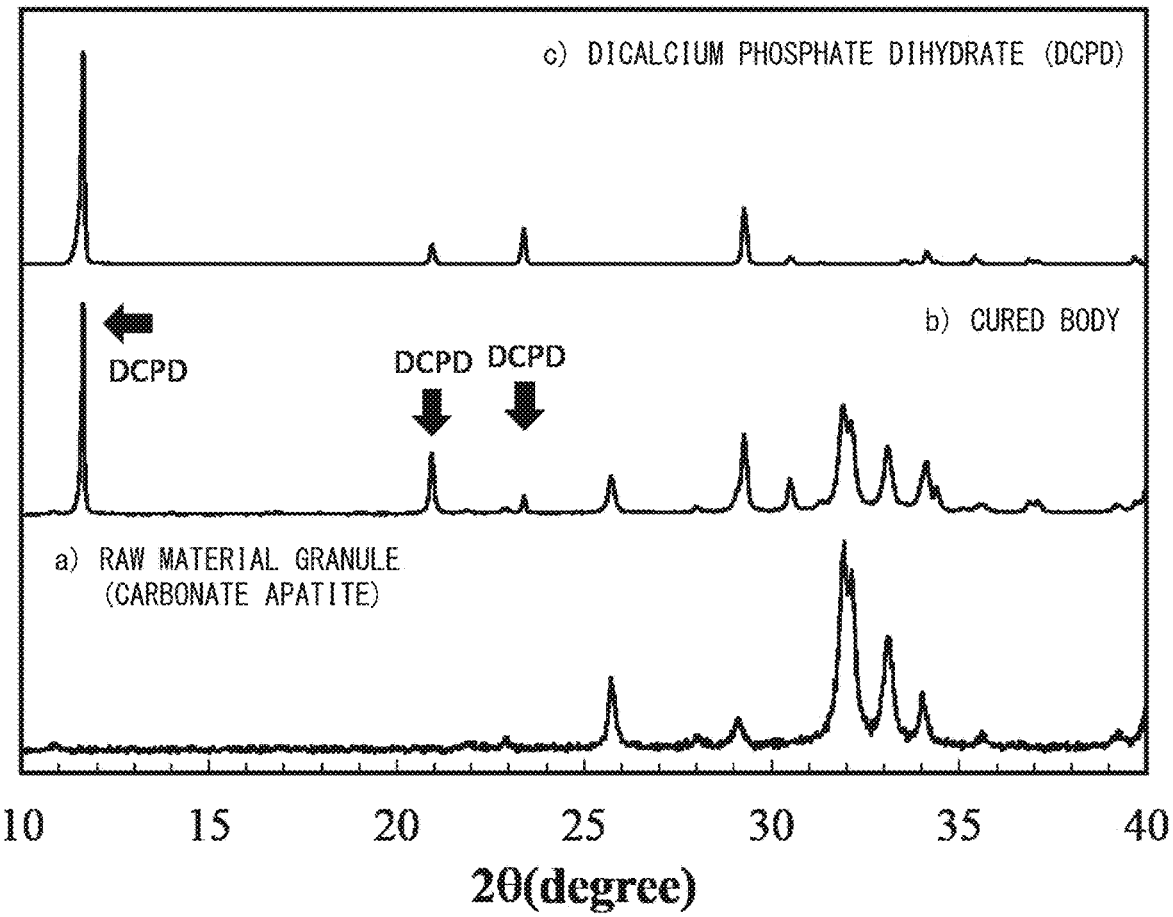

FIG. 43 shows powder X-ray diffraction patterns of carbonate apatite granules (a) used for production, produced cured bodies (b), and calcium hydrogen phosphate (c) in Example 42.

Figure 44:
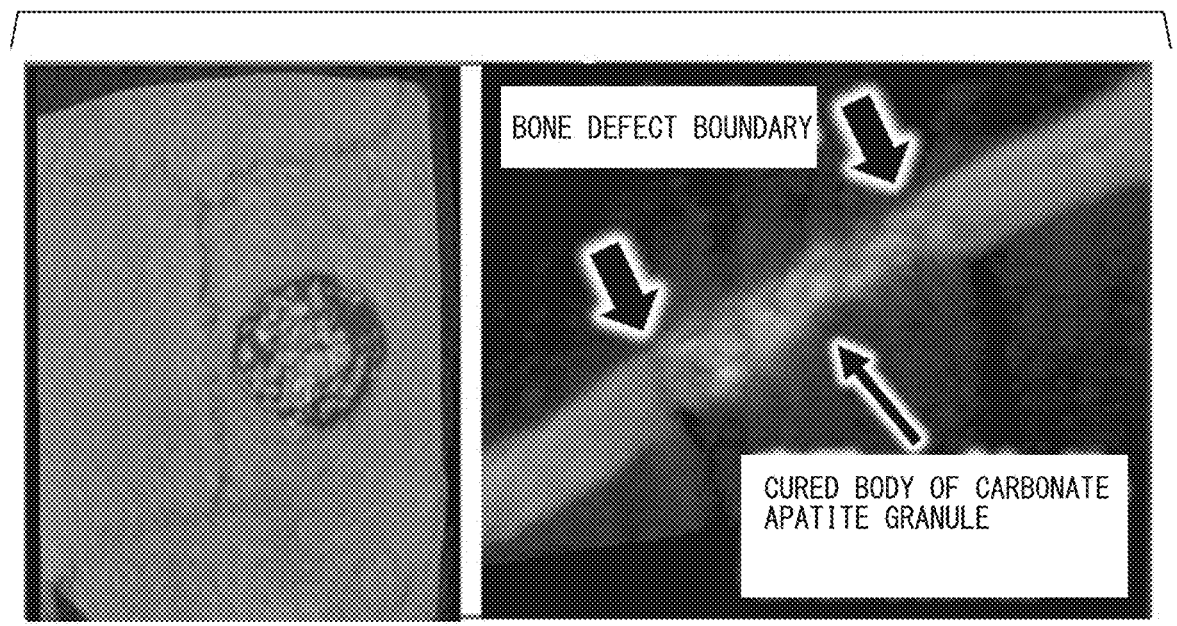

FIG. 44 shows X-ray micro CT images obtained when a cured body is formed on a bone defect of a rat in Example 42.

Figure 45:
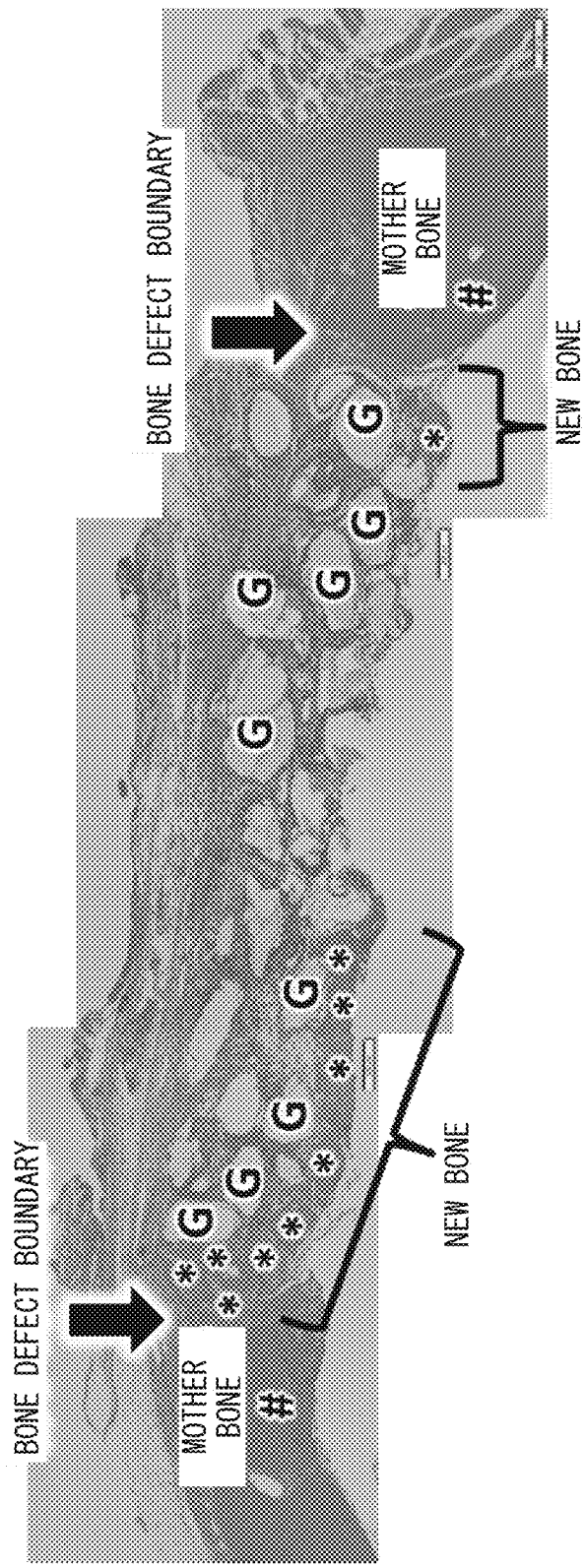

FIG. 45 shows a histopathological image in hematoxy-eosin staining in Example 42.

Figure 46:
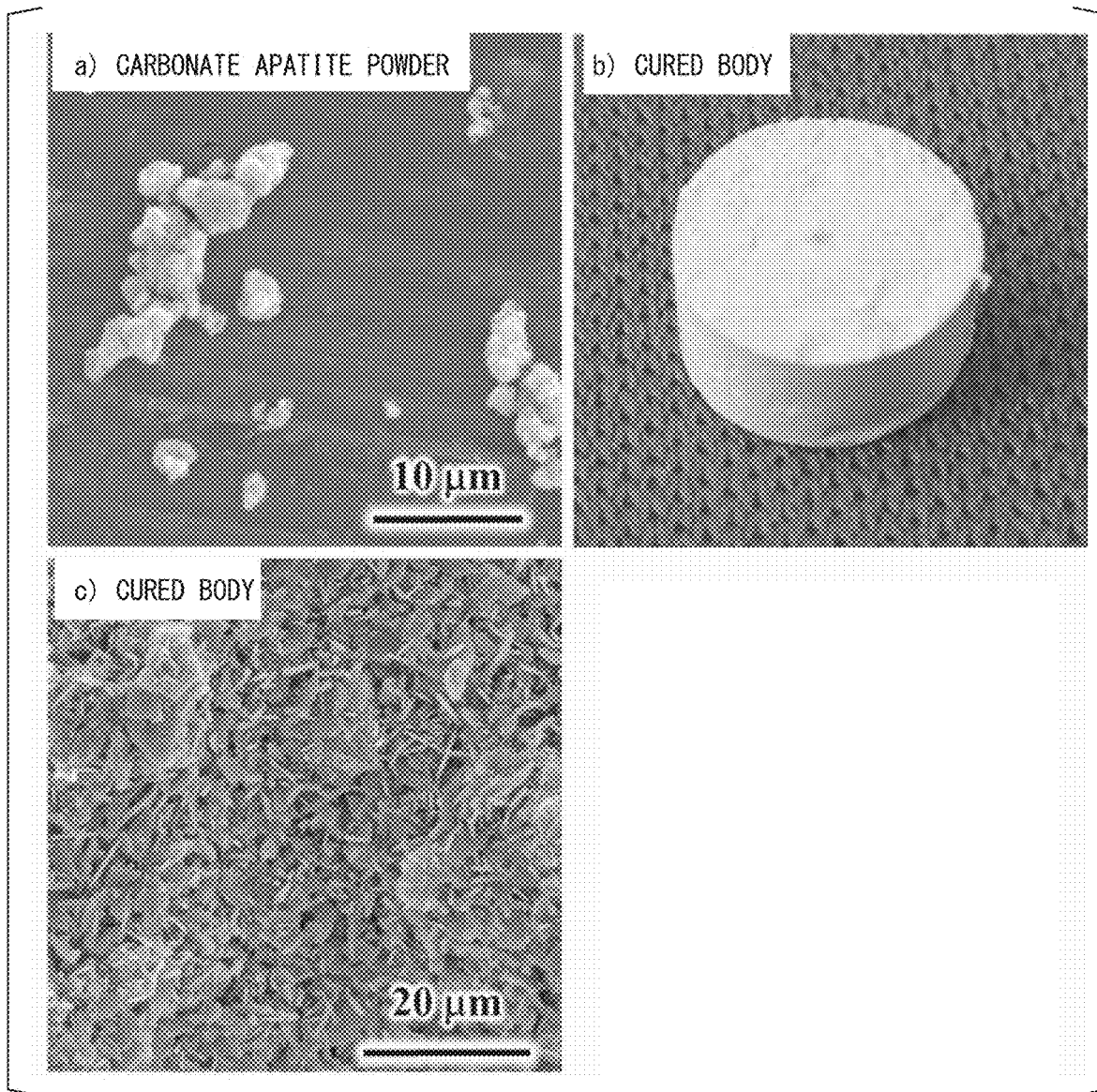

FIG. 46 shows a scanning electron microscope image (a) of carbonate apatite powder used for production, and a picture (b) and a scanning electron microscope image (c) of produced cured bodies in Comparative Example 15.

Figure 47:
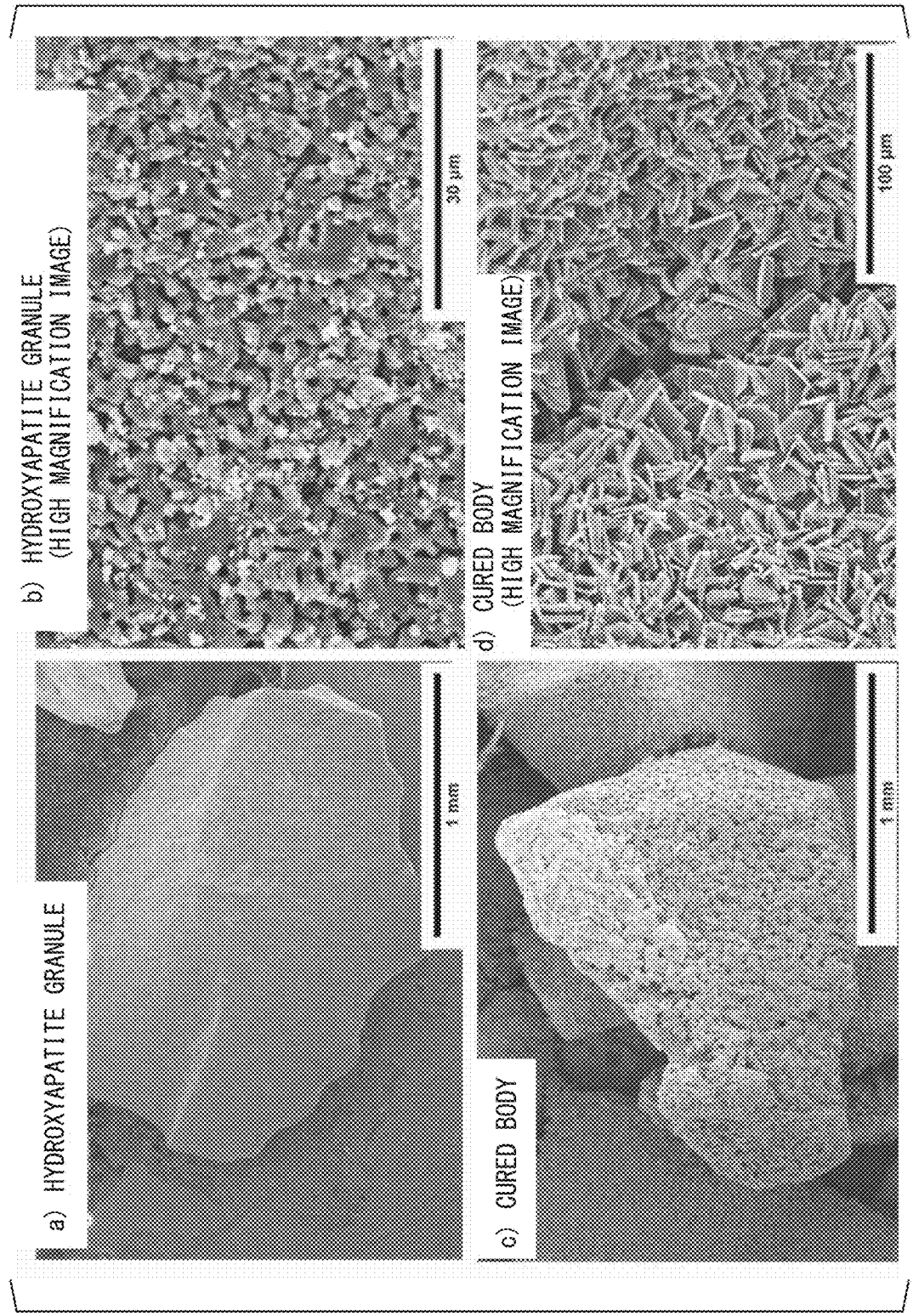

FIG. 47 shows scanning electron microscope images (a and b) of hydroxyapatite granules used for production and scanning electron microscope images (c and d) of produced cured bodies in Example 43.

Figure 48:
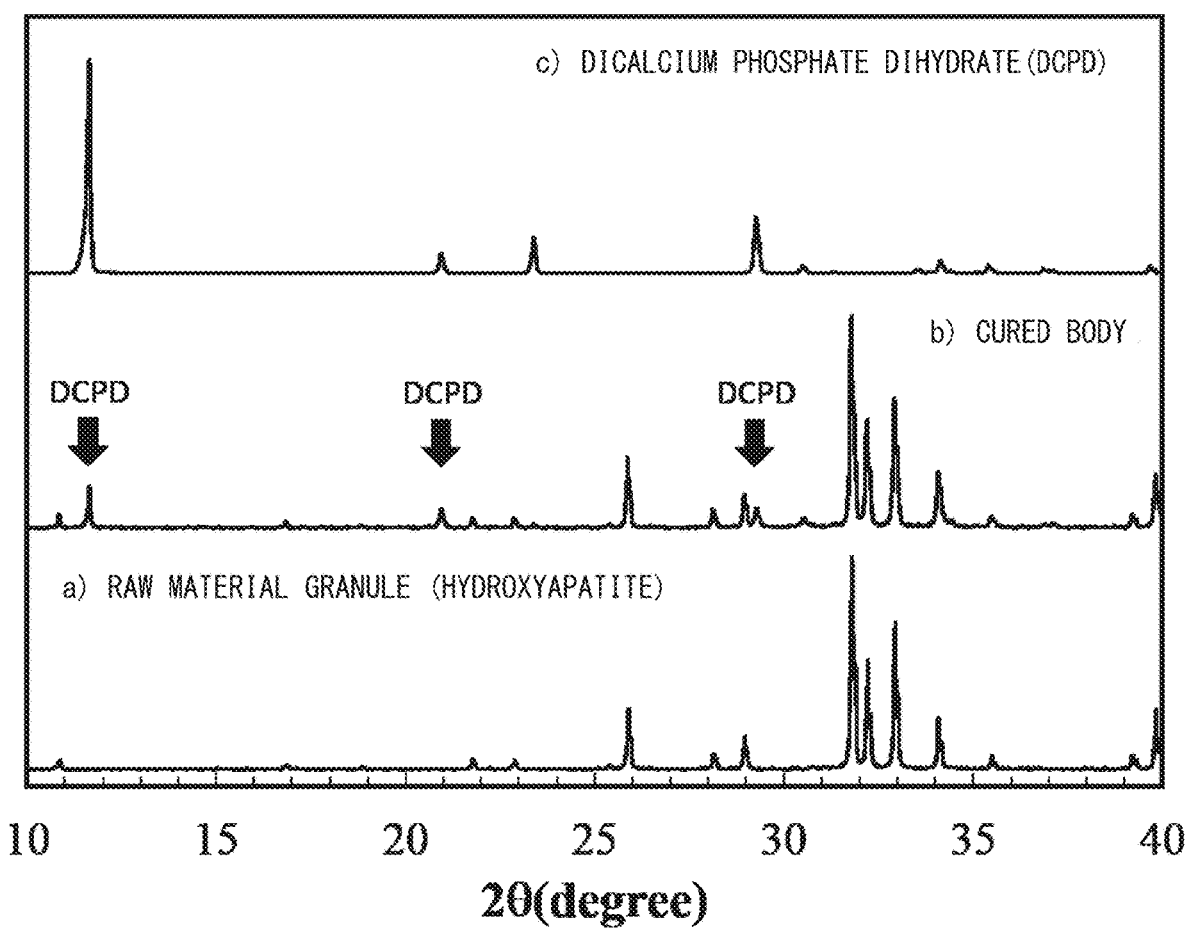

FIG. 48 shows powder X-ray diffraction patterns of hydroxyapatite granules (a) used for production, produced cured bodies (b) and calcium hydrogen phosphate (c) in Example 43.

Figure 49:
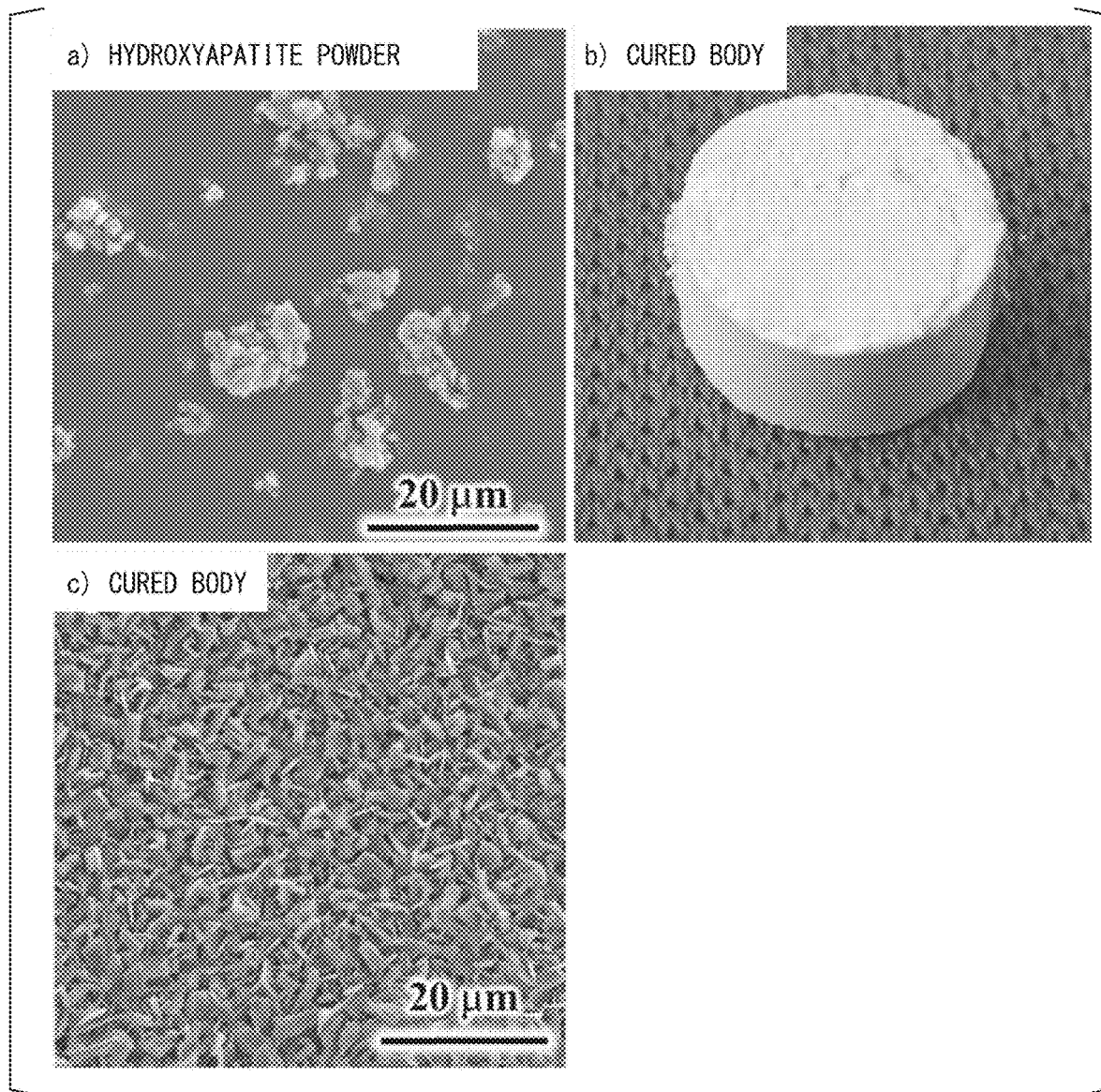

FIG. 49 shows a scanning electron microscope image (a) of hydroxyapatite powder used for production, and a picture (b) and a scanning electron microscope image (c) of produced cured bodies in Comparative Example 16.

Figure 50:
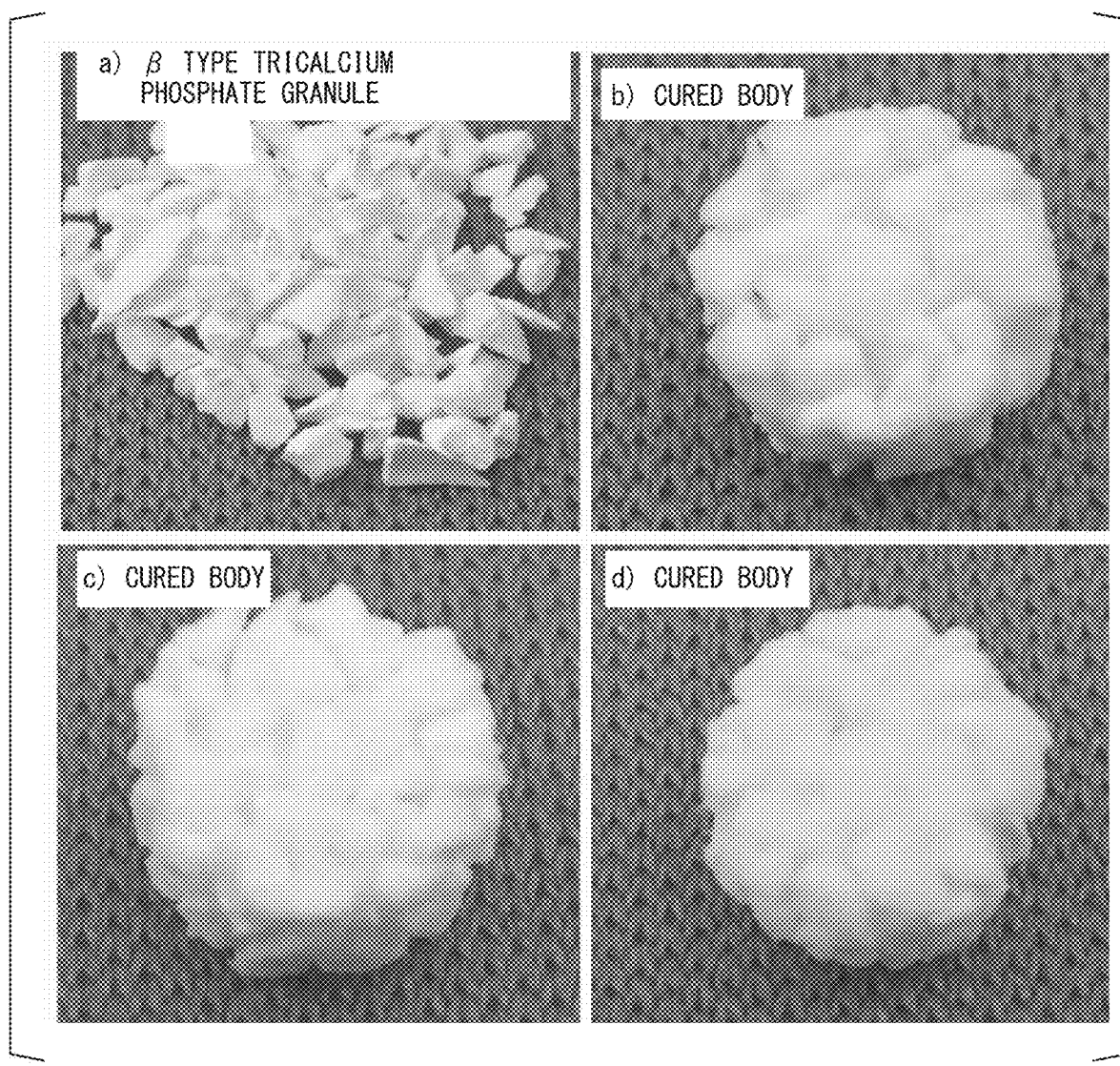

FIG. 50 shows a picture (a) of β-type tricalcium phosphate granules used for production and pictures (b to d) of produced cured bodies in Example 44.

Figure 51:
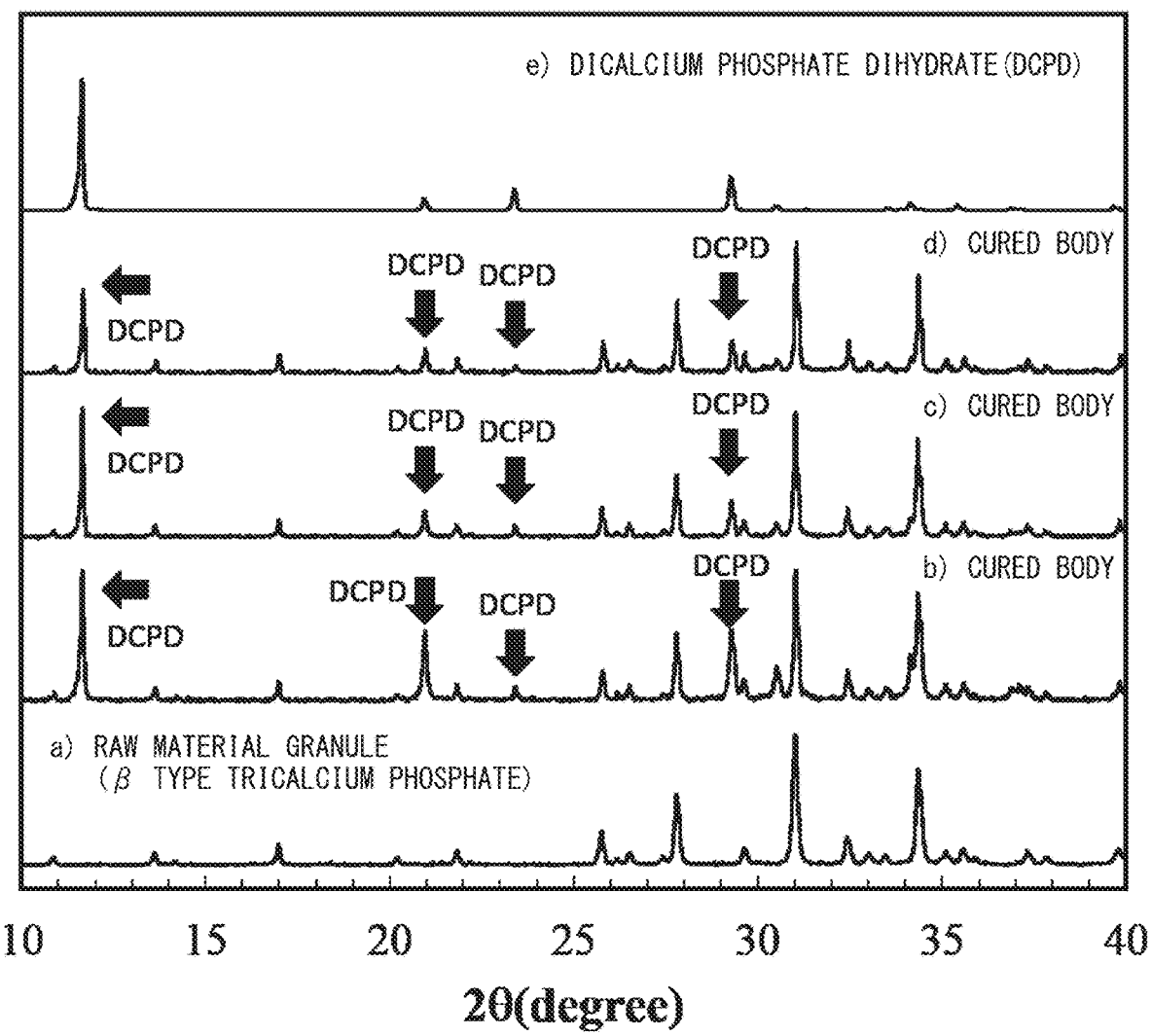

FIG. 51 shows powder X-ray diffraction patterns of β-type tricalcium phosphate granules (a) used for production in Example 44, produced cured bodies (b to d), and calcium hydrogen phosphate (e).

Figure 52:
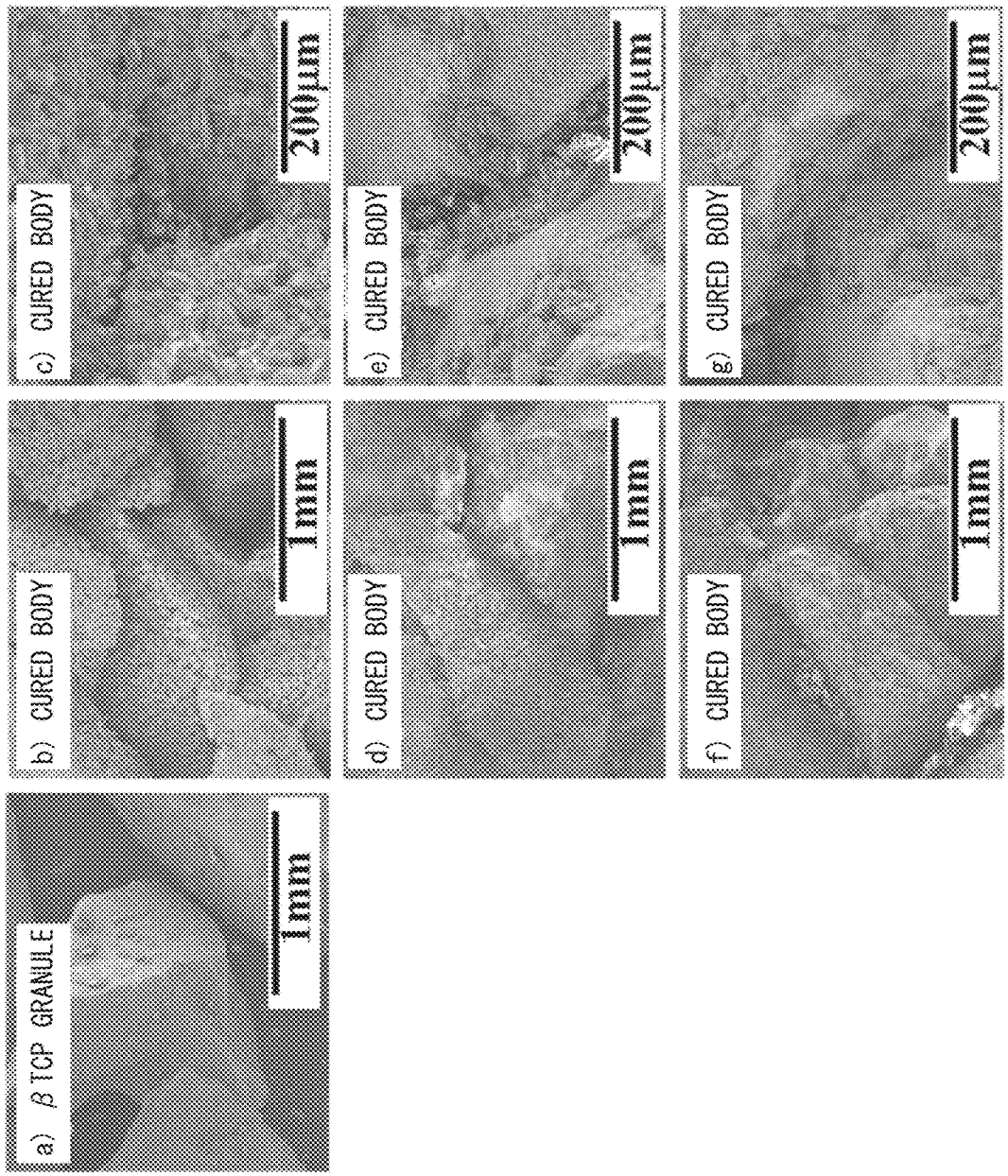

FIG. 52 shows a scanning electron microscope image (a) of β-type tricalcium phosphate granules used for production and scanning electron microscope images (c to g) of produced cured bodies in Example 44.

Figure 53:
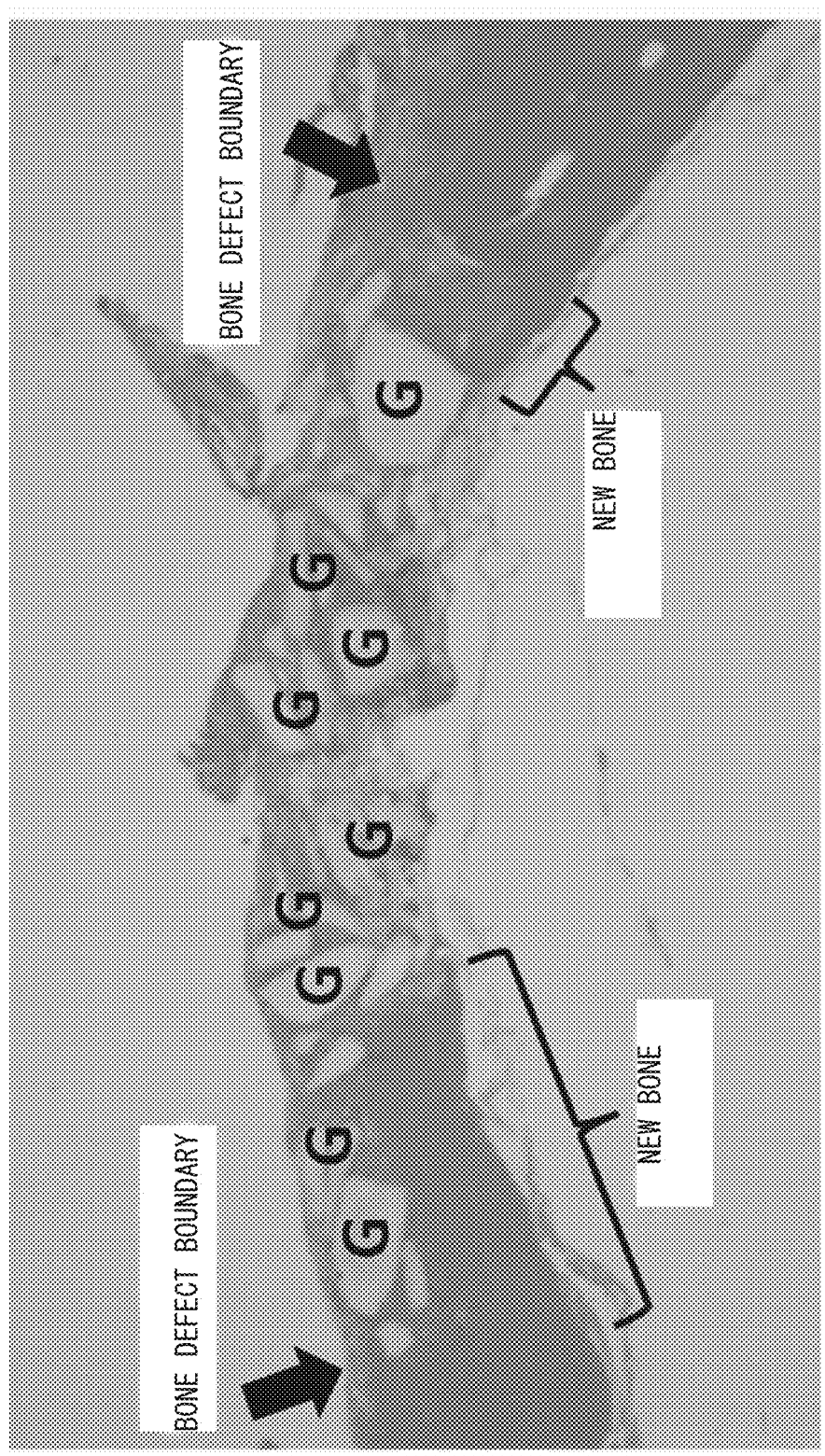

FIG. 53 shows a histopathological image in hematoxy-eosin staining in Example 44.

Figure 54:
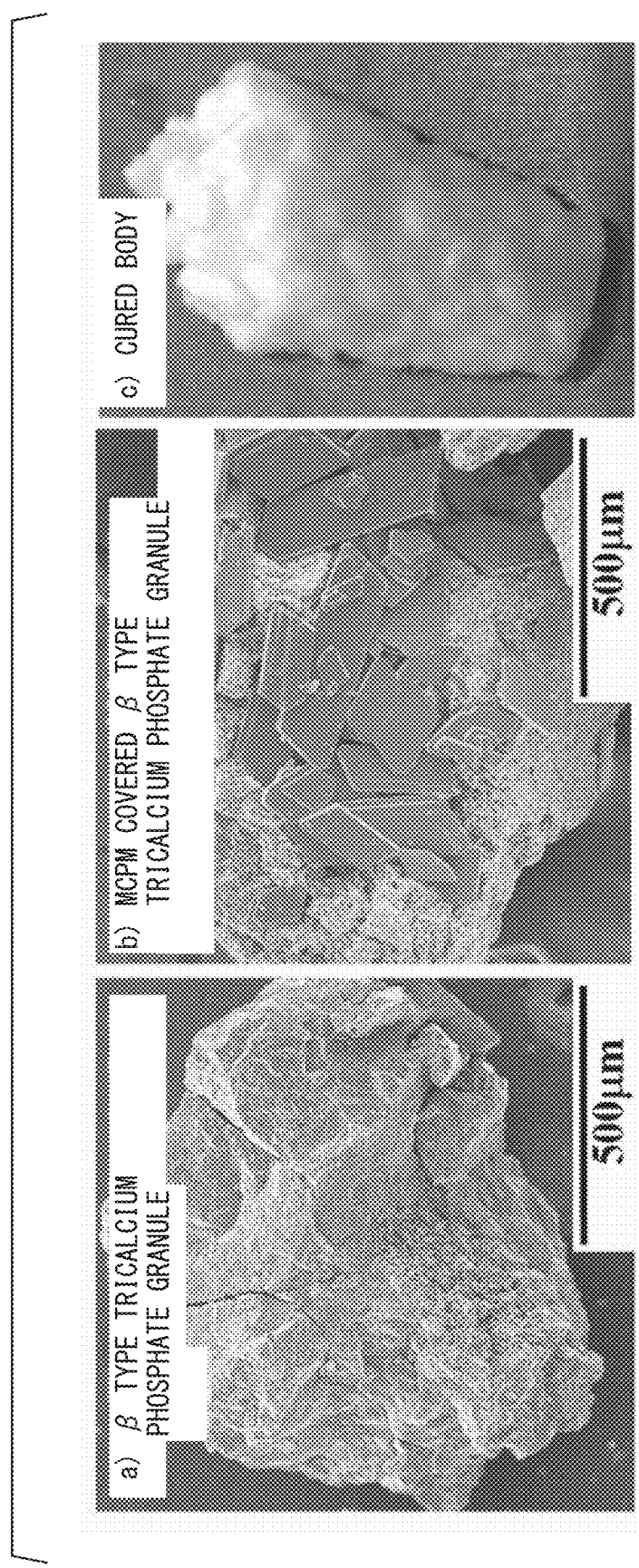

FIG. 54 shows a scanning electron microscope image (a) of β-type tricalcium phosphate granules used for production, a scanning electron microscope image (b) of produced calcium dihydrogen phosphate monohydrate (hereinafter referred to as "MCPM": $Ca(H_2PO_4)_2 \cdot H_2O$)-adhered β TCP granules and a picture (c) of produced cured bodies in Example 45.

Figure 55:
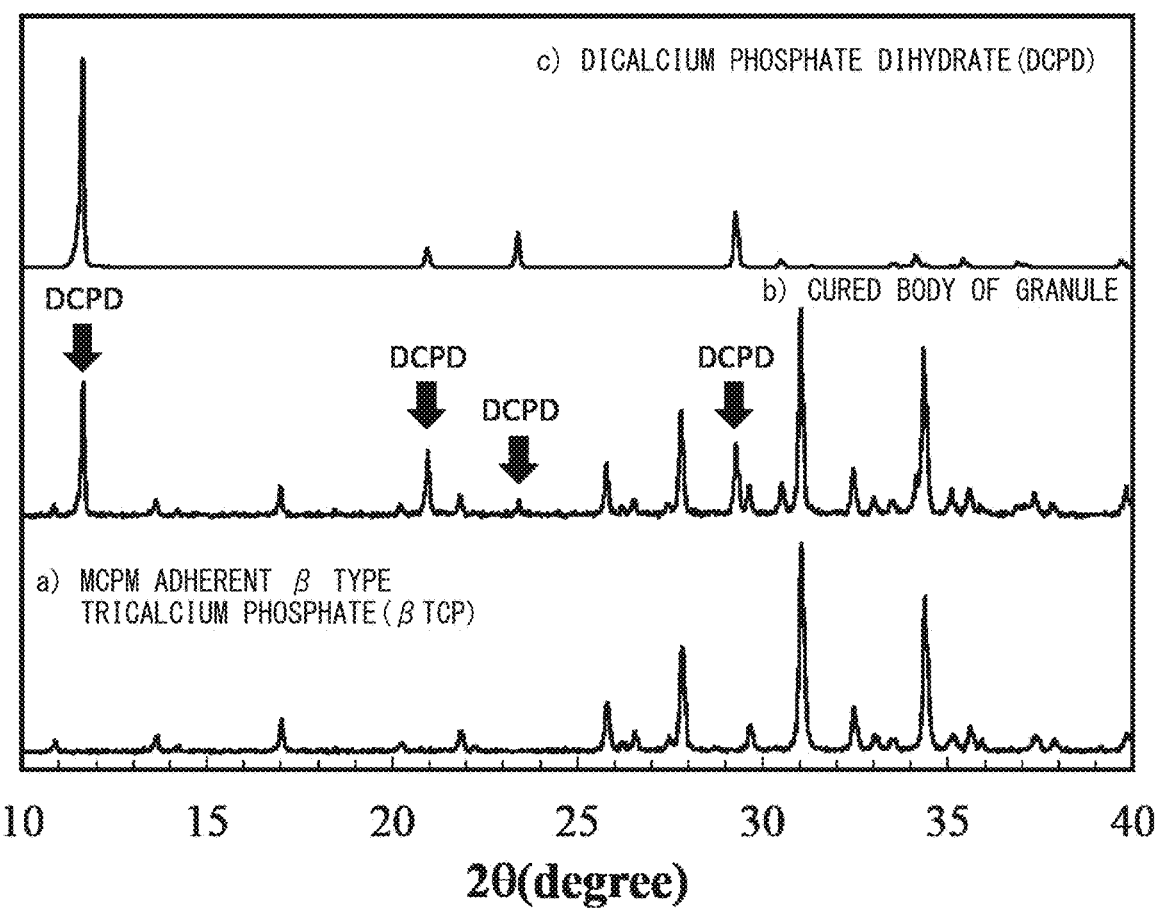

FIG. 55 shows powder X-ray diffraction patterns of β-type tricalcium phosphate granules (a) used for production in Example 45, produced cured bodies (b), and calcium hydrogen phosphate (c).

Figure 56:
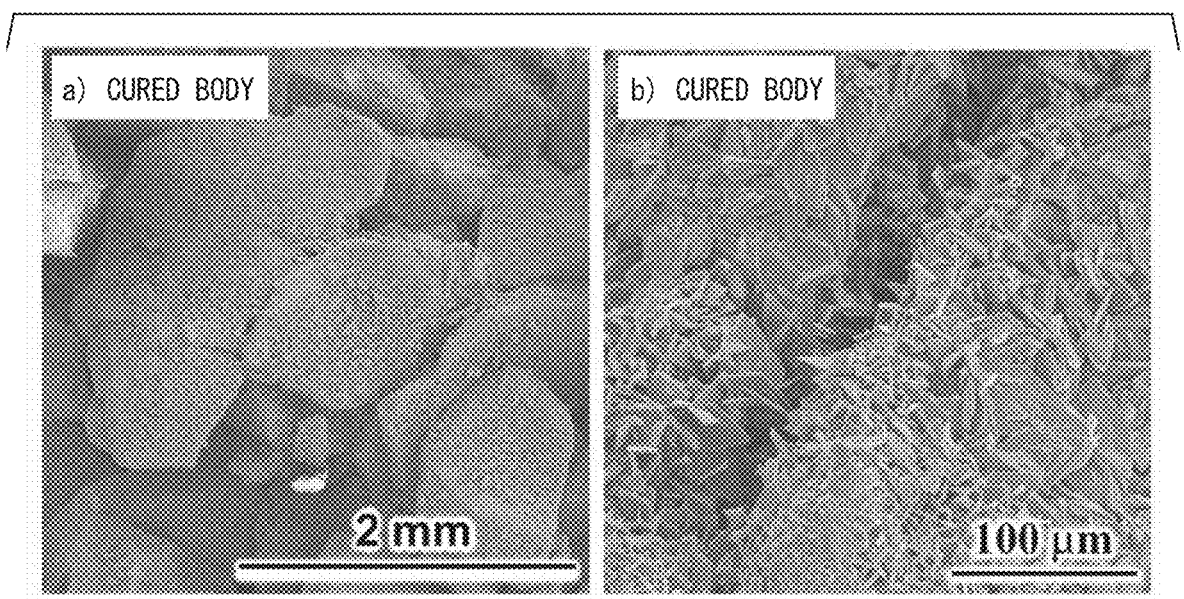

FIG. 56 shows scanning electron microscope images (a and b) of produced cured bodies in Example 45.

Figure 57:
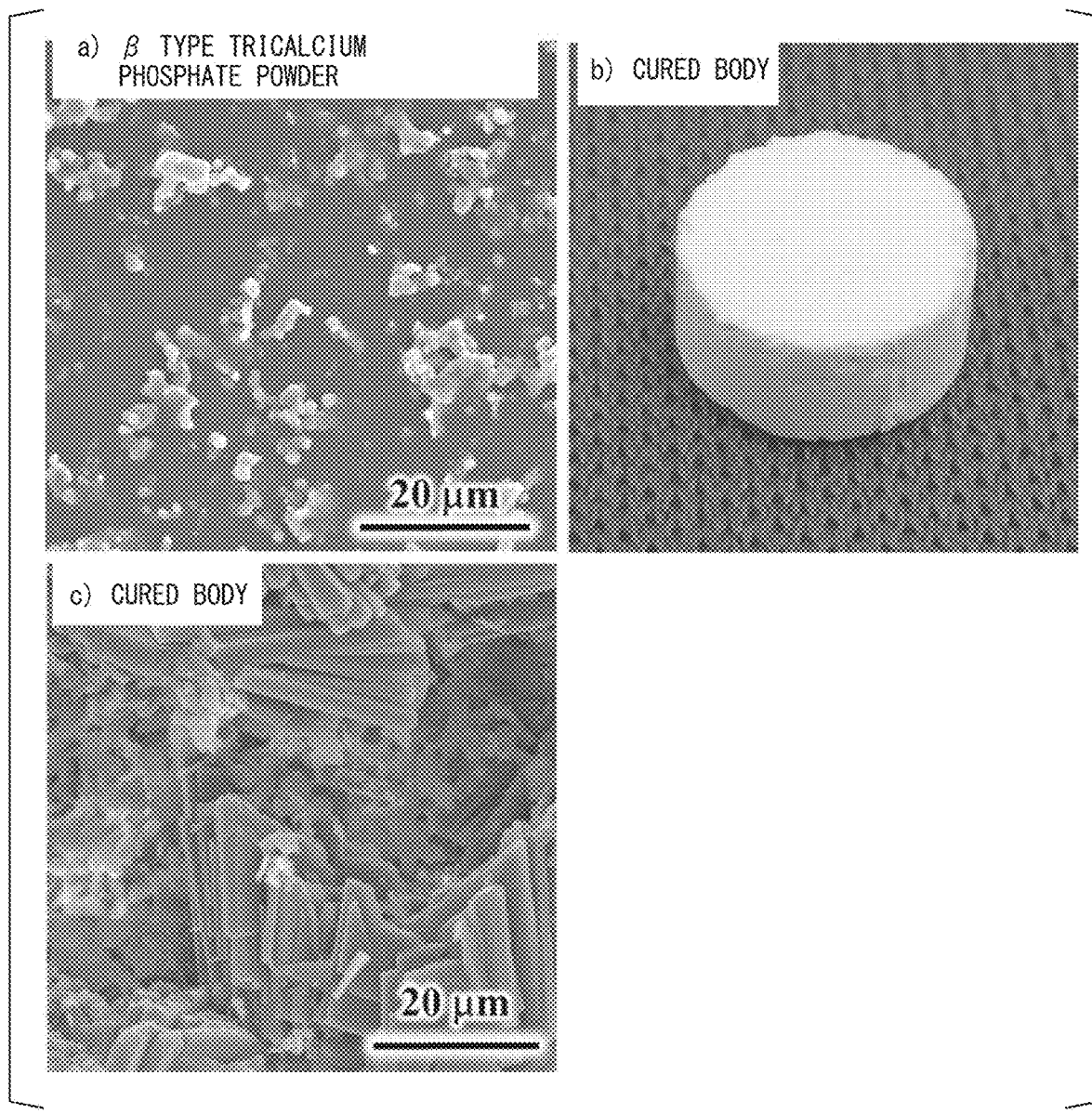

FIG. 57 shows a scanning electron microscope image (a) of β-type tricalcium phosphate granules used for production, and a picture (b) and a scanning electron microscope image (c) of produced cured bodies in Comparative Example 19.

Figure 58:
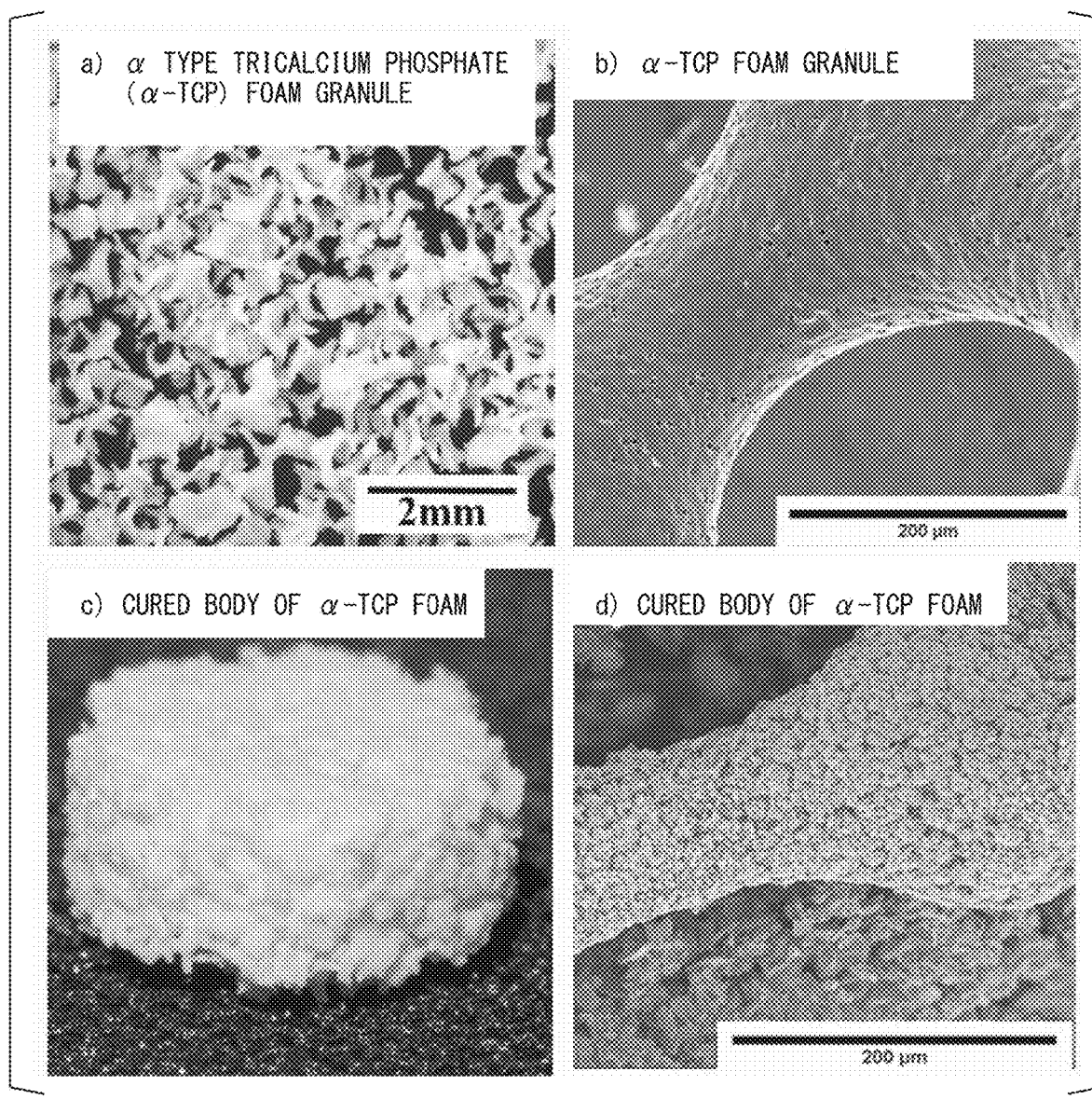

FIG. 58 shows a picture (a) and a scanning electron microscope image (b) of α-type calcium phosphate foam granules used for production, and a picture (c) and a scanning electron microscope image (d) of produced cured bodies in Example 46.

Figure 59:
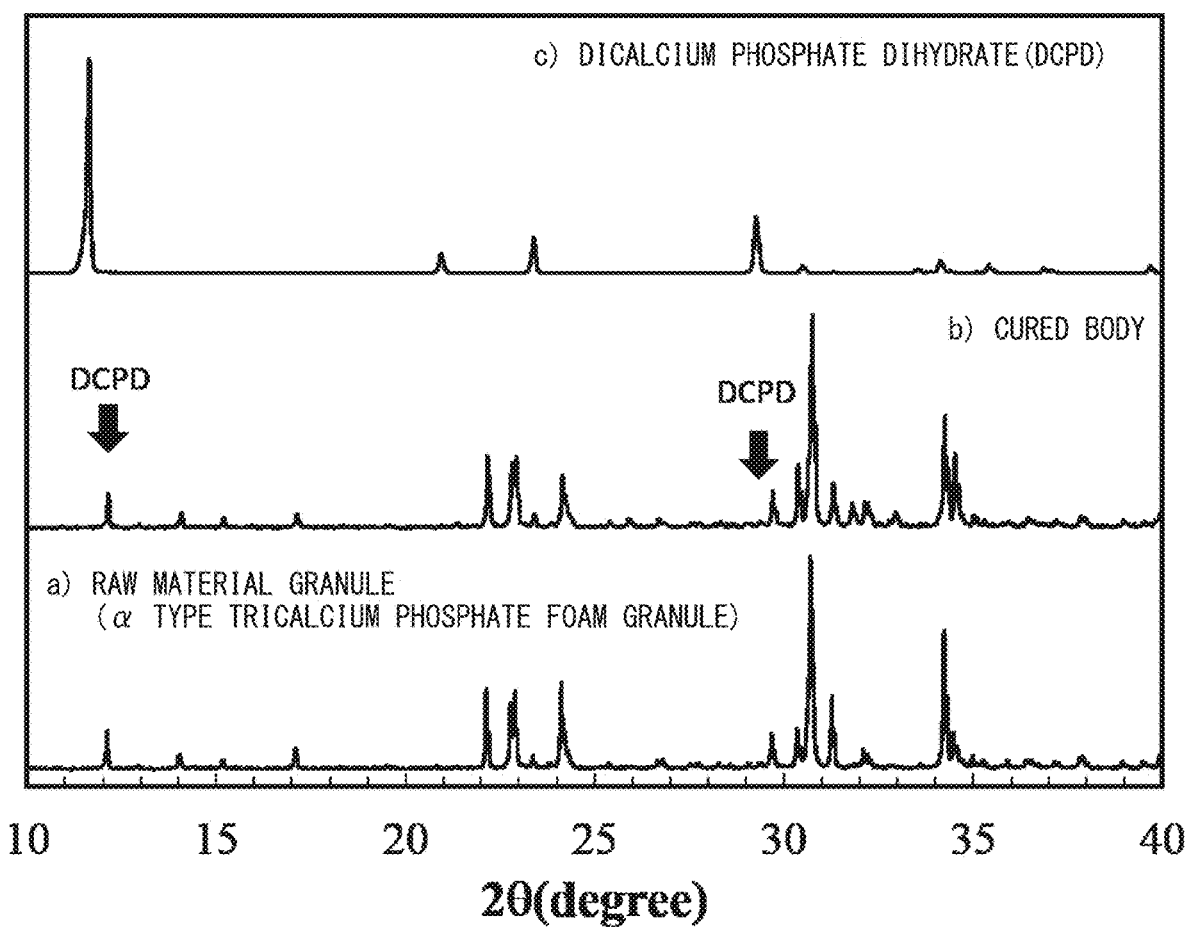

FIG. 59 shows powder X-ray diffraction patterns of α-type calcium phosphate foam granules (a) used for production, produced cured bodies (b) and calcium hydrogen phosphate (c) in Example 46.

Figure 60:
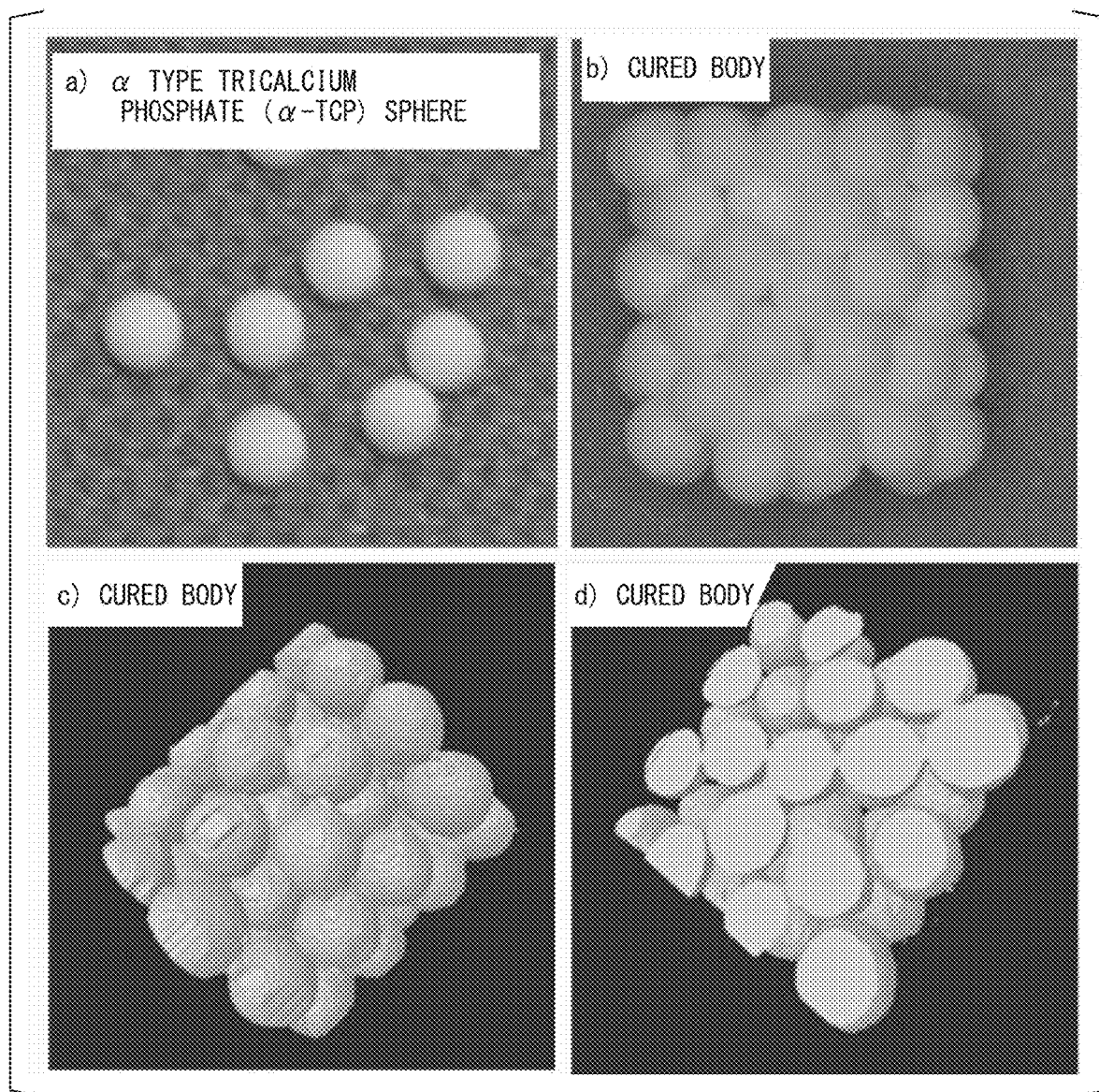

FIG. 60 shows a picture (a) of α-type tricalcium phosphate spheres used for production, and a picture (b), a micro CT image (c), and a cross-sectional micro CT image (d) of produced cured bodies, in Example 47.

Figure 61:
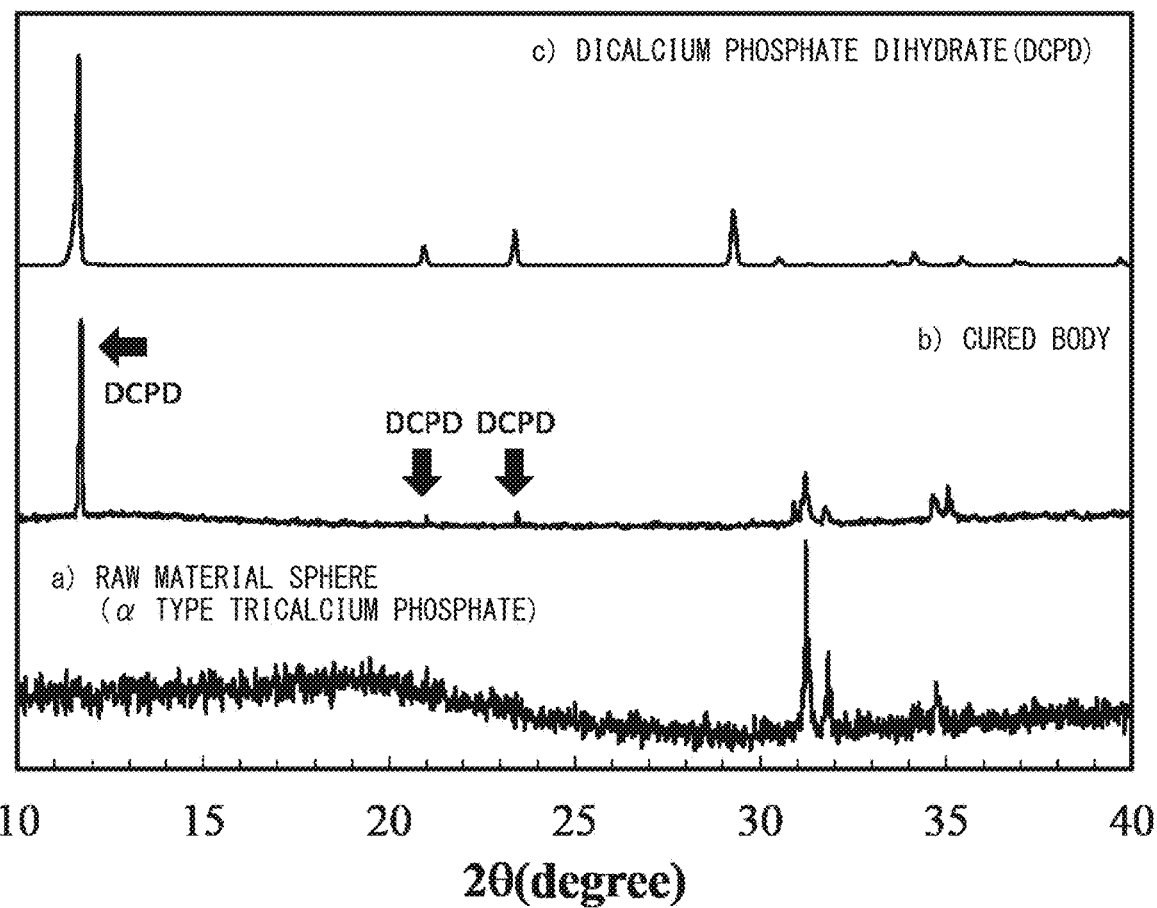

FIG. 61 shows powder X-ray diffraction patterns of α-type tricalcium phosphate spheres (a) used for production, produced cured bodies (b), and calcium hydrogen phosphate (c) in Example 47.

Figure 62:
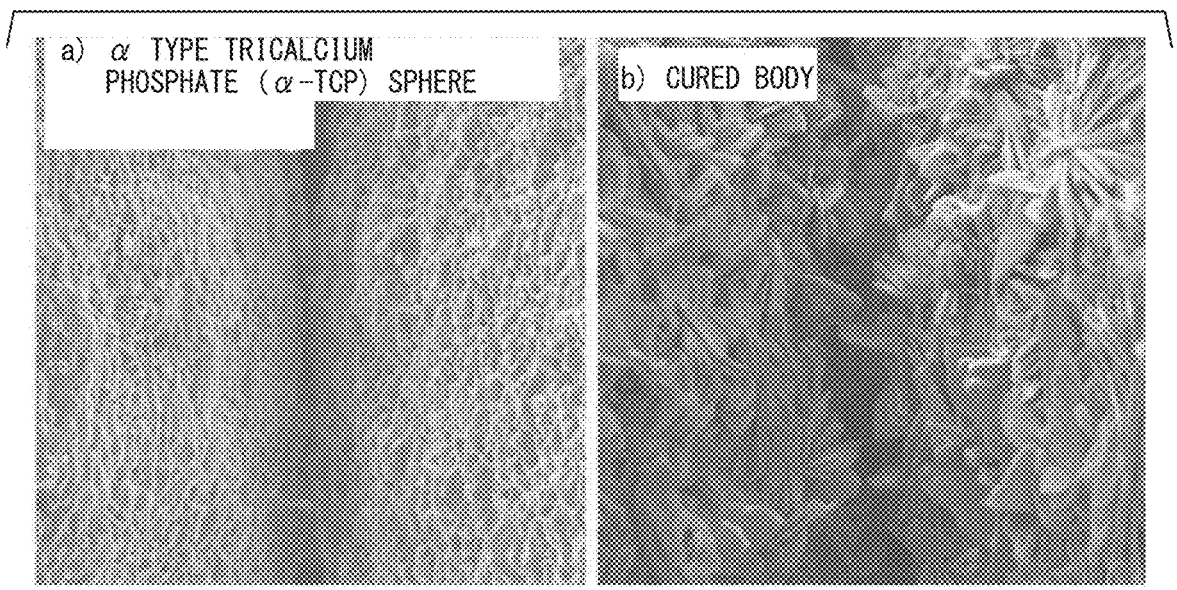

FIG. 62 shows pictures of α-type tricalcium phosphate spheres for cured bodies produced in Example 47 between spheres under a scanning electron microscope.

Figure 63:
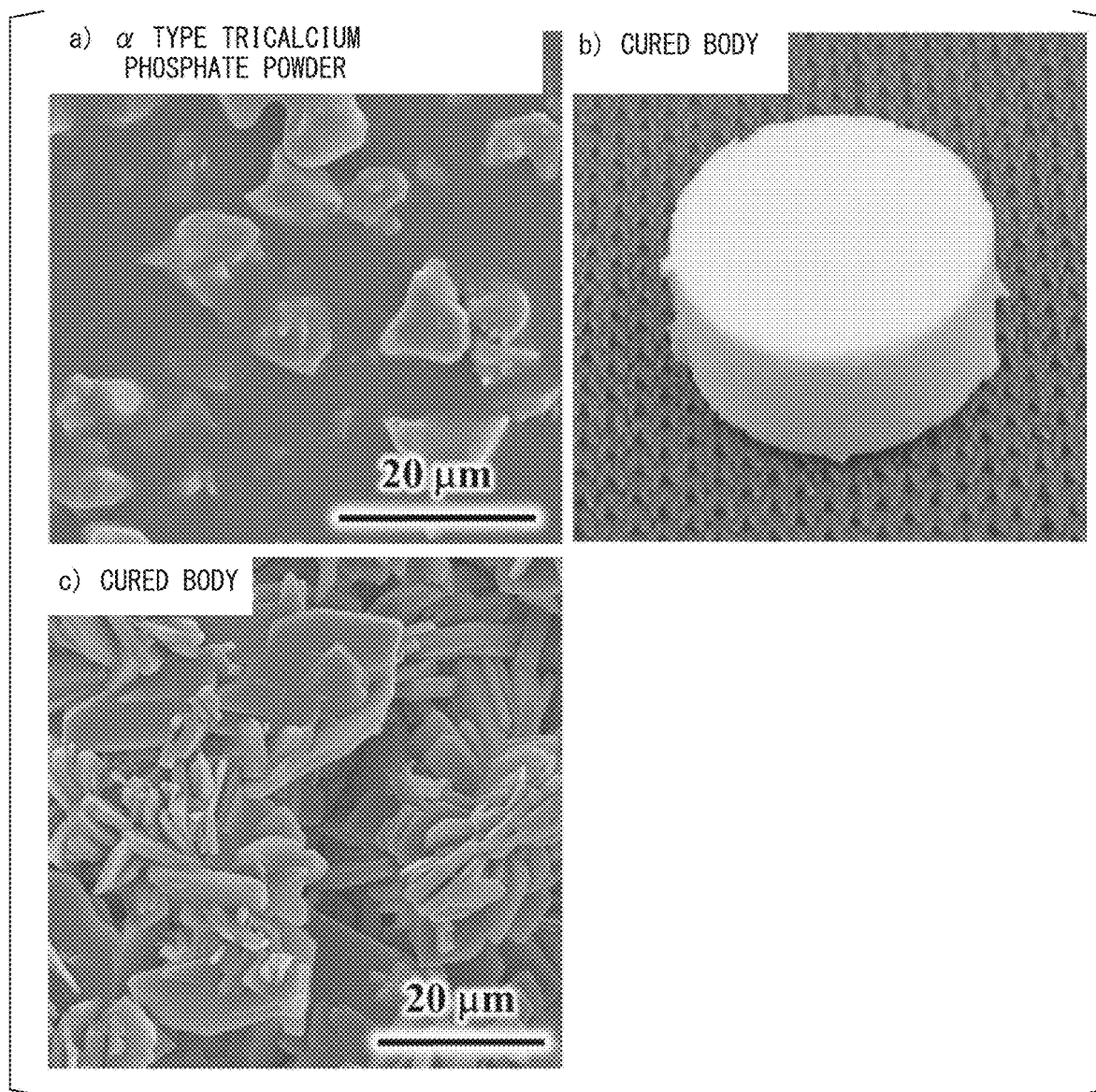

FIG. 63 shows a scanning electron microscope image (a) of α-type tricalcium phosphate powder used for production, and a picture (b) and a scanning electron microscope image (c) of produced cured bodies in Comparative Example 21.

Figure 64:
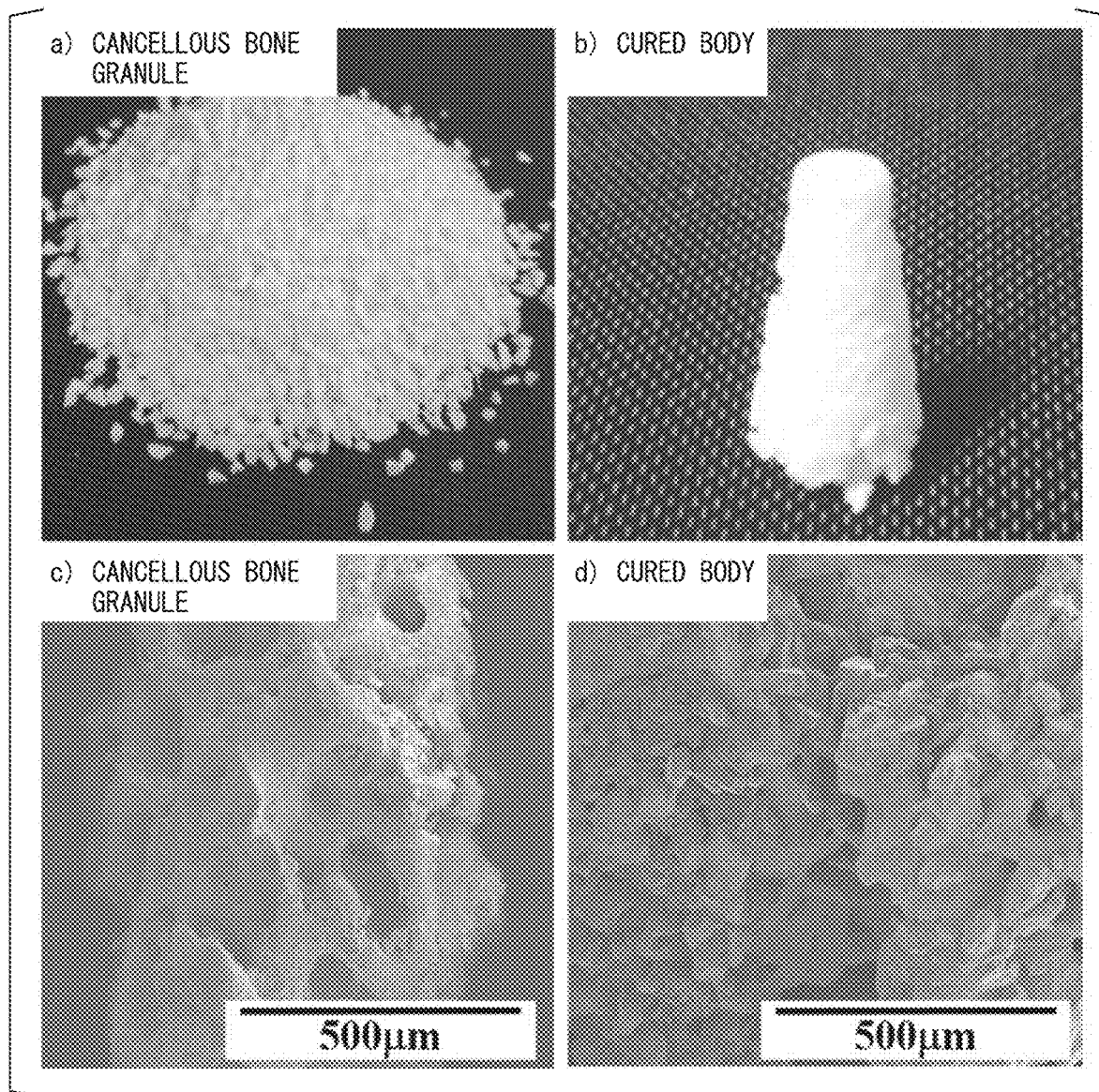

FIG. 64 shows a picture (a) and a scanning electron microscope image (c) of cancellous bone granules used for production, and a picture (b) and a scanning electron microscope image (d) of produced cured bodies in Example 48.

Figure 65:
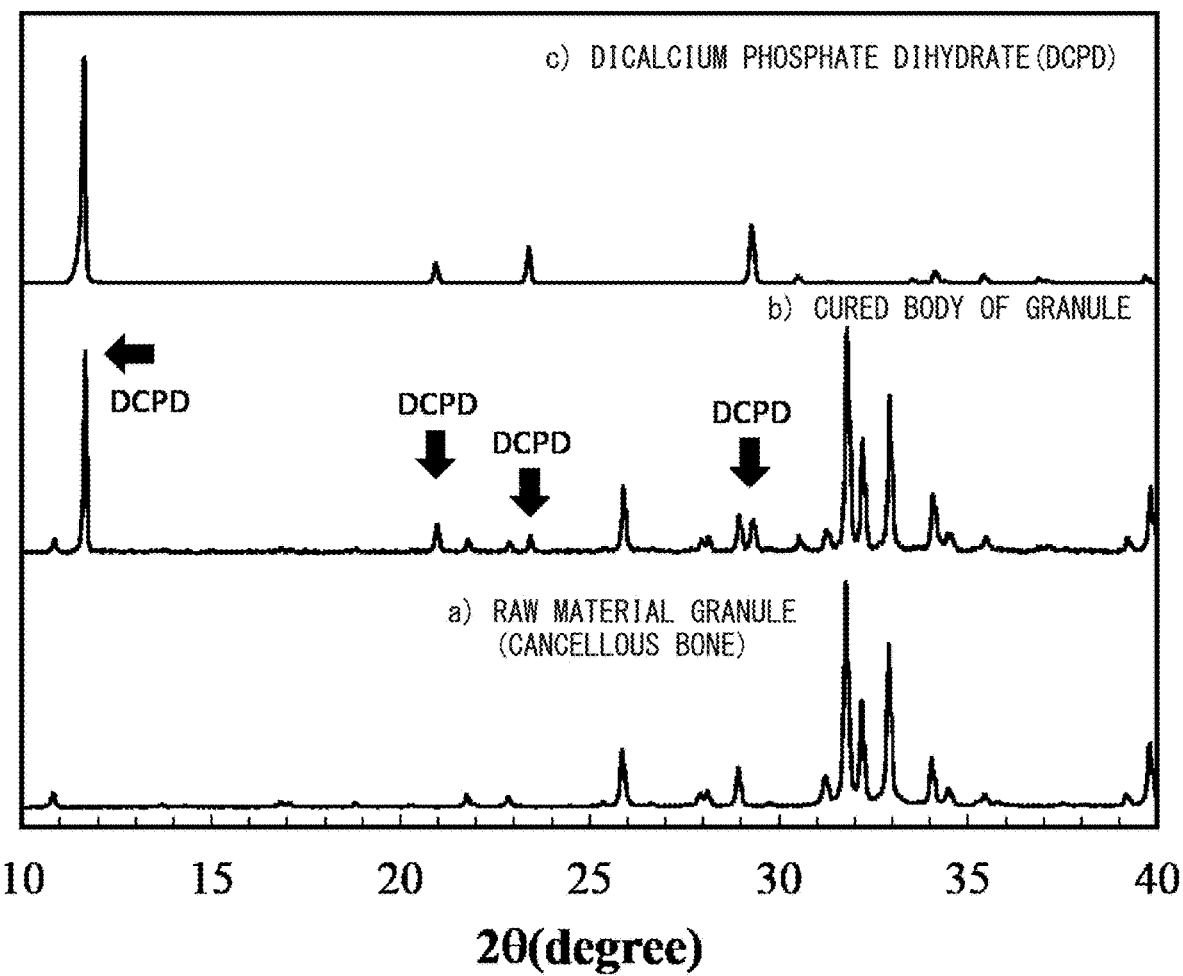

FIG. 65 shows powder X-ray diffraction patterns of cancellous bone granules (a) used for production, produced cured bodies (b), and calcium hydrogen phosphate (c) in Example 48.

Figure 66:
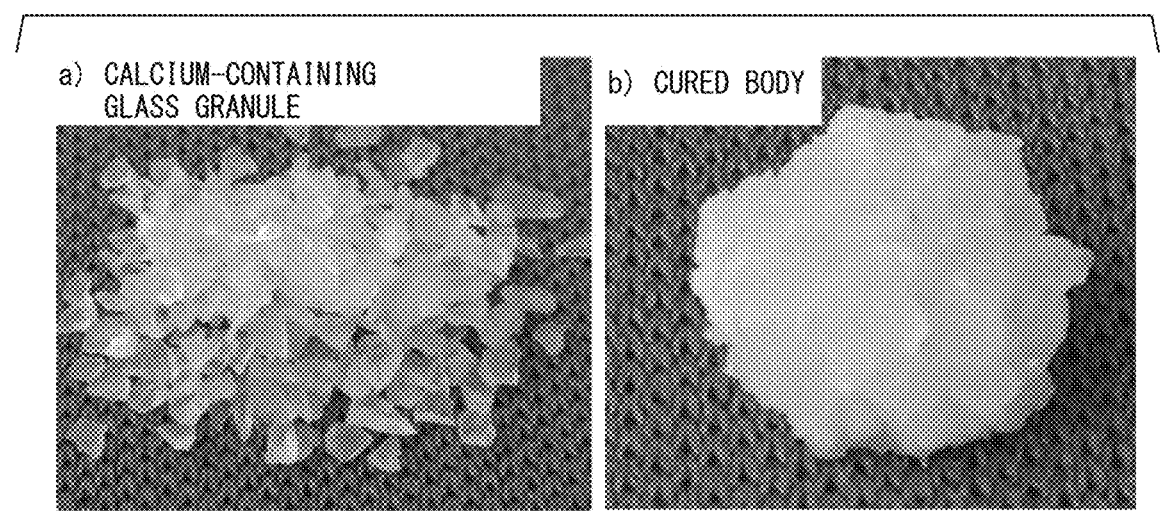

FIG. 66 shows a picture (a) of calcium-containing glass granules used for production and a picture (b) of produced cured bodies in Example 49.

Figure 67:
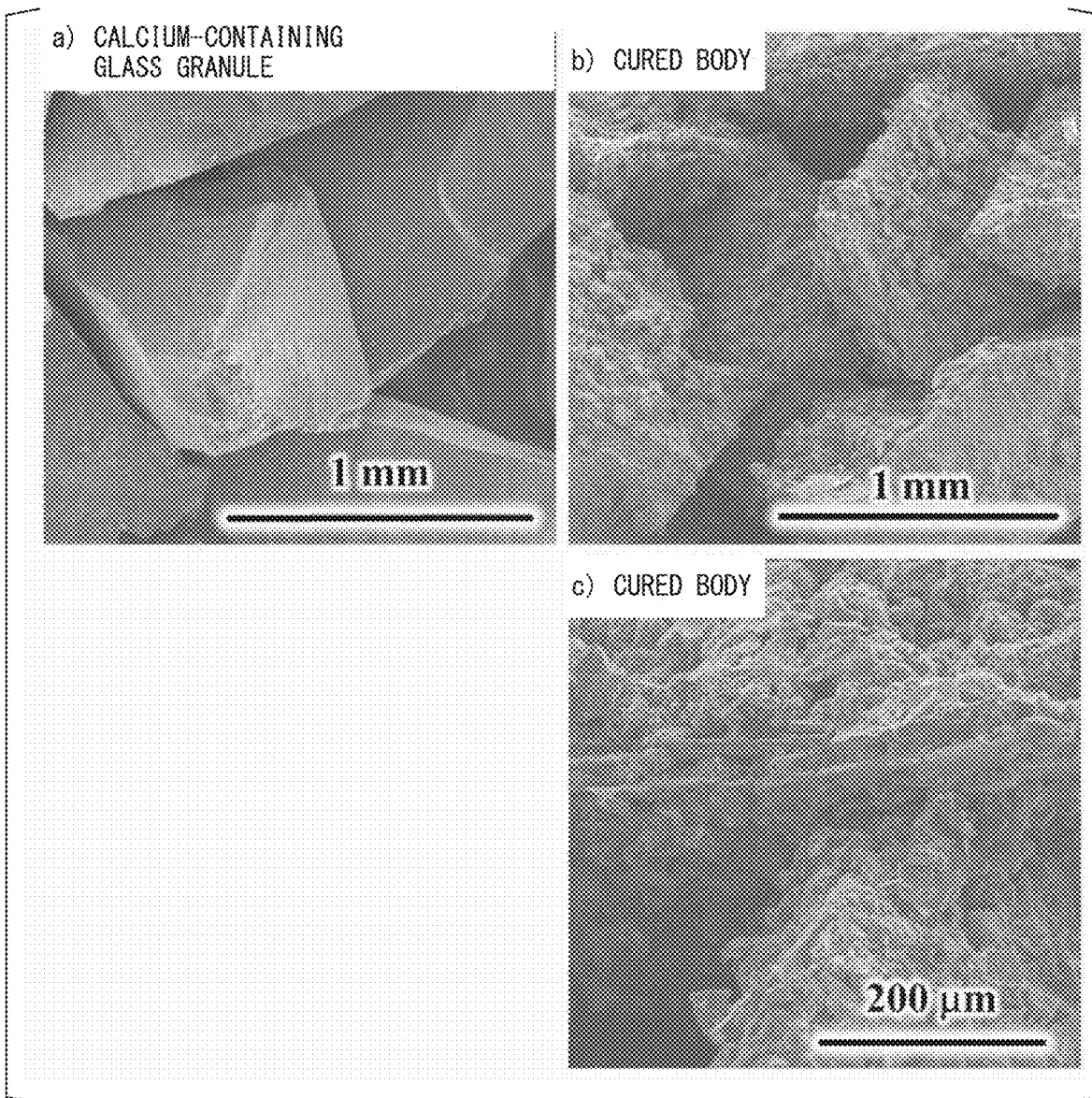

FIG. 67 shows a scanning electron microscope image (a) of cancellous bone granules used for production and scanning electron microscope images (b and c) of produced cured bodies in Example 49.

Figure 68:
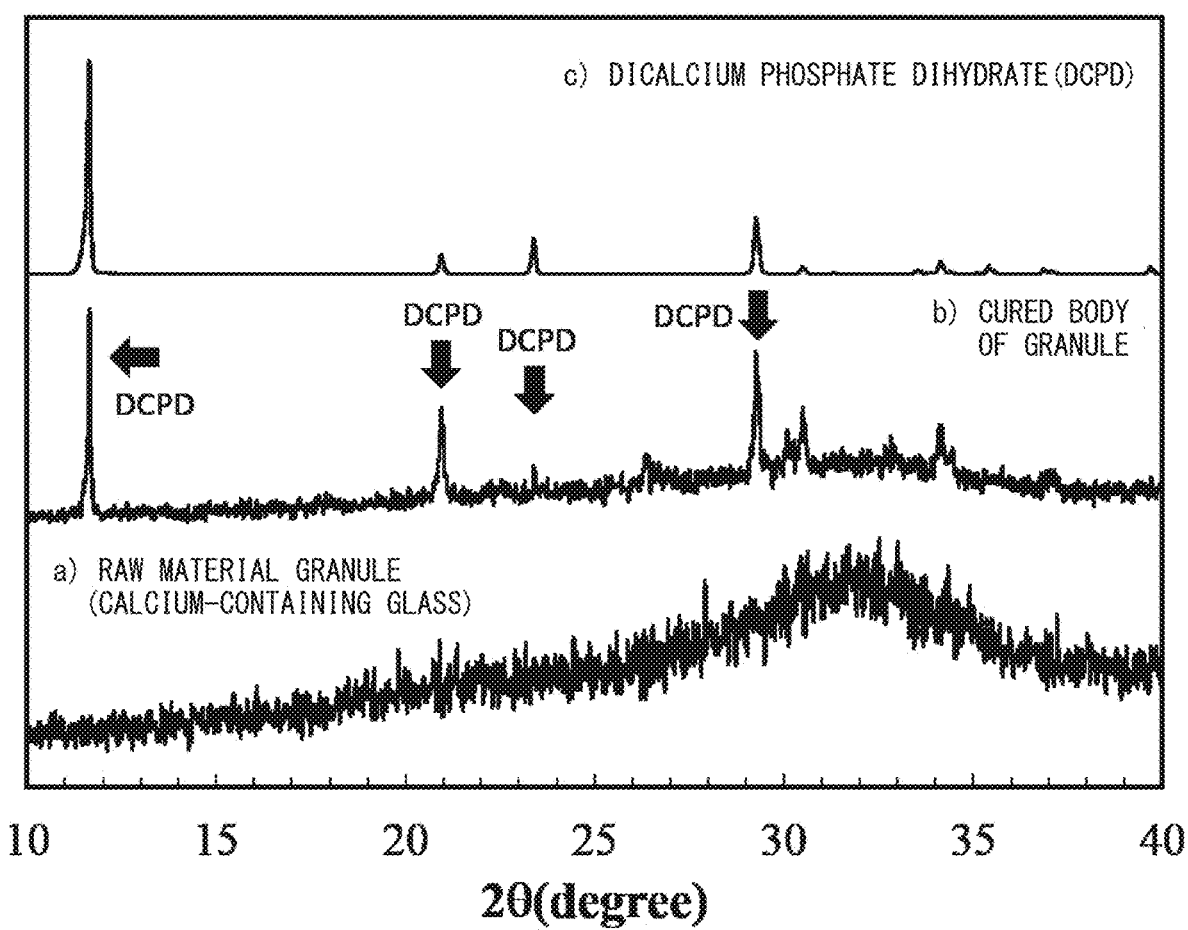

FIG. 68 shows powder X-ray diffraction patterns of calcium-containing glass granules (a) used for production, produced cured bodies (b), and calcium hydrogen phosphate (c) in Example 49.

Figure 69:
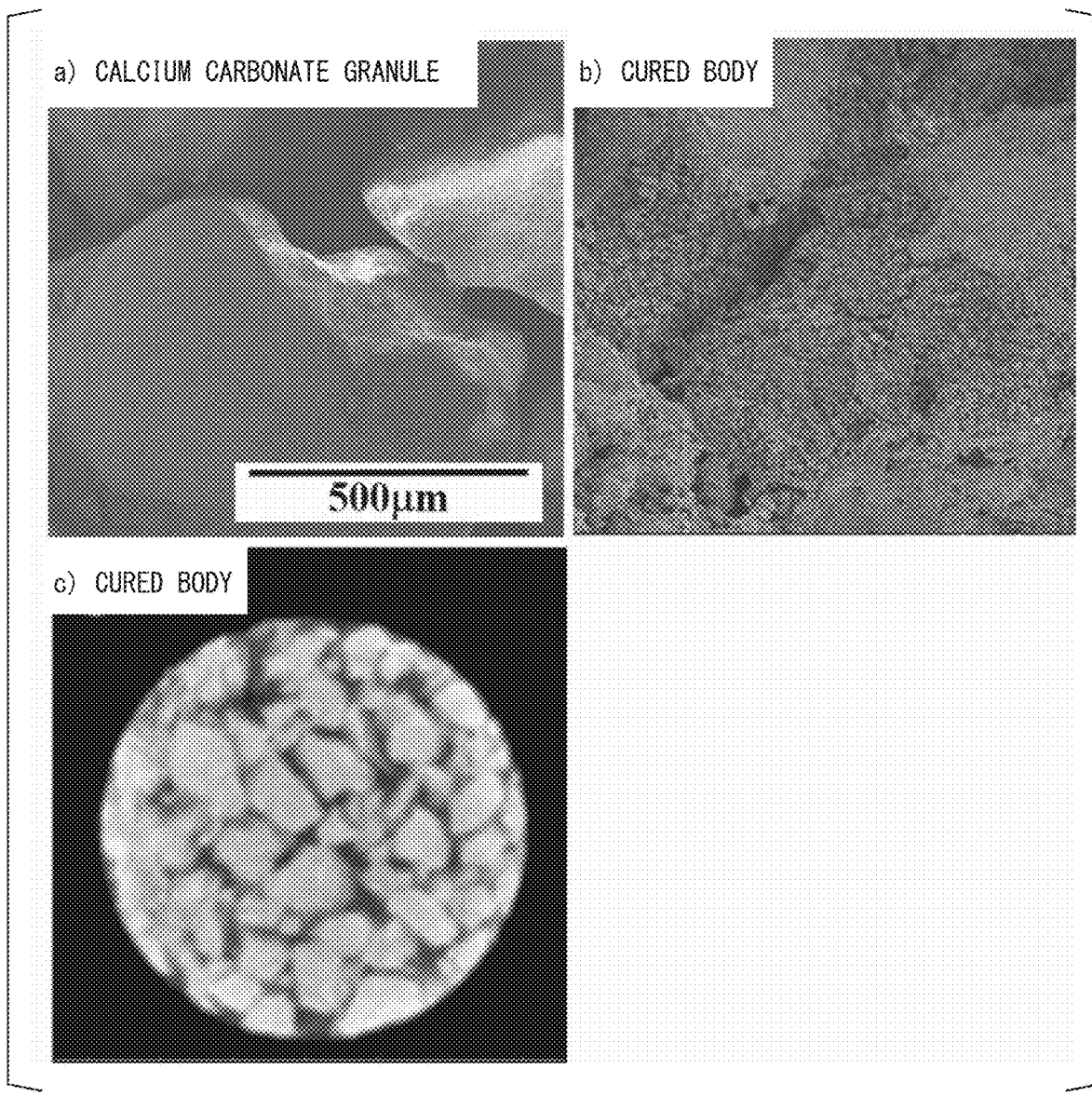

FIG. 69 shows a scanning electron microscope image (a) of calcium carbonate granules used for production, and a scanning electron microscope image (b) and a micro CT image (c) of surfaces of produced cured bodies in Example 50.

Figure 70:
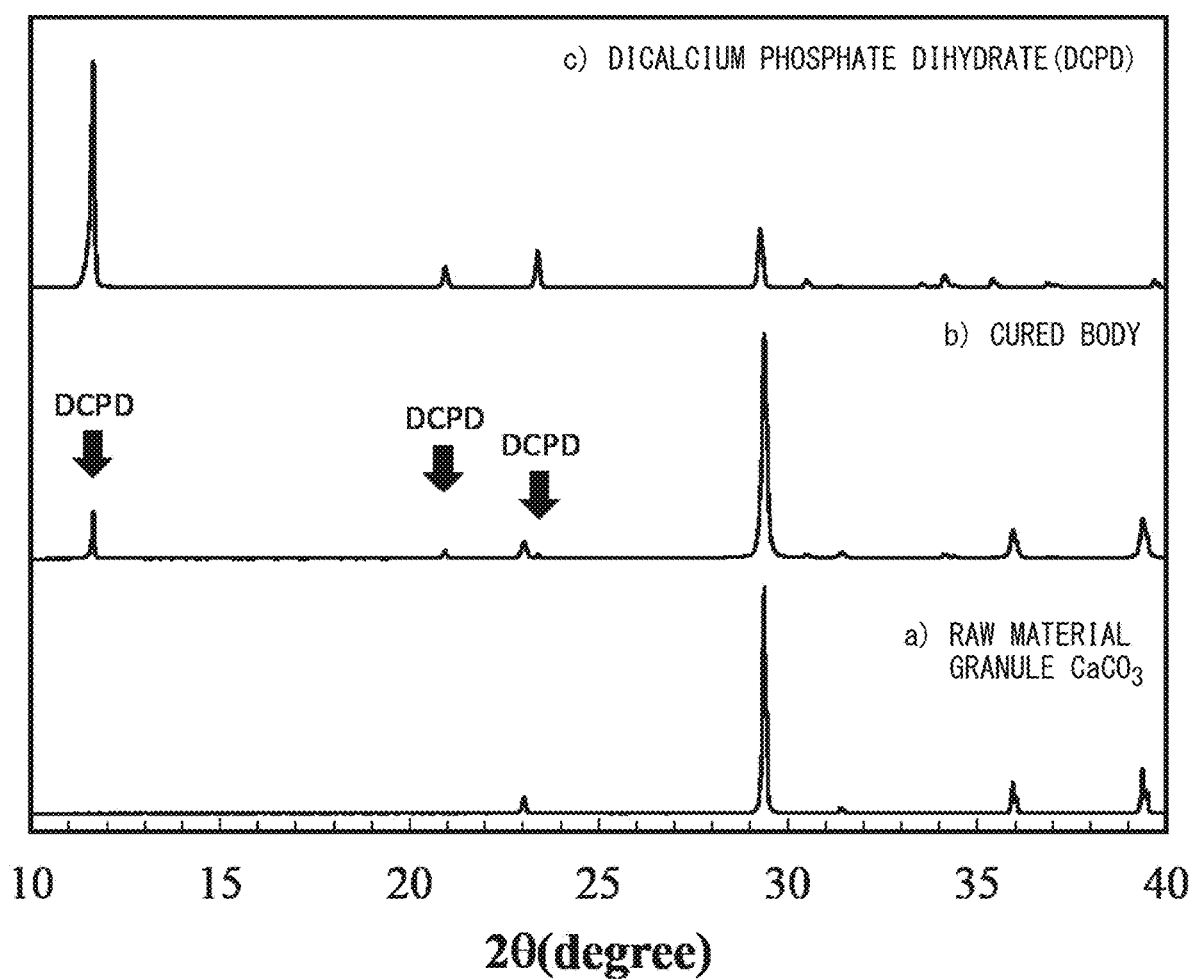

FIG. 70 shows powder X-ray diffraction patterns of calcium carbonate granules (a) used for production, produced cured bodies (b), and calcium hydrogen phosphate (c) in Example 50.

Figure 71:
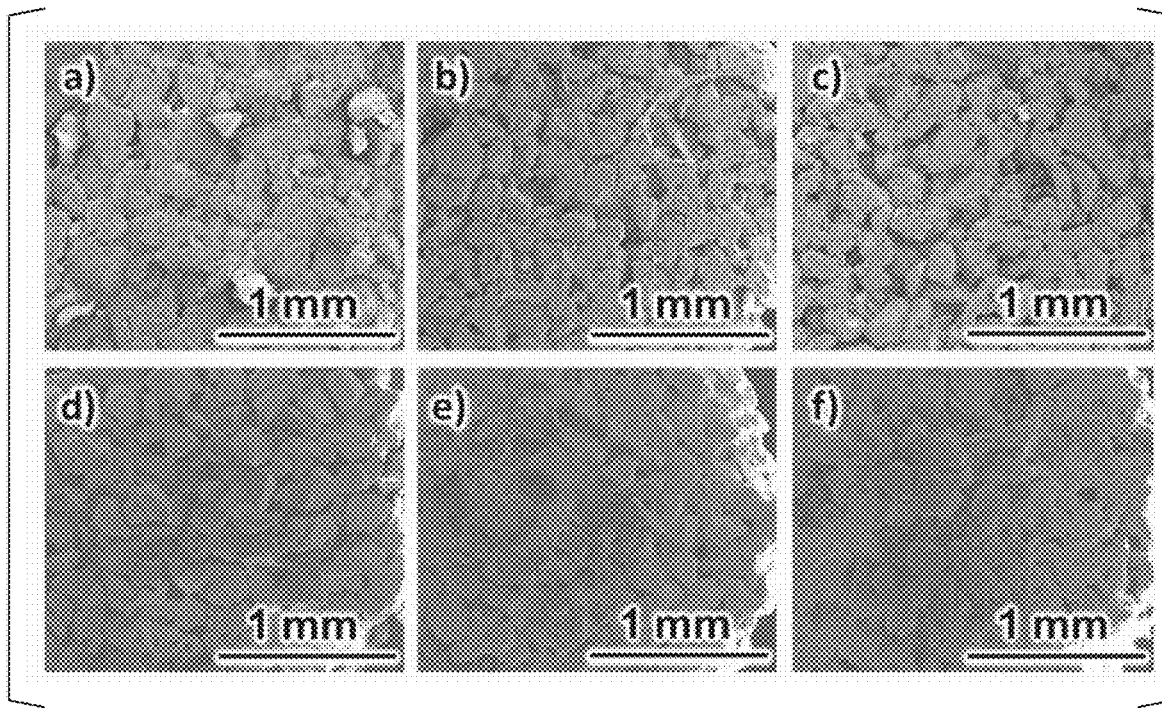

FIG. 71 shows scanning electron microscope images of surfaces of cured bodies (a to c) before they are immersed in a sodium hydrogen carbonate aqueous solution produced and surfaces of cured bodies (d to f) after immersion in Example 51.

Figure 72:
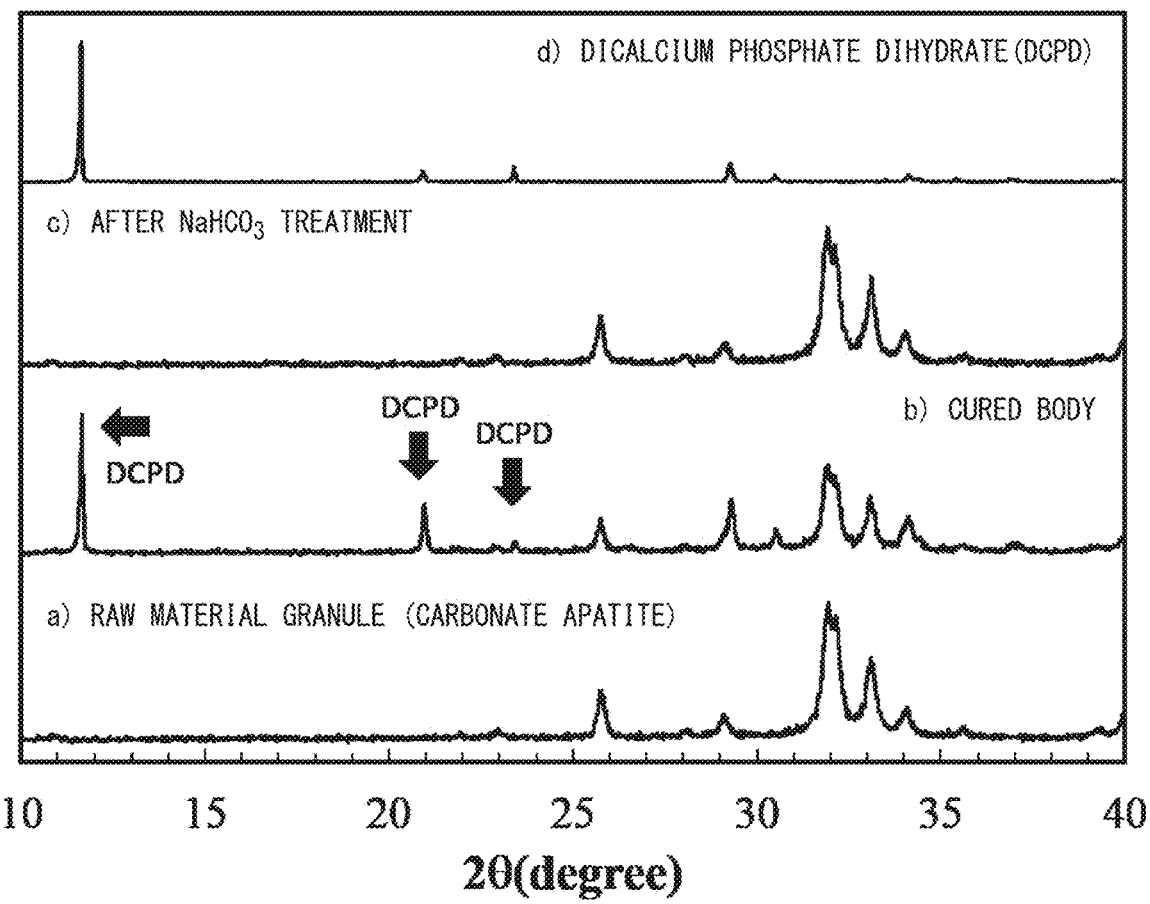

FIG. 72 shows powder X-ray diffraction patterns of carbonate apatite granules (a) used for production, cured bodies (b) before they are immersed in a sodium hydrogen carbonate aqueous solution prepared using a 1 M calcium-phosphoric acid aqueous solution and cured bodies (c) after immersion and calcium hydrogen phosphate (d) in Example 51.

Figure 73:
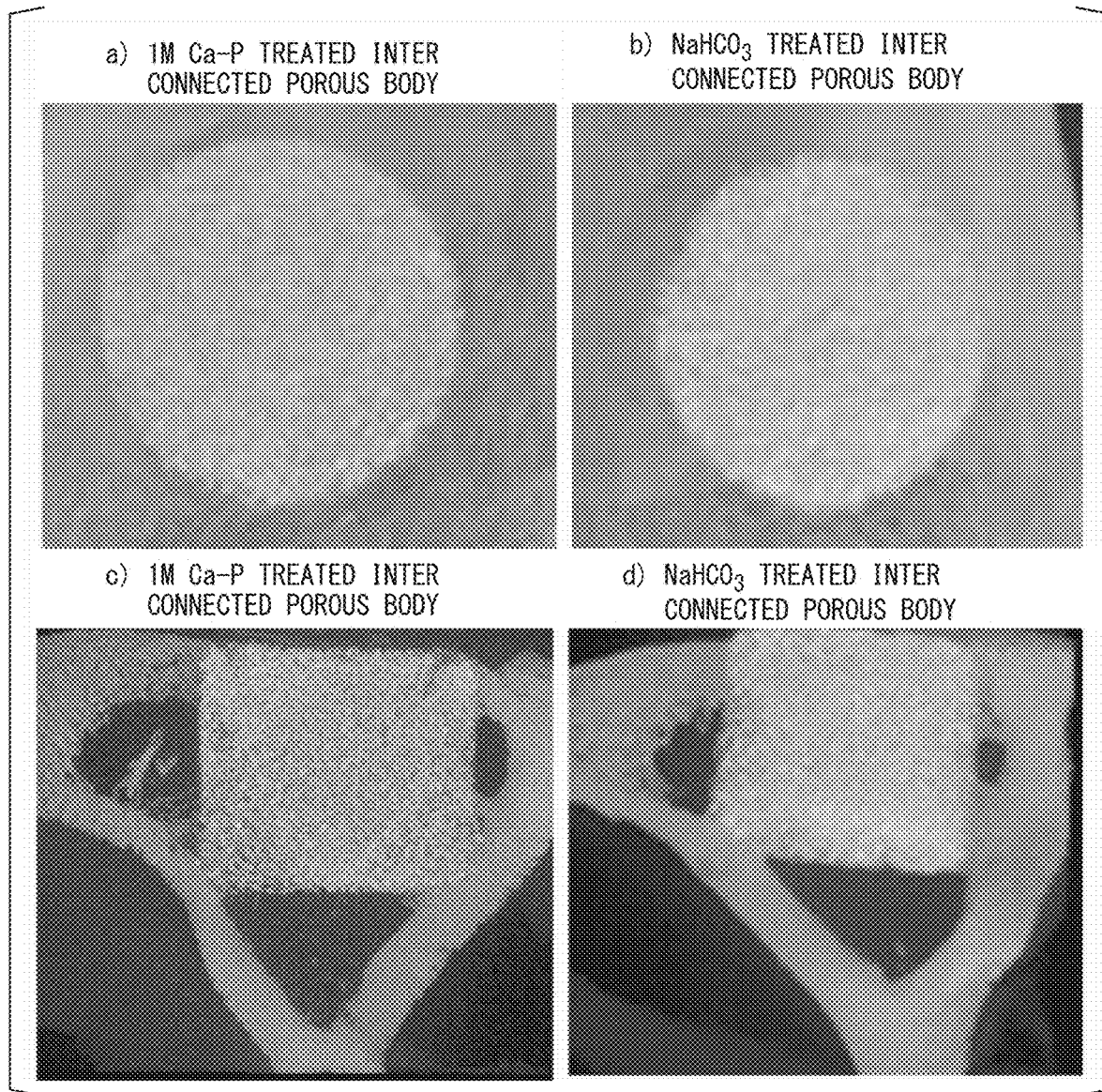

FIG. 73 shows an X-ray micro CT image (a) and picture (c) 1 month after the cured body before being immersed in a sodium hydrogen carbonate aqueous solution prepared using a 1 M calcium-phosphoric acid aqueous solution was implanted in a bone defect of a Japanese white house rabbit and an X-ray micro CT image (b) and a picture (d) 1 month after implantation of the cured body after immersion in Example 51.

Figure 74:
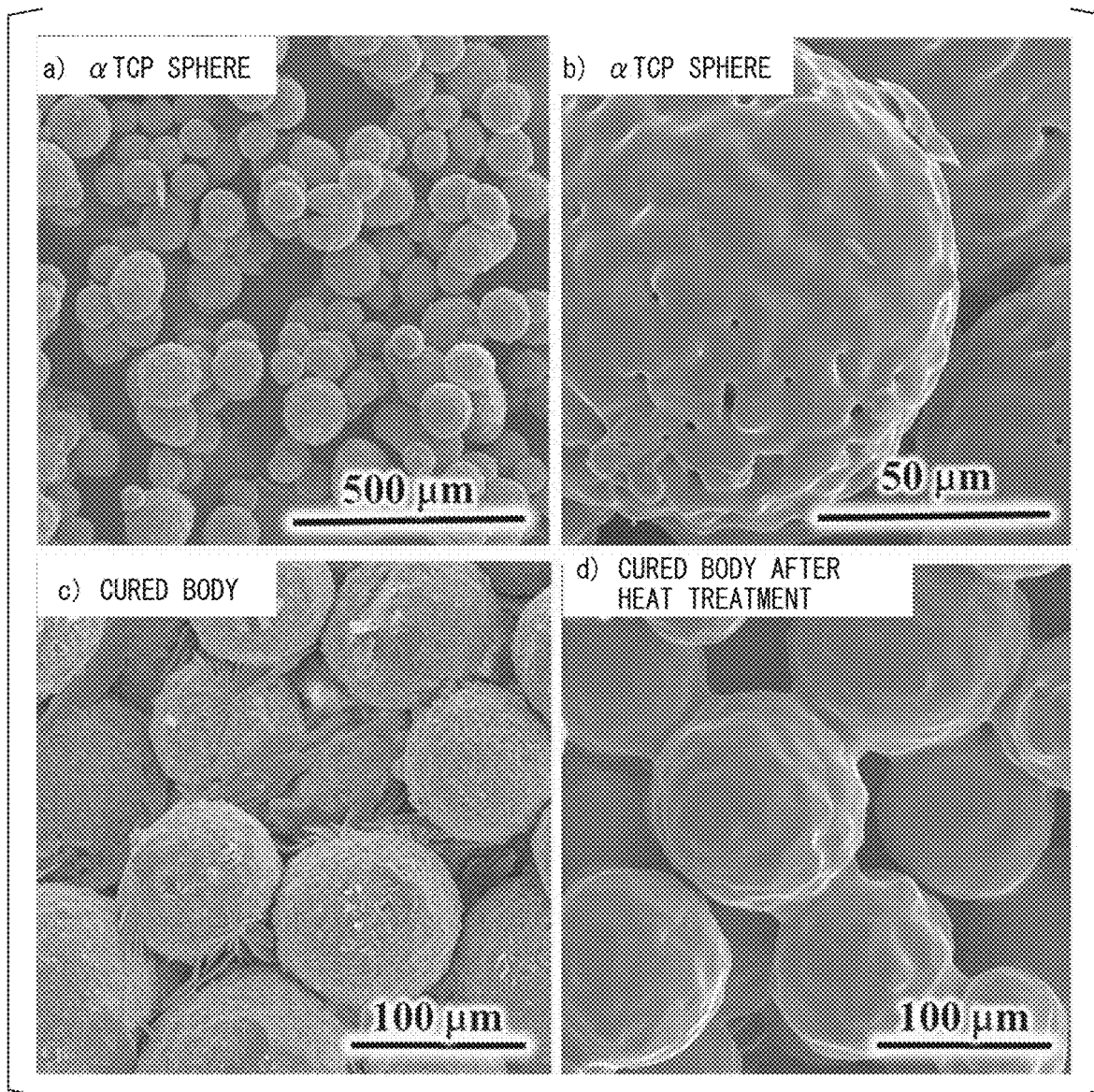

FIG. 74 shows scanning electron microscope images of α-type tricalcium phosphate spheres (a and b) used for production and produced cured bodies (c) before heat treatment and cured bodies (d) after heat treatment in Example 52.

Figure 75:
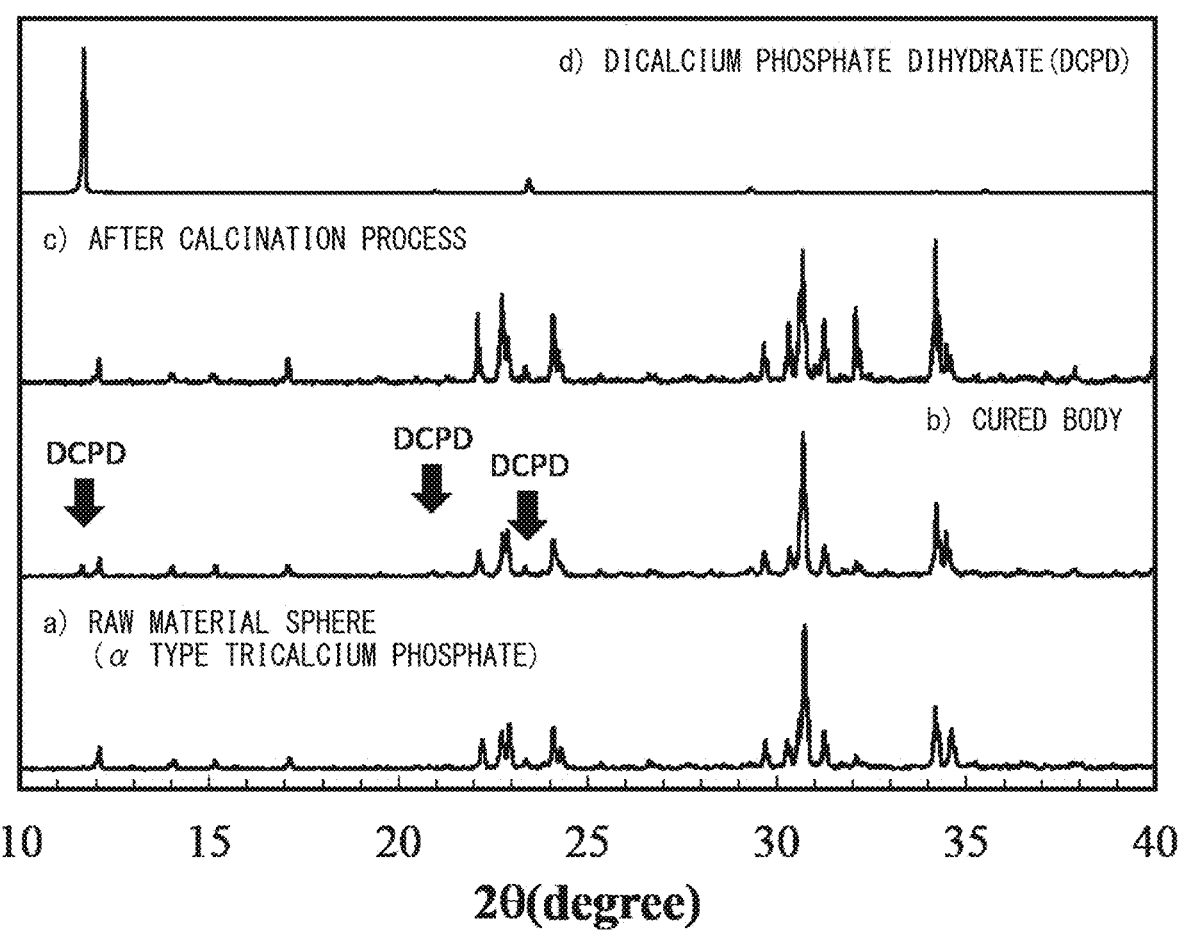

FIG. 75 shows powder X-ray diffraction patterns of α-type tricalcium phosphate spheres (a) used for production, produced cured bodies (b) before heat treatment and cured bodies (c) after heat treatment and calcium hydrogen phosphate (d) in Example 52.

Figure 76:
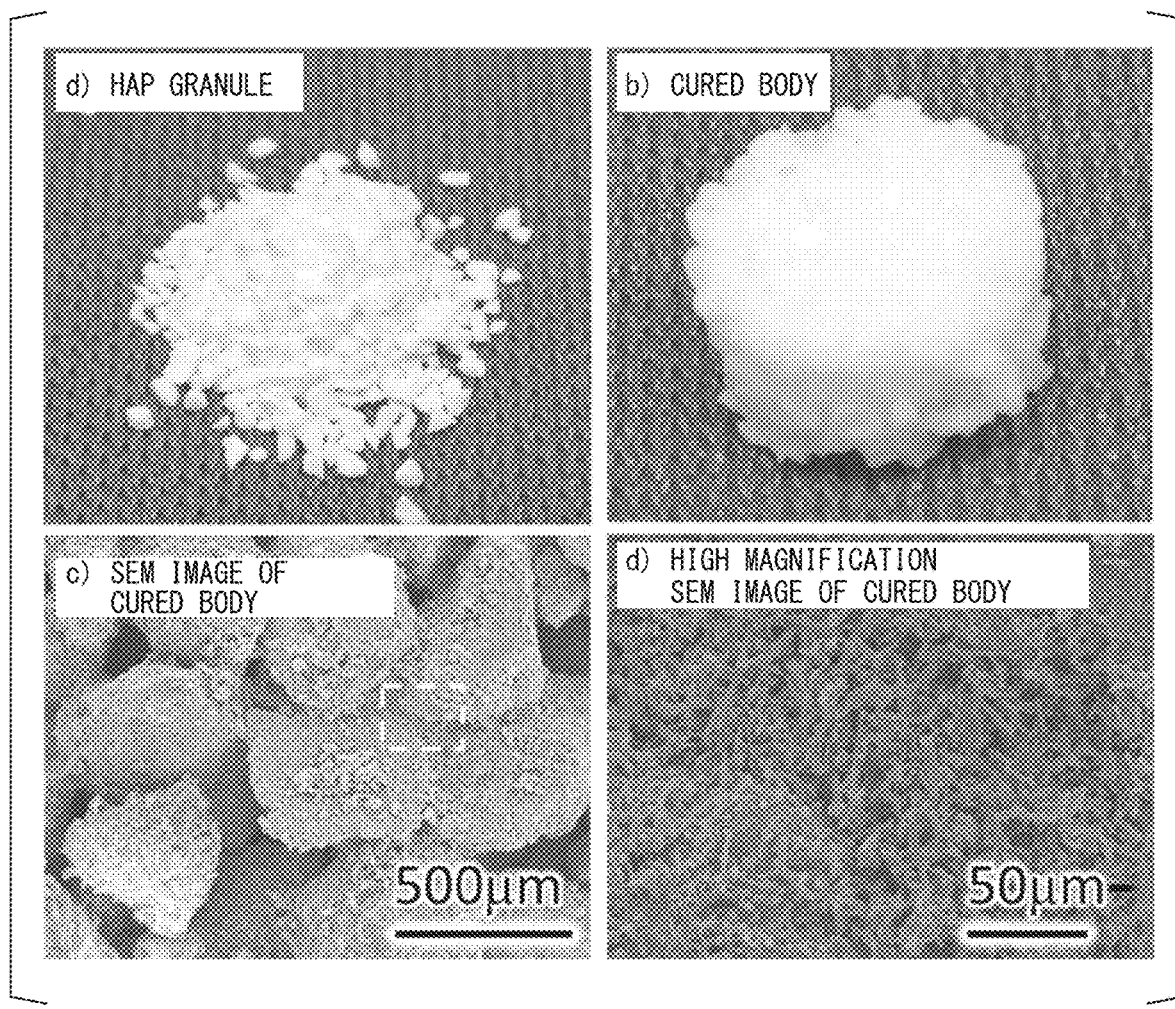

FIG. 76 shows pictures of hydroxyapatite granules (a raw material inorganic compound 9) used for production and interconnected porous bodies produced by curing and a scanning electron microscope image of interconnected porous bodies produced by curing in Example 53.

Figure 77:
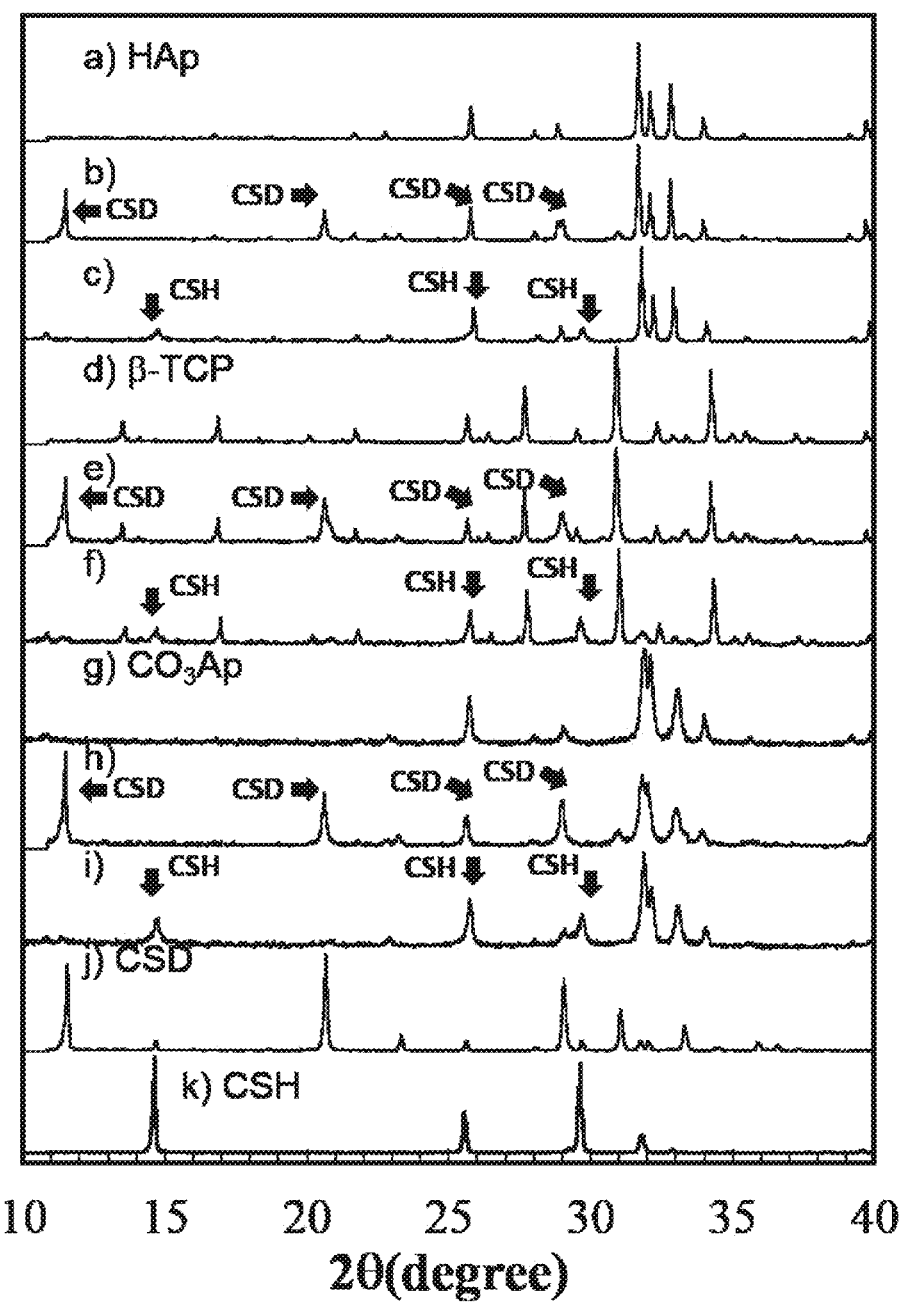

FIG. 77 shows data obtained through powder X-ray diffraction performed in Examples 53 to 58.

Figure 78:
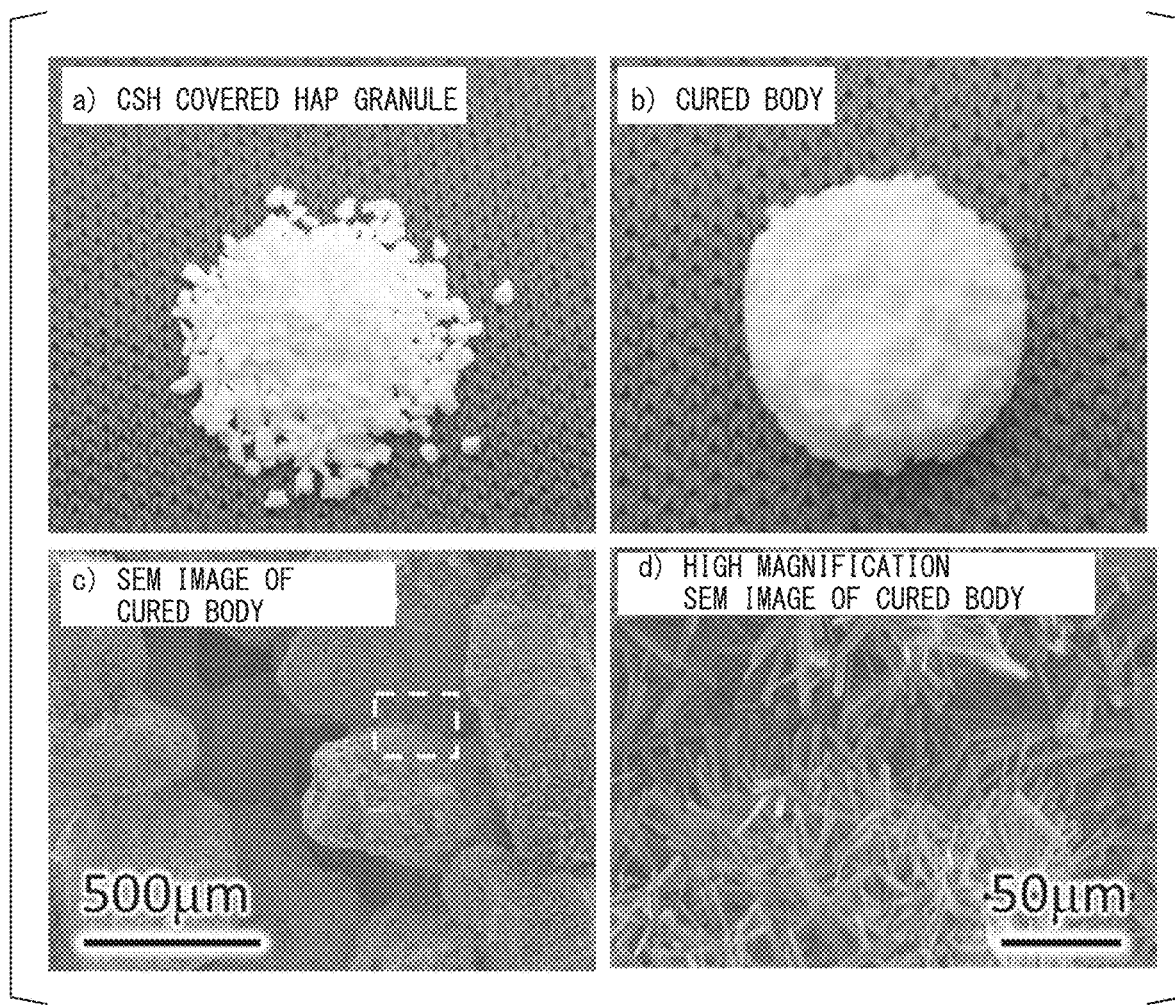

FIG. 78 shows pictures of hydroxyapatite granules (a raw material inorganic compound 9) used for production and interconnected porous bodies produced according to curing and a scanning electron microscope image of interconnected porous bodies produced by curing in Example 54.

Figure 79:
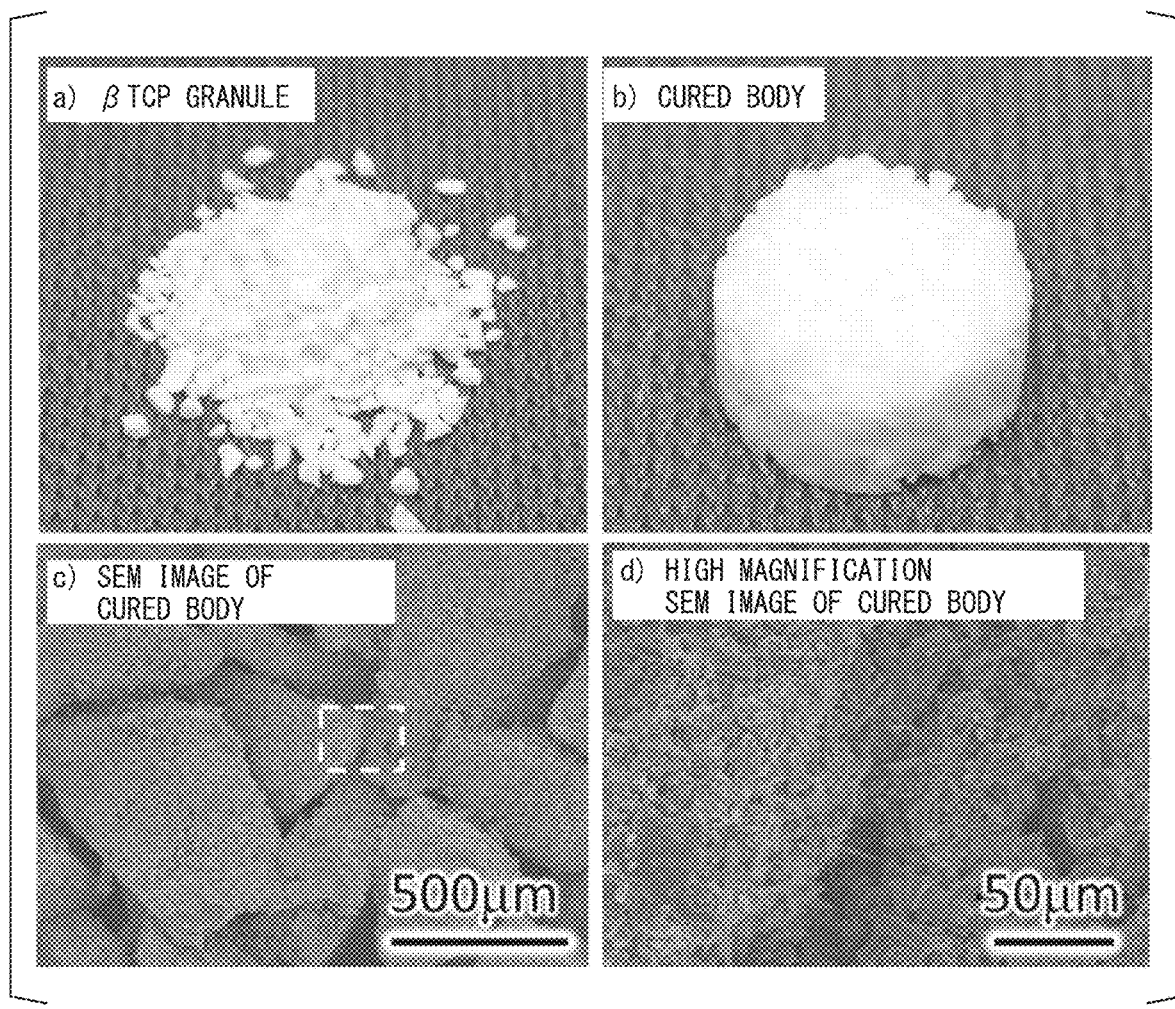

FIG. 79 shows pictures of β-type tricalcium phosphate granules (the raw material inorganic compound 4) used for production and interconnected porous bodies produced according to curing and scanning electron microscope images of interconnected porous bodies produced by curing in Example 55.

Figure 80:
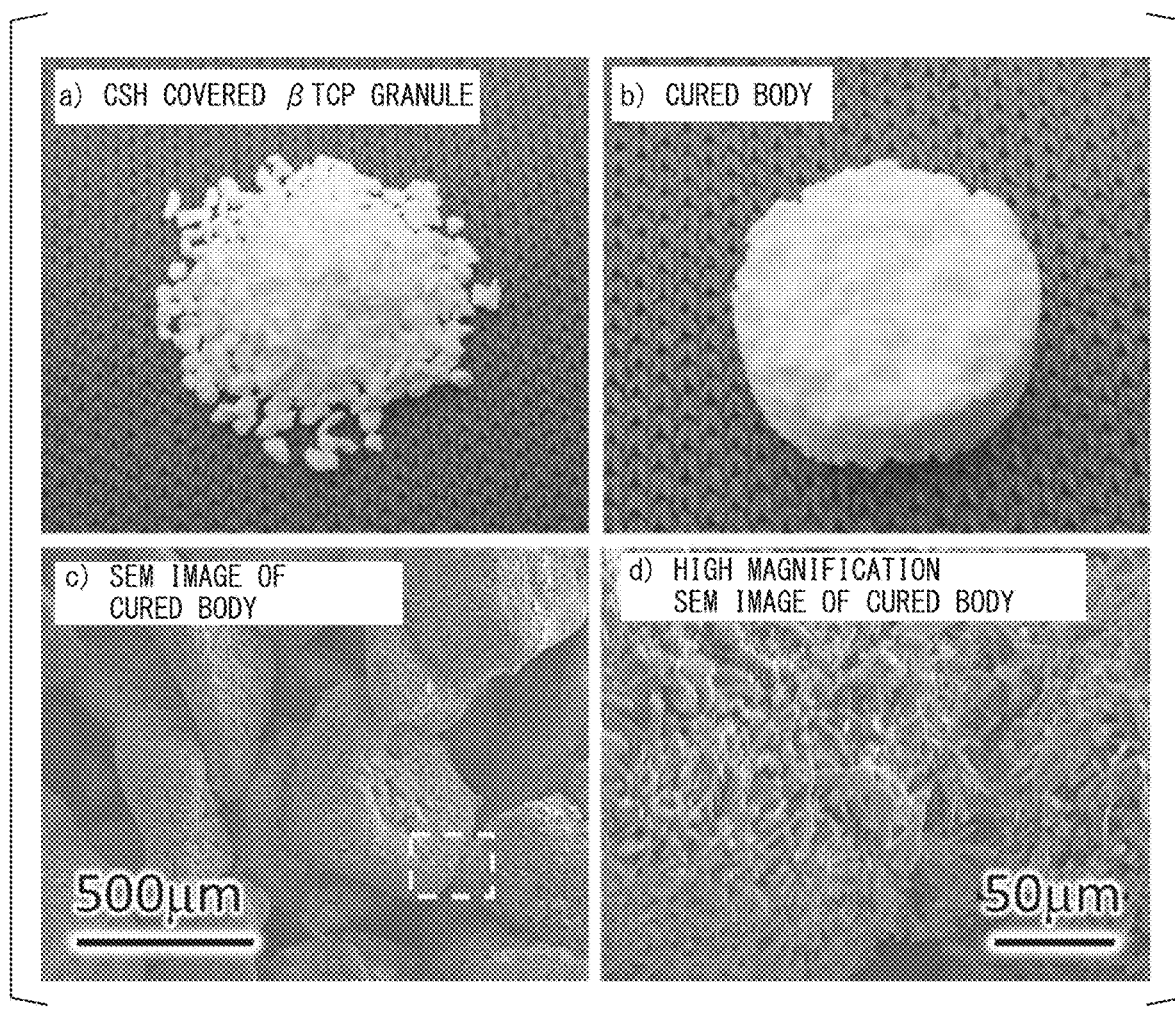

FIG. 80 shows pictures of β-type tricalcium phosphate granules (the raw material inorganic compound 4) used for production and interconnected porous bodies produced according to curing, and scanning electron microscope images of interconnected porous bodies produced by curing in Example 56.

Figure 81:
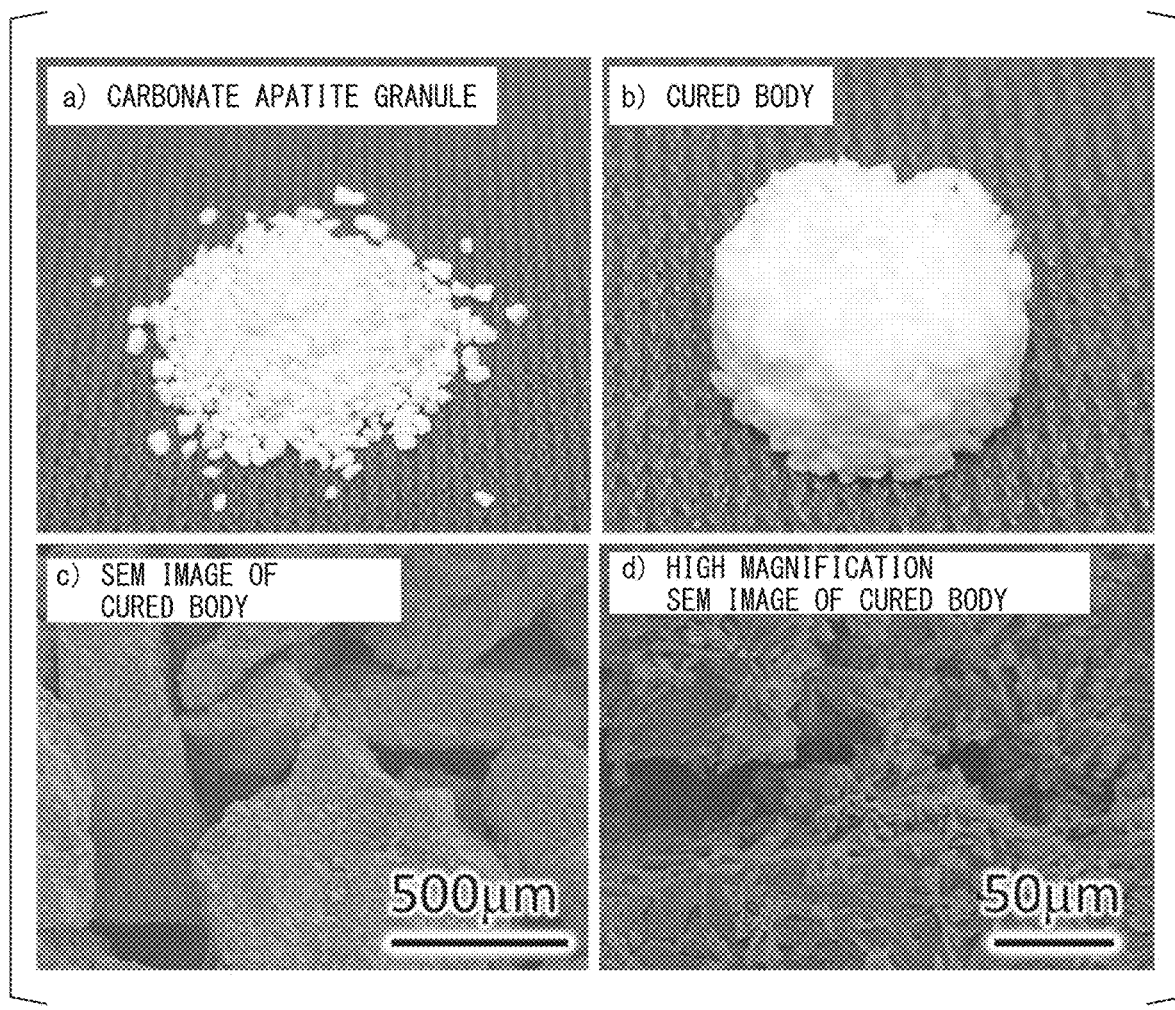

FIG. 81 shows pictures of carbonate apatite granules (a raw material inorganic compound 8) used for production and interconnected porous bodies produced by curing, and scanning electron microscope images of interconnected porous bodies produced by curing in Example 57.

Figure 82:
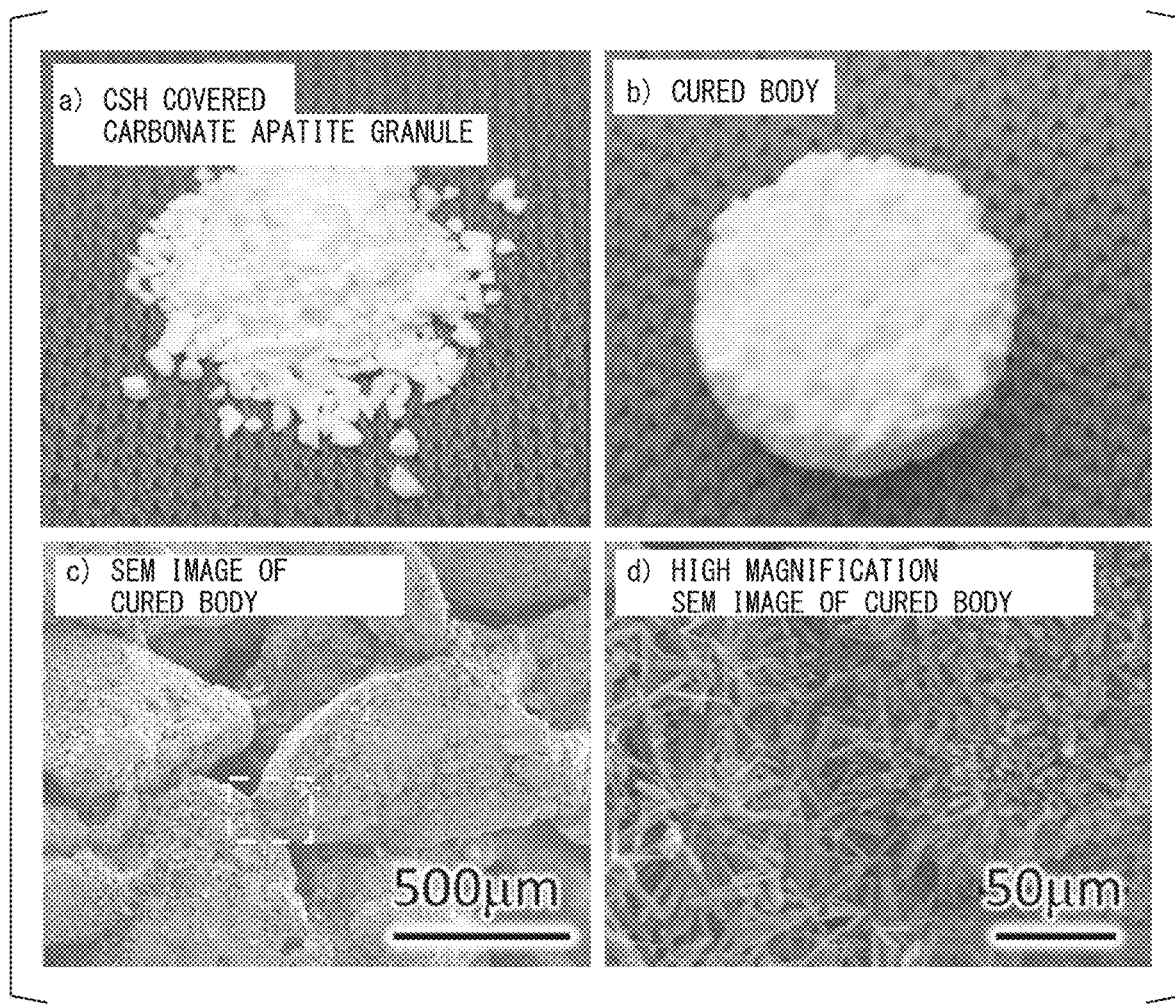

FIG. 82 shows pictures of carbonate apatite granules (a raw material inorganic compound 8) used for production and interconnected porous bodies produced by curing, and scanning electron microscope images of interconnected porous bodies produced by curing in Example 58.

DESCRIPTION OF EMBODIMENTS

Preferable examples of the present invention will be described below but the present invention is not limited to the following examples. Additions, omissions, substitutions and other modifications of the configuration can be made without departing from the scope of the present invention.
[Raw Material Inorganic Compound]

A raw material inorganic compound used in the present invention has a volume that is $10^{-13}$ m$^3$ or more and has a solubility that is 5 or less at 20° C. with respect to water and an electrolyte aqueous solution in which the compound is immersed. The raw material inorganic compound may comprise only a raw material inorganic compound or the raw material inorganic compound may be combined with at least one of a compositing material compound and a support. The compositing material component is an organic substance, a metal, or an inorganic compound other than the raw material inorganic compound.

In addition, the raw material inorganic compound used in the present invention may include a single composition.
[Product Inorganic Compound]

A product inorganic compound produced in the present invention comprises an inorganic compound of which at least one of a cation component and an anion component of the raw material inorganic compound is the same as that of the product inorganic compound and of which a composition is different therefrom. In addition, the product inorganic compound used in the present invention may comprise a single composition.

As will be described below, in the product inorganic compound of the present invention, since an inorganic compound of which at least one of a cation component and an anion component of a raw material inorganic compound is the same as that of the product inorganic compound and of which a composition is different therefrom is an inorganic compound that is precipitated from ion components generated when the raw material inorganic compound is dissolved and ion components in an electrolyte aqueous solution, it is called a precipitated inorganic compound.

The product inorganic compound may comprise only a precipitated inorganic compound or comprise a precipitated inorganic compound formed on a surface of the raw material inorganic compound and an unreacted raw material inorganic compound inside the precipitated inorganic compound.

When the product inorganic compound comprises only a precipitated inorganic compound, the product inorganic compound has a volume that is at least $10^{-13}$ m$^3$ or more, comprises at least grain boundaries other than sinterable grain boundaries, and preserves a form without disintegrating even if it is immersed in water for 24 hours, and has substantially the same composition from the surface to the inside.

Such a product inorganic compound preferably comprises a composition containing at least one selected from the group consisting of a carbonate apatite, vaterite-containing calcium carbonate, aragonite-containing calcium carbonate, calcium hydroxide, calcium fluoride, magnesium hydroxide, and whitlockite.

When the product inorganic compound comprises a precipitated inorganic compound formed on a surface of a raw material inorganic compound and an unreacted raw material inorganic compound inside a precipitated inorganic compound, since the unreacted raw material inorganic compound is covered with the precipitated inorganic compound, it may have a core-shell structure. In this case, the unreacted raw material inorganic compound is referred to as a core portion, and the precipitated inorganic compound is referred to as a surface layer portion. Also, it is not necessary for the precipitated inorganic compound to completely cover the surface of the unreacted raw material inorganic compound. For example, even if a precipitated inorganic compound is formed on one side of a plate-like raw material inorganic compound, the unreacted raw material inorganic compound is referred to as a core portion, and the precipitated inorganic compound is referred to as a surface layer portion.

Such a product inorganic compound has a volume that is $10^{-13}$ m$^3$ or more, comprises at least a core portion and a surface layer portion that covers the core portion and the core portion and the surface layer portion have different compositions, and the surface layer portion includes an inorganic compound that comprises at least grain boundaries other than sinterable grain boundaries and preserves a form without disintegrating even if it is immersed in water for 24 hours, and the inorganic compound of the surface layer portion comprises at least one element included in a composition of the core portion.

In addition, such a product inorganic compound comprises at least a core portion and a surface layer portion that covers the core portion, and has a volume that is $10^{-13}$ m$^3$ or more, and the core portion and the surface layer portion have different compositions, and the core portion has a component the same as that of a raw material inorganic compound and the surface layer portion comprises at least grain boundaries other than sinterable grain boundary and preserves a form without disintegrating even if it is immersed in water for 24 hours and comprises a component in which anions of the inorganic compound are exchanged with anions of an electrolyte aqueous solution or an electrolyte suspension, a component in which cations of the inorganic compound are exchanged with cations of an electrolyte aqueous solution or an electrolyte suspension, or a component that is not included in the raw material inorganic compound and derived from an electrolyte aqueous solution or an electrolyte suspension.

The precipitated inorganic compound is an inorganic compound that is obtained when a raw material inorganic compound is immersed in an electrolyte aqueous solution or an electrolyte suspension, and is an inorganic compound in which an anion component in the raw material inorganic compound and an anion component in the electrolyte aqueous solution or the electrolyte suspension are exchanged, an inorganic compound in which a cation component in the raw material inorganic compound and a cation component in the electrolyte aqueous solution or the electrolyte suspension are exchanged, or an inorganic compound comprising a component (provided that it excludes water, hydrogen, and oxygen) in the electrolyte aqueous solution or the electrolyte suspension that is not included in the raw material inorganic compound is included.

[Core Portion]

In the present invention, at least an inorganic compound included in the core portion preferably comprises at least grain boundaries other than sinterable grain boundaries. In addition, one or both of inorganic compounds of the surface layer portion and the core portion are preferably calcium compounds and inorganic compounds of the core portion preferably comprise at least one selected from the group consisting of calcium phosphate, calcium carbonate, calcium sulfate, an apatite, a calcium-containing glass, a coral, and a bone.

The core portion may or may not comprise a support therein.

[Surface Layer Portion]

In the present invention, inorganic compounds of the surface layer portion preferably comprise at least one selected from the group consisting of vaterite-containing calcium carbonate, aragonite-containing calcium carbonate, whitlockite, calcium hydrogen phosphate, calcium sulfate, calcium carbonate, calcium hydrogen phosphate, calcium hydroxide, and apatite. In addition, the surface layer portion comprises at least calcium sulfate hemihydrate and may have curability. Further, the surface layer portion may comprise granules containing at least calcium sulfate hemihydrate, and may have curability when an aqueous solution containing at least one of sodium ions and sulfate ions is used as a mixing solution.

[Core Portion:Surface Layer Portion]

In the product inorganic compound comprising at least a core portion and a surface layer portion, the release of inorganic ions from the core portion or the surface layer portion may be expected. When a solubility of the core portion is greater than a solubility of the surface layer portion, the release of inorganic ions from the core portion for a relatively long period of time may be expected in many cases. On the other hand, when a solubility of the surface layer portion is greater than a solubility of the core portion, the release of inorganic ions from the surface layer portion for a relatively short period of time is expected. For example, calcium ions released from the core portion or the surface layer portion activate cells such as osteoblasts. In order to provide such a function, a mass ratio between the core portion and the surface layer portion (core portion: surface layer portion) is preferably 97:3 to 50:50, more preferably 97:5 to 50:40, and particularly preferably 97:10 to 50:30.

[Production Method]

In the present invention, an electrolyte aqueous solution or an electrolyte suspension that comprises a component that is a constituent component of a precipitated inorganic compound included in at least a product inorganic compound but is not a constituent component of a raw material inorganic compound as a cation component or an anion component is used.

When the raw material inorganic compound is immersed in the electrolyte aqueous solution or the electrolyte suspension, a precipitated inorganic compound is produced and a product inorganic compound is produced as a result.

In order to understand the content of the present invention, a basic mechanism of the present invention will be described. Note that a production mechanism has not been completely clarified. In addition, the present invention is not limited by the mechanism.

Here, in order to demonstrate the superiority when calcium sulfate is used as a raw material inorganic compound, a case in which an interconnected porous calcium sulfate body is produced from calcium sulfate hemihydrate and polymer-short fibers, and the interconnected porous calcium sulfate body is used as a raw material to produce an interconnected porous calcium carbonate body will be exemplified. Also, in this example, calcium sulfate is a raw material inorganic compound. In this example, the raw material inorganic compound is not combined with a compositing material component and a support.

<Process of Producing a Raw Material Inorganic Compound: Production of an Interconnected Porous Calcium Sulfate Porous Body>

When calcium sulfate hemihydrate is mixed with water, it is cured and forms gypsum dihydrate. Therefore, when calcium sulfate hemihydrate is mixed with polymer-short fibers, calcium sulfate dihydrate containing polymer-short fibers can be produced.

One of features of calcium sulfate is thermal stability. When calcium sulfate dihydrate is heated, for example, at 700° C., it becomes calcium sulfate anhydrate but does not thermally decompose.

On the other hand, polymer-short fibers are incinerated. As a result, a porous calcium sulfate anhydrate body is produced. When a content of short fibers is adjusted, short fibers are brought into contact with each other and an interconnected porous calcium sulfate anhydrate body is produced. Calcium sulfate anhydrate is a compound having a solubility at 20° C. that is greater than 0 and less than 5.

<Process of Immersing a Raw Material Inorganic Compound in an Electrolyte Aqueous Solution or an Electrolyte Suspension>

The raw material inorganic compound is immersed in an electrolyte aqueous solution or an electrolyte suspension. Here, a production method in which a compound is immersed in a sodium carbonate aqueous solution will be exemplified.

A solubility of calcium sulfate anhydrate is about 0.3. Therefore, when calcium sulfate anhydrate is immersed in 100 g of water, calcium ions and sulfate ions corresponding to about 0.3 g of calcium sulfate dihydrate are dissolved in water as shown in Formula (1).

[Chem. 1]

$$CaSO_4 \rightarrow Ca^{2+} + SO_4^{2-} \quad (1)$$

Also, actually, there is calcium sulfate dihydrate whose solubility is lower than calcium sulfate anhydrate. There is a possibility of calcium sulfate anhydrate being hydrated to become calcium sulfate dihydrate. However, for the sake of simplicity, a mechanism will be described herein overlooking the presence of calcium sulfate dihydrate.

At a stage in which calcium sulfate anhydrate is dissolved, when other ions are not present in water, calcium sulfate anhydrate gradually reaches dissolution equilibrium and no additional reaction will occur.

However, when sodium carbonate is dissolved in water, sodium carbonate is ionized as shown in Formula (2) to form sodium ions and carbonate ions, and an equilibrium is established between reactions of calcium ions and carbonate ions.

[Chem. 2]

$$Na_2CO_3 \rightarrow 2Na^+ + CO_3^{2-} \quad (2)$$

Calcium carbonate has a solubility that is about 0.002, which is significantly lower than calcium sulfate anhydrate. Therefore, calcium ions dissolved from calcium sulfate anhydrate are precipitated as calcium carbonate as shown in Formula (3).

[Chem. 3]

$$Ca^{2+} + CO_3^{2-} \rightarrow CaCO_3 \quad (3)$$

In addition, since calcium ions are dissolved from a surface of calcium sulfate anhydrate, calcium carbonate is precipitated on a surface of calcium sulfate anhydrate. It is considered that the dissolution reaction and precipitation reaction continuously occur, and calcium sulfate anhydrate having a high solubility is compositionally converted into calcium carbonate having a lower solubility than calcium sulfate anhydrate, while preserving a macro form. Also, since a calcium carbonate crystal is precipitated, a micro form at a crystal size level is not preserved.

In this manner, since the raw material inorganic compound is partially dissolved in an electrolyte aqueous solution or an electrolyte suspension, and a new inorganic compound is precipitated from a component of a raw material inorganic compound and a component of an electrolyte, an inorganic compound in the newly formed product inorganic compound is referred to as a precipitated inorganic compound in the present invention.

When calcium sulfate is immersed in a sodium carbonate aqueous solution, calcium sulfate is compositionally converted into calcium carbonate while preserving a macro form. This is due to the fact that a solubility of calcium carbonate with respect to an electrolyte solution in which it is immersed is lower than a solubility of calcium sulfate, and a concentration of sulfate ions in the electrolyte aqueous solution increases with the progress of the reaction. As a result, a formation reaction of calcium sulfate shown in Formula (4) also partially progresses. Carbonate ions and sulfate ions competitively react, but the reaction shown in Formula (4) is removed by removing sulfate ions from an electrolyte. Therefore, it is possible to produce a product inorganic compound having a higher purity from the raw material inorganic compound and produce a product inorganic compound in a shorter period of time.

In addition, according to the reaction shown in Formula (3), a concentration of carbonate ions in the electrolyte aqueous solution decreases. As a result, a rate of the precipitation reaction of Formula (3) decreases. When the electrolyte suspension is used in place of the electrolyte aqueous solution, this is preferable because carbonate ions are supplied to the electrolyte aqueous solution according to the reaction of Formula (2).

[Chem. 4]

$$Ca^{2+} + SO_4^{2-} \rightarrow CaSO_4 \quad (4)$$

In order to remove sulfate ions from an electrolyte aqueous solution or an electrolyte suspension, a method in which an electrolyte aqueous solution or an electrolyte suspension is exchanged with a new sodium carbonate aqueous solution during production, a method in which an ion exchange resin is added to an electrolyte aqueous solution or an electrolyte suspension, an adsorption method, an electrodialysis method, a diffusion dialysis method, an electrolysis method and the like are effective.

A temperature of an electrolyte aqueous solution or an electrolyte suspension is very important because it greatly influences properties of a product inorganic compound. Although details will be described below, in general, when the temperature of the electrolyte aqueous solution or the electrolyte suspension is high, since stability is high, a product inorganic compound having excellent stability is produced. On the other hand, when the temperature of the electrolyte aqueous solution or the electrolyte suspension is low, a product inorganic compound having high reactivity is produced.

<Product Inorganic Compound to be Produced>

The product inorganic compound is an interconnected porous calcium carbonate body in which a sulfate ion component that is an anion component of calcium sulfate serving as a raw material inorganic compound and an anion component of sodium carbonate serving as an electrolyte are exchanged.

Note that, in the present invention, when a time for which a raw material inorganic compound is immersed in an electrolyte aqueous solution is set or when a molar ratio between a raw material inorganic compound and an electrolyte included in an electrolyte aqueous solution is adjusted, it is possible to produce a product inorganic compound whose surface composition and internal composition are different.

For example, when calcium carbonate granules are immersed in a disodium hydrogen phosphoric acid aqueous solution, which is an electrolyte aqueous solution, calcium carbonate is dissolved and calcium ions and carbonate ions are released. As a result, while phosphate ions, sodium ions, calcium ions, and carbonate ions coexist in an electrolyte aqueous solution, since the electrolyte aqueous solution is supersaturated with a carbonate apatite, the carbonate apatite is formed on surfaces of calcium carbonate granules.

If the reaction continues under conditions in which sufficient electrolyte components are included, when carbonate apatite granules are immersed in an electrolyte aqueous solution or an electrolyte suspension, calcium carbonate granules are compositionally changed to a carbonate apatite while preserving their forms. However, when a reaction time and the like are controlled, it is possible to produce a product inorganic compound in which calcium carbonate granules are covered with a carbonate apatite. That is, it is possible to produce a product inorganic compound whose core portion is calcium carbonate and whose surface layer portion is a carbonate apatite. In addition, a core-shell type product inorganic compound can be produced even when a molar number of an ion component of an exchange target included in the electrolyte aqueous solution or the electrolyte suspension is less than a molar number of an ion component of an exchange target in the raw material inorganic compound. Such a product inorganic compound becomes an extremely highly functional product according to a combination.

When calcium carbonate having a solubility that is greater than a carbonate apatite becomes a core portion and a carbonate apatite having a solubility that is lower than calcium carbonate and having excellent osteoconductivity becomes a surface layer portion, osteoconductivity is significantly improved compared to when a carbonate apatite is used alone.

Although this mechanism has not been clarified, calcium released from calcium carbonate is speculated to activate osteoblasts.

Also, due to a high adsorption property of a carbonate apatite, when a natural material such as a littleneck clam having a composition of calcium carbonate is used as a raw material inorganic compound, it is not possible to produce a product inorganic compound having excellent tissue compatibility. Therefore, when a carbonate apatite is produced, it is necessary to use an artificial material as a raw material.

If a solubility of the core portion is greater than a solubility of the surface layer portion, if the product inorganic compound is implanted in vivo, a component of the core portion is released through the surface layer portion and osteoblasts may be activated. On the other hand, even if a solubility of the core portion is lower than a solubility of the surface layer portion, cells may be activated according to the same mechanism.

For example, when β-type tricalcium phosphate is immersed in a sodium hydrogen carbonate aqueous solution, which is an electrolyte aqueous solution, it is possible to produce a product inorganic compound whose core portion is β-type tricalcium phosphate and whose surface layer portion is calcium carbonate. When the product inorganic compound is implanted in a bone defect, calcium carbonate having a high solubility is dissolved and calcium ions are released. Osteoblasts are activated due to calcium ions, and bone grows on β-type tricalcium phosphate which is an osteoconductive material. An osteoconduction speed thereof is accelerated compared to when β-type tricalcium phosphate is used alone.

An interconnected porous body is formed according to the same mechanism as the dissolution and precipitation mechanism according to the raw material inorganic compound described above.

For example, β-type tricalcium phosphate granules serving as a raw material inorganic compound are immersed in acidic calcium phosphate serving as an electrolyte aqueous solution.

A solubility of β-type tricalcium phosphate is 5 or less. Therefore, when β-type tricalcium phosphate is immersed in an acidic calcium phosphoric acid aqueous solution, calcium ions and phosphate ions are dissolved in water as shown in Formula (5).

[Chem. 5]

$$Ca_3(PO_4)_2 \rightarrow 3Ca^{2+} + 2PO_4^{3-} \qquad (5)$$

However, the acidic calcium phosphoric acid aqueous solution, which is an electrolyte solution in which β-type tricalcium phosphate is dissolved, is supersaturated with calcium hydrogen phosphate, and calcium hydrogen phosphate is precipitated from the electrolyte solution as shown in Formula (6).

[Chem. 6]

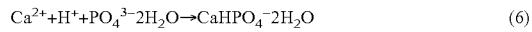

$$Ca^{2+} + H^+ + PO_4^{3-} \cdot 2H_2O \rightarrow CaHPO_4 \cdot 2H_2O \qquad (6)$$

When calcium ions and phosphate ions are supplied from β-type tricalcium phosphate serving as a raw material inorganic compound, surfaces of β-type tricalcium phosphate granules have the highest degree of supersaturation with respect to calcium hydrogen phosphate and the β-type tricalcium phosphate granules are covered with calcium hydrogen phosphate. In this case, when there are a plurality of β-type tricalcium phosphate granules and β-type tricalcium phosphate close to each other, calcium hydrogen phosphate serving as a precipitated inorganic compound is precipitated so that β-type tricalcium phosphate granules are bridged. Since calcium hydrogen phosphate covering β-type tricalcium phosphate granules does not completely occupy a space formed by the β-type tricalcium phosphate granules, an interconnected porous body is formed.

Configurations will be described below.

<Inorganic Compound>

The inorganic compound is a compound other than organic complexes in which carbon atoms are assembled as a skeleton.

<Volume of Raw Material Inorganic Compound>

In the present invention, a raw material inorganic compound having a volume of $10^{-13}$ m$^3$ or more is used. In the present invention, a volume is defined as an amount of a raw material inorganic compound occupying a three-dimensional space. Therefore, even in a porous body, an apparent volume including air and the like inside the porous body is referred to as a volume in the present invention. Even if the volume of the raw material inorganic compound is less than $10^{-13}$ m$^3$, it is possible to produce a product inorganic compound by a production method similar to that of the present invention. However, if the volume is small, a difference from a powder is substantially small, and usefulness is low.

In addition, when the volume of the raw material inorganic compound is less than $10^{-13}$ m$^3$, serious problems, for example, triggering of inflammatory responses, may occur in medical material applications.

<Preferable Volume of Raw Material Inorganic Compound in the Present Invention>

In the present invention, the volume of the raw material inorganic compound is $10^{-13}$ m$^3$ or more, preferably $10^{-12}$ m$^3$ or more, more preferably $10^{-11}$ m$^3$ or more, and most preferably $10^{-10}$ m$^3$ or more. In consideration of operability, a hard tissue reconstruction material has a volume that is preferably $10^{-12}$ m$^3$ or more.

<Content of a Raw Material Inorganic Compound Having a Preferable Constant Volume or More in the Present Invention>

In the present invention, since an essential requirement includes that a product inorganic compound having a volume of $10^{-13}$ m$^3$ or more is produced from a raw material inorganic compound having a volume of $10^{-13}$ m$^3$ or more, a product inorganic compound having a volume of $10^{-13}$ m$^3$ or more can be produced from at least one raw material inorganic compound having a volume of $10^{-13}$ m$^3$ or more, but mixing in of an inorganic compound having a volume of less than $10^{-13}$ m$^3$ in production is not excluded.

However, in consideration of efficiency of production and functionality, in the raw material inorganic compound, a content of an inorganic compound of $10^{-13}$ m$^3$ or more or an inorganic compound having a determined constant volume or more is preferably 10 weight % or more, more preferably 50 weight % or more, and most preferably 90 weight % or more.

<A Preferable Form of a Raw Material Inorganic Compound: Porous Body>

A form of the raw material inorganic compound of the present invention is not particularly limited. Any form such as a cubic shape, a columnar shape, a spherical shape, and an irregular shape is selected according to applications of products.

Meanwhile, it is desirable that a product inorganic compound such as a hard tissue reconstruction material for medical treatment have a porous body in some cases. This is because the merit of the porous body is extremely great in that cells can penetrate into the hard tissue reconstruction material. In particular, an interconnected porous body is particularly preferable because cells easily penetrate into the hard tissue reconstruction material. When a product inorganic compound is used as an adsorbent other than a hard tissue reconstruction material for medical treatment, a porous body and particularly an interconnected porous body is preferable in some cases.

<Porous Body>

A porous body is also called a porous material and refers to a material having many pores therein. On the other hand, a dense body refers to a material having no pores therein. In the present invention, a body having an apparent porosity of 30% or more is defined as a porous body and a body having an apparent porosity of less than 30% is defined as a dense body. The apparent porosity is calculated from an apparent volume and a mass of the material. An apparent volume of the material is calculated from external dimensions and the like. That is, although a pore portion may not be included in a volume of the material; for an apparent volume, pores inside or on a surface of the material are included in the apparent volume. A mass if the material was a dense body is calculated from an apparent volume and a density of the material. A porosity is calculated from a mass of the material and the calculated mass. The porosity can be measured using micro CT and the like.

<Desirable Pores>

When cells and the like are expected to penetrate into a product inorganic compound, not only the porosity but also a shape of pores are important in some cases. One of important factors for the shape of the pores is a diameter of the pores. In consideration of invasion of cells, the diameter of the pores is preferably 20 μm or more and 3000 μm or less, more preferably 50 μm or more and 1000 μm or less, and most preferably 100 μm or more and 500 μm or less.

In addition, an aspect ratio is important in the shape of the pore. The aspect ratio is a ratio of a length of a major axis to a length of a short axis of a pore. The aspect ratio is preferably 2 or more, more preferably 5 or more, and most preferably 10 or more.

In order to form a pore having a high aspect ratio, a method in which a fibrous pore forming material is mixed into a raw material, and the pore forming material is incinerated and thus removed from the raw material is one of suitable methods.

<Interconnected Porous Body>

Among porous bodies, a body in which pores are connected is an interconnected porous body. When light is introduced from one side of a material, interconncting pores can be determined based on whether the light is observed from the other side due to irregular reflection of the light at pore walls.

<Solubility of a Raw Material Inorganic Compound>

A solubility is a value of a mass [g] of a solute soluble in 100 g of a solvent at a certain temperature and is generally an absolute number, but is defined as a mass [g] of an inorganic compound soluble in 100 g of distilled water or an electrolyte aqueous solution at 20° C. in the present invention. When describing simply using solubility, this will refer to solubility in distilled water at 20° C. below.

A solubility of the raw material inorganic compound used in the present invention is greater than 0, and preferably 0.0001 or more and 5 or less. That is, a raw material inorganic compound that dissolves at 5 g or less in 100 g of distilled water or an electrolyte aqueous solution at 20° C. is used as a raw material inorganic compound in the present invention.

<Preferable Solubility of a Raw Material Inorganic Compound>

A solubility of the raw material inorganic compound is greater than 0, and 5 or less and preferably 4 or less, and more preferably 2 or less, and a solubility is most preferably 1 or less.

In the present invention, as a raw material inorganic compound having a solubility that is greater than 0 and 5 or less, calcium sulfate dihydrate, calcium sulfate hemihydrate, calcium sulfate anhydride, calcium hydrogen phosphate dehydrate (dicalcium phosphate dihydrate), calcium hydrogen phosphate anhydrate, tricalcium phosphate, and the like may be exemplified.

<Preferable Raw Material Inorganic Compound: Curable Material>

In the present invention, it is possible to produce a product inorganic compound without substantially changing a macro form of a raw material inorganic compound. Accordingly, formation of a form of the raw material inorganic compound may be important.

In consideration of formation of a form of a raw material inorganic compound, an inorganic compound formed according to curing is a raw material inorganic compound that is extremely excellent as a raw material inorganic compound in the present invention.

As the inorganic compound formed according to curing, calcium sulfate may be exemplified. When calcium sulfate hemihydrate is mixed with water, it is cured to form calcium sulfate dihydrate as shown in Formula (7).

[Chem. 7]

$$CaSO_4 \cdot 0.5H_2O + 1.5H_2O \rightarrow CaSO_4 \cdot 2H_2O \quad (7)$$

Calcium hydrogen phosphate formed from a calcium hydrogen phosphate cement is also an excellent raw material inorganic compound. For example, as shown in Formula (8), a mixture of calcium dihydrogen phosphate and tricalcium phosphate is cured to form calcium hydrogen phosphate dihydrate.

[Chem. 8]

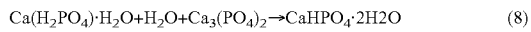

$$Ca(H_2PO_4)\cdot H_2O+H_2O+Ca_3(PO_4)_2 \rightarrow CaHPO_4\cdot 2H2O \quad (8)$$

<Preferable Raw Material Inorganic Compound>

In the present invention, a raw material inorganic compound preferably comprises an alkaline earth metal, more preferably comprises at least one selected from the group consisting of calcium sulfate, calcium carbonate, calcium phosphate, a calcium-containing glass, and a bone, and particularly preferably comprises calcium sulfate anhydrate.

<Preferable Raw Material Inorganic Compound: High Temperature Stability>

In the present invention, it is possible to produce a product inorganic compound without substantially changing a macro form of a raw material inorganic compound. Accordingly, formation of a form of a raw material inorganic compound may be important.

In the product inorganic compound, a porous body, and particularly, an interconnected porous body and the like may be important. In order to produce an inorganic compound porous body as the product inorganic compound, it is necessary to produce a raw material inorganic compound porous body.

One of methods of producing the raw material inorganic compound porous body includes incineration of a pore forming material. Specifically, a polymer-pore forming material is introduced into a raw material inorganic compound and the obtained raw material inorganic compound including the polymer-pore forming material is calcined, and thus the polymer-pore forming material is incinerated. As a result, a porous body inorganic compound can be produced.

Therefore, a stable raw material inorganic compound that is not decomposed at high temperatures is an excellent raw material inorganic compound. The raw material inorganic compound is preferably stable at 700° C. or higher at which a polymer-pore forming material is incinerated, more preferably stable at 800° C. or higher, and most preferably stable at 900° C. or higher.

As the raw material inorganic compound having excellent high temperature stability, tricalcium phosphate, tetracalcium phosphate, and calcium sulfate may be exemplified.

Since calcium sulfate exhibits self-curability and is an inorganic compound having high temperature stability, it is particularly excellent as the raw material inorganic compound of the present invention.

<Particularly Preferable Raw Material Inorganic Compound in the Present Invention>

A particularly preferable raw material inorganic compound in the present invention is an inorganic compound having both curability and high temperature stability, and calcium sulfate may be exemplified.

When calcium sulfate hemihydrate powder is mixed—with water, it is cured to form calcium sulfate dihydrate. The calcium sulfate cured body is dehydrated under thermally stable conditions and is stable at 1000° C. although it becomes calcium sulfate hemihydrate or calcium sulfate anhydrate.

<Preferable Raw Material Inorganic Compound in the Present Invention: A Naturally Derived Material and a Material of Biological Origin>

As the raw material inorganic compound of the present invention, naturally derived materials or materials of biological origin other than artificial materials such as a bone, a calcined bone, a shell, and a coral can be selected. For example, when a bone prosthetic material is produced, a form of bone is ideal and a composition that can be converted while preserving the form of the bone is of great significance.

<Preferable Raw Material Inorganic Compound in the Present Invention: Artificial Material>

Meanwhile, materials other than artificial materials such as materials of biological origin and naturally-derived materials often include impurities, and are not suitable for producing a product inorganic compound. In addition, organic materials are included in many cases. When such an organic material inhibits dissolution of a raw material inorganic compound, a product inorganic compound may be not easily produced. In this case, an artificial material is preferable as the raw material inorganic compound.

<Raw Material Inorganic Compound Including a Compositing Material Component>

In order to increase a mechanical strength of a product inorganic compound, an inorganic compound and a composite material may be combined. The composite material is an organic substance, a metal, or an inorganic compound other than a raw material inorganic compound. In this case, a raw material inorganic compound can be combined with a composite material in a raw material inorganic compound in advance.

<Electrolyte Aqueous Solution or Electrolyte Suspension>

In the present invention, a raw material inorganic compound is treated using an electrolyte aqueous solution or an electrolyte suspension including a component which is not a constituent component of the raw material inorganic compound as cations or anions, and is defined as a compound that is ionized into cations and anions when an electrolyte is dissolved in distilled water in the present invention.

The electrolyte aqueous solution or electrolyte suspension in which a raw material inorganic compound is immersed preferably comprises an alkaline earth metal, an alkali metal, or an ammonia compound. In addition, the electrolyte aqueous solution or the electrolyte suspension preferably comprises at least one selected from the group consisting of carbonate ions, hydrogen carbonate ions, sulfate ions, hydrogen sulfate ions, hydrogen phosphate ions, hydroxide ions, and fluoride ions.

In particular, in the electrolyte in the present invention, as a compound that includes a carbonate compound, a fluorine compound, a chloride, and a hydroxide compound; and sodium carbonate, sodium hydrogen carbonate, sodium hydroxide, potassium hydroxide, ammonia, sodium fluoride, potassium fluoride, and ammonium fluoride may be exemplified.

In the electrolyte aqueous solution or the electrolyte suspension used in the present invention, at least, elements other than hydrogen and oxygen, which are included in a product inorganic compound but not included in a raw material inorganic compound are included.

Since an aqueous solution includes hydrogen and oxygen, if hydrogen or oxygen is not included in the raw material inorganic compound and hydrogen or oxygen is included in the product inorganic compound, determination of whether it is derived from an electrolyte is unclear. Therefore, even if hydrogen or oxygen is not included in the raw material inorganic compound, hydrogen or oxygen is included in the product inorganic compound, and hydrogen or oxygen is included in an electrolyte, when elements other than hydrogen and oxygen, which are included in the product inorganic compound but not included in the raw material inorganic compound, are not included, they are outside the scope of the present invention.

<pH of an Electrolyte Aqueous Solution or an Electrolyte Suspension>

In the present invention, a pH of the electrolyte aqueous solution or an electrolyte suspension may be preferably less than 7. When a pH is less than 7, a solubility of a raw material inorganic compound is generally high. Therefore, a production time is reduced in many cases. In particular, when calcium hydrogen phosphate is formed on at least a surface of a product inorganic compound, it is necessary for a pH of the electrolyte aqueous solution to be set to less than 7. This is because calcium hydrogen phosphate is stable only when a pH is less than 7. When a product composition comprising calcium hydrogen phosphate on at least a surface is produced, essential conditions include that a pH of the electrolyte aqueous solution be less than 7, a pH is preferably 5 or less, a pH is more preferably 3 or less, and a pH is particularly preferably 2 or less. In addition, when calcium sulfate is formed on at least a surface of a product inorganic compound, a pH of the electrolyte aqueous solution is preferably less than 7, a pH is more preferably 5 or less, and a pH is particularly preferably 2 or less. Although a mechanism by which a pH is preferably less than 7 when calcium sulfate is formed on at least a surface of a product inorganic compound from a raw material inorganic compound for production has not been adequately clarified, it is considered to be caused by pH dependence of the solubility of the raw material inorganic compound and calcium sulfate.

In addition, in the present invention, a pH of the electrolyte aqueous solution or the electrolyte suspension may be preferably 7 or more. When a pH is 7 or more, since a solubility of a raw material inorganic compound is generally low and there is less need to strictly control a production time, there is an advantage that an exact product inorganic compound can be produced. In particular, when apatite is formed on at least a surface of a product inorganic compound, a pH of the electrolyte aqueous solution is preferably 7 or more. This is because apatite is stable at a pH of 7 or more. When a product composition including at least a surface is produced, a pH of the electrolyte aqueous solution is preferably 7 or more, a pH is more preferably 9 or more, and a pH is particularly preferably 11 or more. When calcium carbonate is formed on at least a surface of a product inorganic compound, a pH of the electrolyte aqueous solution is preferably 7 or more for the same reason. This is because calcium carbonate is stable at a pH of 7 or more. When a product composition including at least a surface is produced, a pH of the electrolyte aqueous solution is preferably 7 or more, a pH is more preferably 9 or more, and a pH is particularly preferably 11 or more.

<Molar Ratio Between a Raw Material Inorganic Compound and an Electrolyte>

In the present invention, supply of an electrolyte component into an aqueous solution is performed by dissolving or suspending an electrolyte in an aqueous solution.

Since a part of the electrolyte component is used as a component of the product inorganic compound, an amount of an electrolyte added to the aqueous solution is controlled according to a molar ratio with respect to the raw material inorganic compound.

When a product inorganic compound in which anions of the raw material inorganic compound and anions of the electrolyte are completely exchanged is produced, a molar number of an anion component of an exchange target included in the electrolyte aqueous solution or the electrolyte suspension is preferably equal to or greater than a molar number of anions of an exchange target in the raw material inorganic compound.

On the other hand, depending on the product inorganic compound, it may be necessary to produce a nonsingular composition compound in which a part of a raw material inorganic compound is set to a core structure and the outside thereof is covered with another inorganic compound. That is, a product inorganic compound in which an unreacted inorganic compound is covered with a precipitated inorganic compound may be necessary.

Such a product inorganic compound can be produced by adjusting a time for immersing a raw material inorganic compound in an electrolyte aqueous solution, and can also be produced by adjusting a molar ratio between the raw material inorganic compound and the electrolyte.

For example, when a core shell type product inorganic compound in which anions of a raw material inorganic compound and anions of an electrolyte are exchanged on a surface of the raw material inorganic compound is produced, a molar number of ions of an exchange target included in the electrolyte aqueous solution or the electrolyte suspension is preferably less than a molar number of ions of an exchange target in the raw material inorganic compound.

<Concentration of an Electrolyte>

A concentration of an electrolyte influences a rate of a reaction with a raw material inorganic compound and an electrolyte having a higher concentration has a higher reaction rate. This is due to the fact that, when a product inorganic compound is produced, ions eluted from the raw material inorganic compound and ions of the electrolyte react in an electrolyte aqueous solution and are precipitated on a surface of the raw material inorganic compound. For precipitation, the product of ion concentrations of components of the product inorganic compound should be equal to or greater than the solubility product of the product inorganic compound. Therefore, a higher concentration of the electrolyte is preferable.

<Temperature of an Electrolyte Aqueous Solution>

In a stage in which a raw material inorganic compound is immersed in an electrolyte aqueous solution, since the raw material inorganic compound is dissolved, and a component thereof is provided as ions in an aqueous solution, there is basically no need to limit immersion conditions. However, in consideration of production costs, a raw material inorganic compound is preferably immersed in the electrolyte aqueous solution at less than 100° C. In consideration of energy costs, a temperature of the electrolyte aqueous solution is more preferably 90° C. or less, more preferably 70° C. or less, and particularly preferably 10° C. or less.

In addition, depending on the product inorganic compound, high reactivity may be desired. In this case, a temperature at which a compound is immersed in the electrolyte aqueous solution or an electrolyte suspension is preferably greater than 100° C.

In general, when a raw material inorganic compound is immersed in a high temperature electrolyte aqueous solution, since a large amount of crystals is precipitated, a product inorganic compound having low reactivity and excellent stability is obtained. On the other hand, when a raw material inorganic compound is immersed in a low temperature electrolyte aqueous solution, since a small amount of crystals is precipitated, a product inorganic compound having high reactivity is obtained.

In particular, when calcium carbonate or a carbonate apatite is to be formed on at least a surface of the product inorganic compound, functions of the product inorganic compound are significantly different depending on a temperature of the electrolyte aqueous solution.

Calcium carbonate has various forms such as a vaterite, aragonite, and calcite. Vaterite is the most unstable polymorph and is formed when a temperature of the electrolyte aqueous solution is 10° C. or less. Therefore, when a product inorganic compound including vaterite-containing calcium carbonate is produced, it is necessary to set a temperature of an electrolyte to be 10° C. or less. Aragonite is the next most unstable polymorph to vaterite and is formed at 90° C. or less. Therefore, when a product inorganic compound including aragonite-containing calcium carbonate is produced, it is necessary to set a temperature of an electrolyte to 90° C. or less. Calcite is the most stable phase among polymorphs of calcium carbonate. When a stable product inorganic compound is produced, calcite is preferably used as a polymorph of calcium carbonate. Calcium carbonate is generally formed even when a temperature of the electrolyte aqueous solution is 10° C. or less. However, when a more stable calcium carbonate having a different crystallinity is produced, it is necessary to use an electrolyte aqueous solution at greater than 100° C. for production. When a product inorganic compound including calcium carbonate having higher reactivity is produced, it is necessary to use an electrolyte aqueous solution at 90° C. or less and more preferably at 10° C. or less.

When a product inorganic compound including a carbonate apatite on at least a surface of the product inorganic compound is produced, a temperature of the electrolyte is extremely important. This is because reactivity of a carbonate apatite changes significantly depending on crystallinity and crystallinity can be controlled by the temperature. When a carbonate apatite having high activity is produced, an electrolyte aqueous solution at 90° C. or less is preferably used, an electrolyte aqueous solution at 50° C. or less is more preferably used, and an electrolyte aqueous solution at 10° C. or less is most preferably used.

<Crystallite Size>

As an indicator of stability or reactivity of a product inorganic compound, a crystallite size is used. When a crystallite size is larger, a stable product inorganic compound is obtained. When a crystallite size is smaller, a product inorganic compound having higher reactivity is obtained.

When a product inorganic compound including calcium carbonate having excellent reactivity is used, a crystallite size of calcite is preferably less than 110 nm, more preferably 105 nm or less, and most preferably 100 nm or less. When a product inorganic compound including calcium carbonate having excellent stability is used, a crystallite size of calcite is preferably 110 nm or more, more preferably 130 nm or more, and most preferably 150 nm or more.

When a product inorganic compound including a carbonate apatite having excellent reactivity is used, a crystallite size of a carbonate apatite is preferably less than 100 nm, more preferably 50 nm or less, and most preferably 30 nm or less. When a product inorganic compound including a carbonate apatite having excellent stability is used, a crystallite size of a carbonate apatite is preferably 110 nm or more, more preferably 130 nm or more, and most preferably 150 nm or more.

<Product Inorganic Compound>

In the present invention, a volume of a product inorganic compound is $10^{-13}$ m$^3$ or more.

In addition, a composition of the product inorganic compound needs to include a component in which an anion component of a raw material inorganic compound and an anion component of an electrolyte are exchanged, a component in which a cation component of a raw material inorganic compound and a cation component of an electrolyte are exchanged, or a component (provided that it excludes water, hydrogen, and oxygen) that is not included in a raw material inorganic compound but is included in an electrolyte aqueous solution or an electrolyte suspension.

An amount of a component in which an anion component of a raw material inorganic compound and an anion component of an electrolyte are exchanged, a component in which a cation component of a raw material inorganic compound and a cation component of an electrolyte are exchanged, or an electrolyte component (excluding water, hydrogen, and oxygen) that is not included in a composition of a raw material inorganic compound, which is included in the product inorganic compound, is not particularly defined. However, substantially, a component in which an anion component of a raw material inorganic compound and an anion component of an electrolyte are exchanged, a component in which a cation component of a raw material inorganic compound and a cation component of an electrolyte are exchanged, or an electrolyte component (excluding water, hydrogen, and oxygen) that is not included in a composition of a raw material inorganic compound needs to be included in the product inorganic compound.

When it is described that a component is substantially included, adsorption or adhesion is excluded. When the product inorganic compound includes a component in which an anion component of a raw material inorganic compound and an anion component of an electrolyte are exchanged or a component in which a cation component of a raw material inorganic compound and a cation component of an electrolyte are exchanged, a content of the component in which an anion component of a raw material inorganic compound and an anion component of an electrolyte are exchanged or the component in which a cation component of a raw material inorganic compound and a cation component of an electrolyte are exchanged is preferably 1 weight % or more, more preferably 5 weight % or more and most preferably 10 weight % or more.

When an electrolyte component (provided that it excludes water, hydrogen, and oxygen) that is not included in a composition of the raw material inorganic compound is included in the product inorganic compound, a content of the electrolyte component (provided that it excludes water, hydrogen, and oxygen) that is not included in the composition of the raw material inorganic compound is preferably 0.1 weight % or more, more preferably 0.5 weight % or more, and most preferably 1 weight % or more.

Compounds in the present invention are as follows.

<Apatite>

The apatite in the present invention is a compound whose basic structure is $Ca_{10}(PO_4)_6(OH)_2$ and includes apatite of which a part is substituted with another element or void.

<Carbonate Apatite>

The carbonate apatite in the present invention is apatite in which a part or all of phosphate groups or hydroxyl groups of an apatite are substituted with a carbonate group. Apatite in which a phosphate group is substituted with a carbonate group is referred to as a B-type carbonate apatite, apatite in which a hydroxyl group is substituted with a carbonate group is referred to as an A-type carbonate apatite. Also, when a phosphate group is substituted with a carbonate group, Na, K, and the like are often included in a crystal structure, and a compound in which a part of a carbonate apatite is substituted with another element or void is also defined as a carbonate apatite.

<Hydroxide Compound>

The hydroxide compound in the present invention is synonymous with hydroxide and refers to a compound including a hydroxide ion (OH−) as an anion. Here, while ammonia ($NH_3$) does not include a hydroxide ion as an anion, since it becomes ammonium hydroxide ($NH_4OH$) in water, it is defined as a hydroxide compound. As the hydroxide compound, sodium hydroxide (NaOH) and potassium hydroxide (KOH) may be exemplified.

<Calcium Sulfate>

The calcium sulfate in the present invention is a compound including $CaSO_4$ as a composition, and includes an anhydride and hydrates such as a hemihydrate, and a dihydrate.

<Calcium Hydrogen Phosphate>

The calcium hydrogen phosphate in the present invention is calcium orthophosphate including $CaHPO_4$ as a composition, and includes an anhydride and hydrates such as a dihydrate.

<Tricalcium Phosphate>

The tricalcium phosphate in the present invention is calcium orthophosphate including $Ca_3(PO_4)_2$ as a representative composition. There is no limitation to an α-type, a β-type, and the like. In addition, a compound in which some calcium ions are substituted with another metal ion such as a sodium or potassium ion is included.

<Whitlockite>

The whitlockite in the present invention is calcium phosphate which has a crystal structure similar to that of β-type tricalcium phosphate and in which some calcium ions may be substituted with magnesium, zinc, sodium, or potassium. In addition, some $PO_4$'s are often substituted with $HPO_4$. In the present invention, a compound which has a crystallographic tricalcium phosphate structure and in which $HPO_4$ is recognized is defined as whitlockite.

Analysis is performed by a general method. For example, regarding the inclusion of a metal other than calcium, atomic absorption analysis, ICP spectroscopic analysis, colorimetric analysis, fluorescent X-ray analysis, or the like is performed. In addition, regarding the inclusion of hydrogen phosphate, infrared spectroscopy analysis, liquid chromatographic analysis of pyrophosphates that are formed by heating, or the like is performed.

<Tetracalcium Phosphate>

The tetracalcium phosphate according to the present invention is calcium orthophosphate including $Ca_4(PO_4)_2O$ as a representative composition.

<Calcium Carbonate>

The calcium carbonate in the present invention is a compound including $CaCO_3$ as a representative composition. In addition, a compound in which some calcium ions are substituted with another metal ion such as a sodium or magnesium ion is included.

<Calcium Hydroxide>

The calcium hydroxide in the present invention is a compound including $Ca(OH)_2$ as a representative composition.

<Calcium Fluoride>

The calcium fluoride in the present invention is a compound including $CaF_2$ as a representative composition.

<Carbonate Compound>

The carbonate compound in the present invention is a compound including a carbonate ion ($CO_3^{2-}$). Sodium hydrogen carbonate ($NaHCO_3$), sodium carbonate ($Na_2CO_3$), potassium hydrogen carbonate ($KHCO_3$), potassium carbonate ($K_2CO_3$), ammonium hydrogen carbonate (($NH_4$)$HCO_3$), ammonium carbonate (($NH_4$)$_2CO_3$), calcium carbonate ($CaCO_3$), and lithium carbonate ($Li_2CO_3$) may be exemplified.

<Fluoride>

The fluoride in the present invention is a compound including a fluorine ion (F) as an anion. Sodium fluoride (NaF), potassium fluoride (KF), and the like may be exemplified.

In the present invention, a solubility of the raw material inorganic compound is 5 or less. This is because it is necessary to balance dissolution of the raw material inorganic compound and a precipitation reaction of the precipitated inorganic compound. For example, calcium chloride is an inorganic compound, but its solubility in water at 20° C. is 74.5 g and it is a raw material inorganic compound outside the scope of the present invention. Even if calcium chloride is compacted to form a block, when the block is immersed, for example, in a sodium carbonate aqueous solution, a calcium carbonate powder can be produced and a calcium carbonate block cannot be produced. It is assumed that, since a solubility of calcium chloride is greater than 5, a dissolution rate in water is high, and crystal growth of calcium carbonate does not occur on a surface of a calcium chloride powder compacted body.

<Substantial Macro Form>

In the present invention, it is possible to produce a product inorganic compound without substantially changing a macro form of a raw material inorganic compound. The phrase "without substantially changing a macro form of a raw material inorganic compound" defined in the present invention means that, when a raw material inorganic compound and a product inorganic compound are compared, both are macroscopically identical or macroscopically similar.

In addition, "macroscopically identical" in the present invention is defined as a case in which, when a raw material inorganic compound and a product inorganic compound three dimensionally overlap to the highest degree, a non-overlapping volume is 30% or less of a volume of the raw material inorganic compound. Also, a volume and a form are measured using a product inorganic compound that is produced when a raw material inorganic compound is left in an electrolyte aqueous solution or an electrolyte suspension. When a form of a raw material inorganic compound is changed due to rolling or the like, it is excluded from the measurement target.

In addition, in the present invention, it is possible to form an interconnected porous body by bridging a plurality of raw material inorganic compound granules using a precipitated inorganic compound formed on a surface of the raw material inorganic compound. In this case, the preserving of a macro form is satisfied for an individual raw material inorganic compound and one granule that forms a product inorganic compound including an individual precipitated inorganic compound and an internal unreacted inorganic compound, but it is clear that it is not possible to preserve a macro form for a porous body to be produced.

<Preferable Aggregate Form of Raw Material Inorganic Compounds>

A raw material inorganic compound is immersed in an electrolyte aqueous solution. Therefore, it is necessary to preserve a form that does not collapse even when the raw material inorganic compound is immersed in the electrolyte aqueous solution. Since an inorganic powder compacted body collapses when immersed in an electrolyte, generally, it is not used as the raw material inorganic compound. As the raw material inorganic compound, a compound in which crystals are linked and cured or a sintered compound, which has excellent form stability in an electrolyte aqueous solution, is preferable. It is determined whether a compound can be used as a raw material inorganic compound according to whether the compound is able to maintain a volume of $10^{-13}$ m$^3$ or more when immersed in an electrolyte aqueous solution.

<A Preferable Combination of a Raw Material Inorganic Compound and a Product Inorganic Compound>

In the present invention, a raw material inorganic compound having a solubility of 5 or less is immersed in an electrolyte aqueous solution, and a product inorganic compound having a lower solubility with respect to the electrolyte than the raw material inorganic compound in the electrolyte aqueous solution is produced. In this case, the product inorganic compound is preferably the only inorganic compound having a lower solubility than a raw material inorganic compound in the electrolyte aqueous solution.

For example, when a calcium carbonate block is produced, a combination of a calcium sulfate block and sodium carbonate is an excellent combination of a raw material inorganic compound and an electrolyte aqueous solution.

When a calcium carbonate block is produced from a calcium sulfate block, since a component that is included in the calcium carbonate block but is not included in the calcium sulfate block is a carbonate component, the calcium sulfate block is immersed in an electrolyte aqueous solution including a carbonate component, for example, a sodium carbonate aqueous solution. As a result, as described above, the calcium sulfate block becomes the calcium carbonate block while substantially maintaining a macro form. This reaction is expressed by Formula (9) based on Formula (1) to Formula (3). Here, since sodium sulfate has a high solubility and dissolves in water, it is not included in the product inorganic compound. That is, since calcium carbonate which is a product inorganic compound is the only inorganic compound having a lower solubility than calcium sulfate dihydrate which is a raw material inorganic compound in a sodium carbonate aqueous solution, it is possible to produce a high purity calcium carbonate block.

[Chem. 9]

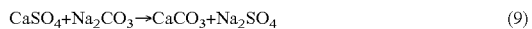

$$CaSO_4 + Na_2CO_3 \rightarrow CaCO_3 + Na_2SO_4 \quad (9)$$

On the other hand, when a calcium carbonate block is produced using a calcium hydrogen phosphate dihydrate block as a raw material inorganic compound, since a component that is included in the calcium carbonate block but is not included in a calcium hydrogen phosphate block is a carbonate component, the calcium hydrogen phosphate block is immersed in an electrolyte aqueous solution including a carbonate component, for example, a sodium carbonate aqueous solution.

Calcium hydrogen phosphate dissolves in an aqueous solution and provides calcium ions, phosphate ions, and the like to an electrolyte aqueous solution as shown in Formula (10). While calcium ions provided from the calcium hydrogen phosphate dihydrate block react with carbonate ions in the electrolyte aqueous solution to produce a calcium carbonate block as shown in Formula (3), phosphate ions are also provided from calcium hydrogen phosphate and apatite is also precipitated as shown in Formula (11). Also, when carbonate ions are present, a carbonate apatite rather than hydroxyapatite is precipitated, but hydroxyapatite will be described for the sake of simplicity. The formation reactions of the calcium carbonate and the apatite are competitive reactions. Therefore, it is not always easy to produce a high purity calcium carbonate block. That is, since calcium carbonate is a product inorganic compound but also apatite is an inorganic compound having a lower solubility than calcium hydrogen phosphate dihydrate which is a raw material inorganic compound in a sodium carbonate aqueous solution, an apatite is also generated and it is not always easy to produce a high purity calcium carbonate block.

[Chem. 10]

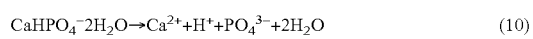

$$CaHPO_4 \cdot 2H_2O \rightarrow Ca^{2+} + H^+ + PO_4^{3-} + 2H_2O \quad (10)$$

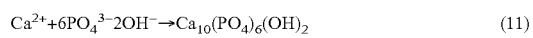

$$Ca^{2+} + 6PO_4^{3-} + 2OH^- \rightarrow Ca_{10}(PO_4)_6(OH)_2 \quad (11)$$

<Preferable Product Inorganic Compound>

In the present invention, it is possible to produce a product inorganic compound without substantially changing a macro form of a raw material inorganic compound. In consideration of effectiveness thereof, a calcium carbonate block or the like is a particularly preferable product inorganic compound.

As described above, calcium carbonate is a skeletal tissue composition of an invertebrate animal, and is clinically applied as a bone prosthetic material. However, collecting natural calcium carbonates such as corals causes damage to the environment and impurity problems are unavoidable. In addition, it is possible to produce a calcium carbonate block by exposing calcium hydroxide to carbon dioxide for curing. However, in this case, it is difficult to introduce a pore forming material which is an organic substance. This is because calcium carbonate starts to decompose at 620° C. in air and is completely decomposed into calcium oxide at 770° C. A polyurethane, polymethyl methacrylic acid and the like which are used as a pore forming material are not incinerated at 620° C. at which decomposition of calcium carbonate starts and are insufficiently incinerated. Therefore, it is difficult to produce calcium carbonate in which pores are controlled.

Meanwhile, calcium sulfate exhibits self-curability and has high stability at high temperatures. Therefore, when, for example, a polyurethane serving as a pore forming material is introduced into calcium sulfate hemihydrate slurry and cured, and the polyurethane is incinerated at 1000° C., it is possible to produce a calcium sulfate porous body. When this calcium sulfate porous body is immersed in a sodium carbonate electrolyte aqueous solution, it is possible to produce a calcium carbonate porous body while preserving a macro form. Therefore, in the present invention, a method of producing a calcium carbonate block from a calcium sulfate block or the like is particularly useful when compared with other calcium carbonate production methods.

In addition, calcium hydroxide is also preferable as a product inorganic compound. In the case of calcium hydroxide, it is extremely difficult to produce calcium hydroxide having a block form and a volume of $10^{-13}$ m$^3$ or more by a method other than the production method of the present invention.

In addition, calcium fluoride is also preferable as a product inorganic compound. Calcium fluoride is collected as fluorite in nature, but is unavoidably contaminated by impurities, and it is necessary to produce an artificial calcium fluoride. A highly functional lens is one of applications of calcium fluoride and uses a property of calcium fluoride transmitting light with a wide range of wavelengths from ultraviolet light to infrared light. A lens including calcium fluoride as a composition is called a fluorite lens. In order to produce a highly functional fluorite lens, a chemically synthesized calcium fluoride block with less impurities is necessary. It is difficult to produce calcium fluoride having a block body by other production methods and production of calcium fluoride in the present invention is highly useful.

<Curable Composition>

In the present invention, a curable composition comprises a plurality of raw material inorganic compounds having a volume of $10^{-13}$ m$^3$ or more and an electrolyte aqueous solution. A component in which the raw material inorganic compound and the electrolyte aqueous solution react and anions of the inorganic compound are exchanged with anions of the electrolyte aqueous solution or the electrolyte suspension or cations of the inorganic compound are exchanged with cations of the electrolyte aqueous solution or the electrolyte suspension or a component that is not included in the raw material inorganic compound and is derived from the electrolyte aqueous solution, or the electrolyte suspension is formed on a surface of the raw material inorganic compound and the formed substance bridges the raw material inorganic compounder to form a porous body.

The porous body to be formed is preferably an interconnected body and preferably comprises at least one selected from the group consisting of calcium hydrogen phosphate, calcium sulfate, and calcium carbonate. In addition, the raw material inorganic compound is preferably at least one selected from the group consisting of calcium phosphate, calcium carbonate, calcium sulfate, calcium hydroxide, calcium fluoride, calcium silicate, a calcium-containing glass, a coral, a shell, and a bone. The electrolyte aqueous solution preferably comprises at least one selected from the group consisting of hydrogen phosphate ions, sulfate ions, and carbonate ions.

In the present invention, the curable composition is preferably used as a material for medical treatment, and specifically, more preferably used as a hard tissue reconstruction material.

<<A Hard Tissue Reconstruction Material for Medical Treatment and a Method of Producing the Same>>

[A Hard Tissue Reconstruction Material for Medical Treatment]

A hard tissue reconstruction material for medical treatment of the present invention comprises at least a core portion and a surface layer portion that covers the core portion. The core portion and the surface layer portion have different compositions. The core portion comprises a calcium component other than calcium hydrogen phosphate, and the surface layer portion comprises calcium hydrogen phosphate.

The hard tissue reconstruction material for medical treatment may be used as, for example, an implant material for hard tissue reconstruction or a bone prosthetic material. The hard tissue reconstruction material for medical treatment is preferably used as a bone prosthetic material.

Configurations will be described below.

<(1) Including at Least a Core Portion and a Surface Layer Portion that Covers the Core Portion>

In the hard tissue reconstruction material for medical treatment of the present invention, "including at least a core portion and a surface layer portion that covers the core portion" is an essential requirement. Therefore, a hard tissue reconstruction material for medical treatment having no covering portion is not included in the present invention.

Meanwhile, in the hard tissue reconstruction material for medical treatment of the present invention, tissue compatibility or osteoconductivity is mainly controlled by the inclusion of the surface layer portion or the core portion. Therefore, at least the core portion and the surface layer portion that covers the core portion are included. In addition to the core portion and the surface layer portion, for example, a support may be provided inside the core portion. The support will be described below.

In addition, the core portion may have a single phase or a plurality of phases.

<(2) a Core Portion and a Surface Layer Portion that have Different Compositions>

In the hard tissue reconstruction material for medical treatment of the present invention, "a core portion and a surface layer portion that have different compositions" is an essential requirement. Since the surface layer portion includes calcium hydrogen phosphate, it is necessary for the core portion not to include calcium hydrogen phosphate or to have a lower concentration of calcium hydrogen phosphate than the surface layer portion. That is, a case in which a divided surface layer portion and core portion have compositions with the same concentration of calcium hydrogen phosphate is outside the scope of the present invention.

<(3) Including Calcium Hydrogen Phosphate in a Surface Layer Portion>

In the present invention, it is necessary to include calcium hydrogen phosphate in the surface layer portion, which is fundamental to the present invention.

Calcium hydrogen phosphate in the present invention is a calcium orthophosphate component whose basic composition is CaHPO$_4$, and an anhydride and a dihydrate may be exemplified. Calcium hydrogen phosphate formed in an aqueous solution of pH 4 or less is often calcium hydrogen phosphate dihydrate (CaHPO$_4$.2H$_2$O). However, calcium hydrogen phosphate in the present invention also includes calcium hydrogen phosphate anhydride (CaHPO$_4$).

Unlike calcium hydrogen phosphate dihydrate, since calcium hydrogen phosphate anhydrate is not hydrated, it has excellent stability. Therefore, a hard tissue reconstruction material for medical treatment in which calcium hydrogen phosphate dihydrate is formed on the surface layer portion may be heated to form calcium hydrogen phosphate anhydrate.

In the present invention, inclusion of calcium hydrogen phosphate in the surface layer portion is required to dissolve calcium hydrogen phosphate in a body fluid and increase a calcium concentration and a phosphate concentration of the surroundings of the hard tissue reconstruction material for medical treatment or a bone defect. In this mechanism, it is not necessary for the surface layer portion to be completely calcium hydrogen phosphate, and a composition of the surface layer portion may be substantially calcium hydrogen phosphate. This is because, even when the core portion is not completely covered with calcium hydrogen phosphate, when the hard tissue reconstruction material for medical treatment of the present invention is implanted in a bone defect, calcium hydrogen phosphate is dissolved in a body fluid so that a calcium concentration and a phosphate concentration of the surroundings of the hard tissue reconstruction material for medical treatment or the bone defect increase.

However, in order to increase a calcium concentration and a phosphate concentration of the surroundings of the hard tissue reconstruction material for medical treatment or the bone defect to a high level, calcium hydrogen phosphate preferably covers 50% or more of a surface area of the core portion, more preferably 80% or more, and most preferably completely covers it.

In the present invention, a thickness of the surface layer portion is not limited for the same reason for which a proportion of a core portion covered with calcium hydrogen phosphate is not limited.

However, in order for calcium hydrogen phosphate to be dissolved in a body fluid and to increase a calcium concentration and a phosphate concentration of the surroundings of the hard tissue reconstruction material for medical treatment or the bone defect, an average converted thickness of the surface layer portion is preferably 1 μm or more, more preferably 5 μm or more, and most preferably 20 μm or more.

In the present invention, the average conversion thickness of the surface layer portion is an average thickness of calcium hydrogen phosphate which is a composition of the surface layer portion. For example, when 80% of the core portion is covered with calcium hydrogen phosphate with a thickness of 10 μm and 20% thereof is not covered, the average conversion thickness is 8 μm.

In addition, an upper limit of the thickness of the surface layer portion is not particularly limited. In consideration of adhesiveness with the core portion or a mechanical strength, 500 μm or less is preferable, 200 μm or less is more preferable, and 100 μm or less is most preferable.

<(4) Including a Calcium Component Other than Calcium Hydrogen Phosphate in a Core Portion>

In a material of the present invention, including a calcium component other than calcium hydrogen phosphate in the core portion is also an essential requirement. A mechanism by which a material satisfying a requirement that a core portion include a calcium component other than calcium hydrogen phosphate has excellent osteoconductivity and tissue compatibility has not been completely clarified. Although the mechanism does not limit the present invention, it is speculated to be related to the fact that calcium is one constituent component of an inorganic composition of bone and calcium plays an important role in osteogenesis.

The calcium component herein is defined as a compound including calcium. As the calcium component, calcium carbonate, calcium sulfate, an apatite, tricalcium phosphate, tetracalcium phosphate, calcium hydrogen phosphate, calcium silicate, a calcium-containing glass, and a bone may be exemplified. Among these, a required calcium component to be included in the core portion is a calcium component other than calcium hydrogen phosphate. The calcium component may be a single calcium compound or a mixture of a plurality of calcium compounds.

A solubility of the core portion including a calcium component is preferably lower than a solubility of calcium hydrogen phosphate of the surface layer portion.

The calcium component is preferably at least one selected from the group consisting of calcium phosphate, calcium carbonate, calcium sulfate, an apatite, a calcium-containing glass, a coral and a bone, more preferably at least one selected from the group consisting of artificially produced calcium phosphate, calcium carbonate, calcium sulfate and a calcium-containing glass, and most preferably at least one selected from the group consisting of a β-type tricalcium phosphate, an α-type tricalcium phosphate, a hydroxyapatite and a carbonate apatite. These calcium components are materials that have already been reported or are anticipated to have usefulness as bone prosthetic materials.

Calcium phosphate in the present invention is a salt of phosphoric acid and calcium. Calcium orthophosphate, calcium metaphosphate, and condensed calcium phosphate may be exemplified. Since calcium orthophosphate exhibits relatively excellent osteoconductivity and tissue compatibility, calcium orthophosphate is preferable among calcium phosphates.

Calcium orthophosphate in the present invention is a salt of orthophosphoric acid and calcium. For example, tetracalcium phosphate, apatites including hydroxyapatite and a carbonate apatite, α-type tricalcium phosphate, and β-type tricalcium phosphate may be exemplified.

Among calcium orthophosphates, an apatite and tricalcium phosphate are particularly preferable because they are known to have excellent osteoconductivity and tissue compatibility.

Apatite in the present invention is a compound whose basic structure is $A_{10}(BO_4)_6C_2$. Examples of A include $Ca^{2+}$, $Cd^{2+}$, $Sr^{2+}$, $Ba^{2+}$, $Pb^{2+}$, $Zn^{2+}$, $Mg^{2+}$, $Mn^{2+}$, $Fe^{2+}$, $Ra^{2+}$, $H^+$, $H_3O^+$, $Na^+$, $K^+$, $AL^{3+}$, $Y^{3+}$, $Ce^{3+}$, $Nd^{3+}$, $La^{3+}$, $C^{4+}$, and a void. Examples of $BO_4$ include $PO_4^{3-}$, $CO_3^{2-}$, $CrO_4^{3-}$, $AsO_4^{3-}$, $VO_4^{3-}$, $UO_4^{3-}$, $SO_4^{2-}$, $SiO_4^{4-}$, $GeO_4^{4-}$, and a void. Examples of C include $OH^-$, $OD^-$, $F^-$, $Br^-$, $BO^{2-}$, $CO_3^{2-}$, $O^{2-}$, and a void. In the present invention, the core portion including at least calcium is an essential requirement, at least some A's need to be calcium.

Note that $A_{10}(BO_4)_6C_2$ is a structural formula of apatite, and $Ca_{10}(PO_4)_6(OH)_7$ is a basic structural formula of a calcium phosphate-based apatite. However, the present invention is not limited to the basic structural formulas. For example, in the case of calcium phosphate-based apatite, Ca-deficient apatite $Ca_{10-x}(HPO_4)_x(PO_4)_{6-x}(OH)_{2-x}$, a carbonate apatite, and substitute apatite are known, and all of these are apatites defined in the present invention.

Among apatites in the present invention, an apatite including a hydroxyl group is referred to as a hydroxyapatite. A representative structure of hydroxyapatite is $Ca_{10}(PO_4)_6(OH)_2$ that is described above as a basic structural formula of calcium phosphate-based apatite.

Among apatites defined in the present invention, an apatite including a carbonate group is referred to as a carbonate apatite, which is generally an apatite in which some or all of phosphate groups or hydroxyl groups of the calcium phosphate-based apatite are substituted with a carbonate group. An apatite in which a phosphate group is substituted with a carbonate group is referred to as a B-type carbonate apatite. An apatite in which a hydroxyl group is substituted with a carbonate group is referred to as an A-type carbonate apatite. Here, according to the substitution of a phosphate group with a carbonate group, in order to obtain a charge balance for an apatite, Na, K or the like is often included in a crystal structure. In the present invention, a carbonate apatite in which a part of a carbonate apatite is substituted with another element or void is also defined as a carbonate apatite. A carbonate apatite is one type of apatite. Carbonate apatites include an apatite including a hydroxyl group. In the present invention, in order to distinguish between hydroxyapatites and a carbonate apatite, when there is a need to distinguish an apatite as a hydroxyapatite or a carbonate apatite, masses of hydroxyl groups and carbonate groups in the apatite are compared. When a mass of hydroxyl groups of the apatite is greater than a mass of carbonate groups, the apatite is classified as a hydroxyapatite. When a mass of carbonate groups of the apatite is equal to or greater than that of hydroxyl groups, the apatite is classified as a carbonate apatite.

Apatite is known as a material having excellent tissue compatibility and osteoconductivity and is a typical bone prosthetic material. Both hydroxyapatites and carbonate apatites have excellent tissue compatibility and osteoconductivity, and the carbonate apatite is known to have better osteoconductivity. In addition, in general, hydroxyapatite cannot replace bone or takes a considerably long time to replace bone. However, a carbonate apatite replaces bone. Therefore, a carbonate apatite is preferably used to satisfy "quickly replacing hone" which is one desirable property of a hard tissue reconstruction material for medical treatment.

Hydroxyapatite and carbonate apatite granules are produced by a known method.

The "tricalcium phosphate" in the present invention is one calcium orthophosphate component whose representative composition is $Ca_3(PO_4)_2$ and includes a compound in which some calcium ions are substituted with another metal ion such as a sodium or potassium ion. Tricalcium phosphate includes a high temperature stable phase α-type tricalcium phosphate and a low temperature stable phase β-type tricalcium phosphate. Although an α'-type tricalcium phosphate is also known, α'-type tricalcium phosphate is also defined as α-type tricalcium phosphate in the present invention.

α-type tricalcium phosphate and β-type tricalcium phosphate have the same composition, but their solubilities greatly differ, and behaviors in vivo are totally different. β-type tricalcium phosphate has a low solubility and is clinically applied as a bone replacement material. Therefore, β-type tricalcium phosphate is generally more preferable than α-type tricalcium phosphate.

On the other hand, α-type tricalcium phosphate has a high solubility and is used as a component of bioactive cement. However, when an amount of bone defect is not large or in the case of a porous body, α-type tricalcium phosphate may be preferably used for the core portion rather than β-type tricalcium phosphate.

A method of producing tricalcium phosphate granules or a tricalcium phosphate block is not particularly defined, but a known method is generally used. For example, a calcium hydrogen carbonate powder and a calcium hydrogen phosphate powder may be mixed such that a molar ratio between calcium and phosphorus is 3:2 and compacted. In the case of α-type tricalcium phosphate, calcination is performed at 1,200° C. that is a higher temperature than 1,180° C. that is an α-β phase transition temperature. In the case of β-type tricalcium phosphate, calcination is performed at 1000° C. that is a lower temperature than 1,180° C. that is an α-β phase transition temperature.

The calcium carbonate in the present invention is one calcium component whose basic composition is $CaCO_3$. In addition, a compound in which some Ca is substituted with another element such as Mg is also defined as the calcium carbonate in the present invention.

As the carbonate apatite, polymorphs such as calcite, vaterite, and aragonite are known. Ho ever, in the present invention, a type of polymorph is not limited.

However, behaviors of the carbonate apatite in vivo differ according to the polymorph. Vaterite has excellent bioabsorbability because it has a high solubility and dissolution rate. Since calcite has a lower solubility and dissolution rate than vaterite, it is useful when slower bone replacement than that with vaterite is desired. In addition, aragonite has an intermediate solubility and dissolution rate between calcite and vaterite, and is useful when an intermediate bone replacement rate between them is desired.

A method of producing calcium carbonate granules or a calcium carbonate block is not particularly defined but a known method is generally used. For example, a calcium hydroxide powder compacted body may be exposed to carbon dioxide for production and calcium carbonate may be sintered under a carbon dioxide gas atmosphere for production.

The calcium sulfate according to the present invention is one calcium component whose basic composition is $CaSO_4$, and a hemihydrate and a dihydrate are also known. Both are produced by a known method.

The calcium-containing glass in the present invention is one calcium component, and is a calcium-containing glass or glass ceramic, and is produced by a known method in which a calcium-containing glass component is melted and rapidly cooled. Calcium-containing crystallized glass obtained by pulverizing, calcining and crystallizing calcium-containing glass is also defined as the calcium-containing glass in the present invention. $Na_2O$—$CaO$—$SiO_2$—$P_2O_5$-based glass (representative composition includes $Na_2O$ at 24.5 mass %, CaO at 24.5 mass %, $SiO_2$ at 45 mass %, and $P_2O_5$ at 6 mass %) called Bioglass (registered trademark) and crystallized glass (representative composition includes MgO at 4.6 mass %, CaO at 44.7 mass %, $SiO_2$ at 34.0 mass %, $P_2O_5$ at 16.2 mass %, and $CaF_2$ at 0.5 mass %) called Cerabone (registered trademark) A-W may be exemplified. These calcium-containing glasses are produced by a known method.

Coral is known to include calcium carbonate as an inorganic main component. In the present invention, coral or a material treated with coral is defined as one of calcium components. Treatment of coral includes cleaning and removal of organic substances. A component obtained by treating coral and including no calcium is outside the scope of the present invention.

Bone includes calcium. In the present invention, bone and treated bone are defined as one of calcium components. An autograft bone collected from one, an allograft bone collected from a human other than one, and a xenograft bone collected from an animal other than a human may be exemplified. In addition, a calcined bone and a freeze-dried bone which have been subjected to a calcination process and a freeze-drying process in order to inhibit an antigen-antibody reaction are included. In both, an inorganic composition is a carbonate apatite and includes calcium. Among bones called demineralized freeze-dried bones, a bone in which calcium is completely removed is a bone in which an inorganic component is completely removed from a bone and does not correspond to a bone in the present invention. On the other hand, among bones called demineralized freeze-dried bone, a demineralized freeze-dried bone in which calcium is partially removed and calcium remains is a bone of the present invention.

<Support>

The hard tissue reconstruction material for medical treatment of the present invention may include a support inside the core portion. The support is generally used to increase a mechanical strength. As a composition of the support, a metal, a polymer, and a ceramic may be exemplified.

Metals are materials that are generally used for dental implants and are often the first choice since they have a high mechanical strength. Since a material of the present invention is used as a support, the material is not particularly limited. However, in consideration of ensuring safety when the surface layer portion and the core portion are dissolved due to severe infection and the like and the support is exposed in vivo, titanium, a titanium alloy, stainless steel, and a cobalt chromium alloy are preferable. In particular, titanium or a titanium alloy is a more preferable material because it has good compatibility with a calcium component.

A polymer may be preferable as the support because it has excellent flexibility. Since requirements of the support vary depending on cases, a type of polymer is not limited. In consideration of a mechanical function, an aromatic polyether-ketone, a polyimide, and a polysulfone are preferable.

An aromatic polyether ketone is a polymer having a linear polymer structure in which benzene rings is linked by an ether and a ketone. Polyether ether ketone (PEEK), polyether ketone (PEK), polyether ether ketone ketone (PEEKK), and polyether ketone ester may be exemplified.

A polyimide is a general term for polymers including an imide bond in its repeating unit. In consideration of mechanical properties, an aromatic polyimide such as Kapton H in which an aromatic compound is directly connected by an imide bond is preferable.

A polysulfone is a polymer including a sulfonyl group in its repeating structure. In consideration of mechanical properties, a polymer including an aromatic group is preferable.

A ceramic may be preferable as the support because it has excellent tissue compatibility. Since requirements of the support vary depending on cases, a type of ceramic is not limited. In consideration of a mechanical function, an alumina and a zirconia are preferable.

<Size>

Among hard tissue reconstruction materials for medical treatment, since an implant material for hard tissue reconstruction needs structure, there is no limitation on the size of pieces thereof.

Among hard tissue reconstruction materials for medical treatment, a bone prosthetic material is also used in the form of granules or a block. Surprisingly, it has been found that a bone prosthetic material of the present invention having a small size causes an inflammatory response. Although the mechanism has not been adequately clarified, when the size of the bone prosthetic material is small, since a specific surface area of the bone prosthetic material is large, due to dissolution of calcium hydrogen phosphate on a surface layer, a concentration of calcium, a concentration of phosphate, and a pH are likely to be changed by a great amount.

As results of extensive studies, it was found that, when a volume is $10^{-13}$ m$^3$ or more, no inflammatory response was caused. In consideration of ensuring high level safety, a volume is more preferably $10^{-12}$ m$^3$ or more and most preferably $10^{-11}$ m$^3$ or more.

<Porous Body>

A form of a material of the present invention is not particularly limited. At least one of the core portion and the support may be preferably a porous body.

In particular, when the bone prosthetic material of the present invention is used for a case in which bone replacement is desired, the core portion is preferably a porous body and more preferably an interconnected porous body. It is speculated that cells invade into the bone prosthetic material.

[Method of Producing a Hard Tissue Reconstruction Material for Medical Treatment]

A method of producing a hard tissue reconstruction material for medical treatment of the present invention comprises a covering step in which a core portion is brought in contact with an acidic aqueous solution to form a surface layer portion. The core portion comprises a calcium component other than calcium hydrogen phosphate. The acidic aqueous solution has a pH that is 5 or less. The acidic aqueous solution comprises a phosphate component when the core portion does not include a phosphate component. According to the covering step, a surface layer portion including calcium hydrogen phosphate is formed.

In addition, preferably, the method of producing a hard tissue reconstruction material for medical treatment of the present invention further comprises a surface layer portion adjusting step in which a part of the calcium hydrogen phosphate included in the formed surface layer portion is dissolved in a solvent to adjust a thickness or a form of the surface layer portion.

The method of producing a hard tissue reconstruction material for medical treatment of the present invention is not limited by a mechanism of action thereof, and it is conceivable that a part of a composition of the core portion and a part of components of the acidic aqueous solution may undergo a dissolution and precipitation type reaction and thus a surface layer portion including calcium hydrogen phosphate may be formed to cover a surface of the core portion.

Among calcium phosphates, calcium hydrogen phosphate needs to be stable in an aqueous solution having a pH of 5 or less. In addition, in order to form calcium hydrogen phosphate, a phosphate component and a calcium component are required as raw materials.

Therefore, if the core portion includes not only a calcium component but also a phosphate component, when the core portion comes in contact with an acidic aqueous solution, a phosphate component, a calcium component, and an acidic environment necessary for forming calcium hydrogen phosphate are provided. Therefore, for example, it is possible to produce the hard tissue reconstruction material for medical treatment of the present invention by performing immersion in an acidic aqueous solution including neither a phosphate component nor a calcium component such as hydrochloric acid.

On the other hand, when the core portion does not comprise phosphate, even when a material of the core portion is brought into contact with an acidic solution having a pH of 5 or less, a phosphate component necessary for forming calcium hydrogen phosphate is not supplied to a reaction site. Therefore, in order to form calcium hydrogen phosphate, it is necessary to bring the core portion into contact with an acidic aqueous solution including a phosphate component for production.

For example, when hard tissue reconstruction material granules for medical treatment in which β-type tricalcium phosphate granules are used for the core portion and a composition of at least a part of the surface layer portion is calcium hydrogen phosphate are produced, the β-type tricalcium phosphate granules are immersed in an acidic aqueous solution. The β-type tricalcium phosphate immersed in the acidic aqueous solution is dissolved in the acidic aqueous solution from the surface, and calcium ions and phosphate ions are released in the acidic aqueous solution. In addition, hydrogen ions are provided from the acidic aqueous solution. When the core portion comprises β-type tricalcium phosphate, since phosphate ions and calcium ions are supplied according to the dissolution of the core portion, it is not necessary for the acidic aqueous solution to include phosphate ions.

The β-type tricalcium phosphate granules are dissolved in an acidic aqueous solution. As a result, an acidic solution near the core portion becomes supersaturated with calcium hydrogen phosphate, and calcium hydrogen phosphate dihydrate is precipitated on a surface of the β-type tricalcium phosphate granules to form the surface layer portion. As a result, a hard tissue reconstruction material granule for medical treatment in which the core portion includes β-type tricalcium phosphate and the surface layer portion includes calcium hydrogen phosphate is produced.

The hard tissue reconstruction material for medical treatment of the present invention can be produced by bringing a core portion into contact with an aqueous solution satisfying the requirements of both (1) being an acidic aqueous solution including both a phosphate component and a calcium component in compositions of a core portion and an acidic aqueous solution, and (2) being an acidic aqueous solution having a pH of 5 or less. However, in order to efficiently form calcium hydrogen phosphate on the surface layer portion, concentrations of a phosphate component and a calcium component around the core portion preferably increase. Therefore, a production method in which a core portion is brought into contact with an aqueous solution satisfying the requirements of both (1) being an acidic aqueous solution including both a phosphate component and a calcium component in compositions of a core portion and an acidic aqueous solution, and (2) being an acidic aqueous solution having a pH of 5 or less is preferable.

Since calcium hydrogen phosphate is stable in an acidic aqueous solution having a pH of 5 or less, it is necessary for a pH of the acidic aqueous solution to be brought into contact with the core portion to be 5 or less.

However, in order to more efficiently form calcium hydrogen phosphate on a surface layer of the core portion, a pH is preferably 4.5 or less, a pH is more preferably 4 or less, and a pH is most preferably 3 or less.

On the other hand, if a pH of an acidic aqueous solution when it is brought into contact with the core portion is too low, calcium dihydrogen phosphate rather than calcium hydrogen phosphate is in a thermodynamically stable phase. Therefore, when the acidic aqueous solution comes in contact with the core portion, a pH of the acidic aqueous solution is desirably 1.5 or more which is a range in which calcium hydrogen phosphate is stable. However, the calcium component of the core portion is often an alkaline salt. Therefore, when a calcium component of the core portion comes in contact with an acidic aqueous solution, the calcium component is dissolved and a pH of the acidic aqueous solution increases. Therefore, in the present invention, a lower limit of a pH of the acidic aqueous solution is not determined. However, in order to efficiently form calcium hydrogen phosphate on a surface on the core portion, a pH is preferably 1 or more, a pH is more preferably 1.5 or more, and a pH is most preferably 2 or more.

In the present invention, a phosphate concentration and a calcium concentration in the acidic aqueous solution are not particularly limited because they are imparted from the core portion as described above. However, in consideration of efficient production, it is desirable that a solution be saturated with calcium hydrogen phosphate. When a solubility of calcium hydrogen phosphate measured when a temperature, a solvent and the like are determined is set as $C_0$ and a dissolution concentration of a prepared calcium phosphate solution with respect to calcium hydrogen phosphate is set as $C_1$, a degree of saturation is defined as $\sigma=(C_0-C_1)/C_0$. The degree of saturation is preferably 0.5 or less, more preferably 0.1 or less, and most preferably 0.0 or less. Also, when $\sigma$ is 0.0, it indicates that a solution is in a saturated state. When $\sigma$ is a negative value, it indicates that a solution is in a supersaturated state.

In the present invention, even if a suspension is used in place of an aqueous solution, it is substantially the same because the core portion reacts with the aqueous solution. Therefore, the core portion may be brought into contact with a suspension for production.

In addition, in the present invention, even if an alcohol or the like is added to an acidic aqueous solution, it is substantially the same as an acidic aqueous solution. This is because calcium ions, phosphate ions and the like do not easily dissolve in an alcohol and water is substantially responsible for a reaction.

[Action and Effect]

A mechanism by which the hard tissue reconstruction material for medical treatment of the present invention excellently satisfies requirements of desirable properties of a hard tissue reconstruction material for medical treatment of the above hard tissue reconstruction material for medical treatment has not been completely clarified. The present invention is not limited to a mechanism of action in which the hard tissue reconstruction material for medical treatment of the present invention has excellent osteoconductivity.

However, a mechanism by which the hard tissue reconstruction material for medical treatment of the present invention is a hard tissue reconstruction material for medical treatment that highly satisfies requirements of desirable properties of a hard tissue reconstruction material for medical treatment including (1) excellent tissue compatibility, (2) excellent osteoconductivity, (3) quickly replacing bone, (4) exhibiting an appropriate mechanical strength, and (5) being able to be produced at low cost is speculated to be as follows.

A presumed mechanism by which a material of the present invention has excellent desirable properties for a hard tissue reconstruction material for medical treatment will be described below.

<(1) Excellent Tissue Compatibility>

The hard tissue reconstruction material for medical treatment of the present invention is a hard tissue reconstruction material for medical treatment, satisfying all requirements of (1) comprising at least a surface layer portion and a core portion, (2) having a surface layer portion and a core portion that have different compositions, (3) having a composition of a surface layer portion that is calcium hydrogen phosphate, and (4) having a core portion that comprises a calcium component. Therefore, a composition of the surface layer portion is calcium hydrogen phosphate. The hard tissue reconstruction material for medical treatment is implanted in vivo and used. It is known that tissue compatibility depends on a composition of the surface layer. It is also known that calcium hydrogen phosphate has excellent tissue compatibility.

When calcium hydrogen phosphate of the surface layer portion is absorbed or dissolves, a material of the core portion comes into contact with the human body. However, in the material of the present invention, the core portion is a material including a calcium component, and it is known that a material including a calcium component has generally excellent tissue compatibility. In addition, if a support is included, the support is produced using a material that does not exhibit a detrimental effect on tissues such as titanium, a titanium alloy, stainless steel, and a cobalt chromium alloy.

Since materials of both of the surface layer portion and the core portion or all of materials of the surface layer portion, the core portion, and the support are materials having excellent tissue compatibility, it is speculated that a desirable property of a hard tissue reconstruction material for medical treatment which is "(1) excellent tissue compatibility" will be satisfied.

<(2) Excellent Osteoconductivity>

The reason why the hard tissue reconstruction material for medical treatment of the present invention highly satisfies "(2) excellent osteoconductivity," which is an important desirable property of a hard tissue reconstruction material for medical treatment is speculated to be that a composition of the surface layer portion of the hard tissue reconstruction material for medical treatment of the present invention is calcium hydrogen phosphate and the core portion is a material including a calcium component such as an apatite, calcium phosphate, and calcium carbonate.

Calcium hydrogen phosphate is a calcium phosphate which has a relatively high solubility and dissolves when it is implanted in vivo and phosphate ions and calcium ions are provided to a surface of the hard tissue reconstruction material for medical treatment. "(2) Excellent osteoconductivity" is speculated to be obtained by either or both of phosphate ions and calcium ions that activate osteoblasts. This mechanism is similar to that of a highly osteoconductive biphasic calcium phosphate including a hydroxyapatite and a β-type tricalcium phosphate. However, since calcium hydrogen phosphate is a more highly acidic calcium phosphate than β-type tricalcium phosphate, improvement of osteoconductivity due to combining this was not considered. However, surprisingly, it is found that osteoconductivity is improved by covering with calcium hydrogen phosphate which is a highly acidic calcium phosphate.

In addition, in a biphasic calcium phosphate including a hydroxyapatite and a β-type tricalcium phosphate, it is considered that it is necessary for the hydroxyapatite and the β-type tricalcium phosphate to come in contact with a body fluid at the same time. This is considered to be caused by the fact that phosphate ions and calcium ions released while the β-type tricalcium phosphate dissolves activate osteoblasts, and at the same time, osteoblasts need to be adhered to a hydroxyapatite having excellent osteoconductivity.

However, surprisingly, it is found that a material covered with calcium hydrogen phosphate that dissolves in vivo exhibits excellent osteoconductivity.

A mechanism by which the hard tissue reconstruction material for medical treatment of the present invention exhibits excellent osteoconductivity may be due to an effect obtained when an apatite including a biological component is formed on a core portion surface in addition to the above-described mechanism in which phosphate ions and calcium ions from calcium hydrogen phosphate activate osteoblasts. That is, calcium hydrogen phosphate of the surface layer portion of the hard tissue reconstruction material for medical treatment of the present invention dissolves in vivo, and calcium ions and phosphate ions are provided near the hard tissue reconstruction material for medical treatment. The body fluid has a buffering effect and also includes carbonate ions and a physiologically active substance. The surroundings of the hard tissue reconstruction material for medical treatment of the present invention are supersaturated with a carbonate apatite. As a result, a carbonate apatite or an amorphous calcium phosphate including a physiologically active substance is precipitated on a surface of the hard tissue reconstruction material for medical treatment of the present invention. The carbonate apatite has superior osteoconductivity to the hydroxyapatite. In addition, a carbonate apatite or an amorphous calcium phosphate including a physiologically active substance has greater osteoconductivity than a material including no physiologically active substance.

"(2) Excellent osteoconductivity" is considered to be satisfied according to such a mechanism.

<(3) Quickly Replacing Bone>

"(3) Quickly replacing bone," which is an important desirable property of a hard tissue reconstruction material for medical treatment, is obtained because calcium hydrogen phosphate of the surface layer portion is a bioabsorbable material when there is no non-bioabsorbable support and the core portion is a bioabsorbable material.

<(4) Exhibiting an Appropriate Mechanical Strength>

"(4) Exhibiting an appropriate mechanical strength," which is an important desirable property of a hard tissue reconstruction material for medical treatment, is obtained according to an appropriate mechanical strength of the core portion, a link between the surface layer portion and the core portion, and a mechanical strength of the surface layer portion in the case of a bone prosthetic material. Therefore, it is necessary to select a calcium-containing material with an appropriate mechanical strength for the core portion. While calcium hydrogen phosphate has a mechanical strength that is not so high, it is sufficient when it is used for the surface layer portion. When the core portion and calcium hydrogen phosphate are not linked, the surface layer portion separates from the core portion, and a mechanical strength of the hard tissue reconstruction material for medical treatment as a whole is not able to be guaranteed. However, when calcium hydrogen phosphate and the core portion are linked, an appropriate mechanical strength of the hard tissue reconstruction material for medical treatment is ensured.

In the case of a hard tissue implant material, mechanical properties of a support are important. In addition, a bonding strength between the support and the core portion is one important factor. Further, factors necessary for a bone prosthetic material for medical treatment are required.

<(5) being Able to be Produced at Low Cost>

"(5) Being able to be produced at low cost," which is an important desirable property of a hard tissue reconstruction material for medical treatment, is obtained when production can be performed according to a simple production process without using an expensive BMP or bFGF.

<<A Curable Inorganic Compound, a Porous Body, and a Method of Producing the Same, a Surface Apatitized Porous Body and a Method of Producing the Same, a Calcined Porous Body and a Method of Producing the Same, and a Surface Apatitized Calcined Porous Body and a Method of Producing the Same>>

[Curable Composition for Forming a Calcium Hydrogen Phosphate-Containing Porous Body]

A curable composition for forming a calcium hydrogen phosphate-containing porous body of the present invention is a curable composition comprising granules containing a calcium component (provided that it excludes calcium dihydrogen phosphate), in which 70 mass % or more of the granules have a particle size of 100 μm or more and 10 mm or less.

Configurations will be described below.

<Granules>

A curable composition of the present invention includes granules containing a calcium component (provided that it excludes calcium dihydrogen phosphate is excluded).

In a general curable composition, a powder is used rather than granules. However, in the present invention, granules are selected.

(Particle Size)

A granule generally refers to a particle whose particle size is greater than a that of a powder. Since the object of the present invention is formation of a porous body, the size of the granules is important. Therefore, in the present invention, a particle having a size of 100 μm or more is defined as a granule. In general, while a particle having a size of less than 100 μm is also referred to as a granule, this particle is excluded from the scope of the present invention.

When the curable composition of the present invention is used, it is necessary to cure granules to form pores between the granules and granules are brought into contact with water and cured. As a method of bringing them in contact with water, for example, a method in which water is dropped after granules are filled into a bone defect, and the granules are brought into contact with water and cured, and a method in which granules are mixed with water before they are filled into a bone defect and the granules are brought into contact with water and cured may be exemplified. That is, granules are dispersed in water and a calcium component and a phosphate component are reacted under an acidic environment, calcium hydrogen phosphate is formed and the granules are cured. Therefore, as the curable composition of the present invention, for example, a form of a combination of granules including a calcium component and water including a phosphate component may be exemplified.

In addition, a phosphate component necessary for a curing reaction between granules is provided between the granules, is brought into contact with a body fluid or other moisture, and thus the granules can be cured. Therefore, the curable composition of the present invention may have a form in which granules are included but water is not included.

The particle size of the granules of the present invention is defined according to whether the granules pass through mesh openings of a sieve with a particle size.

For example, a particle size of granules that pass through a sieve having a mesh opening of 500 μm but do not pass through a sieve having a mesh opening of 100 μm is defined as a size greater than 100 μm and smaller than 500 μm.

Since the form of the particles is not necessarily a spherical shape, it is not possible to completely control a particle size using a sieve. However, in the present invention, as described above, according to whether they pass through a sieve, granules or a powder is defined and a particle size of granules is defined.

Since a porous body is formed by linking granules by a curing reaction, the size of the granules is important in the curable composition. When the particle size of the granules is less than 100 μm, pores may become smaller and invasion by cells or a body fluid may be insufficient. On the other hand, when a volume of granules is greater than 10 mm, applicable bone defects are limited and practicality is low.

In consideration of formation of a porous body, 70 mass % or more of granules have a particle size of 100 or more and 10 mm or less. 70 mass % or more of granules preferably have a particle size of 200 μm or more and 3 mm or less, more preferably have a particle size of 250 μm or more and 2.5 mm or less, and most preferably have a particle size of 300 μm or more and 2 mm or less.

In order to efficiently form an interconnected porous body, it is preferable that particle sizes of individual granules be similar.

When granules are classified into a group of 100 μm or more and 300 μm or less, a group of greater than 300 μm and 600 μm or less, a group of greater than 600 μm and 1 mm or less, a group of greater than 1 mm and 2 mm or less, a group of greater than 2 mm and 3 mm or less, or a group of greater than 3 mm and 10 mm or less, a mass of granules included in any group is preferably 50% or more, more preferably 70% or more and most preferably 90% or more with respect to the total number of granules.

Since a pore is formed in an interval between a granule and a granule by linking the granules, the size of the granules is important. However, when a pore formed in an interval between a granule and a granule is filled with a powder, a part or all of the pore may be blocked. Therefore, 70 mass % or more of granules have a particle size of 100 μm or more and 10 mm or less.

However, in consideration of effective formation of the pores, 80 mass % or more of granules preferably have a particle size of 100 μm or more and 10 mm or less, 90 mass % or more of granules more preferably have a particle size of 100 μm or more and 10 mm or less, and 95 mass % or more of granules most preferably have a particle size of 100 μm or more and 10 mm or less.

Similarly in the case in which particle sizes are classified into a particle size of 200 μm or more and 3 mm or less, a particle size of 250 μm or more and 2.5 mm or less, or a particle size of 300 μm or more and 2 mm or less, 80 mass % or more of granules are preferably in such a range, 90 mass % or more of granules are more preferably in such a range, and 95 mass % or more of granules are most preferably in such a range.

The shape of the granules is not particularly limited. However, in consideration of formation of interconnecting pores, a spherical shape or a shape having a protrusion structure such as a tetrapod and a foam granule are preferable.

Foam granules are obtained, for example, by crushing porous body foam into a granular form, and are useful when a high porosity filling material is prepared. For example, porous body foams in the following literature may be exemplified.

Satoshi Karashima, Akari Takeuchi, Shigeki Matsuya, Koh-ichi Udoh, Kiyoshi Koyano, Kunio Ishikawa. Fabrication of low-crystallinity hydroxyapatite foam based on the setting reaction of α-tricalcium phosphate foam. J Biomed Mater Res. 2009, VoL. 88A, pp. 628-633.

For granules to be porous body is effective when a porous body obtained from the curable composition of the present invention is expected to be replaced to bone. A porous body form of granules is preferably an interconnected porous body, but an independent porous body may be effective.

In the present invention, a volume of granules necessary for a purpose of forming an interconnected porous body between granules by linking the granules to each other is an essential requirement.

In order to achieve this purpose, a porosity formed by space other than granules is preferably 20% or more, more preferably 40% or more, and most preferably 60% or more.

(Calcium Component)

Granules include a calcium component (provided that calcium dihydrogen phosphate is excluded).

A role of granules in the curable composition is for forming pores between granules by the granules being linked. In order to link granules by calcium hydrogen phosphate, it is necessary for granules to be brought into contact with an aqueous solution having a pH of 4 or less and dissolved and at least calcium ions need to be supplied to a reaction site. Accordingly, calcium hydrogen phosphate is formed on a surface of the granule. Gaps between granules are cured by bridging by calcium hydrogen phosphate.

Therefore, including a calcium component is an essential requirement of granules included in the curable composition.

The calcium component is a calcium-containing compound (provided that calcium dihydrogen phosphate is excluded) or a mixture including such a compound. As the calcium component, calcium phosphate, calcium carbonate, calcium sulfate, calcium hydroxide, calcium fluoride, calcium silicate, a calcium-containing glass, a coral, a shell and a bone may be exemplified.

Including calcium in granules is an essential requirement. However, in consideration of tissue compatibility of a cured body, and mechanical properties, and production of an interconnected porous body by post processing, tetracalcium phosphate, an apatite, tricalcium phosphate, calcium carbonate, calcium sulfate, calcium metaphosphate, calcium pyrophosphate, a calcium-containing glass, and a bone are preferable.

Among these, a hydroxyapatite, a carbonate apatite, an α-type tricalcium phosphate, a β-type tricalcium phosphate, a calcium-containing glass, and a bone are more preferable, and a carbonate apatite, a β-type tricalcium phosphate and a bone are most preferable.

Among granules, β-type tricalcium phosphate, a carbonate apatite and bone (an isolated bone) are known to replace bone by remodeling in a bone defect and integrating with an existing bone. When it is desired for a cured body to replace bone in vivo, β-type tricalcium phosphate, a carbonate apatite and bone are preferable.

Tetracalcium phosphate is a compound whose basic structure is $Ca_4(PO_4)_2O$, and is obtained, for example, when calcium carbonate serving as a calcium compound and secondary calcium hydrogen phosphate ($CaHPO_4$) serving as a phosphate component are mixed such that a molar ratio between calcium and phosphate is 2.0 and calcined at 1500° C.

In general, since a block form tetracalcium phosphate is produced by calcination, it is possible to adjust a particle size when pulverizing is performed. It is possible to produce tetracalcium phosphate having a desired volume by adjusting pulverizing conditions and by simply sieving as necessary.

Among apatites, hydroxyapatites have a basic structure of $Ca_{10}(PO_4)_6(OH)_2$ and include apatites of which a part is substituted with another element or void.

A carbonate apatite is an apatite in which some or all of phosphate groups or hydroxyl groups of a hydroxyapatite are substituted with a carbonate group. An apatite in which a phosphate group is substituted with a carbonate group is referred to as a B-type carbonate apatite. An apatite in which a hydroxyl group is substituted with a carbonate group is referred to as an A-type carbonate apatite. Also, when a phosphate group is substituted with a carbonate group, Na, K and the like are often included in a crystal structure and thus the carbonate apatite includes a carbonate apatite in which a part thereof is substituted with another element or void.

A carbonate apatite is considered to be an apatite in which a part of a hydroxyapatite is substituted with a carbonate group. However, in the present invention, in order to distinguish a bone replacement material, an apatite comprising a carbonate group is defined as a carbonate apatite.

Among apatites, in consideration of tissue compatibility and osteoconductivity, a hydroxyapatite and a carbonate apatite are preferable. In consideration of bone replacement, a carbonate apatite is more preferable. A carbonate apatite replaces bone by bone remodeling.

Hydroxyapatite and carbonate apatite granules are produced by known methods.

Tricalcium phosphate is a calcium phosphate component whose representative composition is $Ca_3(PO_4)_2$ and includes a compound in which some calcium ions are substituted with another metal ion such as a sodium ion. Tricalcium phosphate includes a high temperature stable phase α'-type tricalcium phosphate, an α-type tricalcium phosphate and a low temperature stable phase β-type tricalcium phosphate.

A method of producing tricalcium phosphate granules or a tricalcium phosphate block is not particularly defined, but a known method is generally used. For example, a calcium hydrogen carbonate powder and a calcium hydrogen phosphate powder may be mixed such that a molar ratio between calcium and phosphorus is 3:2 and compacted. In the case of α-type tricalcium phosphate, calcination is performed at 1200° C. In the case of β-type tricalcium phosphate, calcination is performed at 1000° C. It is possible to adjust a particle size when pulverizing is performed when a sintered body is pulverized to produce granules. It is possible to produce tricalcium phosphate having a desired volume by adjusting pulverizing conditions or sieving as necessary.

While it is possible to form a porous body using either α-type tricalcium phosphate or β-type tricalcium phosphate, α-type tricalcium phosphate has high solubility in vivo and often dissolves before bone is formed. On the other hand, while β-type tricalcium phosphate is known to have inferior reactivity to α-type tricalcium phosphate, since a solubility in vivo is appropriate, β-type tricalcium phosphate is clinically applied as a bone replacement material. Therefore, in the present invention, when a porous body for replacing bone is produced, β-type tricalcium phosphate is more preferable.

Calcium carbonate is a compound whose basic composition is $CaCO_3$. Polymorphs such as calcite, vaterite, and aragonite are known. However, in the present invention, a type of polymorph is not limited. In addition, a compound in which some of Ca is substituted with another element such as Mg is also defined as calcium carbonate in the present invention.

A method of producing calcium carbonate granules or a calcium carbonate block is not particularly defined but a known method is generally used. For example, a calcium hydroxide powder compacted body may be exposed to carbon dioxide for production and calcium carbonate may be sintered under a carbon dioxide gas atmosphere for production.

The calcium sulfate according to the present invention is a compound whose basic composition is $CaSO_4$ and a hemihydrate and a dihydrate are also known. Both are produced by a known method.

Calcium metaphosphate is a calcium salt of metapyrophosphoric acid ($PO_3$) which is a condensed pyrophosphate. Calcium metaphosphate and the like may be exemplified.

Calcium pyrophosphate is a calcium salt of pyrophosphoric acid which is a condensed pyrophosphate. Calcium pyrophosphate ($CaP_2O_7$) and the like may be exemplified.

A calcium-containing glass is a calcium-containing glass or glass ceramic and is produced by a known method in which a calcium-containing glass component is melted and rapidly cooled. Calcium-containing crystallized glass obtained by pulverizing, calcining and crystallizing calcium-containing glass is also defined as a calcium-containing glass in the present invention. $Na_2O$—$CaO$—$SiO_2$—$P_2O_5$-based glass (representative composition includes $Na_2O$ at 24.5 mass %, $CaO$ at 24.5 mass %, $SiO_2$ at 45 mass %, and $P_2O_5$ at 6 mass %) called Bioglass (registered trademark) and crystallized glass (representative composition includes MgO at 4.6 mass %, CaO at 44.7 mass %, $SiO_2$ at 34.0 mass %, $P_2O_5$ at 16.2 mass %, and $CaF_2$ at 0.5 mass %) called Cerabone (registered trademark) A-W may be exemplified. These calcium-containing glasses are produced by a known method.

Bone is defined as a calcium-containing bone. An autogenic bone collected from one, an allogeneic bone collected from a human other than one, and a heterogenic bone collected from an animal other than a human may be exemplified. In addition, a calcined bone and a freeze-dried bone which have been subjected to a calcination process and a freeze-drying process in order to inhibit an antigen-antibody reaction are included.

In both, an inorganic composition is a carbonate apatite and includes calcium. Among bones called demineralized freeze-dried bones, a bone in which calcium is completely removed is a bone in which an inorganic component is completely removed from a bone and does not correspond to a bone in the present invention. On the other hand, among bones called demineralized freeze-dried bones, a demineralized freeze-dried bone in which calcium is partially removed and calcium remains is a bone of the present invention.

As a calcium component in the granules, only one type may be included or a combination of two or more types may be included.

(Calcium Dihydrogen Phosphate)

Preferably, the granules further comprise calcium dihydrogen phosphate.

Calcium dihydrogen phosphate is $Ca(H_2PO_4)_2$. Calcium dihydrogen phosphate monohydrate $Ca(H_2PO_4)_2 \cdot H_2O$ and calcium dihydrogen phosphate anhydrate $Ca(H_2PO_4)_2$ are known and these are referred to as calcium dihydrogen phosphate without being distinguished in the present invention.

In addition, calcium dihydrogen phosphate may also be referred to as primary calcium phosphate.

When the curable composition of the present invention is used, even if granules do not come into contact with an aqueous solution having a pH of 4 or less, if calcium dihydrogen phosphate and a calcium component coexist in the granules, the curable composition is cured according to contact with a body fluid, physiological saline, or distilled water. This is because, as can be understood from the fact that calcium dihydrogen phosphate is a salt of a dihydrogen phosphate ion ($H_2PO_4^-$), calcium dihydrogen phosphate is a readily soluble acidic calcium phosphate.

When granules and calcium dihydrogen phosphate coexist, when the calcium dihydrogen phosphate dissolves, for example, in contact with distilled water, a pH of a reaction site becomes 4 or less. Calcium ions are supplied to a reaction site when some of the granules dissolve, and calcium ions and hydrogen phosphate ions are supplied to the reaction site according to the dissolution of the calcium dihydrogen phosphate.

When a concentration product of calcium ions and hydrogen phosphate ions exceeds a concentration product of calcium hydrogen phosphates, a solution of the reaction site is supersaturated with calcium hydrogen phosphate dihydrate ($CaHPO_4 \cdot 2H_2O$) that has the most thermodynamically stable phase in an acidic range of a pH of 4 or less, and calcium ions and phosphate ions are precipitated on surfaces of granules as calcium hydrogen phosphate. Since calcium dihydrogen phosphate is also precipitated on a surface on which granules come in contact with each other, a granule and another granule are bridged by calcium hydrogen phosphate and the granules are cured.

[Porous Body]

The porous body of the present invention is a porous body that is produced from the above-described curable composition and comprises calcium hydrogen phosphate.

Granules are cured to form an interconnected porous body in which calcium hydrogen phosphate is formed on surfaces of the granules and in gaps between the granules. The body is effective for a treatment through which a bone defect is directly reconstructed by performing curing inside the bone defect. However, the body can be used as scaffold of a regenerative drug by being cured ex vivo.

(Calcium Hydrogen Phosphate)

Calcium hydrogen phosphate is a compound whose basic composition is $CaHPO_4$ and an anhydride and a dihydrate are known. Calcium hydrogen phosphate formed in an aqueous solution having a pH of 4 or less is often calcium hydrogen phosphate dihydrate ($CaHPO_4 \cdot 2H_2O$), and is calcium hydrogen phosphate anhydride ($CaHPO_4$) according to temperature conditions.

(Production Method)

A method of producing a porous body comprises a step in which the above-described curable composition is dispersed in water and calcium hydrogen phosphate is formed, and either or both of granules included in the curable composition and the water include a phosphate component. In the production method, granules are linked by calcium hydrogen phosphate formed by reacting a calcium component included in the granule with the phosphate component and the curable composition is cured.

Here, as a method in which a curable composition is dispersed in water, a method in which water is dropped after granules are filled into a bone defect and a method in which granules are mixed with water before they are filled into a bone defect—may be exemplified.

In order to form calcium hydrogen phosphate, it is necessary to satisfy the two conditions that a component for forming calcium hydrogen phosphate be supplied to a reaction site and a pH of the reaction site be a pH at which calcium hydrogen phosphate is formed.

In order to supply a component for forming calcium hydrogen phosphate to a reaction site, it is necessary to supply a component which is $CaHPO_4$ that is a basic chemical formula of calcium hydrogen phosphate to the reaction site. That is, it is necessary to include both a calcium component and a phosphate component in a combination of granules and liquid components.

In the present invention, since granules include a calcium component, if either or both of granules and water include a phosphate component, it is possible to form calcium hydrogen phosphate. Therefore, a phosphate component may not be included in granules but be present in water, a phosphate component may be present in granules but may not be present in water, and a phosphate component may be present both in granules and water.

In addition, the phosphate component is preferably calcium dihydrogen phosphate. Also, more preferably, calcium dihydrogen phosphate is present in granules. Also, particularly preferably, calcium dihydrogen phosphate is present in surfaces of granules.

Also, calcium hydrogen phosphate includes hydrogen in addition to calcium and phosphate. However, since hydrogen is supplied from water, there is no need to consider hydrogen in general. In addition, when a pH is 4 or less, phosphate is present as a hydrogen phosphate ion ($HPO_4^{2-}$). Therefore, when both a calcium component and a phosphate component are included in a combination of granules and liquid components, this is substantially the same as when all constituent components of calcium hydrogen phosphate are included.

In order to form calcium hydrogen phosphate according to a reaction between granules and water, the reaction site needs to be supersaturated with calcium hydrogen phosphate and water preferably includes both calcium and phosphate. In addition, more preferably, the product of a calcium concentration and a phosphate concentration is high.

That is, when a calcium ion concentration and a hydrogen phosphate ion concentration of the reaction site exceed the solubility product of calcium hydrogen phosphate, a solution is supersaturated with calcium hydrogen phosphate, and calcium hydrogen phosphate is precipitated on surfaces of granules. Since calcium hydrogen phosphate is formed on surfaces of granules, it is also formed between granules, and it is speculated that the granules are cured by granules being bridged by calcium hydrogen phosphate.

In order to form calcium hydrogen phosphate, a pH of the reaction site is preferably 2 or more and 4 or less. This is because a pH at which calcium hydrogen phosphate is in a stable phase is 2 or more and 4 or less. When a pH is greater than 4, an apatite is in a stable phase. When a pH is lower than 2, calcium dihydrogen phosphate is in a stable phase. Therefore, a pH of water is preferably 4 or less.

Calcium dihydrogen phosphate is $Ca(H_2PO_4)_2$. Calcium dihydrogen phosphate monohydrate $Ca(H_2PO_4)_2 \cdot H_2O$ and calcium dihydrogen phosphate anhydrate $Ca(H_2PO_4)_2$ are known and these are referred to as calcium dihydrogen phosphate without being distinguished in the present invention.

In addition, calcium dihydrogen phosphate may also be referred to as primary calcium phosphate.

Calcium hydrogen phosphate is formed when a pH is 4 or less. However, in consideration of clinical operability, a curing time is preferably within 30 minutes. Therefore, formation of calcium hydrogen phosphate should proceed quickly. In addition, when a certain amount of calcium hydrogen phosphate or more is not formed, linking between granules becomes insufficient. As a result, a mechanical strength of a cured body is reduced.

When a pH of the reaction site is low, a supply amount of a calcium component or a calcium component and a phosphate component based on the dissolution of granules increases. As a result, it is advantageous in shortening a curing time and formation of a large amount of calcium hydrogen phosphate.

Therefore, a pH of water is preferably 3.5 or less, more preferably 3 or less, and most preferably 2.5 or less.

When a pH is lower than 2, calcium hydrogen phosphate is in an unstable phase and calcium dihydrogen phosphate $(Ca(H_2PO_4)_2 \cdot H_2O)$ is in a stable phase. Therefore, a pH of the reaction site is preferably 2 or more. However, since calcium hydrogen phosphate is formed on surfaces of granules including a calcium component, it is almost impossible to measure a pH of the reaction site. In addition, even if a pH of water is lower than 2, a pH increases as calcium-containing granules dissolve. Therefore, even if a pH of water is lower than 2, since calcium hydrogen phosphate is formed according to a reaction with granules including a calcium component, setting a lower limit of a pH of water is not always suitable.

Meanwhile, in consideration of a detrimental effect on tissue due to water that comes in contact with tissues, a pH of water is preferably 0.3 or more, more preferably 0.5 or more and most preferably 0.7 or more.

If granules include not only a calcium component but also a phosphate component such as β-type tricalcium phosphate $(Ca_3(PO_4)_2)$, when they come in contact with an aqueous solution having a pH of 4 or less, some of tricalcium phosphate granules dissolve, and calcium ions and hydrogen phosphate ions are supplied to the reaction site. When a concentration product of calcium ions and hydrogen phosphate ions exceeds the solubility product of calcium hydrogen phosphate, a solution of the reaction site is supersaturated with calcium hydrogen phosphate dihydrate $(CaHPO_4 \cdot 2H_2O)$ that is thermodynamically in the most stable phase in an acidic range of a pH of 4 or less, and calcium ions and hydrogen phosphate ions are precipitated on surfaces of granules as calcium hydrogen phosphate. Since calcium hydrogen phosphate is also precipitated on a surface on which granules come in contact with each other, a granule and another granule are bridged by calcium hydrogen phosphate and the granules are cured.

If granules do not include a phosphate component such as calcium carbonate granules, when they are brought into contact with an aqueous solution having a pH of 4 or less and cured, it is necessary to include a phosphate component in the aqueous solution. As described above, this is because a curing reaction of granules is due to the formation of calcium hydrogen phosphate dihydrate and it is necessary to supply a phosphate component necessary for forming calcium hydrogen phosphate dihydrate from an aqueous solution.

For example, when calcium carbonate granules including no phosphate component are brought into contact with water including a phosphate component and having a pH 4 or less, some of calcium carbonate granules dissolve and calcium ions are supplied to the reaction site. On the other hand, hydrogen phosphate ions are supplied from water including a phosphate component.

When a concentration product of calcium ions and hydrogen phosphate ions exceeds the solubility product of calcium hydrogen phosphate, a solution of the reaction site is supersaturated with calcium hydrogen phosphate dihydrate $(CaHPO_4 \cdot 2H_2O)$ that is thermodynamically in the most stable phase in an acidic range of a pH of 4 or less, and calcium ions and hydrogen phosphate ions are precipitated on surfaces of calcium carbonate granules as calcium hydrogen phosphate. When calcium hydrogen phosphate is also precipitated on a surface on which calcium carbonate granules come in contact with each other, a calcium carbonate granule and another calcium carbonate granule are bridged by calcium hydrogen phosphate and thus the calcium carbonate granules are cured.

Even if granules do not come into contact with an aqueous solution having a pH of 4 or less, if calcium dihydrogen phosphate coexists, curing is performed due to contact with a body fluid, physiological saline, or distilled water. This is because, as can be understood from the fact that calcium dihydrogen phosphate is a salt of a dihydrogen phosphate ion $(H_2PO_4^-)$, calcium dihydrogen phosphate is a readily soluble acidic calcium phosphate.

When granules and calcium dihydrogen phosphate coexist, when the calcium dihydrogen phosphate dissolves, for example, in contact with distilled water, a pH of a reaction site becomes 4 or less. Calcium ions are supplied to the reaction site when some of the granules dissolve, and calcium ions and hydrogen phosphate ions are supplied to the reaction site according to the dissolution of the calcium dihydrogen phosphate.

When a concentration product of calcium ions and hydrogen phosphate ions exceeds a concentration product of calcium hydrogen phosphates, a solution of the reaction site is supersaturated with calcium hydrogen phosphate dihydrate $(CaHPO_4 \cdot 2H_2O)$ that has the most thermodynamically stable phase in an acidic range of a pH of 4 or less, and calcium ions and phosphate ions are precipitated on surfaces of granules as calcium hydrogen phosphate. Since calcium dihydrogen phosphate is also precipitated on a surface on which granules come in contact with each other, a granule and another granule are bridged by calcium hydrogen phosphate and the granules are cured.

Calcium hydrogen phosphate is in a stable phase when a phosphate component and a calcium component are present in a reaction site and a pH is 2 or more and 4 or less.

However, in order for calcium hydrogen phosphate to be precipitated, an aqueous solution in the reaction site needs to be supersaturated with calcium hydrogen phosphate. For supersaturation, a product of a calcium ion concentration, a phosphate ion concentration, and a hydrogen ion concentration in the reaction site needs to be greater than the solubility product of calcium hydrogen phosphate. When calcium-containing granules include a calcium component and a phosphate component, both a calcium component and a phosphate component are supplied to the reaction site according to a reaction with water, and the reaction site becomes quickly supersaturated with calcium hydrogen phosphate. In addition, in order to obtain a high degree of supersaturation, water preferably includes a calcium component, and more preferably includes both a calcium component and a phosphate component.

The curable composition is used as follows. Calcium ions and hydrogen phosphate ions are supplied so that a solution of a reaction site is supersaturated with calcium hydrogen phosphate in a pH range in which calcium hydrogen phosphate is thermodynamically in the most stable phase. Therefore, calcium hydrogen phosphate is formed on surfaces of granules and granules are cured by the granules being bridged by calcium hydrogen phosphate. Therefore, in a combination of granules and an aqueous solution having a pH of 4 or less, supply of a calcium component and a phosphate component to the reaction site is an essential requirement. However, a case in which a calcium component and a phosphate component are included in granules and a calcium component and a phosphate component are additionally included in an aqueous solution has no problems, and is actually preferable. This is because it is possible to supply a larger amount of a calcium component and a hydrogen phosphate component to the reaction site or supply more quickly them. As a result, a concentration product of calcium ions and hydrogen phosphate ions exceeds the solubility product of calcium hydrogen phosphate more quickly. A solution of the reaction site is supersaturated with calcium hydrogen phosphate dihydrate ($CaHPO_4 \cdot 2H_2O$) that is thermodynamically in the most stable phase in an acidic range of a pH of 4 or less, and calcium ions and hydrogen phosphate ions are precipitated on surfaces of granules as calcium hydrogen phosphate.

For the same reason, water used in the curing reaction preferably includes at least one of phosphate and calcium. Even if water does not include a phosphate component or a calcium component, when some of the granules dissolve in water, calcium ions are supplied to the reaction site from granules. When granules include not only a calcium component but also a phosphate component, some of the granules dissolve in water, and calcium ions and hydrogen phosphate ions are supplied to the reaction site from the granules. When a concentration product of calcium ions and hydrogen phosphate ions of the reaction site exceeds the solubility product of calcium hydrogen phosphate, a solution of the reaction site is supersaturated with calcium hydrogen phosphate dihydrate ($CaHPO_4 \cdot 2H_2O$) that is thermodynamically in the most stable phase in an acidic range of a pH of 4 or less, and calcium ions and hydrogen phosphate ions are precipitated on surfaces of granules as calcium hydrogen phosphate. However, when water includes neither phosphate nor calcium, it takes time until a concentration product of calcium ions and hydrogen phosphate ions in a solution that functions as a reaction site exceeds the solubility product of calcium hydrogen phosphate.

When water includes at least one of phosphate and calcium, it is advantageous to increase a concentration product of calcium ions and hydrogen phosphate ions, and calcium hydrogen phosphate is quickly precipitated. Therefore, water preferably includes at least one of phosphate and calcium.

For the same reason, water preferably includes phosphate and calcium. This is because, when an aqueous solution functioning as a reaction site initially includes phosphate and calcium, a concentration product of calcium ions and hydrogen phosphate ions of the reaction site easily exceeds the solubility product of calcium hydrogen phosphate, and calcium hydrogen phosphate is easily precipitated.

Even if calcium and phosphate are present in an aqueous solution having a pH of 4 or less in which calcium hydrogen phosphate is thermodynamically in the most stable phase, no calcium hydrogen phosphate is precipitated from the solution until a product of a calcium ion concentration and a hydrogen phosphate ion concentration exceeds the solubility product of calcium hydrogen phosphate. That is, when a product of a calcium ion concentration and a hydrogen phosphate ion concentration of the reaction site is smaller than the solubility product of calcium hydrogen phosphate, the reaction site is unsaturated with calcium hydrogen phosphate.

When a product of a calcium ion concentration and a hydrogen phosphate ion concentration of the reaction site is equal to the solubility product of calcium hydrogen phosphate, the reaction site is saturated with calcium hydrogen phosphate.

When a product of a calcium ion concentration and a hydrogen phosphate ion concentration of the reaction site is smaller than the solubility product of calcium hydrogen phosphate, the reaction site is supersaturated with calcium hydrogen phosphate.

A degree of saturation with respect to a salt in a solution is represented by a common logarithm of a value obtained by dividing an activity product of a salt in a solution by the solubility product of a salt (a dissolution equilibrium constant of a salt), that is, a degree of saturation with respect to a salt=Log(an activity product of a salt in a solution÷the solubility product of a salt).

In this case, when a value of a degree of saturation of a salt is a positive value, a solution is supersaturated with the salt. When a value of a degree of saturation is zero, a solution is saturated with a salt. When a degree of saturation has a negative value, a solution is unsaturated with a salt. Also, an activity is obtained by multiplying an activity coefficient of a salt by a concentration of a salt and is an ion concentration of a salt that is substantially involved in a precipitation reaction.

When water includes phosphate and calcium, this is preferable in consideration of a precipitation ability of calcium hydrogen phosphate. However, in order to precipitate a larger amount of calcium hydrogen phosphate, ideally, water is supersaturated or saturated with calcium hydroxide; that is, a degree of saturation of water with respect to calcium hydrogen phosphate is positive or zero.

A value of a degree of saturation of the reaction site is preferably −1 or more and a value of a degree of saturation is more preferably −0.5 or more.

In the curable composition of the present invention, calcium ions and hydrogen phosphate ions are supplied so that a solution of a reaction site is supersaturated with calcium hydrogen phosphate in a pH range in which calcium hydrogen phosphate is thermodynamically in the most stable phase. Therefore, calcium hydrogen phosphate is formed on surfaces of granules and granules are cured by granules being bridged by calcium hydrogen phosphate.

Therefore, even if there is no aqueous solution having a pH of 4 or less, the curable composition of the present invention is formed in a combination of granules and calcium dihydrogen phosphate. This is because calcium dihydrogen phosphate is a water-soluble acidic calcium phosphate salt. That is, calcium dihydrogen phosphate is dissolved when it comes in contact with a body fluid, physiological saline, or water and forms an aqueous solution having a pH of 4 or less. The granules dissolve in an aqueous solution having a pH of 4 or less formed by dissolution of calcium dihydrogen phosphate. A product of a calcium ion concentration and a hydrogen phosphate ion concentration of the aqueous solution serving as a reaction site exceeds the solubility product of calcium hydrogen phosphate and calcium hydrogen phosphate is precipitated on surfaces of calcium granules. Granules are cured by the granules being bridged by the precipitated calcium hydrogen phosphate.

When a curable composition includes a combination of granules and calcium dihydrogen phosphate, water is not necessary for a curing reaction. When the curable composition including a combination of granules and calcium dihydrogen phosphate is filled into a bone defect, it is cured by a body fluid and the like and it is particularly useful in consideration of clinical applications.

When the curable composition of the present invention comprises calcium dihydrogen phosphate, a portion in which calcium dihydrogen phosphate is present is not particularly limited. A case in which it is mixed with granules as a powder, a case in which it is mixed with granules as a granule, a case in which it is adhered to surfaces of granules, and a case in which it is suspended in water may be exemplified.

Calcium dihydrogen phosphate granules are produced by a known granule preparation method such as compacting, gently pulverizing and sieving. Compared to when calcium dihydrogen phosphate is used as a powder, when calcium dihydrogen phosphate granules are used, it is possible to produce a curable composition having a high bulk density and excellent operability is provided. In addition, compared to when a calcium dihydrogen phosphate powder is used, since it takes time until dissolution is completed, a curing reaction can continue for a relatively long period of time, a time in which operation is possible increases, and calcium hydrogen phosphate is formed even after initial curing. Therefore, there is an advantage such as an increase in a mechanical strength of a cured body.

In particular, when a particle size of calcium dihydrogen phosphate granules is 100 µm or more, this is preferable since operability is improved, and a time in which operation is possible and a mechanical strength of a cured body significantly increase.

When calcium dihydrogen phosphate is adhered to granules, it is useful to quickly precipitate calcium hydrogen phosphate and uniformly precipitate calcium hydrogen phosphate on surfaces of granules. A production method in which calcium dihydrogen phosphate is adhered to surfaces of granules is not particularly limited. For example, a method in which granules including a calcium component is immersed in a calcium dihydrogen phosphate suspension and dried and a production method in which granules including a calcium component are immersed in a solvent and a calcium dihydrogen phosphate powder is applied may be cited.

A curable composition in which calcium dihydrogen phosphate is adhered to granules through a water-soluble polymer is useful in consideration of storage stability. A method in which calcium dihydrogen phosphate is adhered to granules through a water-soluble polymer is not particularly limited.

For example, a calcium dihydrogen phosphate powder may be suspended in a water-soluble polymer aqueous solution or an alcohol solution and granules may be immersed in the suspension solution. When granules are extracted from the solution in which a calcium dihydrogen phosphate powder is suspended and dried, it is possible to produce granules in which calcium dihydrogen phosphate is adhered through a water-soluble polymer.

The water-soluble polymer is not particularly limited. For example, starches such as amylum, corn starch, oxidized starch, and modified starch; carbohydrates such as mannan and pectin; seaweed such as agar and alginic acid; microbial mucilage such as dextran and pullulan; proteins such as glue and gelatin; celluloses such as carboxylmethyl cellulose, hydroxymethyl cellulose, and hydroxyethyl cellulose, and polyacrylic acid, polyacrylamide, polyvinyl alcohol, polyethyleneimine, polyethylene oxide, polyethylene glycol, polypropylene oxide, polypropylene glycol, and polyvinylpyrrolidone may be exemplified.

Since water serves as a reaction site in which calcium hydrogen phosphate is formed, it is necessary for water to form an aqueous solution having a pH of 4 or less during a curing reaction. However, a suspension including calcium dihydrogen phosphate is used to form an aqueous solution having a pH of 4 or less during a curing reaction.

In addition, in order to improve operability and the like, a solvent such as an alcohol and a compound such as a polymer may be added to water.

The curable composition of the present invention is cured by granules being bridged including a calcium component by calcium hydrogen phosphate. Therefore, formation of calcium hydrogen phosphate on at least some of granules is an essential requirement.

[Surface Apatitized Porous Body]

The surface apatitized porous body of the present invention is a surface apatitized porous body which is produced from the above-described porous body and in which at least a part of calcium hydrogen phosphate of a surface is apatitized.

The surface of a porous body is preferably a porous body having a surface that is apatitized by a hydroxyapatite or a carbonate apatite which has superior biocompatibility to a porous body of calcium hydrogen phosphate without change. The apatitization is preferably carbonate apatitization in consideration of bone replacement.

A method of producing a surface apatitized interconnected porous body comprises a step in which the above-described porous body is immersed in an aqueous solution having a pH of 8 or more and at least a part of calcium hydrogen phosphate present on a surface of the interconnected porous body is apatitized.

This is because, in an aqueous solution having a pH of greater than 4, an apatite rather than calcium hydrogen phosphate is in a thermodynamically stable phase, and calcium hydrogen phosphate has a composition that is converted into an apatite due to a dissolution precipitation type reaction. In an aqueous solution having a pH of greater than 4, since an apatite is thermodynamically in a stable phase, calcium hydrogen phosphate is gradually changed to an apatite, but this takes time. Therefore, immersing in an aqueous solution having a pH of 8 or more is practical and preferable.

In order for an interconnected porous body whose surface is covered with calcium hydrogen phosphate produced in the curable composition of the present invention to be immersed in an aqueous solution having a pH of 8 or more so that at least a part of the surface of the interconnected porous body for medical treatment is apatitized, an aqueous solution having a pH of 8 or more preferably comprises at least one of a calcium component and a carbonate component.

This is because, when a composition of calcium hydrogen phosphate is converted into an apatite due to a dissolution precipitation type reaction, preferably, a calcium component is additionally supplied, and when a composition of calcium hydrogen phosphate is converted into a carbonate apatite due to a dissolution precipitation type reaction, it is necessary to additionally supply a carbonate component.

When an aqueous solution having a pH of 8 or more includes a carbonate component, calcium hydrogen phosphate is carbonate-apatitized. The carbonate component is not particularly limited. For example, sodium hydrogen carbonate, sodium carbonate, and carbon dioxide may be exemplified.

An aqueous solution including a carbonate component and having a pH of 8 or more is easily prepared by dissolving sodium carbonate. However, calcium dissolved in an aqueous solution having a pH of 8 or more is limited in consideration of a relation to solubility. Therefore, calcium is supplied to an aqueous solution as a suspension and an amount of calcium that is consumed when a phase is converted from calcium hydrogen phosphate into an apatite is preferably compensated for from calcium supply according to the dissolution from the suspension.

[Calcined Porous Body and Surface Apatitized-Calcined Porous Body]

The calcined porous body of the present invention is a calcined porous body that is produced from the above-described porous body including calcium hydrogen phosphate and is obtained by calcining the porous body.

In addition, the surface apatitized-calcined porous body of the present invention is a surface apatitized-calcined porous body that is produced from the above-described surface apatitized-porous body and is obtained by calcining the surface apatitized-porous body.

(Production Method)

Both calcined porous bodies are obtained in a process in which calcination is performed at 700° C. or higher.

While granules cured by bridging by calcium hydrogen phosphate form a porous body, when the porous body is calcined at 700° C. or higher, calcium hydrogen phosphate reacts with granules and the granules are more firmly linked. Therefore, this is useful for producing a porous body having an excellent mechanical strength.

It is necessary for a calcination temperature to be 700° C. or higher. 800° C. or higher is preferable, 900° C. or higher is more preferable, and 1000° C. or higher is most preferable.

[Action and Effect]

While a mechanism of action for effects of the present invention is not limitedly interpreted, when the present invention is a curable composition that highly satisfies requirements of "(1) being cured at a body temperature, (2) being cured within 30 minutes, (3) being a cured body having a compressive strength of 10 kPa or more, (4) having a porosity of 10 volume % or more, (5) at least a part of a porous body is interconnected, and (6) does not exhibit a detrimental effect on tissue," the action mechanism is speculated to be as follows.

A curing reaction of the present invention is speculated to be as follows. In a pH range in which calcium hydrogen phosphate is thermodynamically in the most stable phase, calcium ions and hydrogen phosphate ions are supplied so that a solution of the reaction site is supersaturated with calcium hydrogen phosphate. Therefore, calcium hydrogen phosphate is formed on surfaces of granules and granules are cured by granules being bridged by calcium hydrogen phosphate.

In addition, in this case, when granules have a predetermined size or larger, interconnected pores are formed between granules.

<<Bone Prosthetic Material and Method of Producing the Same>>

[Requirements of the Present Invention]

First, objective requirements of the present invention will be briefly described.

<(A) Exhibiting Excellent Tissue Compatibility>

Exhibiting excellent tissue compatibility is important for a bone prosthetic material to be implanted in vivo. A material that does not exhibit excellent tissue compatibility and exhibits a detrimental effect on tissue is not easily used as a material for medical treatment and is not easily used as a bone prosthetic material. In general, a bone prosthetic material is implanted into a laboratory animal and histological analysis is performed. However, if an inflammatory response is caused when a material is implanted subcutaneously, the material has fundamentally low tissue compatibility and has low usefulness as a bone prosthetic material.

<(B) Exhibiting Excellent Osteoconductivity>

Osteoconductivity is a property of forming a bone on a surface of a material when the material is implanted near a bone defect and is a property of linking a material and bone without intervening fibrous connective tissues under preferable conditions. Since the present invention relates to a bone prosthetic material, it is important for the material to exhibit excellent osteoconductivity.

Bone conduction occurs on a surface of a material. One major factor influencing whether osteoconduction occurs or a degree of osteoconduction is a composition of a surface of a material. An apatite and the like are known to exhibit osteoconductivity. However, the reason why an apatite exhibits osteoconductivity has not been clarified.

<(C) Replacing Bone>

Bone has a biological function such as hematopoiesis in addition to a mechanical function. Therefore, it is often desirable that a bone prosthetic material replaces bone. In order for the bone prosthetic material to replace bone, it is necessary for a process in which absorption in vivo is performed and a process in which bone is formed to proceed in a well-balanced manner. Therefore, a material that quickly replaces bone is a material that has excellent osteoconductivity and is easily absorbed. Absorption includes osteoclast absorption and absorption based on physicochemical dissolution. As a material that is absorbed in osteoclasts in vivo or physicochemically dissolved, a carbonate apatite, an α-type tricalcium phosphate, a β-type tricalcium phosphate, and calcium carbonate are known.

Also, maintaining a mechanical strength may have a priority. In such a clinical case, bone replacement is not necessary.

<(D) not Dissolving in a Physiological Environment>

When a bone replacement material for medical treatment is implanted in vivo, it comes in contact with body fluids. Since osteoblasts that form a bone and osteoclasts that absorb a material do not migrate to a surface of the material when implantation is initialized, a behavior of a bone prosthetic material in vivo is only a physicochemical behavior. When a material dissolves in such a situation, since it is difficult for a function as a bone prosthetic material to be exhibited, it is important that a material does not dissolve in this physiological environment. As a material that does not dissolve in a physiological environment, a hydroxyapatite and a carbonate apatite may be exemplified.

<E> being Able to be Produced at Low Cost>

It is desirable that a bone replacement material for medical treatment be able to be produced at low cost similarly to other materials. In order for production at low cost, it is preferable that a special treatment not be performed, a processing temperature not be high, a hydrothermal treatment and the like not be required, and a processing time be short. In addition, it is also important not to use an expensive growth factor drug to improve osteoconductivity.

[Bone Prosthetic Material]

Next, a configuration of the bone prosthetic material of the present invention will be described.

The bone prosthetic material of the present invention comprises a core portion and a surface layer portion that covers the core portion. The surface layer portion comprises an apatite. The core portion is an artificial material that includes either or both of calcium phosphate and calcium carbonate. The bone prosthetic material has a volume of $10^{-13}$ m$^3$ or more.

The bone prosthetic material is used to reconstruct or regenerate a damaged bone or promote the reconstruction or regeneration.

Configurations will be described below.

<Core Portion and Surface Layer Portion that Covers the Core Portion>

The surface layer portion in the present invention refers to a portion of a surface of the bone prosthetic material. In addition, the surface layer portion comprises an apatite.

On the other hand, the core portion refers to an inside covered with the surface layer portion. In addition, the core portion is an artificial material that comprises either or both of calcium phosphate and calcium carbonate. The core portion may be a single composition or a mixture. The core portion may be additionally divided into a plurality of phases. As an example in which the core portion is additionally divided into a plurality of phases, a case in which a powder of either or both of calcium phosphate and calcium carbonate is adhered to a framework made of a polymer or the like is used for the core portion may be exemplified.

In the present invention, since compositions of the core portion and the surface layer portion are different they may be distinguished from each other. Both a hydroxyapatite and a carbonate apatite are apatites, but their compositions are different. For example, a hydroxyapatite covered with a carbonate apatite has a core portion and a surface layer portion whose compositions are different and both can be distinguished from each other.

In addition, even if one component of the core portion and a composition of the surface layer portion are the same, when the core portion is formed of a plurality of compositions, the entire composition of the core portion and the entire composition of the surface layer portion are different, and both can be distinguished from each other. For example, when the core portion is formed of a mixture of calcium carbonate and a carbonate apatite in order to improve conductivity and the surface layer portion is formed of a carbonate apatite, both a part of the core portion and a composition of the surface layer portion comprise a carbonate apatite. However, since the core portion has a composition that is a mixture of a carbonate apatite and calcium carbonate, both can be distinguished from each other.

In addition, as the carbonate apatite, various carbonate apatites in which carbonate group contents are different are known. However, also if the core portion and the surface layer portion are formed of carbonate apatites, when both have different carbonate group contents, both can be distinguished from each other.

The thickness of the surface layer portion is not particularly limited. In consideration of a balance between production costs and functionality, 0.1 µm or more and 100 µm or less is preferable, 0.2 pan or more and 50 µm or less is more preferable, and 0.5 µm or more and 30 µm or less is most preferable.

<Surface Layer Portion>

The surface layer portion comprises an apatite.

The inclusion of an apatite in the surface layer portion is related to requirements of (A) exhibiting excellent tissue compatibility, (B) exhibiting excellent osteoconductivity, (C) replacing bone, and (D) not dissolving in a physiological environment. In consideration of more highly satisfying the requirements, the surface layer portion is preferably formed of an apatite.

(Apatite)

An apatite is a compound whose basic structure is $A_{10}(BO_4)_6C_2$. Examples of A include $Ca^{2+}$, $Cd^{2+}$, $Sr^{2+}$, $Ba^{2+}$, $Pb^{2+}$, $Zn^{2+}$, $Mg^{2+}$, $Mn^{2+}$, $Fe^{2+}$, $Ra^{2+}$, $H^+$, $H_3O^+$, $Na^+$, $K^+$, $AL^{3+}$, $Y^{3+}$, $Ce^{3+}$, $Nd^{3+}$, $La^{3+}$, $C^{4+}$, and a void. Examples of $BO_4$ include $PO_4^{3-}$, $CO_3^{2-}$, $CrO_4^{3-}$, $AsO_4^{3-}$, $VO_4^{3-}$, $UO_4^{3-}$, $SO_4^{2-}$, $SiO_4^{4-}$, $GeO_4^{4-}$, and a void. Examples of C include $OH^-$, $OD^-$, $F^-$, $Br^-$, $BO^{2-}$, $CO_3^{2-}$, $O^{2-}$, and a void. In the present invention, since the core portion includes at least calcium, at least some A's needs to be calcium.

The hydroxyapatite in the present invention has a stoichiometric composition that is $Ca_{10}(PO_4)_6(OH)_2$, and comprises hydroxyl groups. A Ca-deficient apatite having a composition of $Ca_{10-X}(HPO_4)_X(PO_4)_{6-X}(OH)_{2-X}$ is also a hydroxyapatite.

A carbonate apatite is an apatite in which some or all of phosphate groups or hydroxyl groups of the hydroxyapatite are substituted with a carbonate group, and one in which a phosphate group is substituted with a carbonate group is referred to as a B-type carbonate apatite. one in which a hydroxyl group is substituted with a carbonate group is referred to as an A-type carbonate apatite. An apatite including both a hydroxyl group and a carbonate group may be referred to as a carbonate-containing hydroxyapatite, and is defined as one type of carbonate apatite in the present invention for simplicity of description.

An apatite is known to exhibit excellent tissue compatibility. In addition, since a surface composition of a material comes into contact with the human body, the surface composition of the material is closely related to a tissue reaction. Therefore, the bone prosthetic material of the present invention comprising an apatite in the surface layer portion satisfies the requirement of (A) exhibiting excellent tissue compatibility.

In the bone prosthetic material of the present invention, since the surface layer portion comprises an apatite, osteoconductivity of the bone prosthetic material is ensured.

An apatite in which silicon is fused to further improve osteoconductivity of the apatite itself and the like has been reported (for example, Non-Patent Literature 1). Surprisingly, it is found that a carbonate apatite has superior osteoconductivity to hydroxyapatites that have been clinically applied so far.

Although the reason why a carbonate apatite has superior osteoconductivity to a hydroxyapatite has not been completely adequately clarified, in vivo bone being a carbonate apatite rather than a hydroxyapatite, and a carbonate apatite being closer to in vivo bone is speculated to be one factor.

Since a carbonate apatite has superior osteoconductivity to a hydroxyapatite, when a surface layer in the bone prosthetic material of the present invention is formed of a carbonate apatite rather than a hydroxyapatite, it is preferable in consideration of osteoconductivity.

Since an apatite is absorbed by osteoclasts, an apatite included in a surface layer portion replaces bone in vivo.

Among apatites, since a carbonate apatite is absorbed by osteoclasts more easily than a hydroxyapatite, it is preferable in consideration of bone replacement properties. While the mechanism has not been adequately clarified, since osteoclasts absorb a material while insides of Howship's lacunae remain in an acidic environment, it is speculated that a carbonate apatite having a high solubility in an acidic environment is absorbed by osteoclasts more easily than a hydroxyapatite.

Since a body fluid is supersaturated with an apatite, the apatite included in the surface layer portion does not dissolve in a physiological environment.

(Calcium Hydrogen Phosphate)

Preferably, the surface layer portion additionally includes calcium hydrogen phosphate.

When the surface layer portion includes calcium hydrogen phosphate, it is possible to further improve bone replacement properties of the bone prosthetic material.

In addition, the surface layer portion more preferably includes a calcium hydrogen phosphate and includes an interconnected porous body. When the surface layer portion includes calcium hydrogen phosphate and includes an interconnected porous body, it is possible to further improve bone replacement properties of the bone prosthetic material.

Calcium hydrogen phosphate is a compound whose basic composition is $CaHPO_4$ and an anhydride and a dihydrate thereof are known. Calcium hydrogen phosphate formed in an aqueous solution having a pH of 4 or less is often calcium hydrogen phosphate dihydrate ($CaHPO_4.2H_2O$), and is calcium hydrogen phosphate anhydride ($CaHPO_4$) according to temperature conditions.

<Core Portion>

The core portion is an artificial material that comprises either or both of calcium phosphate and calcium carbonate. This is important for the bone prosthetic material to exhibit excellent tissue compatibility. While a mechanism of action by which calcium phosphate and calcium carbonate exhibit excellent tissue compatibility has not been completely adequately clarified, since invertebrate animals select calcium carbonate as a skeletal structure and vertebrate animals select an apatite as a skeletal structure, the superiority of calcium phosphate and calcium carbonate can be found from an evolutionary perspective.

In addition, in order to further enhance tissue compatibility, the core portion preferably comprises an artificial material that includes either or both of calcium phosphate and calcium carbonate.

A coral-derived material is clinically applied as a bone prosthetic material. As an apatite that is used for a bioimplant material such as an artificial tooth and an artificial bone, a natural shell has been proposed (for example, Patent Literature 4). However, in the bone prosthetic material of the present invention, when the core portion is an "artificial material" that comprises either or both of calcium phosphate and calcium carbonate, excellent tissue compatibility is exhibited.

(Artificial Material)

In the core portion of the bone prosthetic material of the present invention, a naturally collected mineral itself such as a limestone, an apatite, and diatomaceous earth or a powder obtained without purifying a mineral and the like are not used. For example, since a calcium carbonate powder such as light calcium carbonate obtained when limestone is heated to form a calcium oxide and the calcium oxide reacts with water includes impurities other than the calcium carbonate, it is a natural product, and is not used for the core portion of the bone prosthetic material of the present invention.

Natural products include natural materials derived from living things other than minerals. Natural materials derived from living things are natural materials that an organism forms. All of an autogenic bone, an allogeneic bone, and a heterogenic bone are natural materials derived from living things and are natural products. A shell that a shellfish forms and coral that a coral worm forms are natural materials derived from living things and are natural products.

In the present invention, even if a material is derived from a natural product, when the material is purified and substantially includes no impurities, the material is defined as a material that is artificially produced from a chemically synthesized material. An artificially produced material refers to a material produced using chemical materials for manufacture including substantially no impurities as raw materials according to a sintering or chemical method.

That is, in the present invention, a material is defined as a natural product or an artificial material according to whether it substantially includes impurities. When a material substantially includes impurities, the material is a natural product. When a material substantially includes no impurities, the material is an artificial material.

Here, impurities refer to compounds other than either or both of calcium phosphate and calcium carbonate.

A proportion of impurities included in an artificial material is preferably 50 mass % or less, more preferably 25 mass % or less, still more preferably 10 mass % or less, yet more preferably 5 mass % or less and most preferably 1 mass % or less. When the proportion is the above upper limit value or less, the bone prosthetic material has superior biocompatibility.

(Calcium Phosphate)

Calcium phosphate is a salt of phosphoric acid and calcium, which may be exemplified by calcium orthophosphate, calcium metaphosphate, condensed calcium phosphate and the like. Since calcium orthophosphate exhibits relatively excellent osteoconductivity and tissue compatibility, calcium orthophosphate is preferable among calcium phosphates.

Calcium orthophosphate is a salt of orthophosphoric acid and calcium, which may be exemplified by, for example, artificial apatites (provided that compositions thereof are different from that of an apatite included in the surface layer portion) including tetracalcium phosphate, α-type tricalcium phosphate, β-type tricalcium phosphate, a hydroxyapatite and a carbonate apatite.

Among calcium orthophosphates, since an apatite and tricalcium phosphate are known to have excellent osteoconductivity and tissue compatibility, they are particularly preferable.

Tricalcium phosphate is one calcium orthophosphate component whose representative composition is $Ca_3(PO_4)_2$, and includes a compound in which some calcium ions are substituted with another metal ion such as a sodium or potassium ion. Tricalcium phosphate includes a high temperature stable phase α-type tricalcium phosphate and a low temperature stable phase β-type tricalcium phosphate. Although an α'-type tricalcium phosphate is also known, in the present invention, α'-type tricalcium phosphate is one type of α-type tricalcium phosphate.

α-type tricalcium phosphate has a higher solubility than β-type tricalcium phosphate and is not clinically applied as a bone prosthetic material but is used as a component of a bone cement. However, in the present invention, since the core portion is covered with a surface layer portion comprising an apatite, there is no physicochemical dissolution in a physiological environment. Therefore, α-type tricalcium phosphate can function as a bone prosthetic material. After bone is formed on a surface of α-type tricalcium phosphate covered with an apatite, according to osteoconductivity of the apatite of the surface, bone replacement is performed by bone remodeling. However, since it has a greater solubility than β-type tricalcium phosphate, it quickly replaces bone.

On the other hand, β-type tricalcium phosphate has a lower rate of physicochemical dissolution in a physiological environment than α-type tricalcium phosphate. In particular, when Ca of β-type tricalcium phosphate is substituted with Mg etc., since a dissolution rate is low, rapid dissolution is suppressed, and it functions as a bone prosthetic material in vivo more safely. β-type tricalcium phosphate covered with an apatite does not physicochemically dissolve in a physiological environment. However, even after an apatite phase is absorbed by osteoclasts, since dissolution is relatively unlikely, it can be relatively safely used in a portion in which an osteogenic potential is low.

(Calcium Carbonate)

Calcium carbonate is a compound whose composition is $CaCO_3$. Polymorphs such as calcite, vaterite, and aragonite are known. In addition, amorphous calcium carbonate is known.

All of these have excellent tissue compatibility but their behaviors in vivo are different. In addition, a body fluid is unsaturated with any calcium carbonate and calcium carbonate physicochemically dissolves in a physiological environment.

Calcite is in the most stable phase among polymorphs of calcium carbonate. Therefore, a physicochemical dissolution rate after an apatite of apatite covered calcite is absorbed by osteoclasts is the slowest. Therefore, it is easy to balance osteogenesis and calcite absorption and it is effective when a bone defect is relatively large.

Vaterite is in the most unstable phase among polymorphs of calcium carbonate. Therefore, a physicochemical dissolution rate after an apatite of apatite covered vaterite is absorbed by osteoclasts is the fastest. Therefore, it is effective when a bone defect is relatively small and osteogenesis is vigorous and when rapid bone replacement is expected.

Aragonite has intermediate stability between calcite and vaterite. Therefore, aragonite shows an intermediate behavior between both in vivo.

Amorphous calcium carbonate has a higher solubility than vaterite. In addition, since a bulk density is low, a mechanical strength is limited compared to vaterite. Since it dissolves more easily than vaterite, it is suitable when bone replacement equal to or faster than that with vaterite is desired.

Calcium carbonate may be an artificial material or calcium carbonate may be obtained by carbonating calcium oxide, calcium hydroxide or a mixture thereof.

<Core Portion: Surface Layer Portion>

A volume ratio between a core portion and a surface layer portion (core portion:surface layer portion) is preferably 90:10 to 70:30.

In this volume ratio, when the surface layer portion has the above lower limit value or more, it is possible to more highly satisfy requirements of (A) exhibiting excellent tissue compatibility, (B) exhibiting excellent osteoconductivity, (C) replacing bone, and (D) not dissolving in a physiological environment.

On the other hand, when the core portion has the above lower limit value or more, it is possible to more highly satisfy the requirement of (A) exhibiting excellent tissue compatibility.

<Volume>

In general, it is considered that included components determine whether tissue compatibility is excellent. However, in the bone prosthetic material of the present invention, a structural feature that a volume is $10^{-13}$ m$^3$ or more is related to showing excellent tissue compatibility.

As will be described in the following examples, when a bone prosthetic material having a volume of less than $10^{-13}$ m$^3$ was implanted into a rat, an inflammatory response was observed and sufficient tissue compatibility was not observed. On the other hand, when a bone prosthetic material of $10^{-13}$ m$^3$ or more was used, excellent tissue compatibility was observed. A mechanism of action by which a volume of a bone prosthetic material influences tissue compatibility has not been adequately clarified. However, in the present invention, a volume of $10^{-13}$ m$^3$ or more is one important factor in order for excellent tissue compatibility to be exhibited.

<Shape>

The shape of the bone prosthetic material is not particularly limited. For example, granules, a block body, a foam, a dense body, and a porous body may be exemplified.

Among these, a porous body is superior to a dense body from the viewpoint of rapid bone replacement. Although the mechanism for this has not been entirely adequately clarified, it is speculated as being invasion of osteoblasts into a porous body and a decrease in an amount of materials that osteoclasts absorb.

In addition, porous bodies are classified into independent pore porous bodies or interconnected poreporous bodies. However, an interconnected porous body into which cells can migrate is preferable. Additionally, in consideration of migration into cells, an interconnected porous body having interconnected pores of 10 μm or more and 500 μm or less is preferable, an interconnected porous body having interconnected pores of 15 or more and 400 μm or less is more preferable, and an interconnected porous body having interconnected pores of 20 μm or more and 300 μm or less is most preferable.

[Method of Producing a Bone Prosthetic Material]

The method of producing a bone prosthetic material of the present invention comprises an apatite forming step in which an artificial material that comprises either or both of calcium phosphate and calcium carbonate and has a volume of $10^{-13}$ m$^3$ or more is immersed in water having a pH of 7 or more to form an apatite on a surface layer portion, and either or both of the artificial material and the water comprise a phosphate component.

<Artificial Material>

The artificial material comprises either or both of calcium phosphate and calcium carbonate and has a volume of $10^{-13}$ m$^3$ or more.

Calcium phosphate and calcium carbonate are the same as those described above.

In addition, when an artificial material having a volume of $10^{-13}$ m$^3$ or more is used, it is possible to produce a bone prosthetic material having a volume of $10^{-13}$ m$^3$ or more.

<Apatite Forming Step>

The apatite forming step is a step in which an artificial material is immersed in water having a pH of 7 or more to form an apatite on a surface layer portion. Either or both of the artificial material and the water comprise a phosphate component.

The apatite is in a thermodynamically more stable phase than calcium phosphate and calcium carbonate other than an apatite in a solution including a phosphate component having a pH of 7 or more. In addition, in a solution that includes a phosphate component having a pH of 7 or more and additionally includes carbonate groups, a carbonate apatite is a thermodynamically more stable composition than apatite. Therefore, when the core portion having a thermodynamically unstable composition is immersed in an aqueous solution, a part of the core portion dissolves and a component of the core portion is eluted in the aqueous solution. When the aqueous solution to which a component of the core portion is added is supersaturated with an apatite or a carbonate apatite, an apatite or a carbonate apatite are precipitated on a surface of the core portion from the aqueous solution, a material including an apatite or carbonate apatite covered core portion being produced.

Basically, a reaction in the method of producing a bone prosthetic material of the present invention comprises a basic dissolution reaction of the core portion and a reaction in which a component of the dissolved core portion and a component included in water are precipitated. The precipitation reaction occurs due to supersaturation of an apatite in an aqueous phase near the core portion in which the core portion dissolves and is formed.

Therefore, when the core portion comprises no phosphate component, in order for an apatite in an aqueous phase near the core portion to be supersaturated, water needs to include a phosphate component.

On the other hand, when the core portion comprises a phosphate component, since the phosphate component is supplied near the core portion in an aqueous phase according to the dissolution of the core portion, there is no need for water to include a phosphate component. However, even if a material of the core portion includes a phosphate component, the inclusion of a phosphate component in water has no problems and is actually preferable in consideration of an increase in a degree of supersaturation of an apatite in an aqueous phase near the core portion.

When water includes a phosphate component, a concentration of the phosphate component in water is preferably a 0.01 molar concentration or more, more preferably a 0.1 molar concentration or more, and most preferably a 0.5 molar concentration or more.

The phosphate component used in the apatite forming step is not particularly limited. For example, phosphoric acid, trisodium phosphate, disodium hydrogen phosphate, sodium dihydrogen phosphate, tripotassium phosphate, dipotassium hydrogen phosphate, potassium dihydrogen phosphate, triammonium phosphate, diammonium hydrogen phosphate, ammonium dihydrogen phosphate, disodium ammonium phosphate, potassium disodium phosphate, potassium ammonium phosphate, dipotassium sodium phosphate, sodium diammonium phosphate, potassium diammonium phosphate, sodium potassium hydrogen phosphate, sodium ammonium hydrogen phosphate, and ammonium potassium hydrogen phosphate may be exemplified.

Also, aqueous solutions of a phosphoric acid, a phosphate, or sodium dihydrogen phosphoric acid have a pH that is less than 7. When such a phosphate component is used, it is necessary to set a pH to be 7 or more using sodium hydroxide or the like.

When an aqueous solution including such a phosphate component and having a pH of 7 or more is used, calcium phosphate or a carbonate apatite inferior to apatite is produced. However, it has been found that a bone prosthetic material produced using a solution in which an aqueous solution including a phosphate component contains only sodium as a cation, that is, a sodium phosphoric acid aqueous solution has superior tissue compatibility.

Although the reason for this has not been adequately clarified, it is inferred that sodium, potassium, ammonium, and the like replace some calcium in the apatite structure.

When the core portion includes no carbonate component and a carbonate apatite is formed on a surface layer, it is necessary to include a carbonate component in water.

When the core portion comprises a carbonate component, even if water does not include a carbonate component, since a carbonate component is supplied to water according to the dissolution of the core portion, a bone prosthetic material can be produced. However, even if the core portion comprises a carbonate component, the inclusion of a carbonate component in water has no problems and is actually preferable in consideration of an increase in a degree of supersaturation of a carbonate apatite in an aqueous phase near the core portion.

As the carbonate component, carbonates obtained by directly dissolving carbon dioxide in water may be exemplified in addition to carbonates produced by dissolving sodium hydrogen carbonate or sodium carbonate.

A temperature at which an artificial material is immersed in water is not particularly limited.

It has been found that a low-crystallinity apatite has superior osteoconductivity to a highly crystalline apatite and is easily absorbed by osteoclasts in vivo. As a temperature at which an artificial material of the core portion is immersed in water decreases, an apatite formed has lower crystallinity.

Accordingly, a temperature at which an artificial material of the core portion is immersed in water is preferably less than 100° C., more preferably less than 80° C., and most preferably less than 60° C.

As described above, the crystallinity of an apatite that covers the core portion is preferably low in consideration of osteoconductivity and bone replacement. However, when a temperature at which the core portion comes in contact with an aqueous solution is low, it takes time until apatite covered calcium phosphate or calcium carbonate is produced. In order to reduce a production time, a temperature at which a material of the core portion is brought into contact with an aqueous solution is effectively 100° C. or higher. In this case, since the aqueous solution boils at a normal pressure, it is necessary to set a pressure to be higher than one atmosphere.

These conditions are generally referred to as hydrothermal conditions.

<Pretreatment Step>

In the method of producing a bone prosthetic material of the present invention, before the above-described apatite forming step, a pretreatment step in which an artificial material comprising either or both of calcium phosphate and calcium carbonate and having a volume of $10^{-13}$ m$^3$ or more is brought into contact with an aqueous solution having a pH of 5 or less to obtain a preprocessed artificial material in which calcium hydrogen phosphate is formed on at least a part of a surface layer portion of the artificial material may be preferably performed.

When calcium hydrogen phosphate is formed on the surface layer portion of the artificial material on which the pretreatment step is performed, it is possible to perform the apatite forming step in a short time. In addition, when the pretreatment step is performed at a low temperature, a low-crystallinity apatite can be formed.

In addition, when calcium hydrogen phosphate of the surface layer portion partially remains, calcium hydrogen phosphate dissolves when the bone prosthetic material is implanted into a bone defect, a calcium component and a phosphate component are supplied to body fluids, and osteoconductivity is thus improved.

This is due to a relatively high solubility of calcium hydrogen phosphate. When calcium hydrogen phosphate comes in contact with an aqueous solution having a pH of 7 or more, it dissolves and a phosphate component and a calcium component are supplied to an aqueous solution. Since a solubility of calcium hydrogen phosphate is high, calcium and phosphate ions are dissolved in water from the core portion covered with calcium hydrogen phosphate in advance in a short time. Since an apatite is in a thermodynamically stable phase in a pH of 7 or more, a calcium component and a phosphate component supplied from calcium hydrogen phosphate are precipitated as an apatite and the core portion is covered with the apatite. Since a dissolution reaction of calcium hydrogen phosphate occurs at a relatively low temperature, a low-crystallinity apatite is formed.

In order to easily form calcium hydrogen phosphate, the aqueous solution having a pH of 5 or less preferably comprises a phosphate component and a calcium component.

Regarding the phosphate component and the calcium component, the same phosphate component used in the above-described apatite forming step may be exemplified.

[Action and Effect]

According to the present invention, as a bone prosthetic material, it is possible to provide a bone prosthetic material that highly satisfies all requirements of (A) exhibiting excellent tissue compatibility, (B) exhibiting excellent osteoconductivity, (C) replacing bone, (D) not dissolving in a physiological environment, and (E) being able to be produced at low cost.

EXAMPLES

The present invention will be described below in further detail using examples and comparative examples, but the scope of the present invention is not limited to the examples.
(General Conditions)

In examples and comparative examples, general measurement conditions and raw material inorganic compounds are as follows. Also, when conditions are different from these conditions, they will be described separately.
(Powder X-Ray Diffraction)

A D8 ADVANCE type commercially available from BRUKER was used as a powder X-ray diffractometer. An output was 40 kV and 40 mA. CuKα (λ=0.15418 nm) was used as an X-ray source.

A crystallite size was obtained using the Scherrer equation $\{L=K\lambda/(\beta \cos \theta)\}$. Here, L represents a crystallite size and K represents a Scherrer constant that is 0.9. λ represents an X ray wavelength and is 0.15418 nm for CuKα. β represents the full width at half maximum of a diffraction peak in radians. θ denotes a diffraction angle of a diffraction peak. β is calculated using the equation β=b−B from an actual half maximum (b) to be measured using a half maximum (B) of a highly crystalline material. In the present invention, the half maximum (B) of a highly crystalline material obtained from a highly crystalline alumina (Korundoporbe A13-B77) using an X-ray diffractometer was 0.0061°.

A crystallite size of calcite, which is one type of polymorph of calcium carbonate, was obtained from the full width at half maximum of a peak at 2θ=29.4°.

A crystallite size of a carbonate apatite was obtained from the full width at half maximum of a peak at 2θ=25.9°.
(Raw Material Inorganic Compounds)

Raw material inorganic compounds were produced by a known production method.

Sizes of granules were controlled by grading using a sieve. The granule size was described as a mesh opening of the sieve. For example, when granules that passed through a sieve having a mesh opening of 3 mm but failed to pass through a sieve having a mesh opening of 1 mm, the granules were defined as 1 to 3 mm granules.
(Porosity)

The porosity was obtained from an apparent volume and a density and a weight of a material. Here, the apparent volume is a volume that was calculated using the measured length, width, and height of a product and includes a volume of pores. A volume of pores and a density of a material were used to calculate a weight if the material were a dense body and the porosity was calculated from the ratio to the measured weight.

An interconnected porosity was a value measured using micro CT.
(Micro CT)

An interconnected pore proportion and an interconnected porosity (indicated by a proportion of interconnected pores) of the produced product inorganic compound were measured using an X-ray micro CT (called micro CT and referred to as μCT in some cases). Micro CT measurement was performed using a Skyscan1076 (commercially available from Bruker microCT), and an interconnected porosity was obtained using a CT-Analyzer (commercially available from Bruker microCT).
(Volume)

Volumes of the raw material inorganic compound and the product inorganic compound were calculated by measuring a length, a width, and a height when they were rectangular products. Others were measured using the μCT. Also, in the examples, a volume of the product inorganic compound obtained in the examples was $5 \times 10^{-11}$ m$^3$ or more even if it is not particularly described.
(Scanning Electron Microscope Observation)

The forms of the raw material inorganic compound and the product inorganic compound were observed under conditions of an acceleration voltage at 15 kV after gold vapor deposition using a scanning electron microscope (S-3400N, commercially available from Hitachi, Ltd).

Incidentally, since an inorganic compound according to a dissolution precipitation type composition conversion reaction was included in all of the examples, the formation of a grain boundary formed of non-sinterable grain boundaries was observed in all of the examples.
(Raw Material Inorganic Compound 1: Calcium Sulfate Dihydrate Disk)

A calcium sulfate dihydrate disk was produced from calcium sulfate hemihydrate (New Fujirock commercially available from GC). A calcium sulfate hemihydrate powder was mixed with distilled water at a ratio of water mixed in of 0.2, introduced into a split mold while applying vibration, cured in the mold, and a disk-shaped cured body with a diameter of 6 mm and a thickness of 3 mm was obtained.

The cured body was used as a raw material inorganic compound. A volume was about $2\times10^{-7}$ m$^3$. When composition analysis was performed using the powder X-ray diffractometer, a composition of the cured body was calcium sulfate dihydrate (FIG. 1a). By observation using the scanning electron microscope and observation using the micro CT, no interconnected pores having a length of 80 μm or more were observed. A compressive strength of the raw material inorganic compound was 51.6 MPa.

(Raw Material Inorganic Compound 2: CIP Calcium Sulfate Porous Body Block)

Nylon 6 monofilaments with a diameter of 113 μm and a length of about 2 mm were mixed with calcium sulfate hemihydrate at 10 weight % with respect to the total amount and mixed with water so that a ratio of water mixed in with respect to the calcium sulfate hemihydrate was 0.2.

The obtained paste was wrapped with a water-absorbing paper, put into a rubber container, and isostatically pressed using a cold isostatic pressing device at 50 MPa for 10 minutes after air inside the container was decompressed. The result was removed from the device and additionally cured for one hour. Heating to 800° C. was performed at 1° C. per minute and kept at 800° C. for 5 hours. Then, the sample was cooled in a furnace.

The result was cut into 5 mm square cubes using a low speed diamond cutter and used as a product inorganic compound. A volume was about $1.3\times10^{-7}$ m$^3$.

Figure 1:
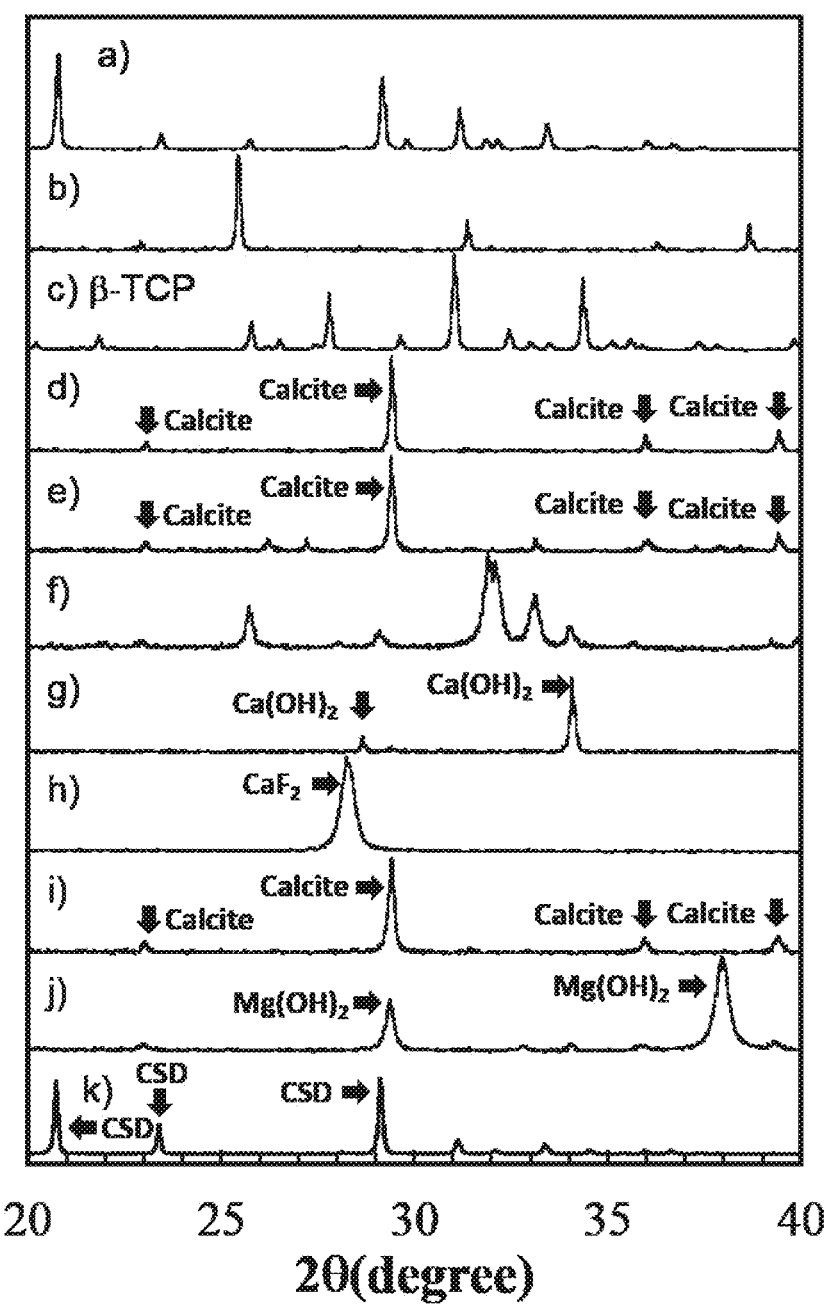
FIG. 1 shows powder X-ray diffraction patterns of raw material inorganic compounds 1 to 3 and product inorganic compounds produced in Examples 1 to 8.
Figure 2:
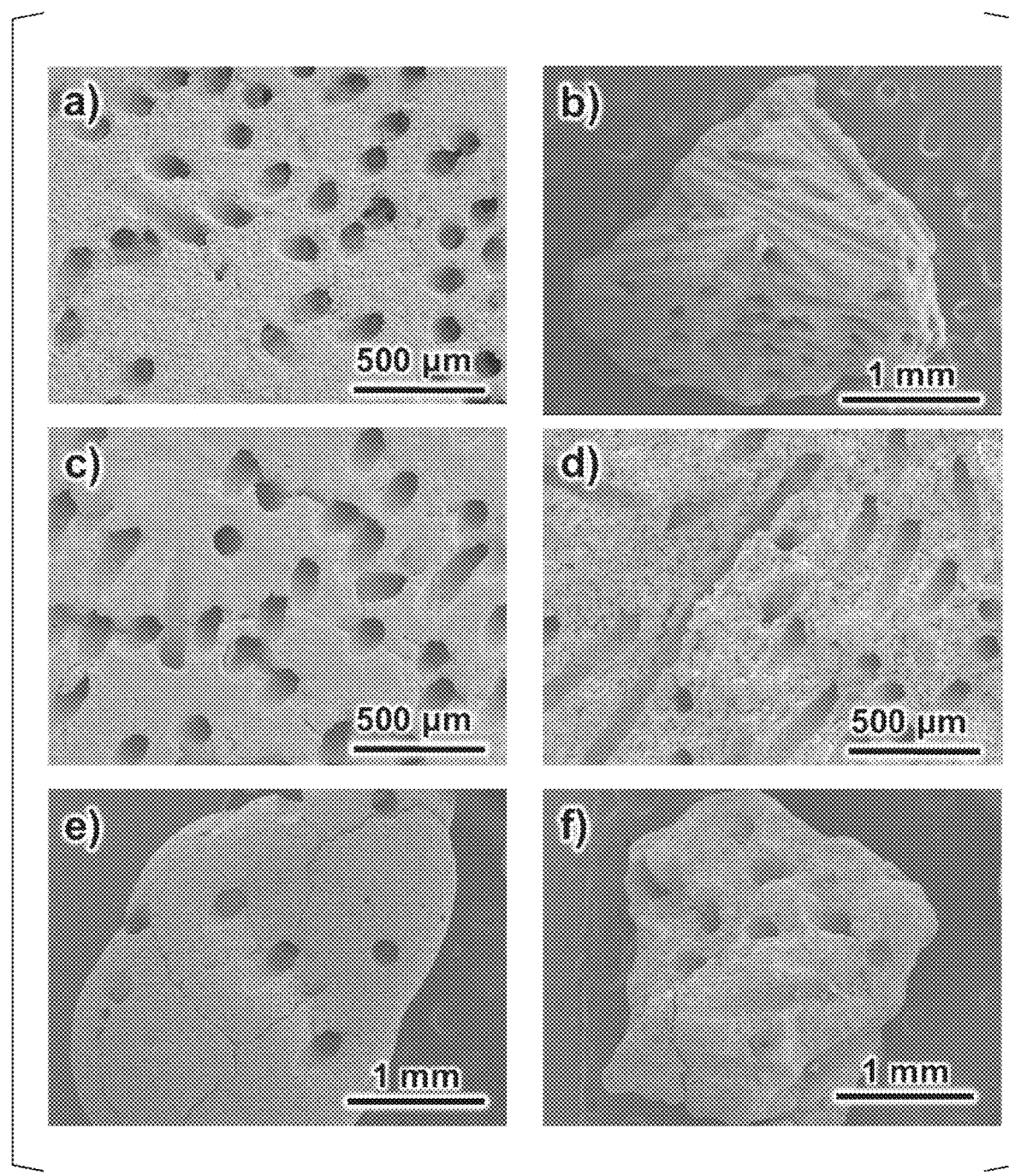
FIG. 2 shows scanning electron microscope images of raw material inorganic compounds 1 to 2 and product inorganic compounds produced in Examples 2 to 5.

When composition analysis was performed using the powder X-ray diffractometer, a composition of the cured body was calcium sulfate anhydrate (b) of FIG. 1). Through the scanning electron microscope image (a) of FIG. 2) of the product inorganic compound and the micro CT, pores with a diameter of 100 μm and a length of at least 2 mm were observed. The aspect ratio of the pore was 20. That is, pores having an aspect ratio of at least 5 or more were observed. A compressive strength of the raw material inorganic compound was 3.3 MPa. It was found that an interconnected porosity was 47% based on the μCT measurement results.

(Raw Material Inorganic Compound 3: Calcium Sulfate Porous Body Granules)

Nylon 6 monofilaments with a diameter of 113 μm and a length of about 2 mm were mixed with calcium sulfate hemihydrate at 10 weight % with respect to the total amount and mixed with water so that a ratio of water mixed in with respect to the calcium sulfate hemihydrate was 0.2. The obtained paste was put into a 5 cm square container and cured for 1 hour while applying vibration. Then, the outside of the cured body removed from the container was removed to about 2 mm. Then, heating was performed to 800° C. at 1° C. per minute and kept at 800° C. for 5 hours. Then, the sample was cooled in a furnace.

The calcined body was pulverized, graded and produced as calcium sulfate porous body granules of 1 to 2 mm. An average volume of the granules was $2\times10^{-9}$ m$^3$.

When composition analysis was performed using the powder X-ray diffractometer, a composition of the cured body was calcium sulfate anhydrite. Through the scanning electron microscope image of the product inorganic compound (b) of FIG. 2) and the micro CT, pores with a diameter of 110 μm and a length of at least 1.7 mm were observed. The aspect ratio of the pore was 15. That is, pores having an aspect ratio of at least 5 or more were observed.

Figure 4:
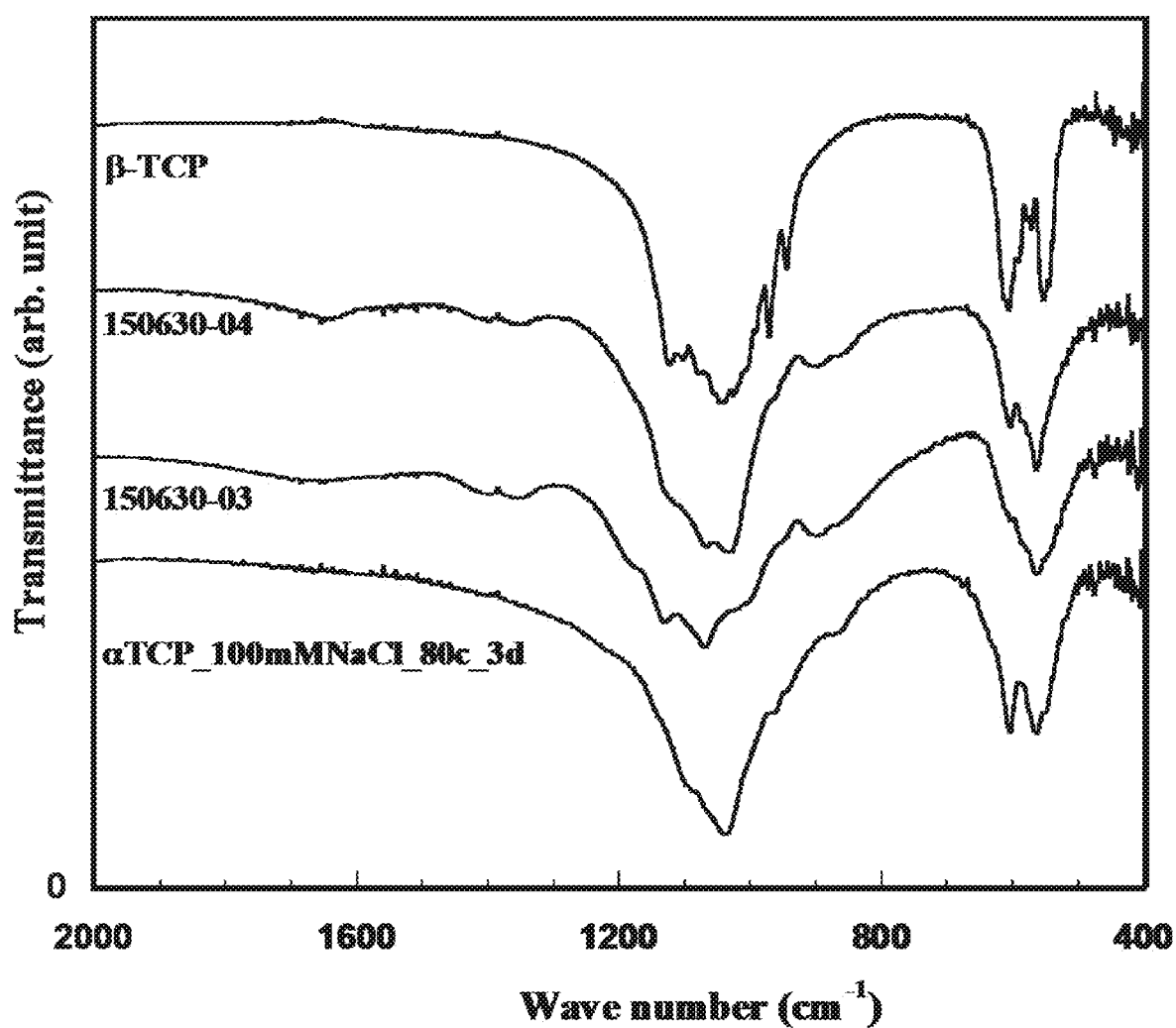
FIG. 4 shows Fourier transform infrared spectrums of a raw material inorganic compound 4, and product inorganic compounds produced in Examples 19, 20, and 22.

(Raw Material Inorganic Compound 4: β-Type Tricalcium Phosphate Granules)

β-type tricalcium phosphate (β-TCP-100) commercially available from Taihei Chemical Industrial Co., Ltd was compacted at 30 MPa and calcined at 1100° C. for 6 hours and a β-type tricalcium phosphate calcined body was produced. The β-type tricalcium phosphate calcined body was pulverized and graded using a sieve. β-type tricalcium phosphate granules of 1 to 2 mm were produced and used as a raw material inorganic compound. An average volume of the granules was $2\times10^{-9}$ m$^3$. Based on powder X-ray diffraction analysis (c) of FIG. 1), it was confirmed that the raw material inorganic compound was β-type tricalcium phosphate. In addition, it was observed that there were no hydrogen phosphate ions based on spectrums (FIG. 4) measured using a Fourier transform infrared spectrophotometer. It was observed that only calcium, phosphorus and oxygen were included based on the composition analysis.

(Raw Material Inorganic Compound 5: α-Type Tricalcium Phosphate Disk)

α-type tricalcium phosphate commercially available from Taihei Chemical Industrial Co., Ltd was compacted at 100 MPa, an α-type tricalcium phosphate powder compacted body was produced and calcined at 1300° C. for 6 hours, and an α-type tricalcium phosphate calcined body with a diameter of 6 mm and a height of 3 mm was used as a raw material inorganic compound. A volume of the sintered body was $2\times10^{-7}$ m$^3$.

(Raw Material Inorganic Compound 6: Calcium Magnesium Carbonate Disk)

Calcium hydroxide and magnesium hydroxide were mixed at a weight ratio of 90:10 and uniaxially pressed at 5 MPa using a mold. The obtained powder compacted body was brought into contact with carbon dioxide at a humidity of 100% at 20° C. and a calcium magnesium carbonate disk was produced. In the produced disk, a diameter was 6 mmΦ and a thickness was 3 mm. A volume of the disk was $2\times10^{-7}$ m$^3$. A composition of the cured body was calcium magnesium carbonate.

(Raw Material Inorganic Compound 7: Calcium Hydrogen Phosphate Dihydrate Calcium Disk)

β-type tricalcium phosphate powder and calcium dihydrogen phosphate powder were mixed at a molar ratio of 1:1. The mixed powder was mixed with water and cured in a split mold. A disk-shaped cured body with a diameter of 6 mm and a thickness of 3 mm was obtained. A volume was $2\times10^{-7}$ m$^3$. When composition analysis was performed using the powder X-ray diffractometer, a composition of the cured body was calcium hydrogen phosphate dihydrate.

(Raw Material Inorganic Compound 8: Carbonate Apatite Granules)

First, calcium carbonate granules were produced. The calcium carbonate granules were prepared such that a calcium hydroxide powder was compacted at 5 MPa and was exposed to carbon dioxide at a humidity of 100% for 24 hours, a block was pulverized and graded, and granules of 300 to 600 μm were produced. The granules were additionally exposed to carbon dioxide at a humidity of 100% for 5 days and the calcium carbonate granules were produced.

Next, the calcium carbonate granules were immersed in a disodium hydrogen phosphoric acid aqueous solution at a 0.5 molar concentration and carbonate apatite granules were produced. An average volume of the granules was $6\times10^{-11}$ m$^3$. It was confirmed that the raw material inorganic compound was a carbonate apatite based on powder X-ray diffraction analysis and Fourier transform infrared spectrophotometer.

(Raw Material Inorganic Compound 9: Hydroxyapatite Granules)

Hydroxyapatite (HAP-100) commercially available from Taihei Chemical Industrial Co., Ltd was compacted at 30 MPa and calcined at 1100° C. for 6 hours, and a hydroxyapatite calcined body was produced. The hydroxyapatite calcined body was pulverized and graded using a sieve. Hydroxyapatite granules of 1 to 2 mm were produced and used as a raw material inorganic compound. An average volume of the granules was $2\times10^{-9}$ m$^3$. It was confirmed that the raw material inorganic compound was a hydroxyapatite through powder X-ray diffraction analysis.

Example 1

A calcium sulfate dihydrate disk (raw material inorganic compound 1) was immersed in a sodium carbonate aqueous solution (50 mL) at a 2 molar concentration at 80° C. for 7 days. There was no change in the apparent form and a volume was $2\times10^{-7}$ m$^3$. Based on composition analysis using the powder X-ray diffractometer, it was confirmed that a composition of the product inorganic compound was calcium carbonate (d) of FIG. 1). A compressive strength of the obtained calcium carbonate was 5 MPa.

Example 2

A calcium sulfate interconnected porous body block (raw material inorganic compound 2) was immersed in a sodium carbonate aqueous solution (50 mL) at a 2 molar concentration at 80° C. for 7 days. There was no change in the apparent form and a volume was $1.3\times10^{-7}$ m$^3$. When composition analysis was performed using the powder X-ray diffractometer, a composition of the product inorganic compound was calcium carbonate (e) of FIG. 1). Through the scanning electron microscope image (c) of FIG. 2) of the product inorganic compound and the micro CT, pores with a diameter of 110 μm and a length of at least 2 mm were observed. The aspect ratio of the pore was 18. That is, pores having an aspect ratio of at least 5 or more were observed. A porosity of the obtained product inorganic compound was 40% and a compressive strength was 2.1 MPa.

Comparative Example 1

Nylon 6 monofilaments with a diameter of 113 μm and a length of about 2 mm were mixed with calcium hydroxide at 10 weight % with respect to the total amount and mixed with water so that a ratio of water mixed in with respect to the calcium hydroxide was 0.2.

The obtained paste was wrapped with a water-absorbing paper, put into a rubber container, and isostatically pressed using a cold isostatic pressing device at 50 MPa for 10 minutes after air inside the container was depressured. The result was removed from the device and additionally dried for 1 hour. Cracks occurred in a drying stage.

The powder compacted body was heated to 800° C. at 1° C. per minute and heated at 800° C. for 5 hours. Then, the sample in a furnace was cooled. Calcium oxide was formed on the calcined body. The calcined body collapsed when immersed in water.

When this comparative example was compared with the calcium sulfate porous body block that was the raw material inorganic compound used in Example 2, the calcium sulfate hemihydrate was cured when mixed with water and the calcium sulfate dihydrate which was the cured body did not thermally decompose even when heated at 800° C. Therefore, it was confirmed that the calcium sulfate porous body block was a unique raw material inorganic compound.

Example 3

The calcium carbonate interconnected porous block produced in Example 2 was immersed in a disodium hydrogen phosphoric acid aqueous solution at a 2 molar concentration at 80° C. for 7 days. There was no change in the apparent form. A volume was $1.3\times10^{-7}$ m$^3$. When composition analysis was performed using the powder X-ray diffractometer (f) of FIG. 1) and the Fourier transform spectrophotometer, a composition of the product inorganic compound was a carbonate apatite. Through the scanning electron microscope image of the product inorganic compound (d) of FIG. 2) and the micro CT, pores with a diameter of 110 μm and a length of at least 2 mm were observed. The aspect ratio of the pore was 18. That is, pores having an aspect ratio of at least 5 or more were observed. A porosity of the obtained product inorganic compound was 38% and a compressive strength was 5.2 MPa.

The obtained carbonate apatite interconnected porous body including pores having an aspect ratio of 5 or more was implanted into a tibia of a rabbit. At a stage 2 weeks after implantation, it was found that bone had invaded into the pores.

Comparative Example 2

A calcium hydroxide powder compacted body was exposed to carbon dioxide to produce a calcium carbonate block. The block was immersed in a disodium hydrogen phosphoric acid aqueous solution at a 2 molar concentration at 80° C. for 7 days and a carbonate apatite block having the same form as in Example 3 was produced. In the carbonate apatite block, there were no pores into which cells can invade and pores having an aspect ratio of at least 5 or more were not observed. At a stage 2 weeks after implantation, osteoconduction was confirmed around the block, but invasion of bone into the block was not observed.

Comparing this comparative example and Example 3, the apatite porous body including pores having an aspect ratio of 5 or more produced in Example 3 was revealed as an excellent bone prosthetic material into which bone can enter.

Example 4

Calcium sulfate porous body granules (a raw material inorganic compound 3) were immersed and rolled in a sodium hydroxide aqueous solution (50 mL) at a 2 molar concentration at 80° C. for 7 days. The exterior was rounded by rolling and there was no change in the apparent form except the rounded exterior. An average volume was $1.8\times10^{-9}$ m$^3$. When composition analysis was performed using the powder X-ray diffractometer, a composition of the product inorganic compound was calcium hydroxide (g) of FIG. 1). Through the scanning electron microscope image of the product inorganic compound (e) of FIG. 2) and the micro CT, pores with a diameter of 110 μm and a length of at least 2 mm were observed. The aspect ratio of the pore was 18. That is, pores having an aspect ratio of at least 5 or more were observed.

Example 5

Calcium sulfate porous body granules (the raw material inorganic compound 3) were immersed and rolled in a sodium fluoride aqueous solution (50 mL) at a 0.5 molar concentration at 80° C. for 10 days. The exterior was rounded by rolling and there was no change in the apparent form except the rounded exterior. An average volume was $1.8\times10^{-9}$ m$^3$. When composition analysis was performed using the powder X-ray diffractometer, it was confirmed that a composition of the product inorganic compound was calcium fluoride (h) of FIG. 1). Through the product inorganic compound scanning electron microscope image (f) of FIG. 2) and the micro CT, pores with a diameter of 110 μm and a length of at least 2 mm were observed. The aspect ratio of the pore was 18. That is, pores having an aspect ratio of at least 5 or more were observed.

Example 6

The calcium hydroxide interconnected porous body produced in Example 4 was used as the raw material inorganic compound and immersed in a sodium carbonate aqueous solution (50 mL) at a 2 molar concentration at 25° C. for 7 days. There was no change in the apparent form and a volume was $1.8 \times 10^{-9}$ m$^3$. When composition analysis was performed using the powder X-ray diffractometer, a composition of the product inorganic compound was calcium carbonate (i) of FIG. 1). Through the scanning electron microscope image of the product inorganic compound and the micro CT, pores with a diameter of 110 μm and a length of at least 1.6 mm were observed. The aspect ratio of the pore was 14. That is, pores having an aspect ratio of at least 5 or more were observed.

Example 7

The calcium hydroxide interconnected porous body produced in Example 4 was used as the raw material inorganic compound and immersed in a magnesium chloride aqueous solution (50 mL) at a 2 molar concentration at 25° C. for 7 days.

There was no change in the apparent form in the produced product inorganic compound. A volume was $1.8 \times 10^{-9}$ m$^3$. When composition analysis was performed using the powder X-ray diffractometer, a composition of the product inorganic compound was magnesium hydroxide (j) of FIG. 1). Through the scanning electron microscope image of the product inorganic compound and the micro CT, pores with a diameter of 110 μm and a length of at least 1.6 mm were observed. The aspect ratio of the pore was 14. That is, pores having an aspect ratio of at least 5 or more were observed.

Example 8

β-type tricalcium phosphate granules (a raw material inorganic compound 4) were immersed in a sodium hydrogen sulfate aqueous solution at a 1 molar concentration at 25° C. for 20 minutes.

There was no change in the apparent form in the produced product inorganic compound. An average volume was $1.8 \times 10^{-9}$ m$^3$. When composition analysis was performed using the powder X-ray diffractometer, a composition of the product inorganic compound was calcium sulfate dihydrate (k) of FIG. 1).

Example 9

Calcium sulfate interconnected porous body granules (the raw material inorganic compound 3) were immersed in a sodium carbonate aqueous solution (50 mL) at a 2 molar concentration at 80° C. for 24 hours.

There was no change in the apparent form in the produced product inorganic compound. A volume was $2 \times 10^{-9}$ m$^3$. When composition analysis was performed using the powder X-ray diffractometer, a composition of the product inorganic compound was calcium carbonate and the polymorph of calcium carbonate was calcite only and vaterite was not detected. Through the scanning electron microscope image of the product inorganic compound and the micro CT, pores with a diameter of 110 μm and a length of at least 2 mm were observed. The aspect ratio of the pore was 18. That is, pores having an aspect ratio of at least 5 or more were observed.

An average diameter of calcium carbonate crystals was 1.9 μm. The full width at half maximum of a peak at 2θ=29.4° measured using the powder X-ray diffractometer was 0.139°. A crystallite size was 105 nm.

Example 10

Calcium sulfate interconnected porous body granules (the raw material inorganic compound 3) were immersed in a sodium carbonate aqueous solution (50 mL) at a 2 molar concentration at 20° C. for 24 hours.

Figure 3:
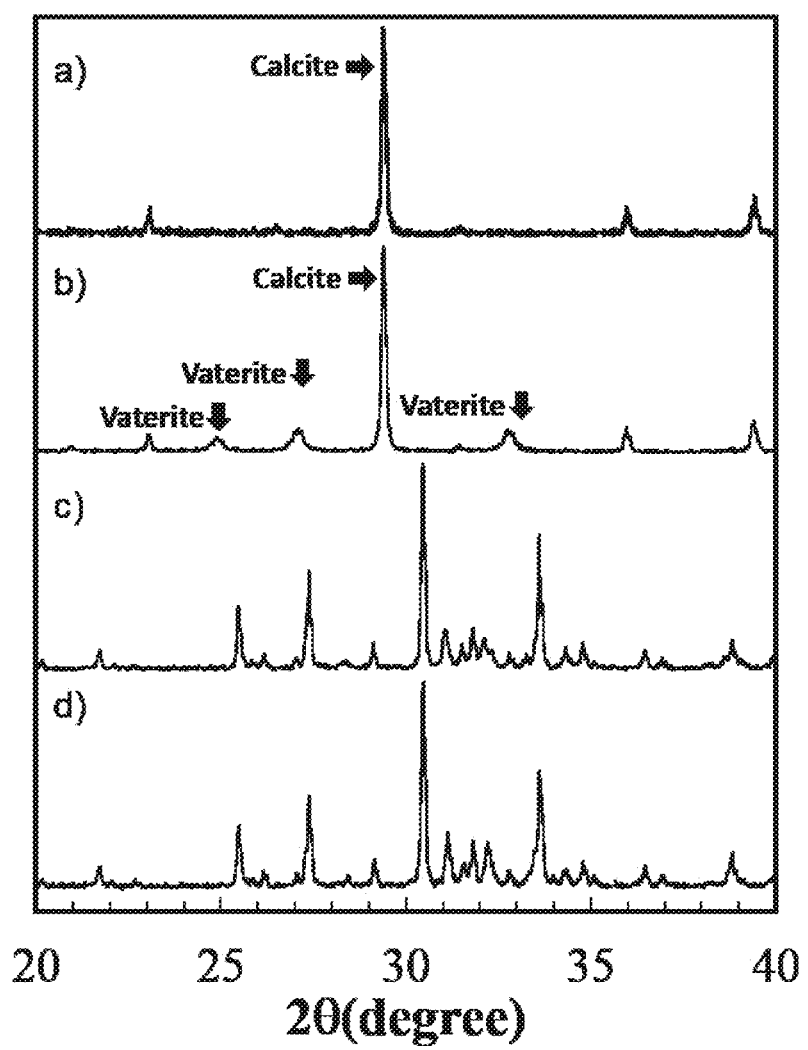
FIG. 3 shows powder X-ray diffraction patterns of product inorganic compounds produced in Examples 10, 11, 19, and 20.

There was no change in the apparent form in the produced product inorganic compound. A volume was $2 \times 10^{-9}$ m$^3$. When composition analysis was performed using the powder X-ray diffractometer, a composition of the product inorganic compound was calcium carbonate, and the polymorph of calcium carbonate was calcite only and vaterite was not detected (a) of FIG. 3). Through the scanning electron microscope image of the product inorganic compound and the micro CT, pores with a diameter of 110 μm and a length of at least 2 mm were observed. The aspect ratio of the pore was 18. That is, pores having an aspect ratio of at least 5 or more were observed.

An average diameter of calcium carbonate crystals was 1.2 μm. The full width at half maximum of a peak at 2θ=29.4° measured using the powder X-ray diffractometer was 0.142°. A crystallite size was 101 nm.

Example 11

Calcium sulfate interconnected porous body granules (the raw material inorganic compound 3) were immersed in a sodium carbonate aqueous solution (50 mL) at a 2 molar concentration at 4° C. for 14 days.

There was no change in the apparent form in the produced product inorganic compound. A volume was $2 \times 10^{-9}$ m$^3$. When composition analysis was performed using the powder X-ray diffractometer, a composition of the product inorganic compound was calcium carbonate and the polymorphs of calcium carbonate were calcite and vaterite (b) of FIG. 3). Through the scanning electron microscope image of the product inorganic compound and the micro CT, pores with a diameter of 110 μm and a length of at least 2 mm were observed. The aspect ratio of the pore was 18. That is, pores having an aspect ratio of at least 5 or more were observed.

An average diameter of calcium carbonate crystals was 0.8 μm. The full width at half maximum of a peak at 2θ=29.4° measured using the powder X-ray diffractometer was 0.147°. A crystallite size was 96 nm.

Example 12

The calcium carbonate interconnected porous body granules (the raw material inorganic compound) produced in Example 11 was immersed in a disodium hydrogen phosphoric acid aqueous solution (50 nit) at a 1 molar concentration at 80° C. for 14 days.

There was no change in the apparent form in the produced product inorganic compound. A volume was $2 \times 10^{-9}$ m$^3$. When composition analysis was performed using the powder X-ray diffractometer and the Fourier transform infrared spectrophotometer, a composition of the product inorganic compound was a carbonate apatite. Through the scanning electron microscope image of the product inorganic compound and the micro CT, pores with a diameter of 110 μm and a length of at least 2 mm were observed. The aspect ratio of the pore was 18. That is, pores having an aspect ratio of at least 5 or more were observed.

A crystallite size of the carbonate apatite measured using the powder X-ray diffractometer was 95 nm.

Example 13

The calcium carbonate interconnected porous body granules (the raw material inorganic compound) produced in Example 11 were immersed in a disodium hydrogen phosphoric acid aqueous solution (50 mL) at a 1 molar concentration at 50° C. for 14 days.

There was no change in the apparent form in the produced product inorganic compound. A volume was $2 \times 10^{-9}$ m$^3$. When composition analysis was performed using the powder X-ray diffractometer and the Fourier transform infrared spectrophotometer, a composition of the product inorganic compound was a carbonate apatite and a small amount of calcium carbonate was also detected. Through the scanning electron microscope image of the product inorganic compound and the micro CT, pores with a diameter of 110 μm and a length of at least 2 mm were observed. The aspect ratio of the pore was 18. That is, pores having an aspect ratio of at least 5 or more were observed.

A crystallite size of the carbonate apatite measured using the powder X-ray diffractometer was 46 nm.

Example 14

The calcium carbonate interconnected porous body granules (the raw material inorganic compound) produced in Example 11 were immersed in a disodium hydrogen phosphoric acid aqueous solution (50 mL) at a 1 molar concentration at 20° C. for 14 days.

There was no change in the apparent form in the produced product inorganic compound. A volume was $2 \times 10^{-9}$ m$^3$. When composition analysis was performed using the powder X-ray diffractometer and the Fourier transform infrared spectrophotometer, a composition of the product inorganic compound was a carbonate apatite and calcium carbonate. Through the scanning electron microscope image of the product inorganic compound and the micro CT, pores with a diameter of 110 μm and a length of at least 2 mm were observed. The aspect ratio of the pore was 18. That is, pores having an aspect ratio of at least 5 or more were observed.

A crystallite size of the carbonate apatite measured using the powder X-ray diffractometer was 24 nm.

Comparing Examples 12, 13, and 14, it was found that, in production of a carbonate apatite from calcium carbonate, the higher the temperature of an electrolyte in which calcium carbonate was immersed, the shorter the time for production. On the other hand, it was found that, when the temperature of the electrolyte was lower, a carbonate apatite having a smaller crystallite size can be produced. When the carbonate apatites of Examples 12, 13, and 14 were implanted in a bone defect formed in a rat skull and histopathologically evaluated after 2 weeks, all of the carbonate apatites showed an excellent tissue reaction and osteoconductivity. However, the invasion of bone into a porous body was particularly superior in the carbonate apatite produced in Example 14, next best in the carbonate apatite produced in Example 13, and the carbonate apatite produced in Example 12 was relatively inferior. Accordingly, it was confirmed that the crystallinity of the carbonate apatite was related to osteoconductivity inside the porous body and a low-crystallinity carbonate apatite has excellent osteoconductivity.

Example 15

Calcium sulfate interconnected porous body granules (the raw material inorganic compound) were immersed in a sodium carbonate aqueous solution (50 mL) at a 2 molar concentration at 4° C. for 7 days.

There was no change in the apparent form in the produced product inorganic compound. A volume was $2 \times 10^{-9}$ m$^3$. When composition analysis was performed using the powder X-ray diffractometer, a composition of the product inorganic compound was mainly calcium carbonate and the polymorphs of calcium carbonate were calcite and vaterite. A part of calcium sulfate remaining was observed. Through the scanning electron microscope image of the product inorganic compound and the micro CT, pores with a diameter of 110 μm and a length of at least 2 mm were observed.

The aspect ratio of the pore was 18. That is, pores having an aspect ratio of at least 5 or more were observed.

An average diameter of calcium carbonate crystals was 0.8 μm. The full width at half maximum of a peak at $2\theta=29.4°$ measured using the powder X-ray diffractometer was 0.147°. A crystallite size was 96 nm.

Example 16

Calcium sulfate interconnected porous body granules (the raw material inorganic compound 3) were immersed in a sodium carbonate aqueous solution (50 mL) at a 2 molar concentration at 4° C. for 7 days.

The sodium carbonate aqueous solution at a 2 molar concentration was replaced every 24 hours.

There was no change in the apparent form in the produced product inorganic compound. A volume was $2 \times 10^{-9}$ m$^3$. When composition analysis was performed using the powder X-ray diffractometer, a composition of the product inorganic compound was calcium carbonate, and the polymorphs of calcium carbonate were calcite and vaterite. Through the scanning electron microscope image of the product inorganic compound and the micro CT, pores with a diameter of 110 μm and a length of at least 2 mm were observed. The aspect ratio of the pore was 18. That is, pores having an aspect ratio of at least 5 or more were observed.

An average diameter of calcium carbonate crystals was 0.8 μm. The full width at half maximum of a peak at $2\theta=29.4°$ measured using the powder X-ray diffractometer was 0.147°. A crystallite size was 96 nm.

Comparing Example 11 and Example 15, it was found that, when the electrolyte aqueous solution in which the product inorganic compound was immersed was replaced during immersing, composition conversion from the raw material inorganic compound to the product inorganic compound was faster.

Example 17

Calcium sulfate interconnected porous body granules (the raw material inorganic compound 3) were immersed in a sodium carbonate aqueous solution (50 mL) at a 2 molar concentration at 4° C. for 7 days. In addition, 20 g of a strong basic ion exchange resin (SA10AOH commercially available from Mitsubishi Chemical Corporation) substituted with carbonate ions in advance was added to an electrolyte aqueous solution.

There was no change in the apparent form in the produced product inorganic compound. A volume was $2\times10^{-9}$ m$^3$. When composition analysis was performed using the powder X-ray diffractometer, a composition of the product inorganic compound was calcium carbonate, and the polymorphs of calcium carbonate were calcite and vaterite. Through the scanning electron microscope image of the product inorganic compound and the micro CT, pores with a diameter of 110 μm and a length of at least 2 mm were observed. The aspect ratio of the pore was 18. That is, pores having an aspect ratio of at least 5 or more were observed.

An average diameter of calcium carbonate crystals was 0.8 μm. The full width at half maximum of a peak at 2θ=29.4° measured using the powder X-ray diffractometer was 0.147°. A crystallite size was 96 nm.

Comparing Example 11 and Example 15, it was found that, when an ion exchange resin was added to an electrolyte aqueous solution, and sulfate ions released from the raw material inorganic compound and not contained in the product inorganic compound were removed, composition conversion from the raw material inorganic compound to the product inorganic compound was faster.

Example 18

A calcium sulfate hemihydrate was mixed with water at a ratio of water mixed in of 0.25 to prepare slurry. A polyurethane foam was immersed in the slurry with excess calcium sulfate slurry being removed, and then cured to cover a surface of the polyurethane foam with calcium sulfate. According to the analysis using the powder X-ray diffractometer, calcium sulfate dihydrate was formed on the surface of the polyurethane foam.

The raw material inorganic compound was immersed in a sodium carbonate aqueous solution at a 1 molar concentration at 4° C. for 1 day.

When analysis was performed using the powder X-ray diffractometer, a composition of the obtained product inorganic compound was calcium carbonate.

A polyurethane foam covered with calcium carbonate was used as the raw material inorganic compound and was immersed in a disodium hydrogen phosphoric acid aqueous solution at a 1 molar concentration at 80° C. for 7 days.

When composition analysis was performed on the obtained product inorganic compound using the powder X-ray diffractometer and the Fourier transform infrared spectrophotometer, a main composition of the product inorganic compound was a carbonate apatite. No change was observed in the internal polyurethane foam.

Example 19

An α-type tricalcium phosphate disk (a raw material inorganic compound 5) was immersed in a sodium chloride aqueous solution (40 mL) at a 0.1 molar concentration at 80° C. for 3 days.

The form of the product inorganic compound after immersing was the same as that before immersing. A volume of the disk was $2\times10^{-7}$ m$^3$. When composition analysis was performed using the powder X-ray diffractometer, a composition of the product inorganic compound was whitlockite (c) of FIG. 3). In addition, in Fourier transform infrared spectroscopy spectrums (FIG. 4), it was found that the product inorganic compound included a hydrogen phosphate group. As the result of ICP plasma analysis, it was found that Na which was an element not included in the raw material inorganic compound was included at 5 weight % in the whitlockite.

Example 20

An α-type tricalcium phosphate disk (the raw material inorganic compound 5) was immersed in a magnesium chloride aqueous solution (40 mL) at a 0.1 molar concentration at 80° C. for 3 days.

The form of the produced product inorganic compound after immersing was the same as that before immersing. A volume of the disk was $2\times10^{-7}$ m$^3$. When composition analysis was performed using the powder X-ray diffractometer, a composition of the product inorganic compound was whitlockite (d) of FIG. 3). In addition, in Fourier transform infrared spectroscopy spectrums (FIG. 4), it was found that the product inorganic compound included a hydrogen phosphate group. As the result of ICP plasma analysis, it was found that magnesium which was an element not included in the raw material inorganic compound was included at 4 weight % in the whitlockite.

Example 21

A calcium magnesium carbonate disk (a raw material inorganic compound 6) was immersed in a disodium hydrogen phosphoric acid aqueous solution at a 1 molar concentration at 150° C. for 7 days and the product inorganic compound was produced.

The form of the produced product inorganic compound after immersing was the same as that before immersing. A volume of the disk was $2\times10^{-7}$ m$^3$. When composition analysis was performed using the powder X-ray diffractometer, a composition of the product inorganic compound was whitlockite. In addition, in Fourier transform infrared spectroscopy spectrums, it was found that the product inorganic compound included a hydrogen phosphate group. As the result of ICP plasma analysis, it was found that magnesium which was an element not included in the raw material inorganic compound was included at 4 weight % in the whitlockite.

Example 22

A calcium hydrogen phosphate dihydrate calcium disk (a raw material inorganic compound 7) was immersed in a disodium hydrogen phosphoric acid aqueous solution at a 1 molar concentration at 80° C. for 7 days and the product inorganic compound was produced.

The form of the produced product inorganic compound after immersing was the same as that before immersing. When composition analysis was performed using the powder X-ray diffractometer, a composition of the product inorganic compound was whitlockite. In addition, in Fourier transform infrared spectroscopy spectrums (FIG. 4), it was found that the product inorganic compound included a hydrogen phosphate group. As the result of ICP plasma analysis, it was found that magnesium which was an element not included in the raw material inorganic compound was included at 4 weight % in the whitlockite.

Example 23

0.5 g of β-type tricalcium phosphate granules (the raw material inorganic compound 4) were immersed in a sodium hydrogen carbonate aqueous solution (50 mL) at a 2 molar concentration at 80° C. for 24 hours.

Figure 5:
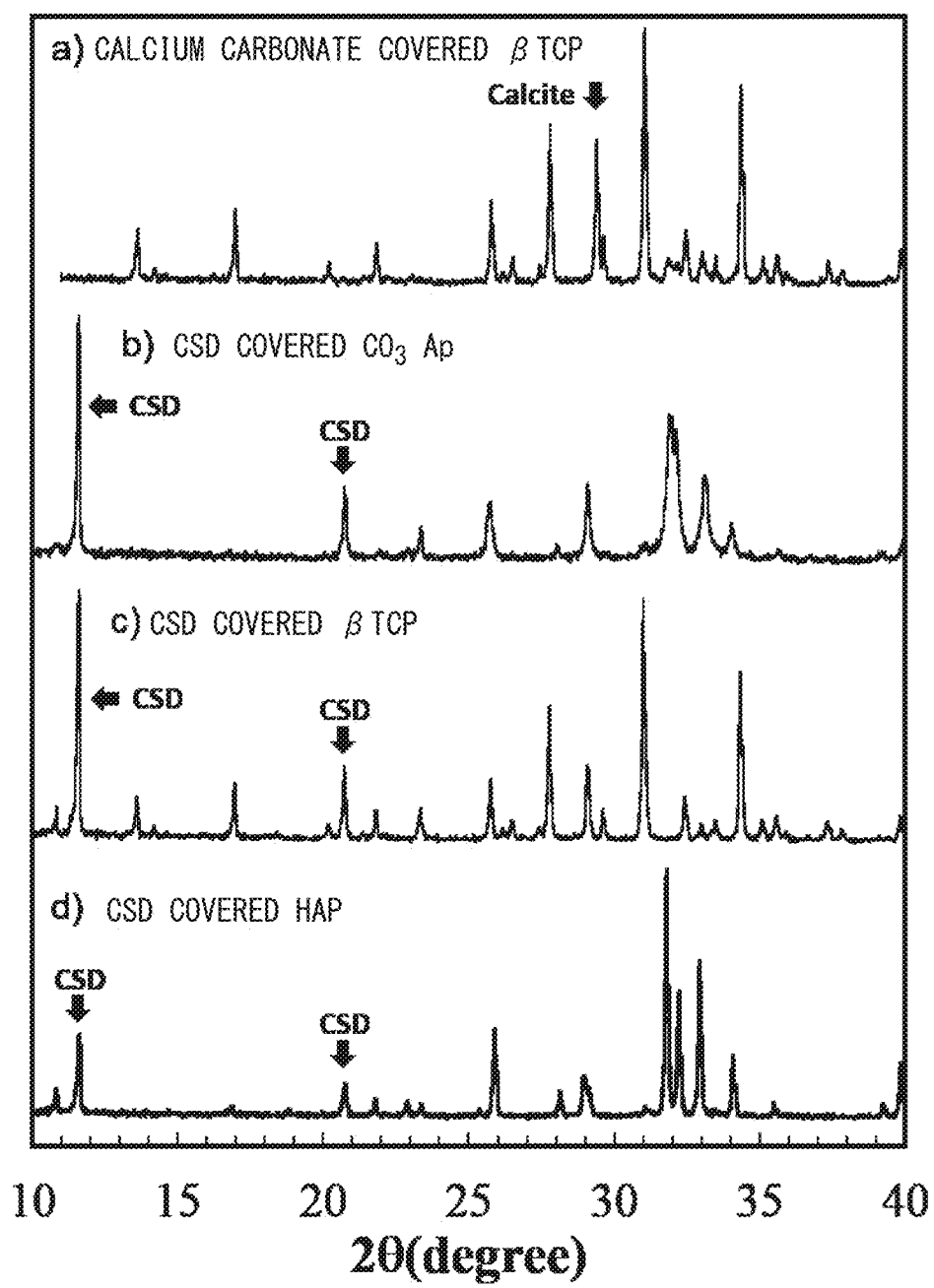
FIG. 5 shows powder X-ray diffraction patterns of product inorganic compounds produced in Examples 23 to 28.

The form of the produced product inorganic compound after immersing was the same as that before immersing. A volume was $2 \times 10^{-9}$ m$^3$. When composition analysis was performed using the powder X-ray diffractometer, a composition of the product inorganic compound was a mixture of β-type tricalcium phosphate and calcium carbonate (a) of FIG. 5). When the product inorganic compound was embedded in a resin, polished and subjected to EDAX analysis, it was found that the surface layer portion was calcium carbonate and the inside was β-type tricalcium phosphate. A thickness of the surface layer portion was 180 An amount of calcium carbonate in the product inorganic compound was 54 weight %.

A bone defect with a diameter of 4 mm formed in a rat skull was reconstructed using the produced calcium carbonate covered β-type tricalcium phosphate granules. Based on a histopathological image after 4 weeks, it was found that the calcium carbonate covered β-type tricalcium phosphate granules serving as the product inorganic compound exhibited excellent tissue compatibility.

In addition, it was confirmed that bone grew on surfaces of the produced calcium carbonate covered β-type tricalcium phosphate granules. An osteogenesis rate was 70%.

Example 24

0.5 g of carbonate apatite granules (raw material inorganic compound 8) were immersed in a sodium hydrogen sulfate aqueous solution (20 mL) at a 0.1 molar concentration at 80° C. for 6 hours.

The form of the produced product inorganic compound after immersing was the same as that before immersing. A volume was $6 \times 10^{-11}$ m$^3$. When composition analysis was performed using the powder X-ray diffractometer, a composition of the product inorganic compound was a mixture of a carbonate apatite and calcium sulfate dihydrate (b) of FIG. 5). When the product inorganic compound was embedded in a resin, polished and subjected to EDAX analysis, it was found that the surface layer portion was calcium sulfate and the inside was a carbonate apatite. A thickness of the surface layer portion was 35 μm. An amount of calcium sulfate in the product inorganic compound was 36 weight %.

A bone defect with a diameter of 4 mm formed in a rat skull was reconstructed using the produced calcium sulfate covered carbonate apatite granule. Based on a histopathological image 4 weeks after implantation, the calcium sulfate covered carbonate apatite granules serving as the product inorganic compound exhibited excellent tissue compatibility.

In addition, it was confirmed that bone grew on surfaces of the produced calcium sulfate covered carbonate apatite granules. An osteogenesis rate was 80%.

Example 25

0.5 g of β-type tricalcium phosphate granules (the raw material inorganic compound 4) were immersed in a sodium hydrogen sulfate aqueous solution (20 mL) at a 0.1 molar concentration at 80° C. for 3 hours.

The form of the produced product inorganic compound after immersing was the same as that before immersing. A volume was $2 \times 10^{-9}$ m$^3$. When composition analysis was performed using the powder X-ray diffractometer, a composition of the product inorganic compound was a mixture of β-type tricalcium phosphate and calcium sulfate dihydrate (c) of FIG. 5). When the product inorganic compound was embedded in a resin, polished and subjected to EDAX analysis, it was found that the surface layer portion was calcium sulfate and the inside was β-type tricalcium phosphate. A thickness of the surface layer portion was 20 μm and an amount of calcium sulfate in the product inorganic compound was 8 weight %.

A bone defect with a diameter of 4 mm formed in a rat skull was reconstructed using the produced calcium sulfate covered β-type tricalcium phosphate granules. Based on a histopathological image, the calcium sulfate covered β-type tricalcium phosphate granules serving as the product inorganic compound exhibited excellent tissue compatibility.

In addition, it was confirmed that bone grew on surfaces of the produced calcium sulfate covered β-type tricalcium phosphate granules. An osteogenesis rate was 75%.

Example 26

0.5 g of hydroxyapatite granules (a raw material inorganic compound 9) were immersed in a sodium hydrogen sulfate aqueous solution (20 mL) at a 0.1 molar concentration at 80° C. for 6 hours.

The form of the produced product inorganic compound after immersing was the same as that before immersing. A volume was $2 \times 10^{-9}$ m$^3$. When composition analysis was performed using the powder X-ray diffractometer, a composition of the product inorganic compound was a mixture of a hydroxyapatite and calcium sulfate dihydrate (d) of FIG. 5). When the product inorganic compound was embedded in a resin, polished and subjected to EDAX analysis, it was found that the surface layer portion was calcium sulfate and the inside was a hydroxyapatite. A thickness of the surface layer portion was 40 μm and an amount of calcium sulfate in the product inorganic compound was 17 weight %.

A bone defect with a diameter of 4 mm formed in a rat skull was reconstructed using the produced calcium sulfate covered hydroxyapatite granules. Based on a histopathological image, it was found that the calcium sulfate covered β hydroxyapatite granules serving as the product inorganic compound exhibited excellent tissue compatibility.

In addition, it was confirmed that bone grew on surfaces of the produced calcium sulfate covered hydroxyapatite granules. An osteogenesis rate was 75%.

Example 27

Calcium hydroxide (commercially available from Nacalai Tesque, Inc.) was compacted at 20 MPa, and reacted at 20° C. with carbon dioxide bubbled into distilled water at 20° C. for 7 days. It was found that the product was calcite crystalline calcium carbonate based on powder X-ray diffraction of the produced material. In addition, it was confirmed that the core portion was a material that satisfied a requirement that a material is artificially produced from calcium hydroxide which is a chemically synthesized material and does not include a natural product.

Next, calcium carbonate was pulverized and sized to 300 μm to 600 μm using a sieve.

The calcium carbonate granules were immersed in a disodium hydrogen phosphate (commercially available from Nacalai Tesque, Inc.) aqueous solution at a 1 molar concentration at 40° C. for 4 hours and 16 hours. A pH of the disodium hydrogen phosphoric acid aqueous solution at a 1 molar concentration was 9.2.

Figure 6:
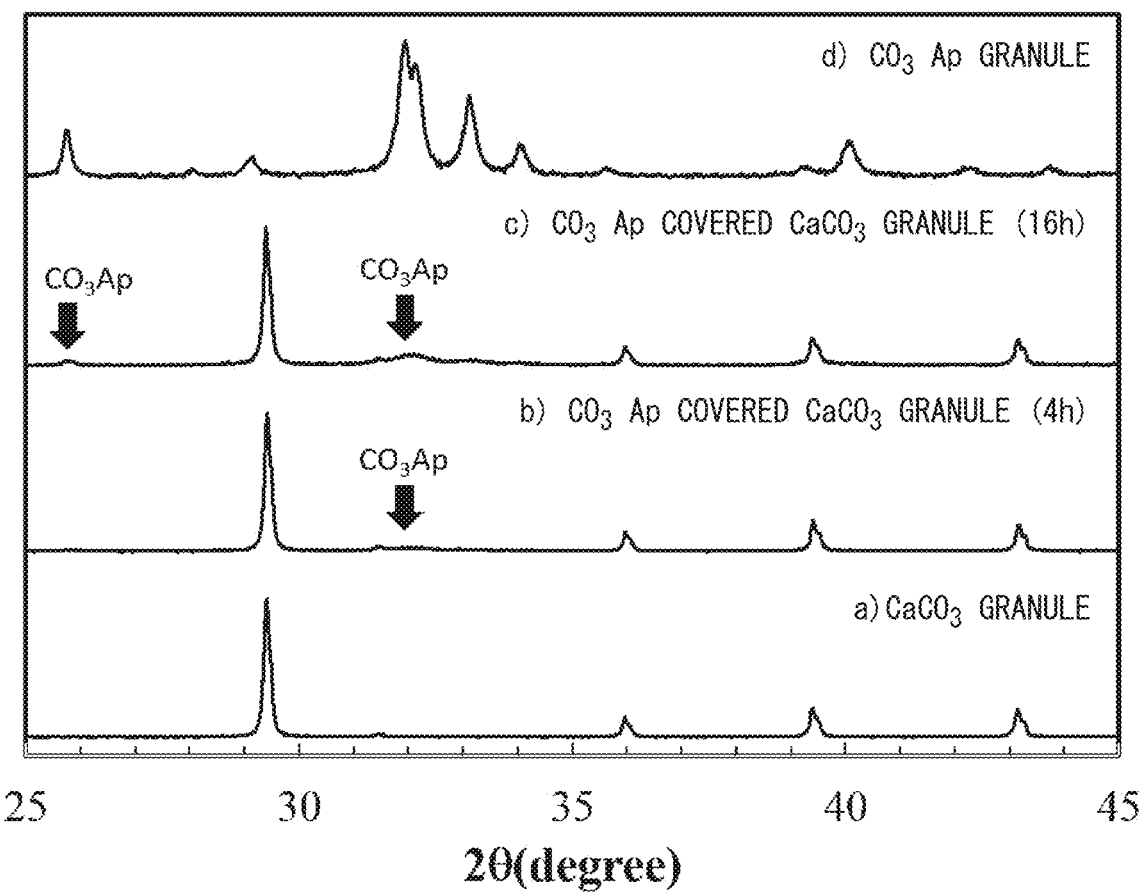
FIG. 6 shows data obtained through powder X-ray diffraction performed in Example 27.

The a) of FIG. 6 shows a powder X-ray diffraction image of calcium carbonate granules. The b) of FIG. 6 shows a powder X-ray diffraction image of granules obtained by treating calcium carbonate granules with a disodium hydrogen phosphoric acid aqueous solution for 4 hours. The c) of FIG. 6 shows a powder X-ray diffraction image of granules obtained by treating calcium carbonate granules with a disodium hydrogen phosphoric acid aqueous solution for 16 hours. The d) of FIG. 6 shows a powder X-ray diffraction image of a carbonate apatite reference sample.

In the granules shown in the b) of FIG. 6 and the c) of FIG. 6, in addition to the diffraction pattern derived from calcium carbonate of the a) of FIG. 6, a carbonate apatite shown in the d) of FIG. 6 is observed. Therefore, it can be understood that calcium carbonate reacts with a disodium hydrogen phosphoric acid aqueous solution and a carbonate apatite is formed. The formation of the carbonate apatite was confirmed from an absorption peak position specific to a carbonate apatite using the Fourier transform spectrophotometer.

Figure 7:
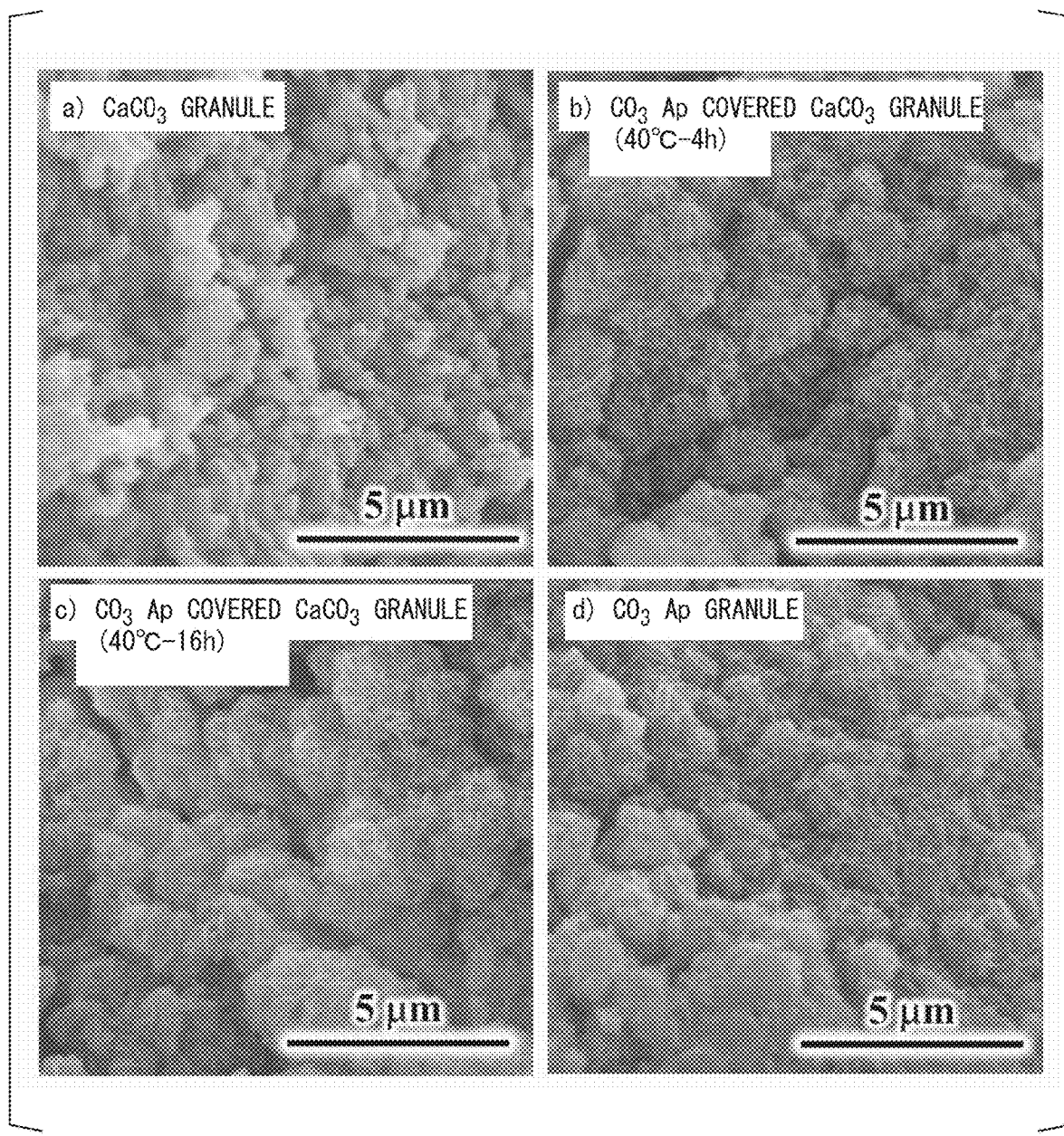
FIG. 7 shows scanning electron microscope images captured in Example 27.

The a) of FIG. 7 shows a scanning electron microscope image of calcium carbonate granules. The b) of FIG. 7 shows a scanning electron microscope image of granules obtained by treating calcium carbonate granules with a disodium hydrogen phosphoric acid aqueous solution for 4 hours. The c) of FIG. 7 shows a scanning electron microscope image of granules obtained by treating calcium carbonate granules with a disodium hydrogen phosphoric acid aqueous solution for 16 hours. The d) of FIG. 7 shows a scanning electron microscope image of carbonate apatite granules. Also, in the d) of FIG. 7, the carbonate apatite granules are granules obtained by treating calcium carbonate granules with a disodium hydrogen phosphoric acid aqueous solution at a 1 molar concentration at 60° C. for 10 days, and it was separately confirmed, based on powder X-ray diffraction that calcium carbonate was not detected and only an apatite phase was observed.

Surface forms of granules of the b) of FIG. 7 and the c) of FIG. 7 were different from surface forms of calcium carbonate shown in the a) of FIG. 7, and the same form as carbonate apatite shown in the d) of FIG. 7 was observed. In addition, it was found from peak areas derived from a carbonate apatite that the granules in the b) of FIG. 7 have a composition including a carbonate apatite at 10 mass % and calcium carbonate at 90 mass % and the granules in the c) of FIG. 7 have a composition including a carbonate apatite at 30 mass % and calcium carbonate at 70 mass %.

Figure 8:
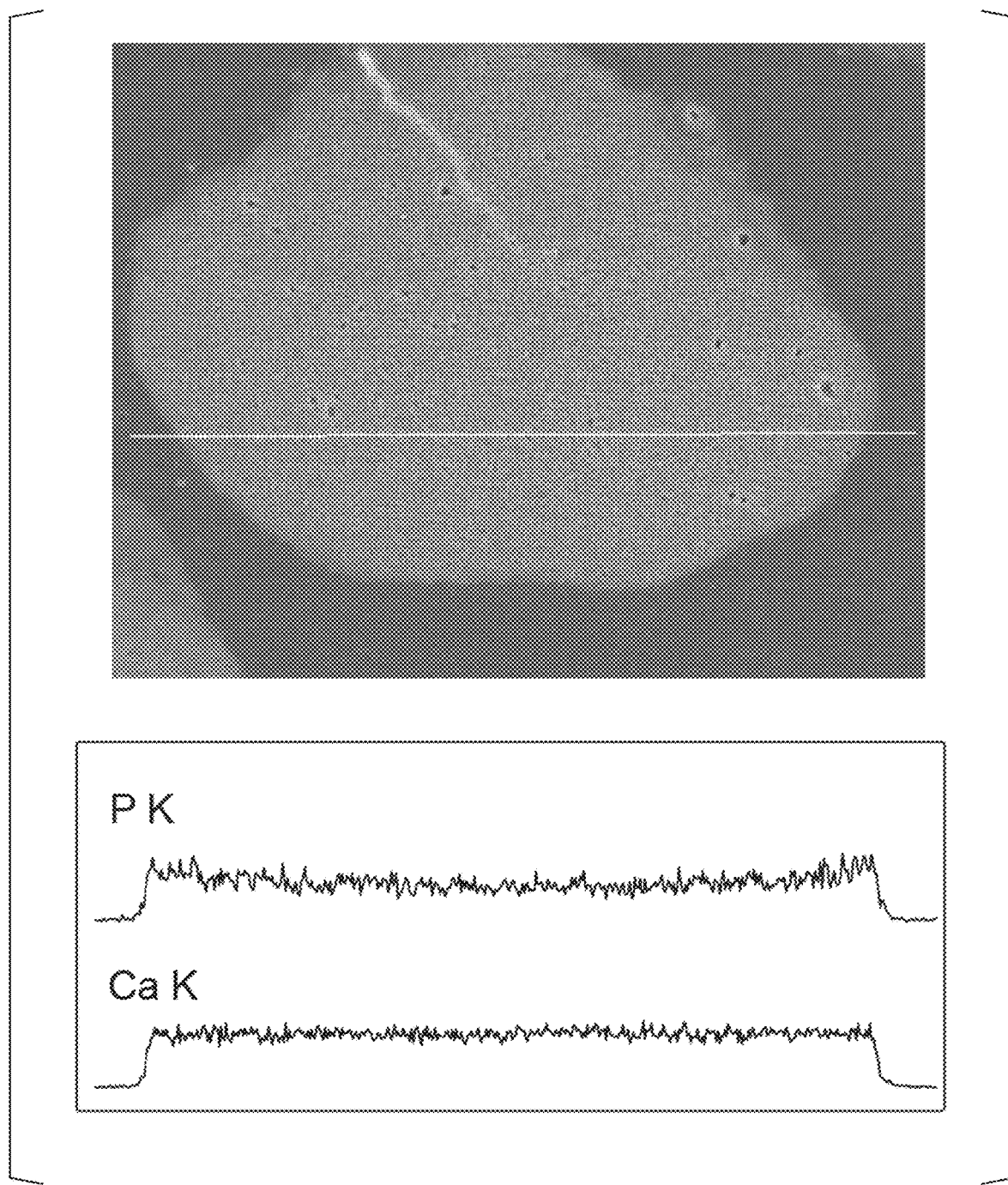
FIG. 8 shows data obtained by element analysis using an energy-dispersive X-ray analyzing device that is performed in Example 27.

FIG. 8 shows a scanning electron microscope image of a cross section of a granule obtained when the calcium carbonate granules shown in the c) of FIG. 6 were treated with a disodium hydrogen phosphoric acid aqueous solution for 16 hours and the granules were embedded in a resin and polished, and the elemental analysis results obtained using an energy-dispersive X-ray analyzing device. The white line part indicates an analysis portion. PK indicates the analysis result for phosphorus and CaK indicates the analysis result for calcium. It was confirmed that phosphorus was observed on surfaces of granules, no phosphorus was observed inside the granule, and no significant difference was detected in calcium.

It can be understood that, theoretically, a reaction occurred on surfaces when calcium carbonate granules reacted in a disodium hydrogen phosphoric acid aqueous solution and it was possible to produce granules of which the surface layer portion was a carbonate apatite and the core portion was calcium carbonate from the scanning electron microscope observation on the surface shown in FIG. 7 and the elemental analysis result obtained using the energy-dispersive X-ray analyzing device and the scanning electron microscope observation on a fractured surface shown in FIG. 8.

A volume of the produced granules was about $10^{-11}$ m$^3$, which was $10^{-13}$ m$^3$ or more.

Figure 9:
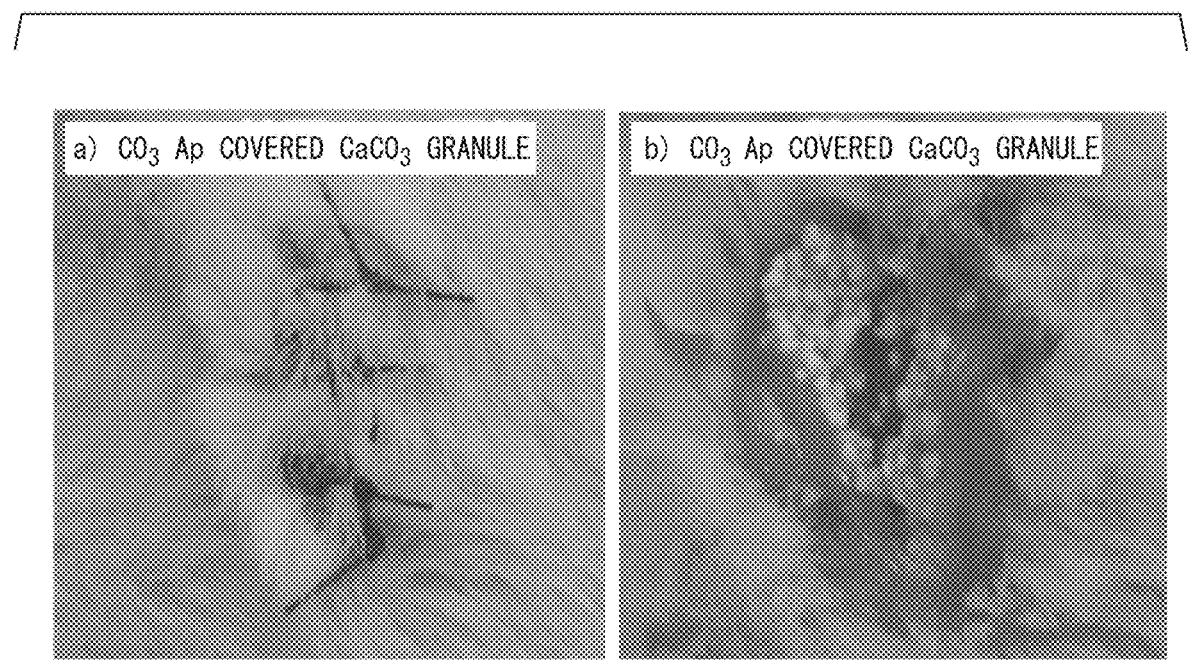
FIG. 9 shows the results according to an implantation test performed in Example 27.

In order to verify tissue compatibility of the produced bone prosthetic material, 0.1 g of granules were implanted subcutaneously into a rat. The a) of FIG. 9 shows the results 1 week after implantation. The b) of FIG. 9 shows the results when the implantation part was cut. Even though carbonate apatite covered calcium carbonate granules were implanted subcutaneously into a rat, no swelling was observed. In addition, when the implantation part was cut, carbonate apatite covered calcium carbonate granules were observed and no inflammatory exudate was observed. Based on such results, it was found that the carbonate apatite covered calcium carbonate granules exhibited excellent tissue compatibility.

Figure 10:
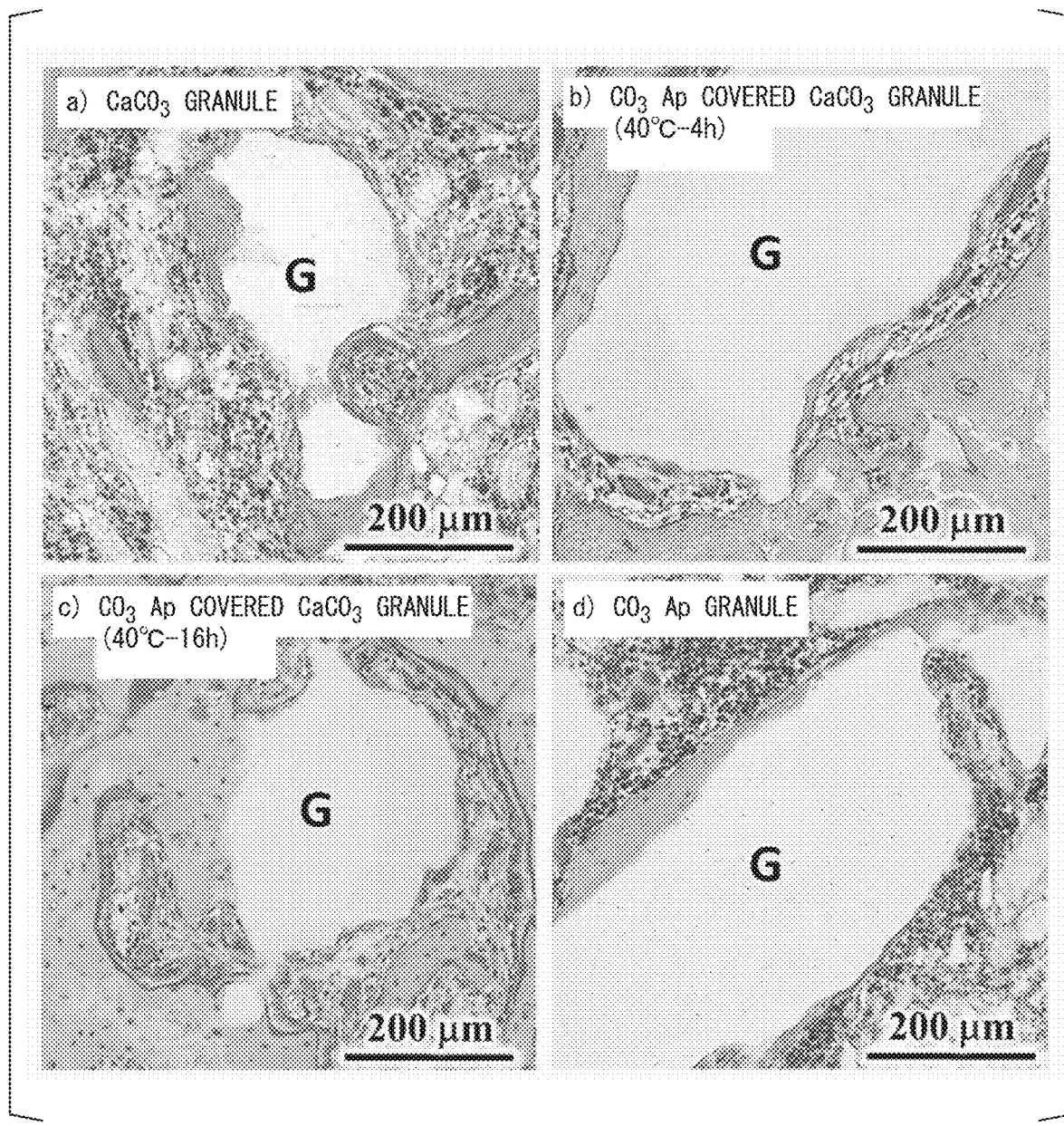
FIG. 10 shows Villanueva-Goldner staining results in an implantation test on a bone defect performed in Example 27.

In order to further examine usefulness of the produced carbonate apatite covered calcium carbonate granules as a bone prosthetic material, a bone defect with a diameter of 6 mm was formed in a skull of a Japanese white house male rabbit using a trephine bar, 10 mass % carbonate apatite covered calcium carbonate granules and 30 mass % carbonate apatite covered calcium carbonate granules were implanted, and histopathological evaluation was performed after 4 weeks and 8 weeks. FIG. 10 shows the results obtained when tissues after 4 weeks were stained with Villanueva-Goldner. In this staining, since the granules dropped off, they were white and mature bone was stained in green.

It was clearly confirmed that the carbonate apatite covered calcium carbonate granules (b) of FIG. 10 and The c) of FIG. 10 of the present invention had a larger amount of mature bone than the calcium carbonate granules (a) of FIG. 10) and the carbonate apatite granules (d) of FIG. 10) that were materials outside the scope of the present invention.

New bone areas after 4 weeks and 8 weeks from the operation are shown in Table 1.

TABLE 1

Usability of carbonate apatite covered calcium carbonate granules for reconstructing house rabbit skull defect.

| Type of granules | New bone area (%) | |
|---|---|---|
| | After 4 weeks | After 8 weeks |
| 10% carbonate apatite covered calcium carbonate | 20 | 27 |
| 30% carbonate apatite covered calcium carbonate | 19 | 25 |
| Calcium carbonate | 14 | 4 |
| Carbonate apatite | 11 | 23 |

In the new bone area 4 weeks after the operation, there was 20% of 10 mass % carbonate apatite covered calcium carbonate granules, and 19% of 30 mass % carbonate apatite covered calcium carbonate granules, but there was 14% of calcium carbonate which was a material outside the scope of the present invention, and 11% of a carbonate apatite which was a material outside the scope of the present invention.

In addition, in the new bone area 8 weeks after the operation, there was 27% 10 mass % carbonate apatite covered calcium carbonate granules, and 25% 30 mass % carbonate apatite covered calcium carbonate granules, but there was 4% calcium carbonate which was a material outside the scope of the present invention and a 23% carbonate apatite which was a material outside the scope of the present invention. It was found that carbonate apatite covered calcium carbonate of the present invention had a superior amount of osteogenesis.

Comparative Example 3

Figure 11:
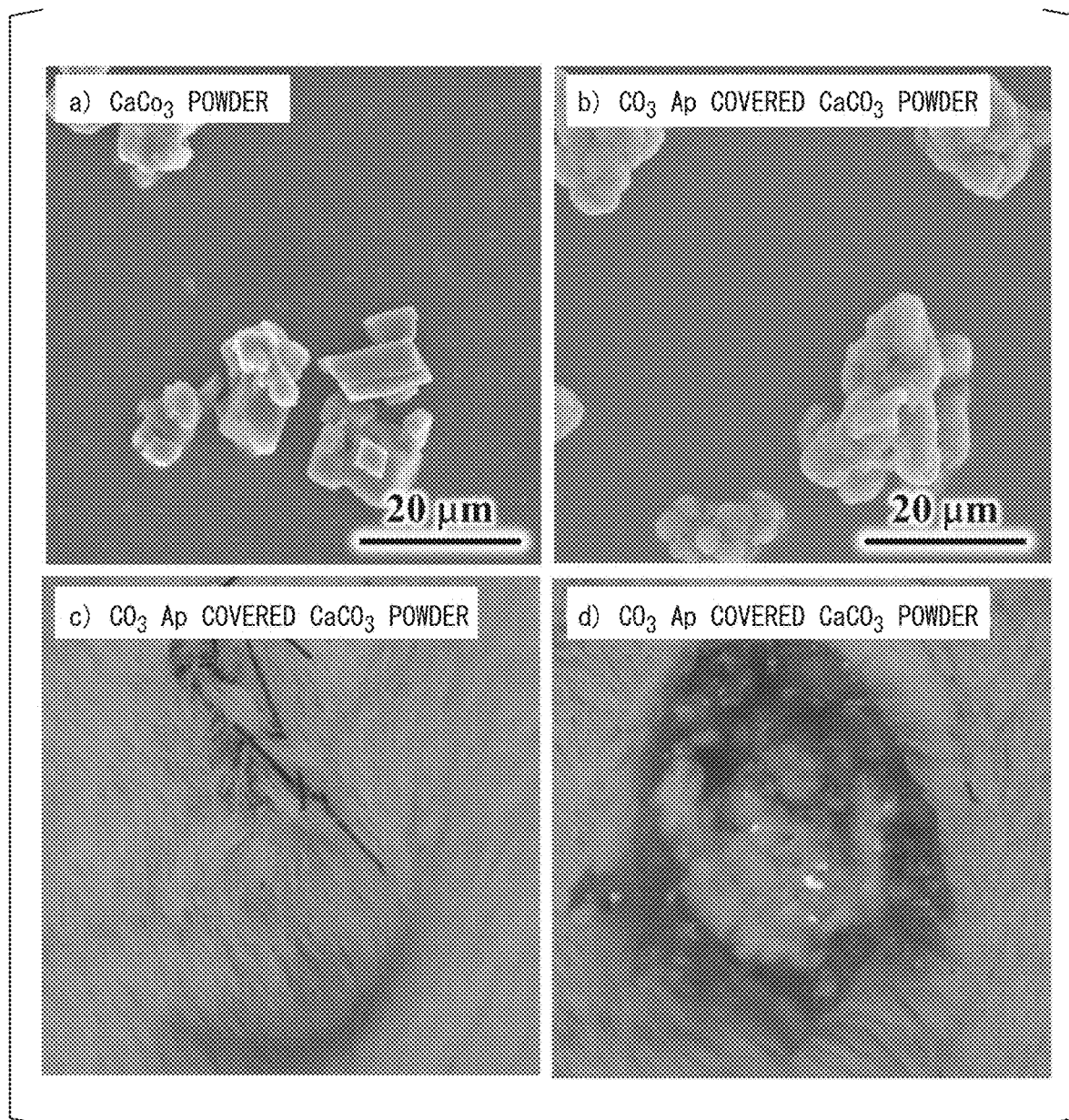
FIG. 11 shows scanning electron microscope images (a and b) captured in Comparative Example 3 and the results (c and d) in an implantation test.

Calcium carbonate powder was immersed in a disodium hydrogen phosphoric acid aqueous solution (pH 9.2) at a 1 molar concentration at 80° C. for 24 hours. The a) of FIG. 11 and the b) of FIG. 11 show scanning electron microscope images of calcium carbonate used for production and the produced powder. Since a volume of the produced powder particles was about $4 \times 10^{-15}$ m$^3$, it was determined as a material having a volume of less than $10^{-13}$ m$^3$ outside the scope of the present invention.

Figure 12:
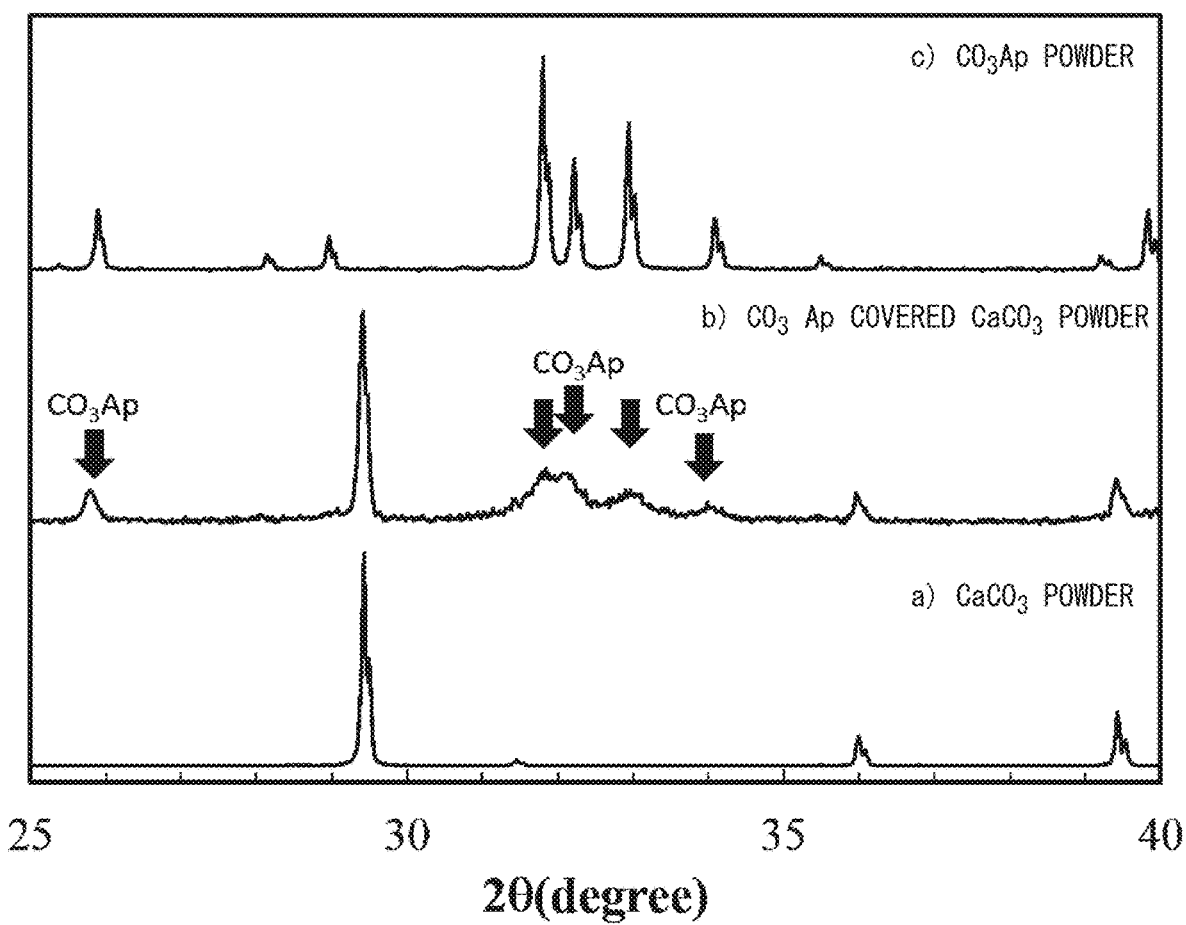
FIG. 12 shows data obtained through powder X-ray diffraction performed in Comparative Example 3.

The a) of FIG. 12 shows a powder X-ray diffraction image of calcium carbonate powder used for production. The b) of FIG. 12 shows a powder X-ray diffraction image of powder obtained by reacting calcium carbonate powder with a disodium hydrogen phosphoric acid aqueous solution. The c) of FIG. 12 shows a powder X-ray diffraction image of a carbonate apatite. The produced powder in the b) of FIG. 12 was determined as a carbonate apatite covered calcium carbonate powder.

In order to verify tissue compatibility of the produced carbonate apatite covered calcium carbonate powder, 0.1 g of the powder was implanted subcutaneously into a rat. The c) of FIG. 11 shows the results 1 week after implantation. The d) of FIG. 11 shows the results when the implantation part was cut. When the carbonate apatite covered calcium carbonate powder was implanted subcutaneously into a rat, swelling was observed. In addition, when the implantation part was cut, a light yellow transparent inflammatory exudate was observed. Based on such results, it was found that the carbonate apatite covered calcium carbonate powder caused an inflammatory response.

In both the products of Example 27 and Comparative Example 3, the surface layer portion was a carbonate apatite and the core portion was calcium carbonate. In addition, in both the produced products, the core portion was an artificially produced material. A difference between them was only a volume. When the carbonate apatite covered calcium carbonate had a volume of less than $10^{-13}$ m$^3$, an inflammatory response was caused.

Comparative Example 4

In order to produce a material including a natural product core portion and a carbonate apatite surface layer portion, littleneck clam shells were pulverized to produce littleneck clam shell powder. It is known that a composition of the littleneck clam shell is calcium carbonate and is aragonite which is one of polymorphs of calcium carbonate. The littleneck clam shell powder was immersed in a disodium hydrogen phosphoric acid aqueous solution at a 1 molar concentration at 80° C. for 24 hours.

Figure 13:
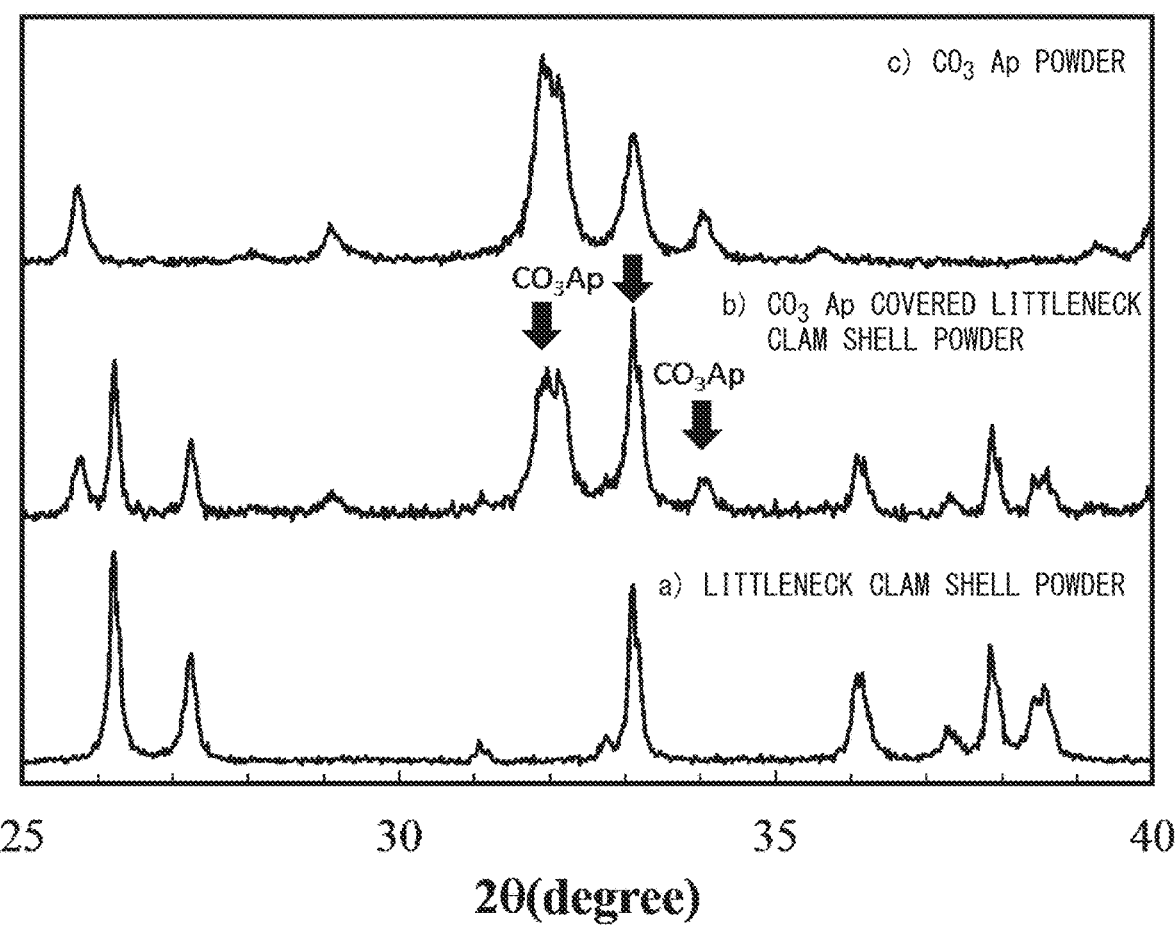
FIG. 13 shows data obtained through powder X-ray diffraction performed in Comparative Example 4.

The a) of FIG. 13 shows a powder X-ray diffraction image of the littleneck clam shell powder. It was confirmed that the littleneck clam shell was aragonite crystalline calcium carbonate.

The b) of FIG. 13 shows an X-ray diffraction image of a product produced by reacting littleneck clam shell powder with a disodium hydrogen phosphoric acid aqueous solution. In addition to a diffraction pattern derived from the littleneck clam shell powder, a diffraction pattern derived from a carbonate apatite shown in the c) of FIG. 13 was observed, and it was confirmed that it was possible to produce a carbonate apatite covered shell powder as a product.

Figure 14:
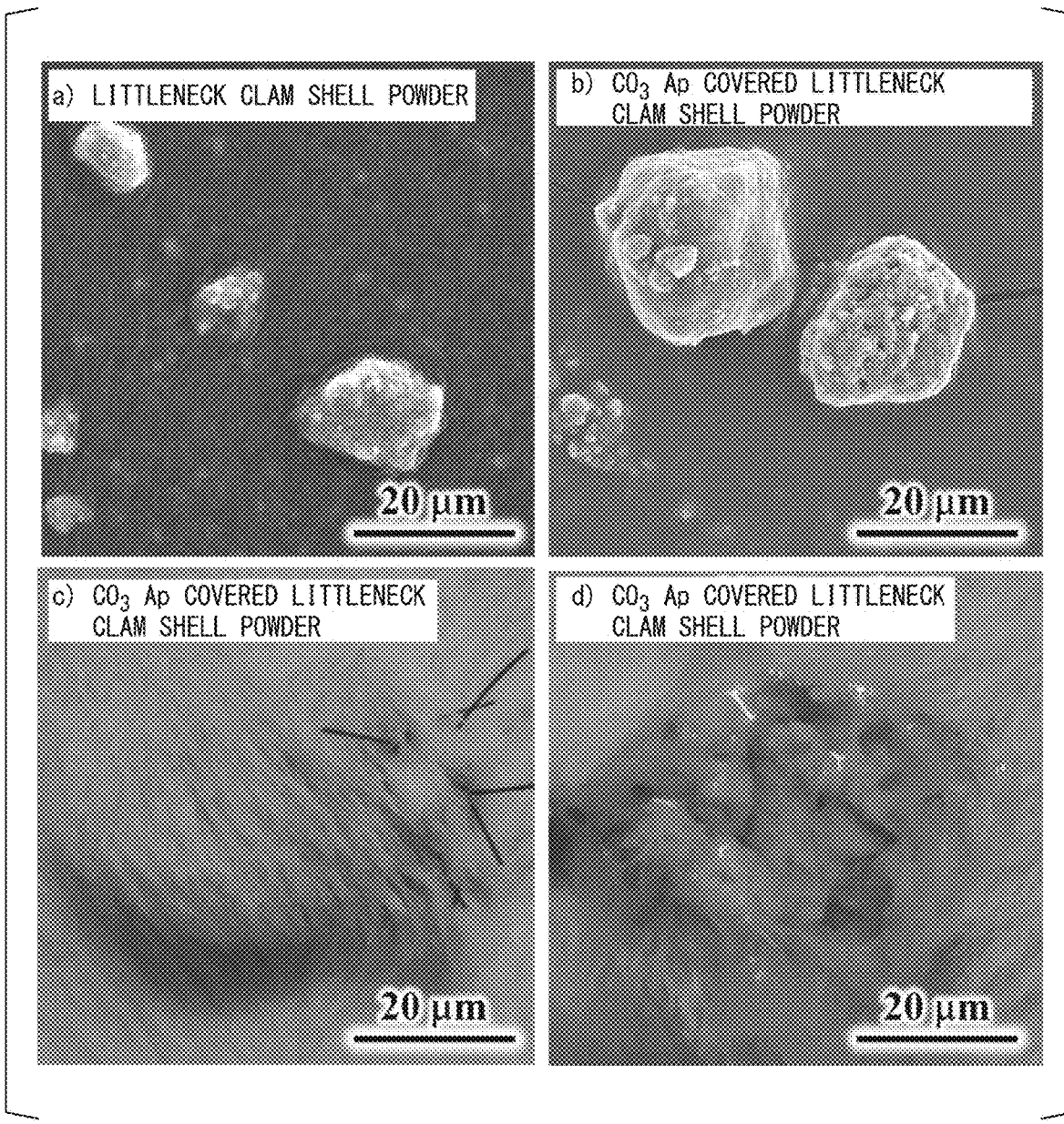
FIG. 14 shows scanning electron microscope images (a and b) captured in Comparative Example 4 and the results (c and d) in an implantation test.

The a) of FIG. 14 and the b) of FIG. 14 show scanning electron microscope images of carbonate apatite covered littleneck clam shell powder produced by reacting littleneck clam shell powder with a disodium hydrogen phosphoric acid aqueous solution. A volume of the carbonate apatite covered littleneck clam shell powder particles was about $6 \times 10^{-15}$ m$^3$ and less than $10^{-13}$ m$^3$. In addition, since the core portion of the produced carbonate apatite covered littleneck clam shell powder was a natural product that was not artificially produced from a chemically synthesized material, it was determined as a material outside the scope of the present invention in consideration of both a volume and an origin of the core portion.

In order to verify tissue compatibility of the produced carbonate apatite covered littleneck clam shell powder, 0.1 g of the powder was implanted subcutaneously into a rat. The c) of FIG. 14 shows the results 1 week after implantation. The d) of FIG. 14 shows the results when the implantation part was cut. When the carbonate apatite covered littleneck clam powder was implanted subcutaneously into a rat, swelling was observed. In addition, when the implantation part was cut, a light yellow transparent inflammatory exudate was observed. Based on such results, it was found that the carbonate apatite covered littleneck clam powder caused an inflammatory response.

Comparative Example 5

In order to produce a material including a natural product core portion and a carbonate apatite surface layer portion, littleneck clam shell were pulverized into granules and sized to 300 μm to 600 μm using a sieve. A volume of the littleneck clam shell granules was about $8 \times 10^{-11}$ m$^3$, which was $10^{-13}$ m$^3$ or more.

Figure 15:
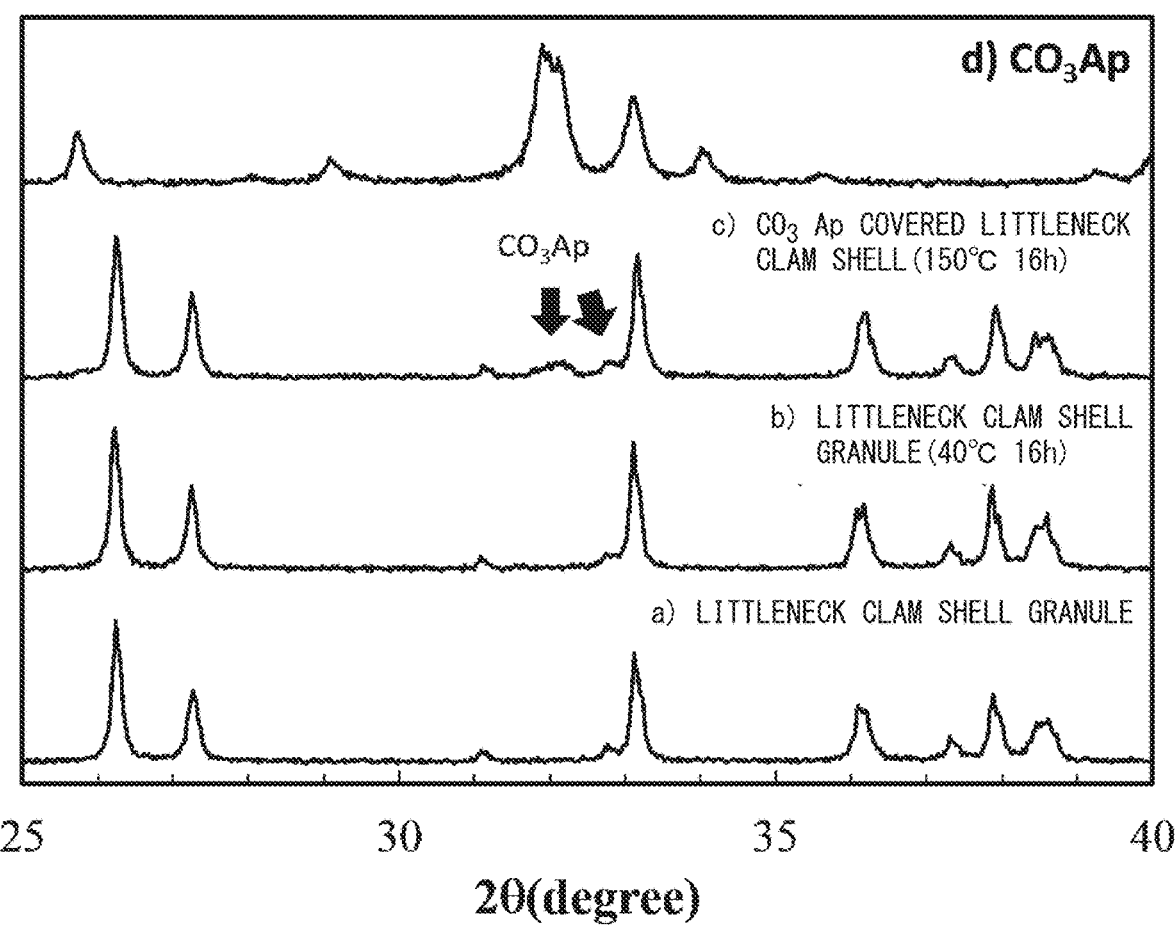
FIG. 15 shows data obtained through powder X-ray diffraction performed in Comparative Example 5.

While littleneck clam shell granules were immersed in a disodium hydrogen phosphoric acid aqueous solution at a 1 molar concentration at 40° C. for 4 hours and 16 hours, the formation of a carbonate apatite was not observed in the powder X-ray diffraction image at all (the b) of FIG. 15). Accordingly, it was confirmed that reactivity of the littleneck clam granules as a natural product with respect to a disodium hydrogen phosphoric acid aqueous solution was significantly lower than that of the artificial calcium carbonate described in Example 27.

In order to produce carbonate apatite covered littleneck clam shell granules, reaction conditions were examined. As a result, it was found that, when a reaction was caused with a disodium hydrogen phosphoric acid aqueous solution at a 1 molar concentration under hydrothermal conditions at 150° C. for 16 hours, it was possible to produce granules whose core portion was a littleneck clam shell as a natural material and whose surface layer portion was a carbonate apatite. The c) of FIG. 15 shows a powder X-ray diffraction image of the product. In addition to the diffraction pattern (a) of FIG. 15) derived from aragonite (calcium carbonate) that was a composition of the littleneck clam shell, a diffraction pattern (d) of FIG. 15) derived from a carbonate apatite was observed.

Figure 16:
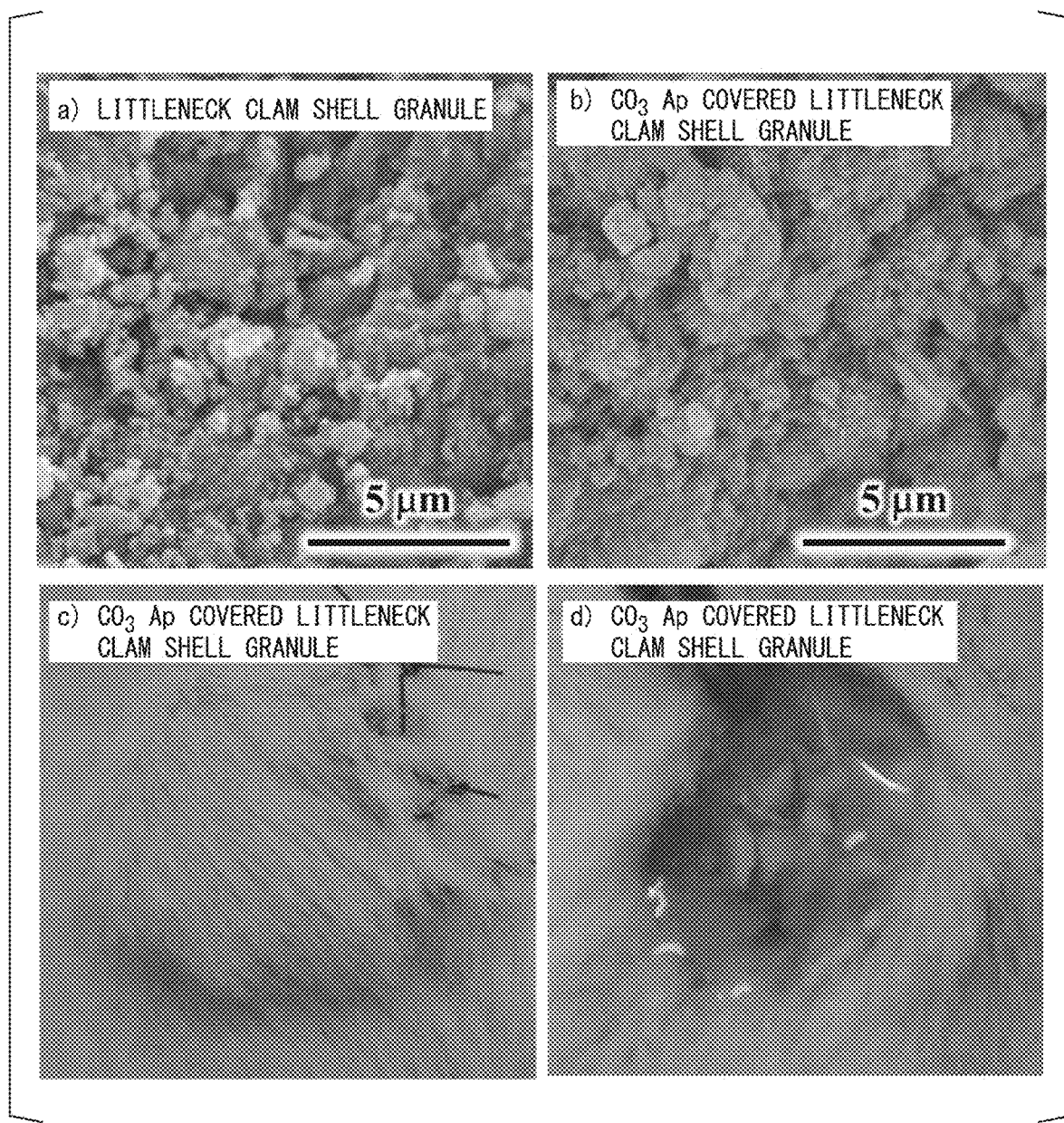
FIG. 16 shows scanning electron microscope images (a and b) captured in Comparative Example 5 and the results (c and d) in an implantation test.

The a) of FIG. 16 shows a scanning electron microscope image of littleneck clam shell granules used for production. The b) of FIG. 16 shows a scanning electron microscope image of a product obtained by performing a reaction with a disodium hydrogen phosphoric acid aqueous solution at a 1 molar concentration under hydrothermal conditions at 150° C. for 16 hours. It was confirmed that characteristic crystals of a carbonate apatite were precipitated on surfaces of the littleneck clam shell granules.

In order to verify tissue compatibility of the produced carbonate apatite covered littleneck clam shell granules, 0.1 g of the granules was implanted subcutaneously into a rat. The c) of FIG. 16 shows the results 1 week after implantation. The d) of FIG. 16 shows the results when the implantation part was cut. When the carbonate apatite covered littleneck clam granules were implanted subcutaneously into a rat, swelling was observed even though surfaces of carbonate apatite covered littleneck clam granules were a carbonate apatite. In addition, when the implantation part was cut, a light yellow transparent inflammatory exudate was observed. Based on such results, it was found that the carbonate apatite covered littleneck clam powder caused an inflammatory response.

A difference between this comparative example and Example 27 is only the composition of the core portion, that is, whether the core portion is a natural product or a product that is artificially produced from a chemically synthesized material. Comparing the two products, it could be understood that it is important for the core portion to be an artificial material and not to include a natural product.

Rat subcutaneous tissue reactions in Example 27 and Comparative Examples 3 to 5 in which a composition of the core portion was calcium carbonate and the surface layer was a carbonate apatite are summarized in Table 2.

TABLE 2

Summary of rat subcutaneous reactions of products in which a core portion is calcium carbonate and a surface layer portion is a carbonate apatite.

|  | Core portion is an artificial material | Core portion is not an artificial material |
|---|---|---|
| Volume is $10^{-13}$ m$^3$ or more | Example 1 o | Comparative Example 3 x |
| Volume is less than $10^{-13}$ m$^3$ | Comparative Example 1 x | Comparative Example 2 x |

In the table, "o" indicates a product in which no swelling and inflammatory exudate was observed and "x" indicates a product in which swelling was observed and an inflammatory exudate was observed when it was cut.

No inflammatory response was caused in a product in which the core portion was calcium carbonate and the surface layer portion was a carbonate apatite only when the requirements that a volume was $10^{-13}$ m$^3$ or more and the core portion was artificially produced from a chemically synthesized material and did not include a natural product were satisfied.

Example 28

A polyurethane foam (HR-50 commercially available from Bridgestone Corporation) was immersed in an α-type tricalcium phosphate (commercially available from Taihei Chemical Industrial Co., Ltd.) suspension (powder-liquid ratio of 0.83) and dried. An α-type tricalcium phosphate powder was adhered to a framework of the polyurethane foam. Then, calcination was performed at 1550° C., the polyurethane foam was incinerated and the α-type tricalcium phosphate was sintered to produce an α-type tricalcium phosphate foam.

Figure 17:
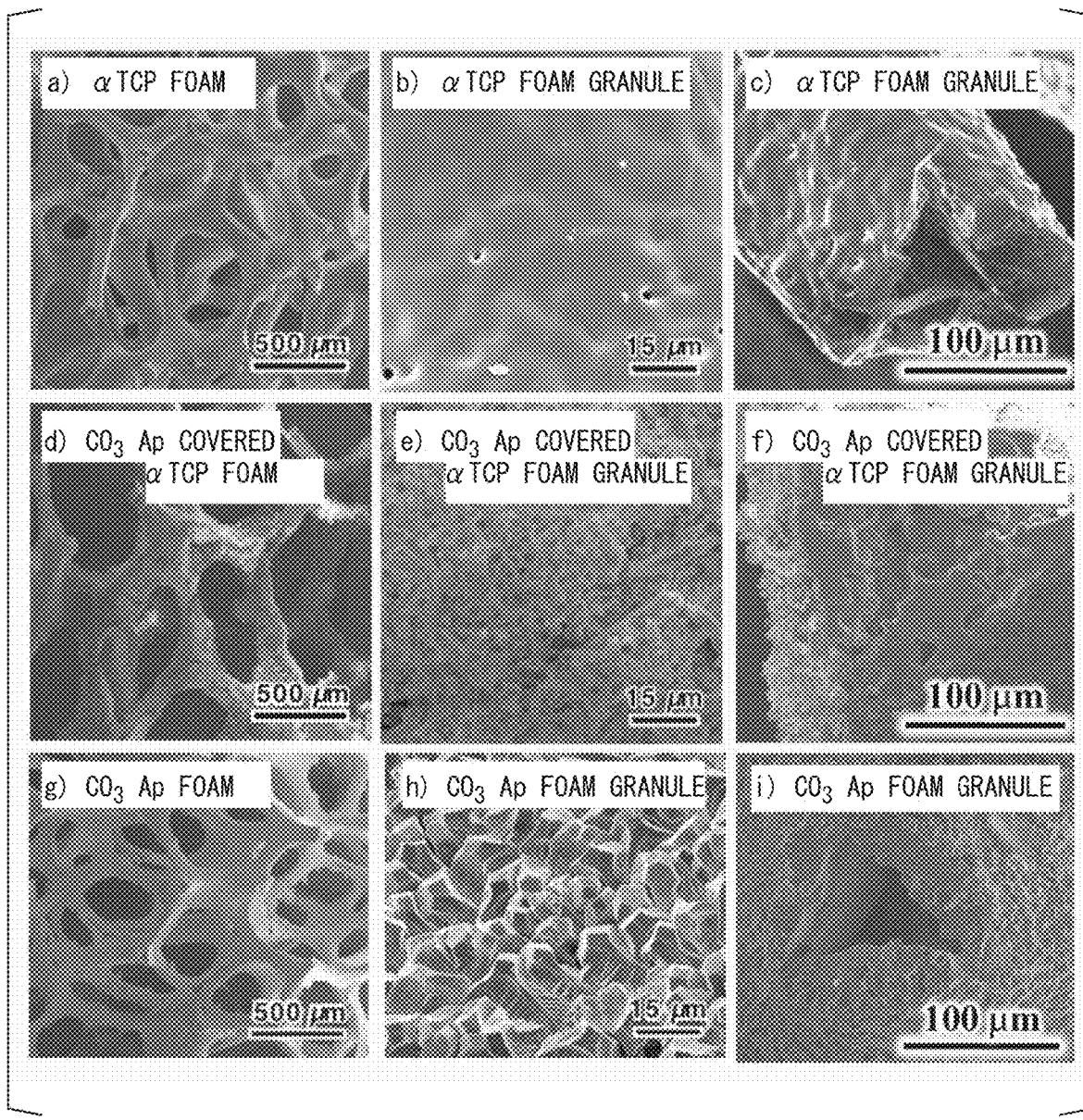
FIG. 17 shows scanning electron microscope images captured in Example 28.

The a) of FIG. 17 to the c) of 17 show scanning electron microscope images of the produced α-type tricalcium phosphate foam. The a) of FIG. 17 is a low-magnification image showing the form of the α-type tricalcium phosphate foam. The b) of FIG. 17 shows a surface of a framework of the α-type tricalcium phosphate foam. The c) of FIG. 17 shows a fractured surface of a framework of the α-type tricalcium phosphate foam.

Next, the α-type tricalcium phosphate foam was immersed in ammonium carbonate ($(NH_4)_2CO_3$) at a 4 molar concentration and treated under hydrothermal conditions at 200° C. A processing time was a maximum of 24 hours. A pH of ammonium carbonate $(NH_4)_2CO_3$ at a 4 molar concentration was 9.9.

According to results of analysis through powder X-ray diffraction, it was found that a composition of the α-type tricalcium phosphate foam was converted into a carbonate apatite over time.

Figure 18:
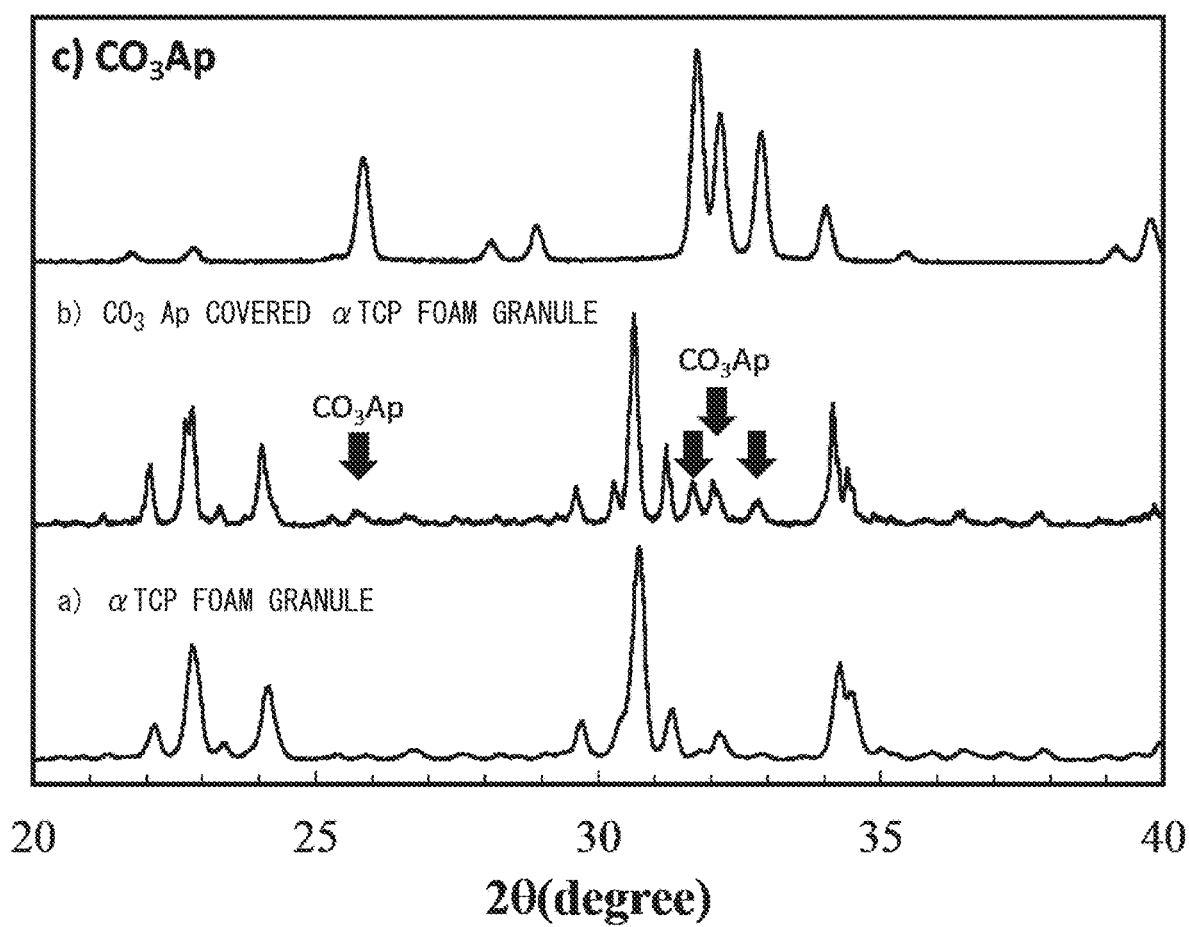
FIG. 18 shows data obtained through powder X-ray diffraction performed in Example 28.

The a) of FIG. 18 shows a powder X-ray diffraction image of the α-type tricalcium phosphate foam. The b) of FIG. 18 shows a powder X-ray diffraction image after treatment for 90 minutes. The c) of FIG. 18 shows a powder X-ray diffraction image after treatment for 24 hours. It could be understood from the powder X-ray diffraction images that, when the α-type tricalcium phosphate foam was immersed in ammonium carbonate ($(NH_4)_2CO_3$) at a 4 molar concentration and hydrothermally treated at 200° C. for 90 minutes, 35% was converted into a carbonate apatite.

The produced carbonate apatite foam was an interconnected porous body. A compressive strength was 5 kPa. Comparing this example and Example 2, it was found that a mechanical strength of the carbonate apatite interconnected porous body produced in Example 2 was extremely high, and a method of introducing and incinerating a fibrous pore forming material was excellent for producing a carbonate apatite interconnected porous body having an excellent mechanical strength.

Next, various foams were pulverized, and foam granules that passed through a sieve having a mesh opening of 3 mm but failed to pass through a sieve having a mesh opening of 1 mm were produced. Since a volume of the foam granules was about $8 \times 10^{-9}$ m$^3$, which was $10^{-13}$ m$^3$ or more.

The d) of FIG. 17 to the f) of FIG. 17 show scanning electron microscope images of granules of the b) of FIG. 18. The g) of FIG. 17 to the i) of FIG. 17 show scanning electron microscope images of granules of the c) of FIG. 18. It could be understood from scanning electron microscope images of fractured surfaces of foam granules shown in c) of FIG. 17, f) of FIG. 17, and i) of FIG. 17 and a powder X-ray diffraction image shown in FIG. 18 that, when the α-type tricalcium phosphate foam was reacted with an ammonium carbonate aqueous solution, it was found that carbonate apatite covered α-type tricalcium phosphate foam granules whose core portion was α-type tricalcium phosphate and whose surface layer portion was a carbonate apatite was obtained.

The fact that crystals formed on surfaces of the α-type tricalcium phosphate foam granules were a carbonate apatite was confirmed when characteristic absorption in a B-type carbonate apatite was observed around 1400 cm$^{-1}$ in infrared spectroscopic analysis in addition to from observation under the scanning electron microscope and analysis using the powder X-ray diffraction image.

A porosity of the obtained carbonate apatite covered calcium carbonate foam was 87%.

In order to verify tissue compatibility of the produced bone prosthetic material, 0.1 g of the foam granules were implanted subcutaneously into a rat. Even though the carbonate apatite covered α-type tricalcium phosphate foam granules were implanted subcutaneously into a rat, no swelling was observed. In addition, when the implantation part was cut, the carbonate apatite covered α-type tricalcium phosphate foam granules were observed and no inflammatory exudate was observed. Based on such results, it was found that the carbonate apatite covered α-type tricalcium phosphate foam granules exhibited excellent tissue compatibility.

In order to further examine usefulness of the produced carbonate apatite covered α-type tricalcium phosphate foam granules, a beagle dog was used to reconstruct a bone defect. A bone defect was formed in a jawbone part three months after tooth extraction. The bone defect was reconstructed using the carbonate apatite covered α-type tricalcium phosphate foam granule. For comparison, reconstruction was performed using α-type tricalcium phosphate foam granules and carbonate apatite foam granules.

Figure 19:
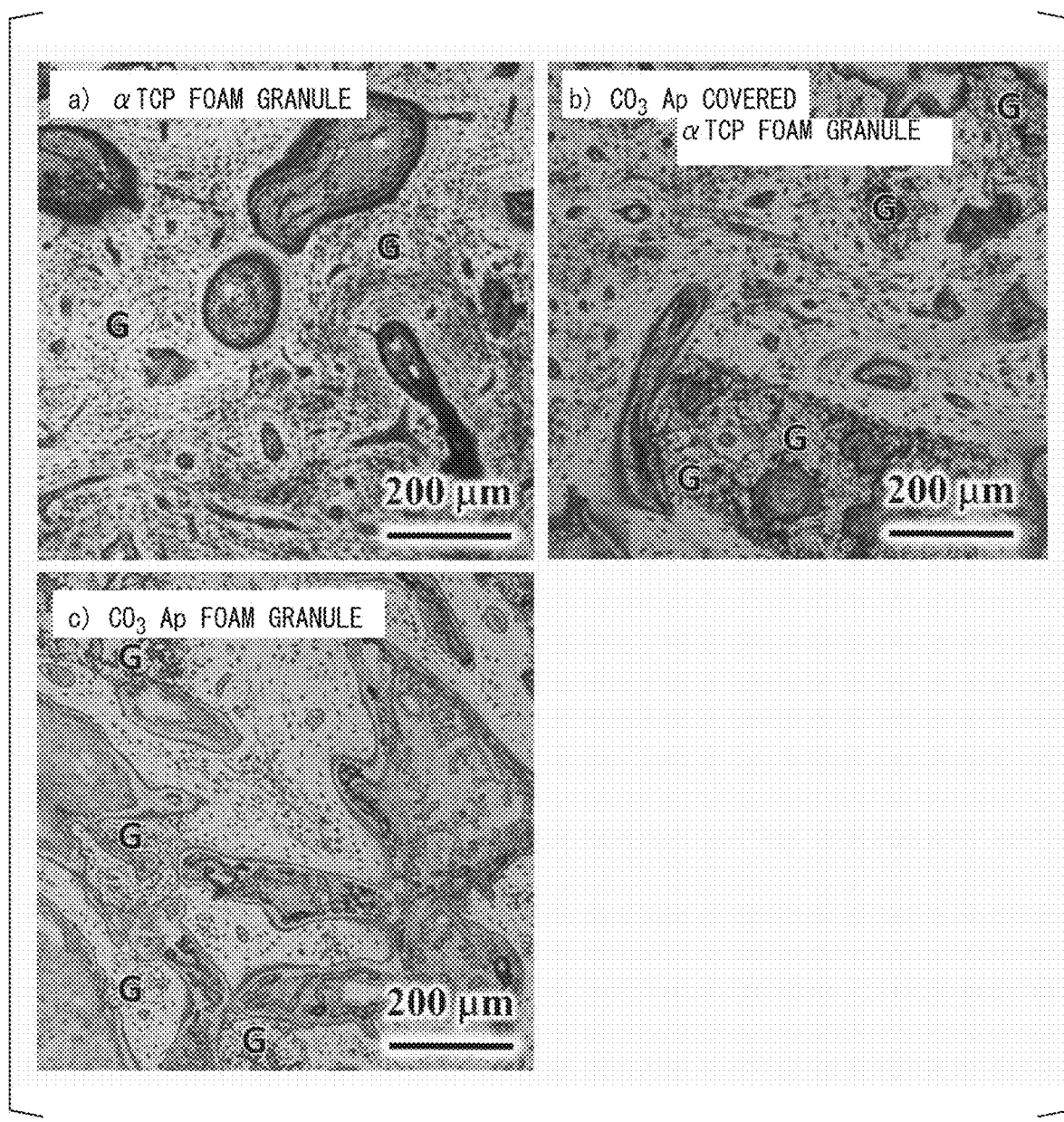
FIG. 19 shows histopathological images in an implantation test performed in Example 28.

FIG. 19 shows a histopathological image three months after implantation. In FIG. 19, G indicates the remaining granules. The a) of FIG. 19 shows pathological tissue of the α-type tricalcium phosphate foam granules. The b) of FIG. 19 shows pathological tissue of the carbonate apatite covered α-type tricalcium phosphate foam granules. The c) of FIG. 19 shows pathological tissue of the carbonate apatite foam granules. All of these were confirmed to exhibit excellent tissue compatibility and osteoconductivity. However, it was confirmed that the carbonate apatite covered α-type tricalcium phosphate foam granules exhibited the largest bone regeneration amount and the carbonate apatite foam granules exhibited the next largest bone regeneration amount, and the amount of osteogenesis was smallest around the α-type tricalcium phosphate foam granules. Bone regeneration rates and proportions of remaining granules three months and six months after implantation are summarized in Table 3.

TABLE 3

Bone regeneration rates and proportions of remaining granules of foam granules for reconstructing beagle dog jawbone.

| Type of foam granules | Bone regeneration rate (%) | | Proportions of remaining granules (%) | |
|---|---|---|---|---|
| | 3 months | 6 months | 3 months | 6 months |
| Carbonate apatite covered α-type tricalcium phosphate | 94 | 97 | 6 | 3 |
| Carbonate apatite covered | 83 | 97 | 9 | 7 |
| α-type tricalcium phosphate | 50 | 56 | 3 | 3 |
| No filling | 47 | 56 | — | — |

It was confirmed that the α-type tricalcium phosphate foam granules which were a material outside the scope of the present invention had a limited bone regeneration rate, but that the granules were absorbed fast. It was confirmed that the carbonate apatite granules which were a material outside the scope of the present invention had a superior bone regeneration rate to the α-type tricalcium phosphate foam granules, but absorption was slower and the proportion of remaining granules was higher than with the α-type tricalcium phosphate foam granules. It was confirmed that the carbonate apatite covered α-type tricalcium phosphate foam granules of the present invention exhibited the highest bone regeneration rate, showed a lower proportion of remaining granules than the α-type tricalcium phosphate foam granules at the $3^{rd}$ month, but showed almost the same proportion of remaining granules as the α-type tricalcium phosphate foam granules after 6 months, and had an amount of bone replacement was the most ideal.

Example 29

Figure 20:
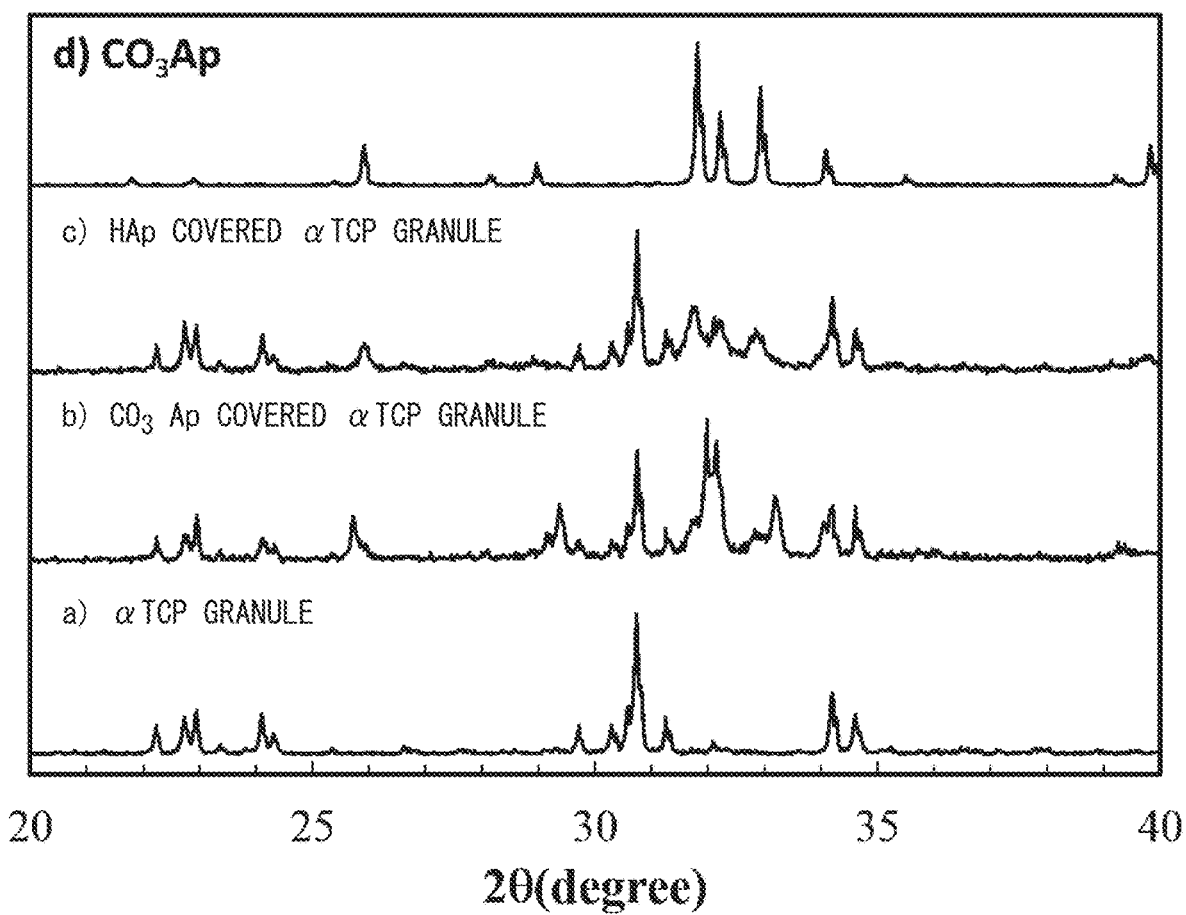
FIG. 20 shows data obtained through powder X-ray diffraction performed in Examples 29 and 30.
Figure 21:
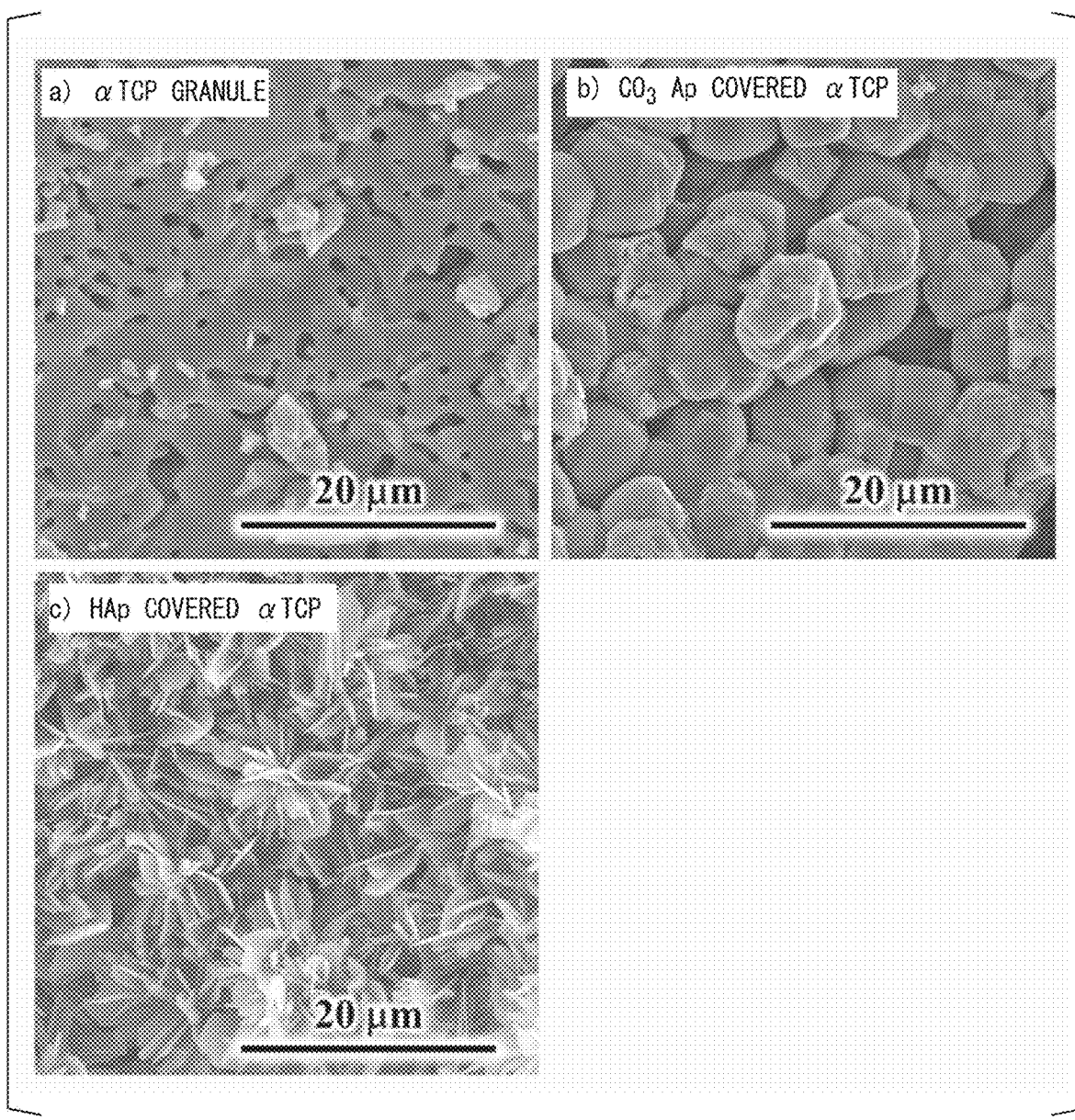
FIG. 21 shows scanning electron microscope images captured in Examples 29 and 30.

A β-type tricalcium phosphate powder (commercially available from Taihei Chemical Industrial Co., Ltd.) was compacted at 50 MPa and calcined at 1400° C. for 6 hours to produce an α-type tricalcium phosphate block. The block was pulverized and sieved to prepare α-type tricalcium phosphate granules of 300 μm to 600 μm. The a) of FIG. 20 shows a powder X-ray diffraction image of the produced α-type tricalcium phosphate granules. The a) of FIG. 21 shows a scanning electron microscope image of surfaces of the granules.

The produced α-type tricalcium phosphate granules were artificially produced from a chemically synthesized material and did not include a natural product.

The produced α-type tricalcium phosphate granules were immersed in a sodium hydrogen carbonate aqueous solution (pH 9.2) with a 1 molar concentration at 80° C. for 24 hours. The b) of FIG. 20 shows a powder X-ray diffraction image of the produced granules. The b) of FIG. 21 shows a scanning electron microscope image of surfaces of the granules.

In the granules shown in b) of FIG. 20, in addition to the diffraction pattern derived from the α-type tricalcium phosphate granules of a) of FIG. 20, the diffraction pattern derived from a carbonate apatite shown in d) of FIG. 20 was observed. Therefore, it was confirmed that the α-type tricalcium phosphate and the sodium hydrogen carbonate aqueous solution had reacted to form a carbonate apatite. The formation of a carbonate apatite was also confirmed from an absorption peak position specific to a carbonate apatite using the Fourier transform spectrophotometer. In addition, the fact that the carbonate apatite covered α-type tricalcium phosphate granules had been produced was confirmed from observation of a fractured surface under a scanning electron microscope.

A volume of the produced carbonate apatite covered α-type tricalcium phosphate granules was about $10^{-11}$ $m^3$, which was $10^{-13}$ $m^3$ or more.

In order to verify tissue compatibility of the produced carbonate apatite covered α-type tricalcium phosphate granules, 0.1 g of the granules was implanted subcutaneously into a rat. No swelling was observed 1 week after implantation. In addition, when the implantation part was cut, the carbonate apatite covered α-type tricalcium phosphate granules were observed and no inflammatory exudate was observed. Based on such results, it was found that the carbonate apatite covered α-type tricalcium phosphate granules exhibited excellent tissue compatibility.

Example 30

The α-type tricalcium phosphate granules produced in Example 29 were immersed in distilled water at 80° C. for 24 hours. The c) of FIG. 20 shows a powder X-ray diffraction image of the produced granules. The c) of FIG. 21 shows a scanning electron microscope image of surfaces of the granules.

In the granules shown in c) of FIG. 20, in addition to the diffraction pattern derived from the α-type tricalcium phosphate granules of a) of FIG. 20, a diffraction pattern derived from hydroxyapatite was observed. Therefore, it was confirmed that the α-type tricalcium phosphate and distilled water had reacted to form hydroxyapatite. The formation of hydroxyapatite was also confirmed from an absorption peak position specific to hydroxyapatite using the Fourier transform spectrophotometer. In addition, the fact that the hydroxyapatite covered α-type tricalcium phosphate granules had been produced was confirmed from observation of a fractured surface using a scanning electron microscope.

A volume of the produced hydroxyapatite covered α-type tricalcium phosphate granules was about $5 \times 10^{-11}$ m$^3$, which was $10^{-13}$ m$^3$ or more.

In order to verify tissue compatibility of the produced hydroxyapatite covered α-type tricalcium phosphate granule, 0.1 g of the granules was implanted subcutaneously into a rat. No swelling was observed 1 week after implantation. In addition, when the implantation part was cut, the hydroxyapatite covered α-type tricalcium phosphate granules were observed and no inflammatory exudate was observed. Based on such results, it was found that the hydroxyapatite covered α-type tricalcium phosphate granules exhibited excellent tissue compatibility.

Example 31

Figure 22:
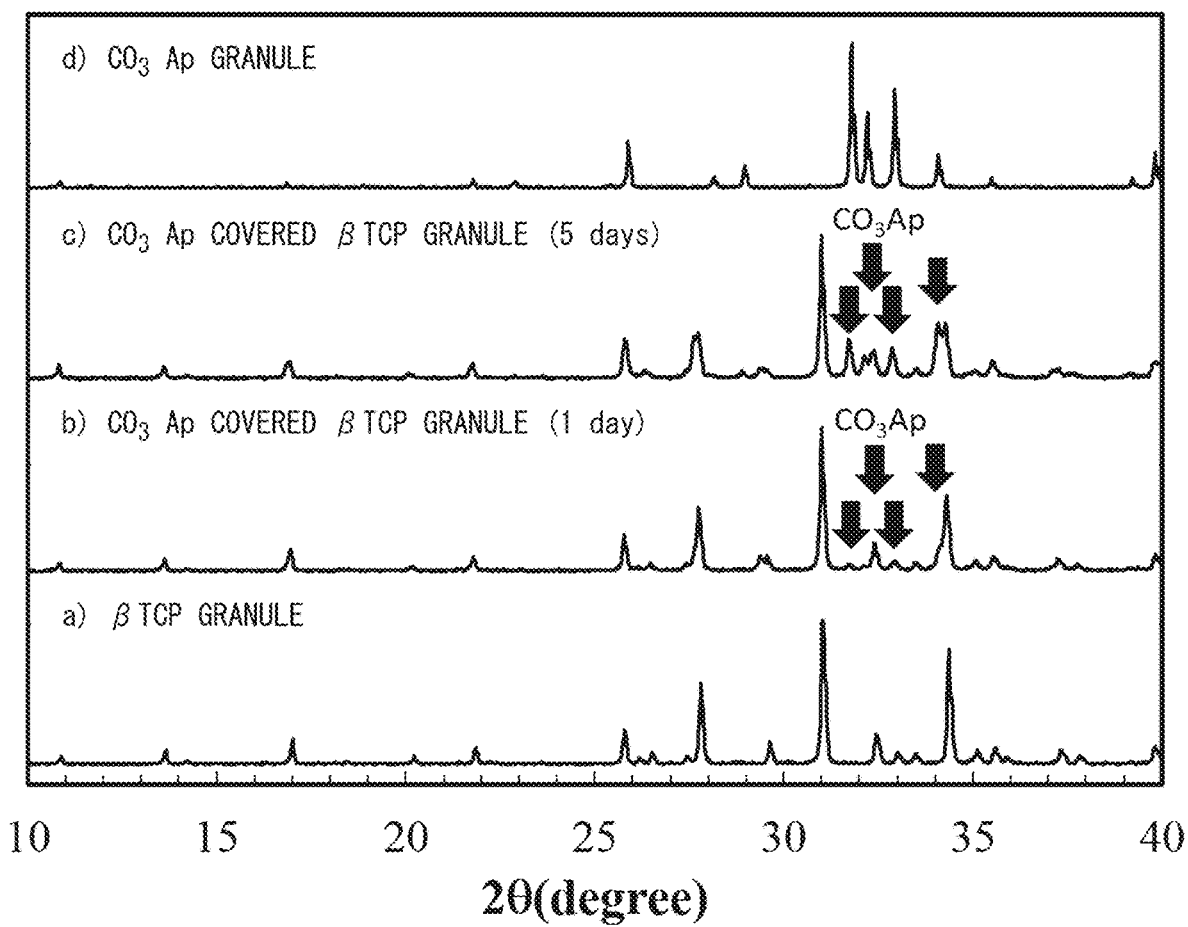
FIG. 22 shows data obtained through powder X-ray diffraction performed in Example 31.
Figure 23:
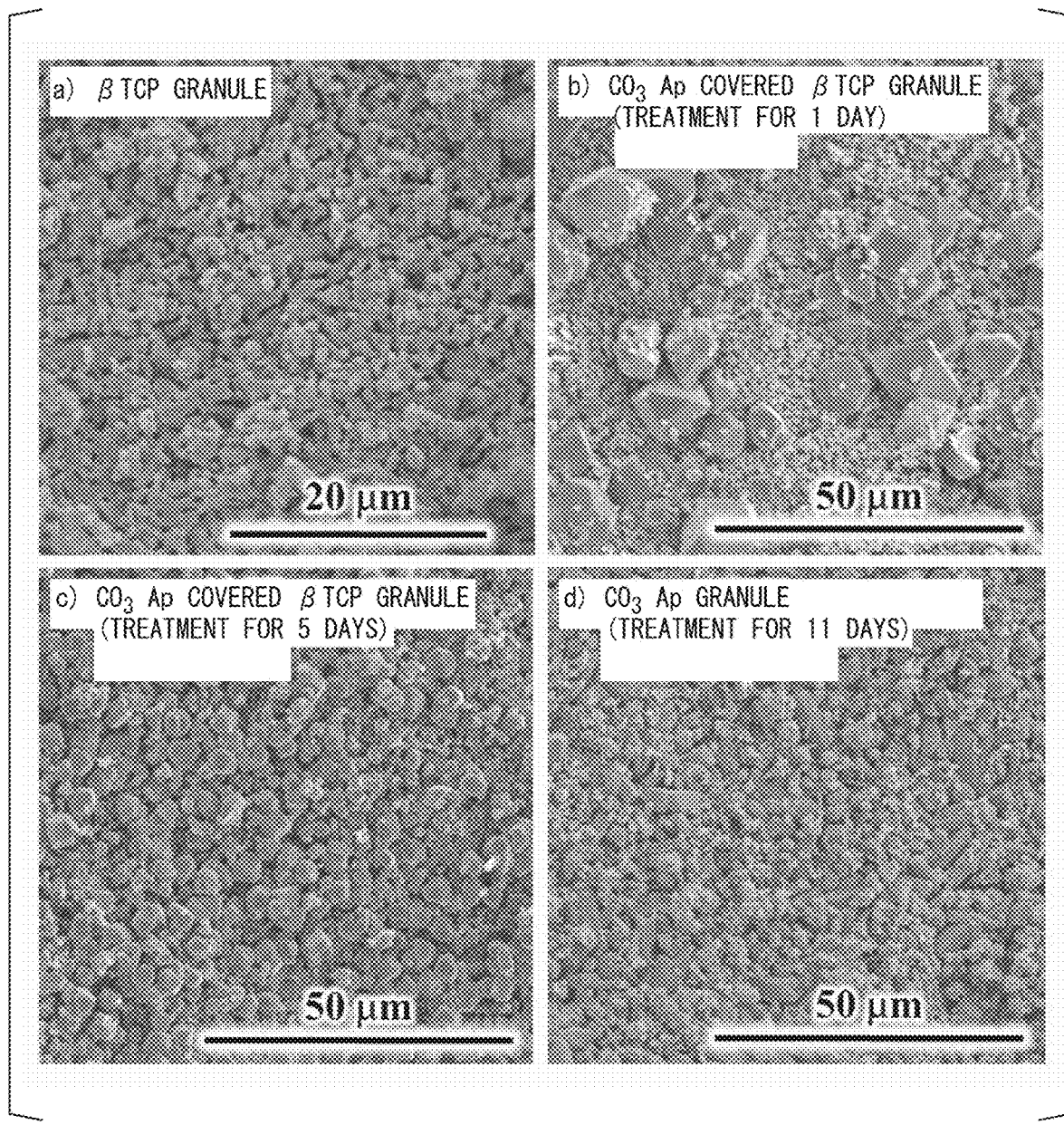
FIG. 23 shows scanning electron microscope images captured in Example 31.

A β-type tricalcium phosphate powder (commercially available from Taihei Chemical Industrial Co., Ltd.) was compacted at 50 MPa and calcined at 1100° C. for 6 hours to produce a β-type tricalcium phosphate block. The block was pulverized and sieved to prepare β-type tricalcium phosphate granules of 300 μm to 600 μm. The a) of FIG. 22 shows a powder X-ray diffraction image of the produced β-type tricalcium phosphate granules. The a) of FIG. 23 shows a scanning electron microscope image of surfaces of the granules.

The produced β-type tricalcium phosphate granules were chemically synthesized and did not include a natural product or a material of biological origin.

The produced β-type tricalcium phosphate granules were immersed in a sodium hydrogen carbonate aqueous solution at a 1 molar concentration at 80° C. for 24 hours. It was confirmed that no change was observed in the powder X-ray diffraction image and the scanning electron microscope image and it was not possible to produce carbonate apatite covered β-type tricalcium phosphate granules under these conditions. Therefore, a reaction was performed in sodium carbonate at a 4 molar concentration at 200° C. under hydrothermal conditions for 1 day and for 5 days. Also, a pH of the sodium carbonate aqueous solution at a 4 molar concentration was 12.0.

The b) of FIG. 22 and c) of FIG. 22 show powder X-ray diffraction images of the produced granules. The b) of FIG. 23 and c) of FIG. 23 show scanning electron microscope images of surfaces of the granules.

In the granules shown in b) of FIG. 22 and c) of FIG. 22, in addition to the diffraction pattern derived from the β-type tricalcium phosphate granules of a) of FIG. 22, the diffraction pattern derived from a carbonate apatite shown in d) of FIG. 22 was observed. Therefore, it was confirmed that the β-type tricalcium phosphate and the sodium carbonate aqueous solution had reacted to form a carbonate apatite. An amount of the formed carbonate apatite was larger after 1 day of reaction (b) of FIG. 22) than after 5 days of reaction (c) of FIG. 22). The formation of a carbonate apatite was also confirmed from an absorption peak position specific to a carbonate apatite using the Fourier transform spectrophotometer. In addition, the fact that the carbonate apatite covered β-type tricalcium phosphate granules had been produced was confirmed from observation of a surface (FIG. 23) or observation of a fractured surface under a scanning electron microscope.

A volume of the produced carbonate apatite covered β-type tricalcium phosphate granules was about $5 \times 10^{-11}$ m$^3$, which was $10^{-13}$ m$^3$ or more.

In order to verify tissue compatibility of the produced carbonate apatite covered β-type tricalcium phosphate granules, 0.1 g of the granule was implanted subcutaneously into a rat. No swelling was observed 1 week after implantation. In addition, when the implantation part was cut, the carbonate apatite covered β-type tricalcium phosphate granules were observed and no inflammatory exudate was observed. Based on such results, it was found that the carbonate apatite covered β-type tricalcium phosphate granules exhibited excellent tissue compatibility.

Example 32

The β-type tricalcium phosphate granules (a) of FIG. 22 and a) of FIG. 23) produced in Example 31 were immersed in an acidic calcium phosphoric acid aqueous solution in which monocalcium dihydrogen phosphate monohydrate (Ca(H$_2$PO$_4$)$_2$·H$_2$O) was dissolved at 25° C. for 15 minutes to a 1 molar concentration in 0.6 molar concentration phosphoric acid. The acidic calcium phosphoric acid aqueous solution was an acidic aqueous solution including calcium at a 1 molar concentration and phosphoric acid at a 2.6 molar concentration. A pH of the acidic calcium phosphoric acid aqueous solution was 1.6.

Figure 24:
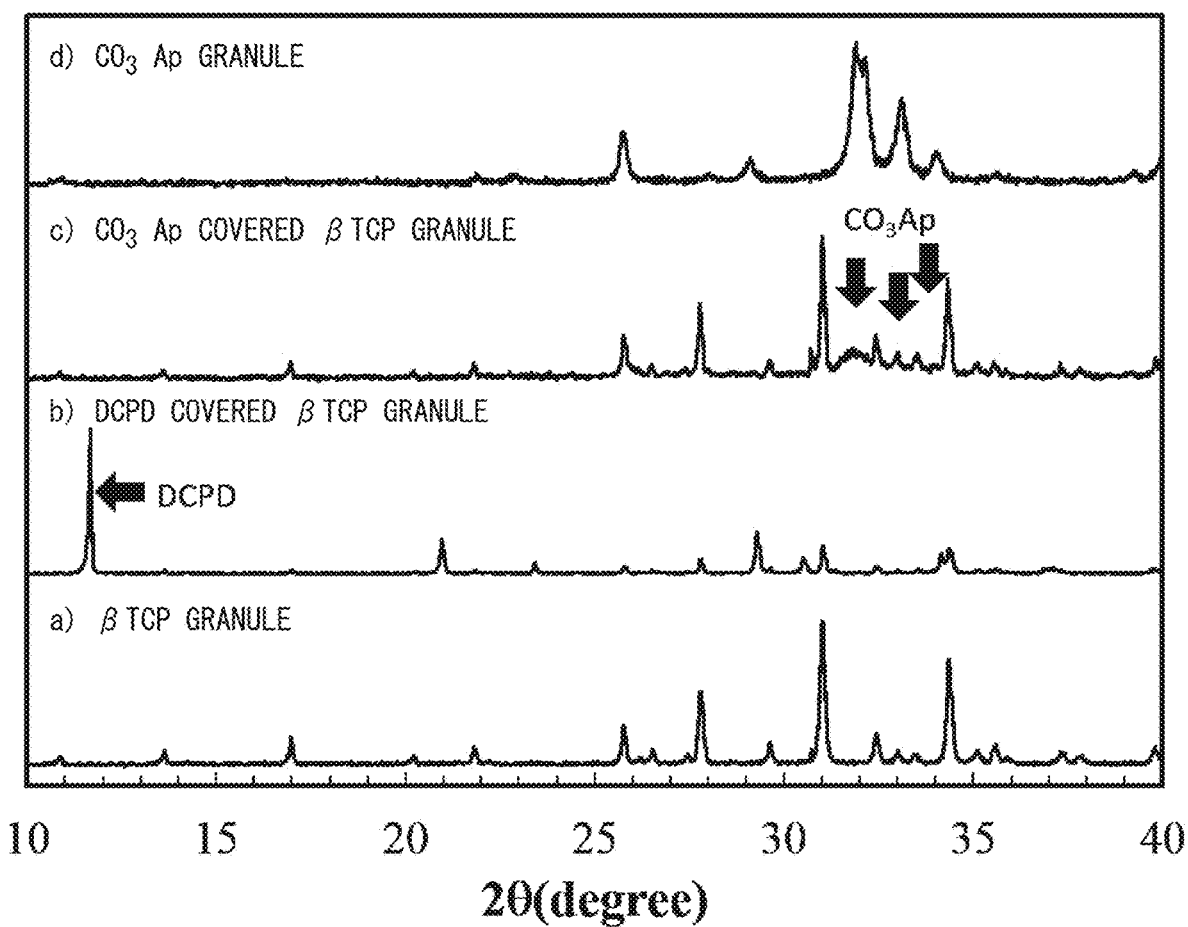
FIG. 24 shows data obtained through powder X-ray diffraction performed in Example 32.
Figure 25:
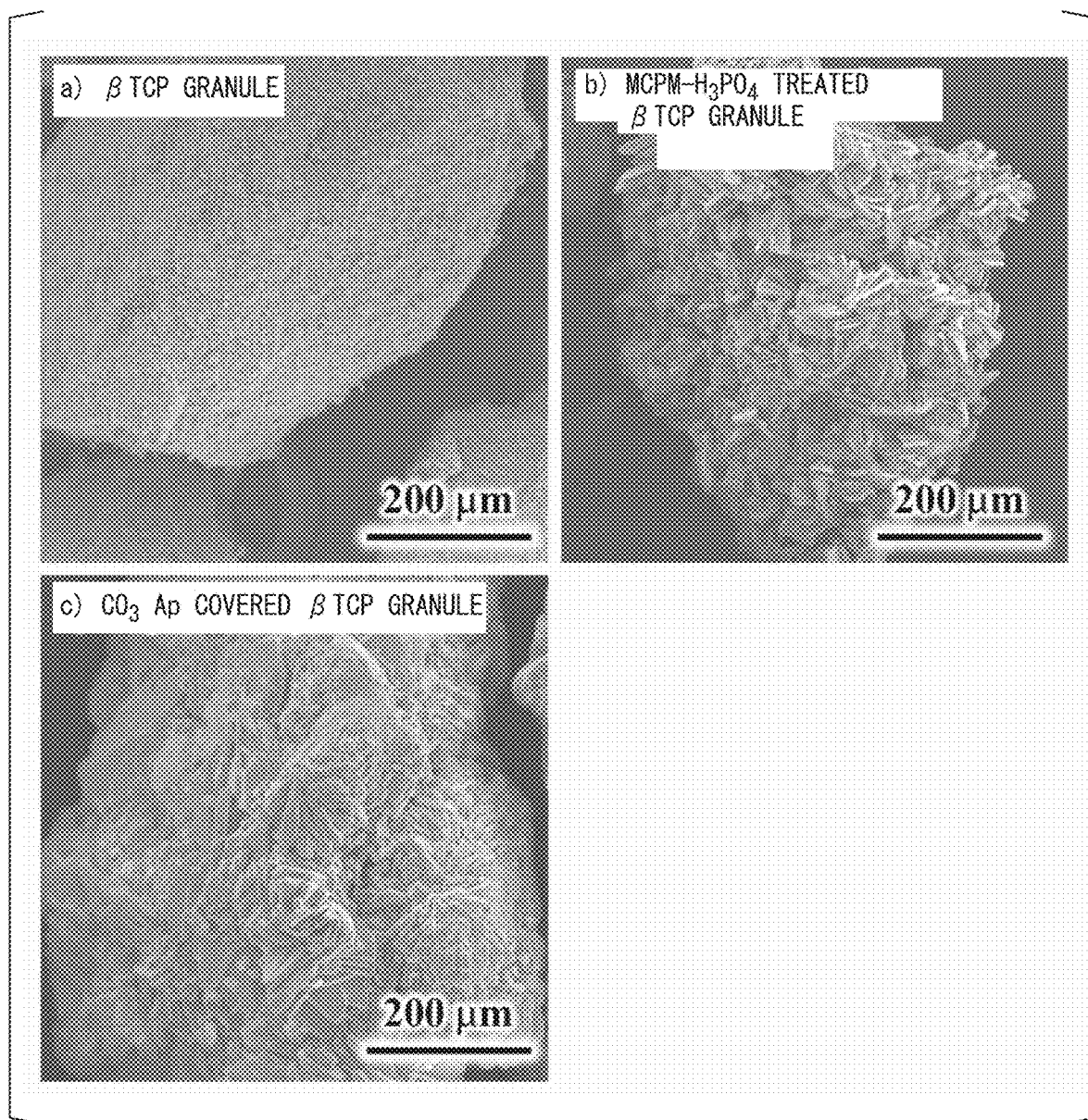
FIG. 25 shows scanning electron microscope images captured in Example 32.

The b) of FIG. 24 shows a powder X-ray diffraction image of the produced granules. The b) of FIG. 25 shows a scanning electron microscope image of surfaces of the granules. In the granules shown in b) of FIG. 24, in addition to the diffraction pattern derived from the β-type tricalcium phosphate granules of a) of FIG. 24, the diffraction pattern derived from calcium hydrogen phosphate dihydrate (CaHPO$_4$.2H$_2$O) was observed. Accordingly, it was confirmed that, when the β-type tricalcium phosphate granules were immersed in the acidic calcium phosphoric acid aqueous solution, the surface was covered with the calcium hydrogen phosphate dihydrate.

Next, the granules were immersed in an aqueous solution including NaHCO$_3$ and Na$_2$HPO$_4$ each with a 0.5 molar concentration at 25° C. for 1 day. The aqueous solution was an aqueous solution including sodium at a 1.5 molar concentration, carbonate with a 0.5 molar concentration, and phosphoric acid at a 0.5 molar concentration. A pH of the aqueous solution was 8.5.

The c) of FIG. 24 shows a powder X-ray diffraction image of the granules produced by this treatment. The c) of FIG. 24 shows a scanning electron microscope image of surfaces of the granules. In the granules shown in c) of FIG. 24, in addition to the diffraction pattern derived from the β-type tricalcium phosphate granules of a) of FIG. 24, the diffraction pattern derived from a carbonate apatite was observed. In addition, the diffraction pattern derived from calcium hydrogen phosphate dihydrate (CaHPO$_4$.2H$_2$O) disappeared. In addition, it was confirmed that surfaces of the granules were covered with characteristic crystals of a carbonate apatite from the scanning electron microscope image (c) of FIG. 20).

Accordingly, it was confirmed that, when the calcium hydrogen phosphate dihydrate covered β-type tricalcium phosphate granules were immersed in the aqueous solution in which NaHCO$_3$ and Na$_2$HPO$_4$ were mixed, calcium hydrogen phosphate dihydrate of the surface became a carbonate apatite and carbonate apatite covered β-type tricalcium phosphate was produced. A volume of the produced carbonate apatite covered β-type tricalcium phosphate granules was about $5 \times 10^{-11}$ m$^3$, which was $10^{-13}$ m$^3$ or more.

Comparing this example and Example 31, it was found that, when the β-type tricalcium phosphate granules having low reactivity were reacted with the acidic calcium phosphate solution, calcium hydrogen phosphate was initially coated thereon, the calcium hydrogen phosphate was then converted into a carbonate apatite, and thus it was possible to produce the carbonate apatite covered β-type tricalcium phosphate granules without strict production conditions such as in a hydrothermal reaction.

In order to verify tissue compatibility of the produced carbonate apatite covered β-type tricalcium phosphate granules, 0.1 g of the granules was implanted subcutaneously into a rat. No swelling was observed 1 week after implantation. In addition, when the implantation part was cut, the carbonate apatite covered β tricalcium phosphate granules were observed and no inflammatory exudate was observed. Based on such results, it was found that the carbonate apatite covered β-type tricalcium phosphate granules exhibited excellent tissue compatibility.

Example 33

Figure 26:
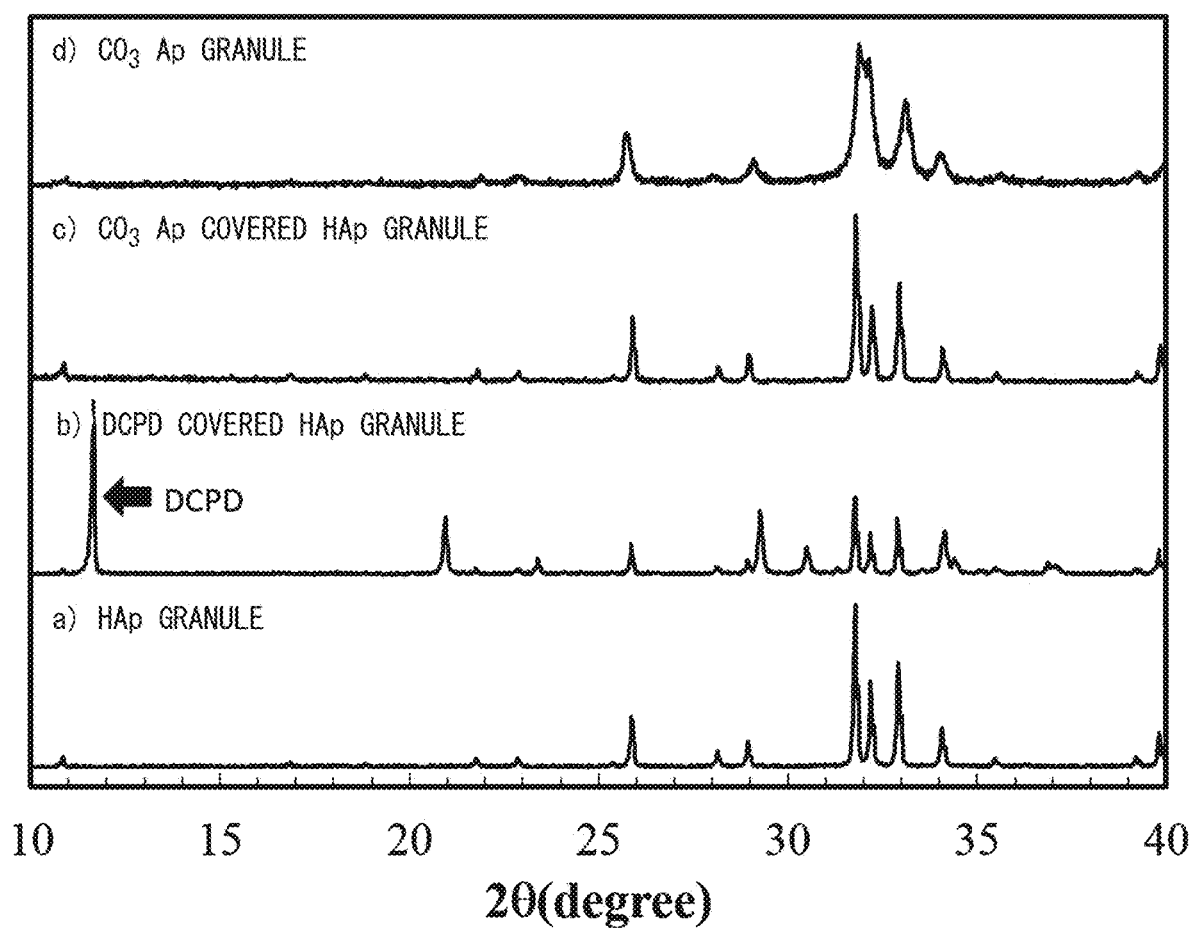
FIG. 26 shows data obtained through powder X-ray diffraction performed in Example 33.
Figure 27:
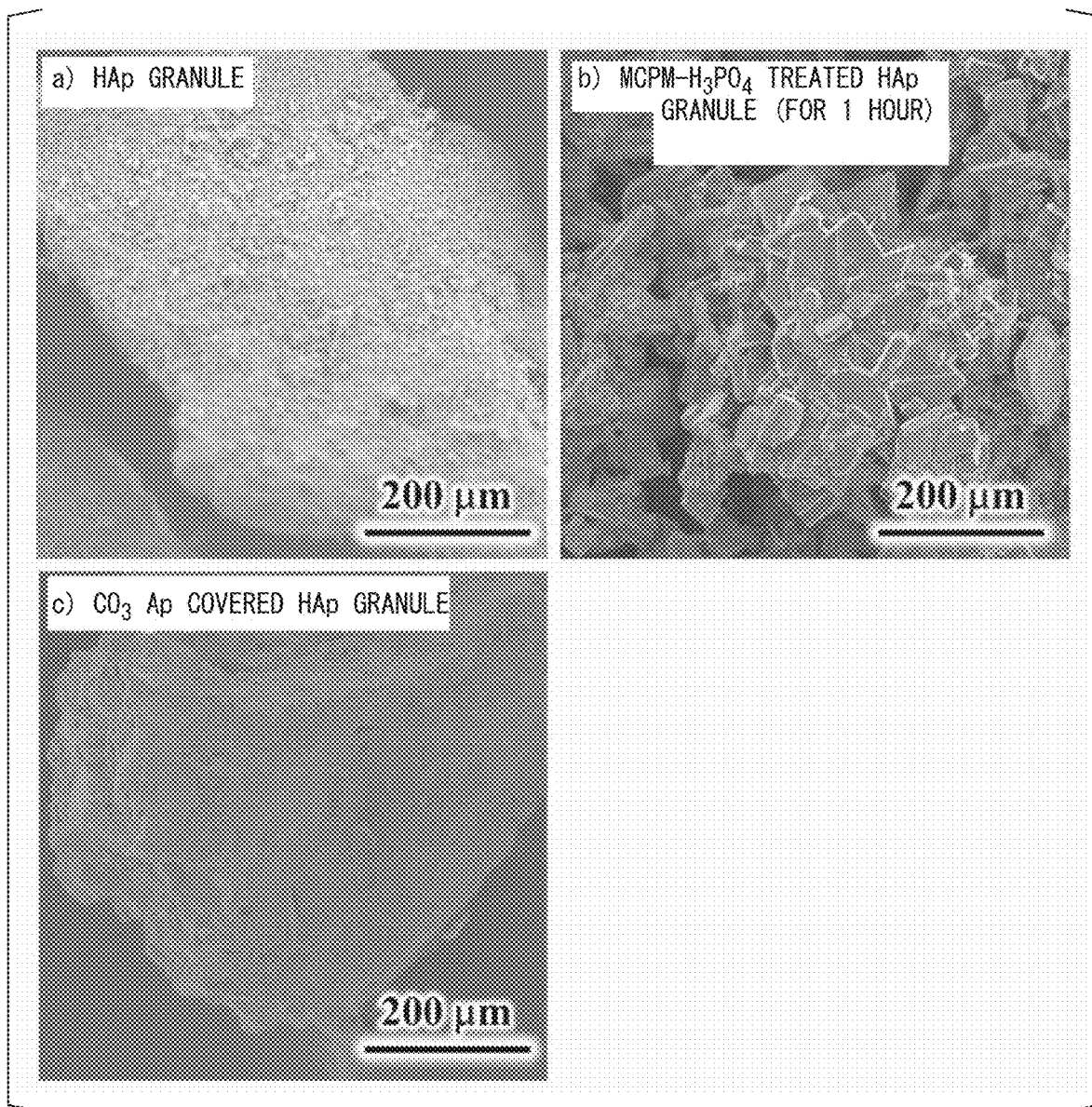
FIG. 27 shows scanning electron microscope images captured in Example 33.

A hydroxyapatite powder (HAP-200 commercially available from Taihei Chemical Industrial Co., Ltd.) was compacted at 50 MPa and calcined at 1100° C. for 6 hours to produce a hydroxyapatite block. The block was pulverized and sieved to prepare hydroxyapatite of 300 μm to 600 μm. The a) of FIG. 26 shows a powder X-ray diffraction image of the hydroxyapatite powder used for production. The a) of FIG. 27 shows a scanning electron microscope image of surfaces of the granules.

The produced hydroxyapatite granule was artificially produced from a chemically synthesized material and did not include a natural product.

The produced hydroxyapatite granules were immersed in the acidic calcium phosphoric acid aqueous solution used in Example 32 at 25° C. for 15 minutes.

The b) of FIG. 26 shows a powder X-ray diffraction image of the produced granules. The b) FIG. 27 shows a scanning electron microscope image of surfaces of the granules. In the granules shown in b) FIG. 26, in addition to the diffraction pattern derived from the hydroxyapatite granules of a) of FIG. 26, the diffraction pattern derived from calcium hydrogen phosphate dihydrate ($CaHPO_4.2H_2O$) was observed. Accordingly, it was confirmed that, when the hydroxyapatite granules were immersed in the acidic calcium phosphoric acid aqueous solution, the surface was covered with calcium hydrogen phosphate dihydrate.

Next, the granules were immersed in an aqueous solution including $NaHCO_3$ and $Na_2HPO_4$ each at a 0.5 molar concentration at 25° C. for 1 day. The aqueous solution was an aqueous solution including sodium at a 1.5 molar concentration, carbonate at a 0.5 molar concentration, and phosphoric acid at a 0.5 molar concentration. A pH of the aqueous solution was 8.5.

The c) of FIG. 26 shows a powder X-ray diffraction image of the granules produced by this treatment. The c) of FIG. 27 shows a scanning electron microscope image of surfaces of the granules. In the granules of c) of FIG. 26, in addition to the diffraction pattern derived from the hydroxyapatite granules of a) of FIG. 26, the diffraction pattern derived from a carbonate apatite was observed. In addition, the diffraction pattern derived from calcium hydrogen phosphate dihydrate ($CaHPO_4.2H_2O$) disappeared. In addition, it was confirmed that surfaces of the granules were covered with characteristic crystals of a carbonate apatite from the scanning electron microscope image.

Accordingly, it was confirmed that, when the calcium hydrogen phosphate dihydrate covered hydroxyapatite granules were immersed in the aqueous solution in which $NaHCO_3$ and $Na_2HPO_4$ were mixed, calcium hydrogen phosphate dihydrate of the surface became a carbonate apatite and carbonate apatite covered hydroxyapatite granules were produced. A volume of the produced carbonate apatite covered hydroxyapatite granules was about $5 \times 10^{-11}$ m$^3$, which was $10^{-13}$ m$^3$ or more.

In order to verify tissue compatibility of the produced carbonate apatite covered hydroxyapatite granules, 0.1 g of the granules was implanted subcutaneously into a rat. No swelling was observed 1 week after implantation. In addition, when the implantation part was cut, the carbonate apatite covered hydroxyapatite granules were observed and no inflammatory exudate was observed. Based on such results, it was found that the carbonate apatite covered hydroxyapatite granules exhibited excellent tissue compatibility.

(Material)

β-type tricalcium phosphate (hereinafter referred to as "β-TCP") granules, an α-type tricalcium phosphate porous body, hydroxyapatite granules, carbonate apatite granules, calcium carbonate granules, calcium-containing glass granules, calcined bone, and hydroxyapatite covered titanium, which serve as core portions of hard tissue reconstruction materials for medical treatment of the present invention exemplified in Examples 34 to 41, were produced by known methods. As the calcium-containing glass, 45S5 glass known as bioglass was selected. The glass includes $SiO_2$, $Na_2O$, CaO, and $P_2O_5$ as constituent components whose mole fractions are 46.13:24.35:26.91:2.60.

(Evaluation Methods)

Examples 34 to 41 and comparative examples for the examples were evaluated as follows. That is, in the case of a bone prosthetic material, a 12-week old Wister SD male rat was used for an animal experiment. At 4 weeks after implantation, the product was excised together with surrounding tissues as a mass and a non-demineralized pathological tissue section was prepared according to a general method. Also, a pathological tissue section was prepared so that a maximum width of the bone defect was obtained. For staining, Villanueva Goldner staining was used.

An osteogenesis rate was defined as a ratio of a sum of lengths of portions in which bone was formed in a horizontal direction to a length (4 mm) of the formed bone defect. That is, a bone defect of 4 mm was defined in the pathological tissue section. When both bone ends on the brain side were connected by a straight line, a portion in which bone was formed in a direction perpendicular to the straight line was defined as an osteogenic region and a portion in which no bone was formed in a direction perpendicular to the straight line was defined as a non-osteogenic region. The osteogenesis rate was obtained by dividing a length of the osteogenic region by the length (4 mm) of the bone defect and expressed as %. While this evaluation method is not preferable for evaluating a total amount of osteogenesis, this method is preferable when a bone prosthetic material remains or when initial osteoconductivity is evaluated.

In the case of a hard tissue reconstruction implant material, a 12-week old Wister SD male rat was used for an animal experiment. At 4 weeks after implantation, the product was excised together with surrounding tissues as a mass and a non-demineralized pathological tissue section was prepared according to a general method. Also, the pathological tissue section was prepared so that a maximum width of the bone defect was obtained.

For staining, Villanueva Goldner staining was used.

A bone contact ratio was calculated by dividing a length of a portion to which a bone was linked around the hard tissue reconstruction implant material by an external dimension of the hard tissue reconstruction implant material implanted into a bone. The ratio was expressed as %.

Composition analysis was performed using the powder X-ray diffractometer. A D8 ADVANCE type powder X-ray diffractometer commercially available from BRUKER was used. An output was 40 kV and 40 mA. CuKα ($\lambda$=0.15418 nm) was used as an X-ray tube. The detected calcium hydrogen phosphate dihydrate (dicalcium phosphate dihydrate) was expressed as DCPD.

Example 34

β-TCP granules that passed through a sieve having a mesh opening of 800 μm but failed to pass through a sieve having a mesh opening of 500 were produced. In addition, an acidic solution in which monocalcium dihydrogen phosphate was dissolved at 50 mmol/L in 25 mmol/L phosphoric acid was produced. A pH of the acidic solution was 2.2. The β-TCP granules were immersed in the acidic solution at 25° C. for 4 hours and calcium hydrogen phosphate covered β-TCP granules were obtained.

Figure 28:
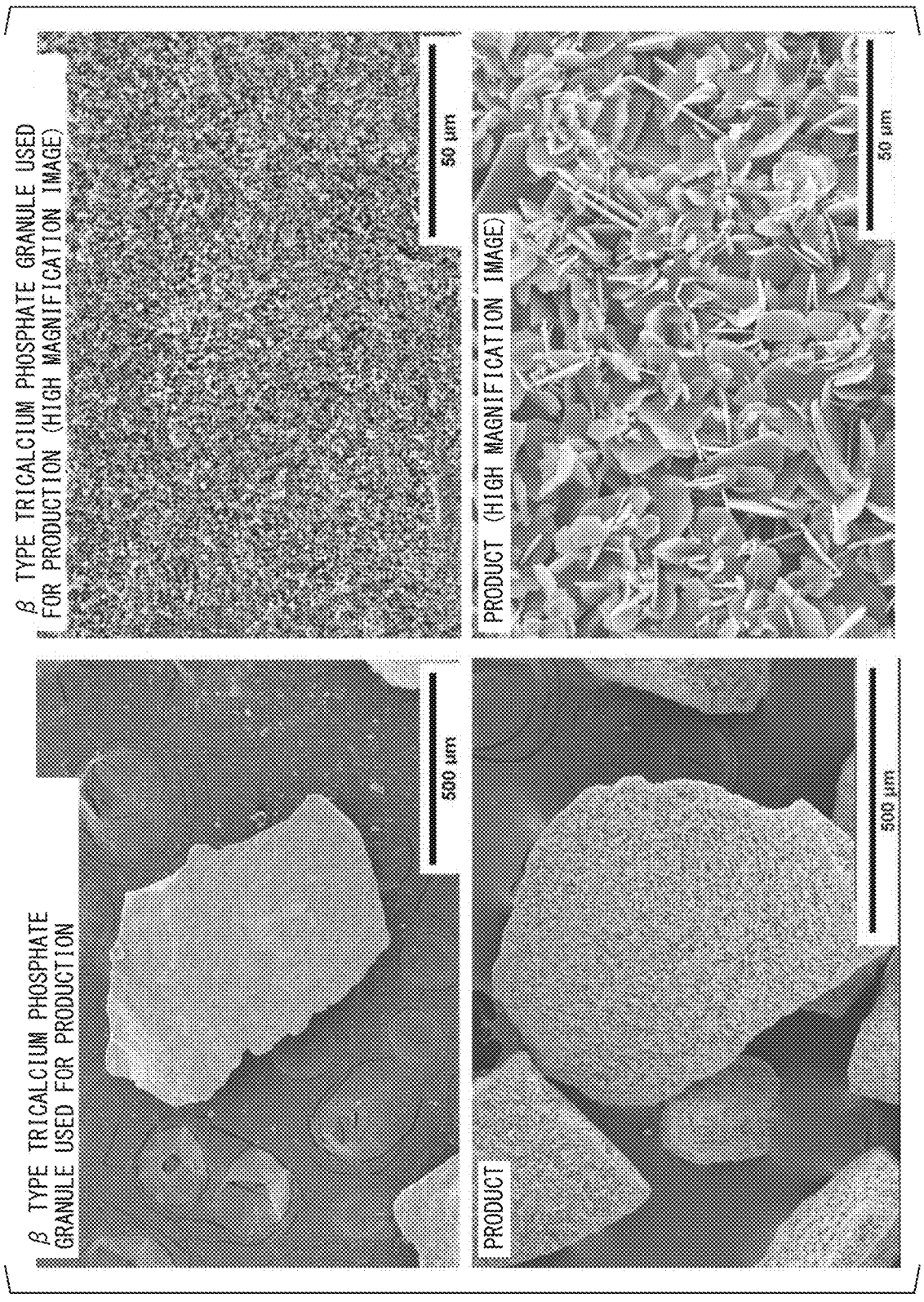
FIG. 28 shows pictures of β-type tricalcium phosphate granules used as a raw material in Example 34 (upper portion) and produced calcium hydrogen phosphate covered β-type tricalcium phosphate granules (lower portion) under a scanning electron microscope.

The upper portions in FIG. 28 show scanning electron microscopic pictures of β-TCP granules used as a raw material inorganic compound. The lower portions in FIG. 28 show scanning electron microscopic pictures of the produced calcium hydrogen phosphate covered β-TCP granules. It was confirmed that the calcium hydrogen phosphate covered β-TCP granules were formed in phases different from forms of raw material β-TCP granules. Based on the scanning electron microscopic picture of fractured surfaces of the produced granules, it was also confirmed that the material was composed of a surface layer portion and a core portion. The core portion of an active cross section was dense and columnar crystals were aggregated in the surface layer portion. In addition, an average conversion thickness of the surface layer portion was 10 μm. A coverage rate of the surface layer portion was 100%. As a result of EDAX analysis, it was confirmed that a Ca/P ratio of the core portion was 1.5 and a Ca/P ratio of the surface layer portion was 10. The core portion and the surface layer portion were firmly adhered. In addition, the product exhibited a sufficient mechanical strength for clinical applications as a bone prosthetic material.

Figure 29:
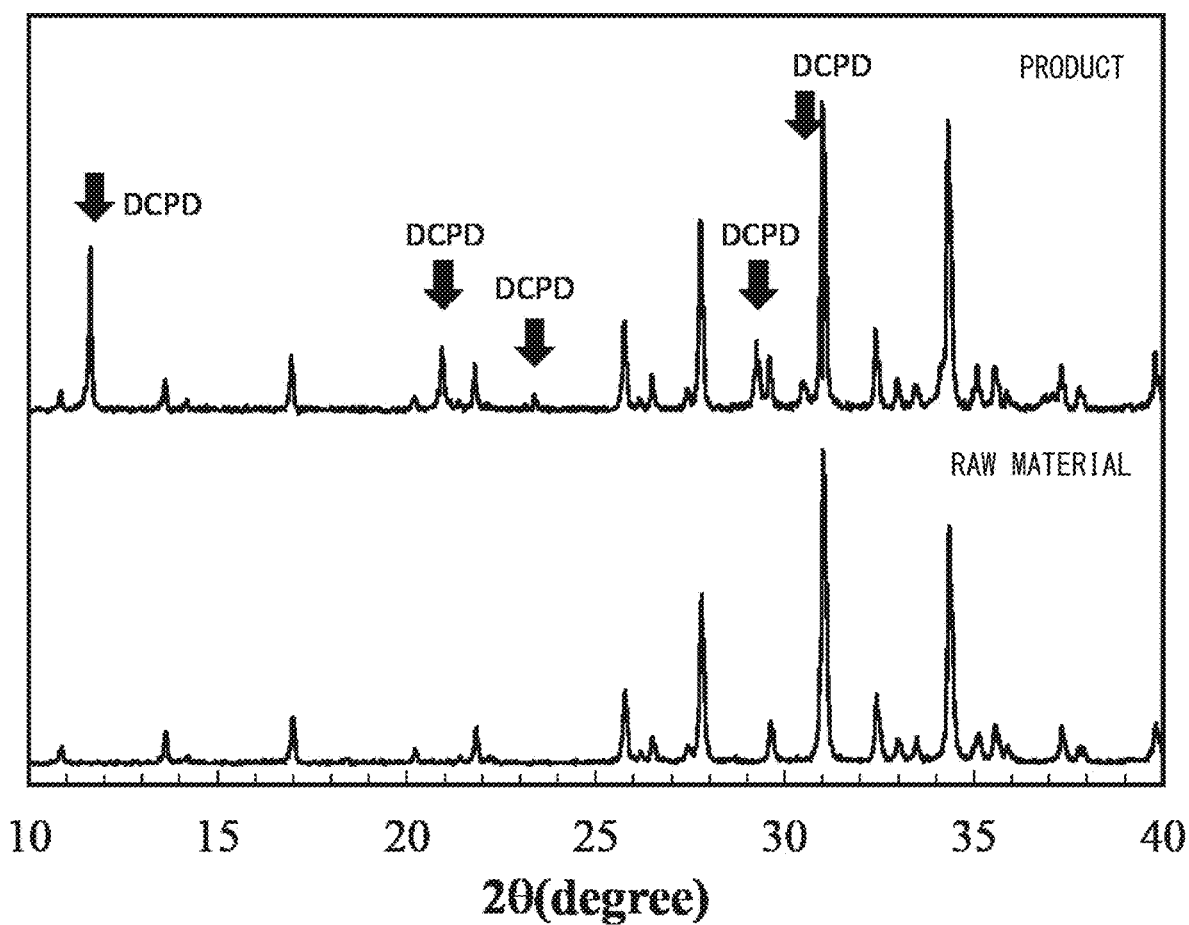
FIG. 29 shows X-ray diffraction patterns of calcium hydrogen phosphate covered β-type tricalcium phosphate granules produced in Example 34 (upper portion) and β-type tricalcium phosphate granules used as a raw material (lower portion).

The upper portion in FIG. 29 shows a powder X-ray diffraction pattern of the produced calcium hydrogen phosphate covered β-TCP granules. The lower portion in FIG. 29 shows a powder X-ray diffraction pattern of the β-TCP granules used for production. In the product, in addition to peaks derived from β-TCP, peaks derived from calcium hydrogen phosphate dihydrate were detected. In the product, a content of calcium hydrogen phosphate dihydrate was 24 mass %.

Based on such results, it was found that a granular material including the surface layer portion whose composition was calcium hydrogen phosphate and the core portion whose composition was β-TCP was produced.

Figure 30:
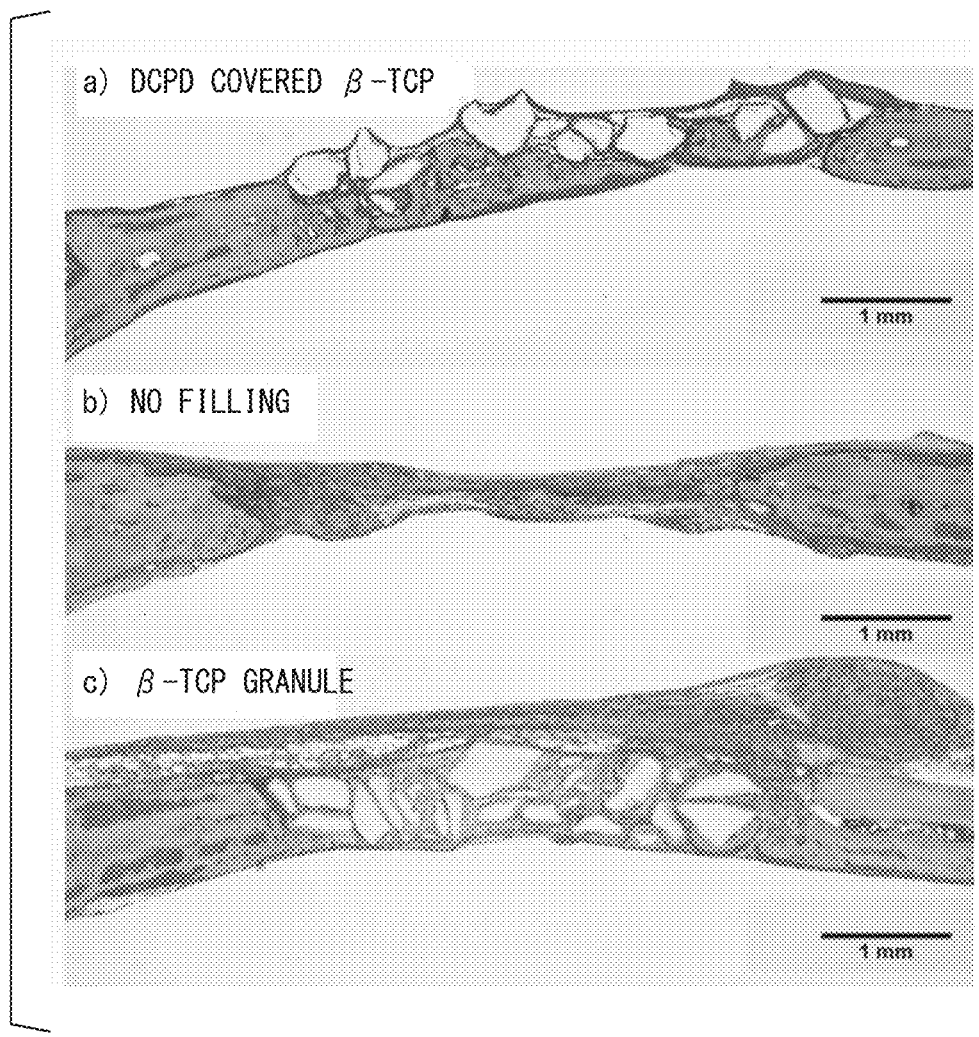
FIG. 30 shows pathological tissue section images of calcium hydrogen phosphate covered β-type tricalcium phosphate granules produced in Example 34 four weeks after implantation (upper portion), with no filling in Comparative Example 6 (middle portion), and 4 weeks after implantation of β-type tricalcium phosphate granules in Comparative Example 6 (lower portion) in a rat bone defect model.

A bone defect with a diameter of 4 mm formed in a rat skull was reconstructed using the produced calcium hydrogen phosphate covered β-TCP granules. The a) of FIG. 30 shows a pathological tissue section 4 weeks after implantation. It was found that the produced calcium hydrogen phosphate covered β-TCP granules exhibited excellent tissue compatibility. In addition, it was confirmed that bone grew on surfaces of the produced calcium hydrogen phosphate covered β-TCP granules. An osteogenesis rate was 93%.

Based on the above results, it was found that the produced calcium hydrogen phosphate covered β-TCP granules were a hard tissue reconstruction material for medical treatment having excellent osteoconductivity, and particularly a bone prosthetic material. In addition, since a composition of a core material was β-TCP granules which are a bioabsorbable material, it was found that the material was a bone replacement material.

Comparative Example 6

In order to clarify superiority of the calcium hydrogen phosphate covered β-TCP granules in Example 34, the same experiment as in Example 34 was performed without using the calcium hydrogen phosphate covered β-TCP granules. In addition, in order to clarify superiority of the calcium hydrogen phosphate covered β-TCP granules, a bone defect was reconstructed using β-TCP granules not covered with calcium hydrogen phosphate outside the scope of the present invention in the same manner as in Example 34.

As shown in b) of FIG. 30, it was found that, when the bone prosthetic material of the present invention was not used, new bone formation was observed from both ends of the bone defect, but hardly any bone was formed on the bone defect and the bone defect was not treated. A bone regeneration rate was 21%.

As shown in c) of FIG. 30, when the bone defect was reconstructed using the β-TCP granules, new bone formation was observed from both ends of the bone defect and osteoconduction to the periphery of the β-TCP granules was also observed. However, a bone regeneration rate was 57%, which was lower than in Example 34.

Since such results were inferior to those of the product in Example 34, it was confirmed that the calcium hydrogen phosphate covered β-TCP granules in Example 34 were excellent as a hard tissue reconstruction material for medical treatment.

Example 35

A polyurethane foam was immersed in an α-type tricalcium phosphate suspension and calcined at 1500° C. to produce an α-type tricalcium phosphate porous body.

In addition, an acidic solution in which calcium dihydrogen phosphate was dissolved at 1 mol/L in 1 mol/L phosphoric acid was produced. A pH of the acidic solution was 2.0.

The α-type tricalcium phosphate porous body was immersed in the acidic solution at 25° C. for 15 minutes and a calcium hydrogen phosphate covered α-type tricalcium phosphate porous body was obtained.

Figure 31:
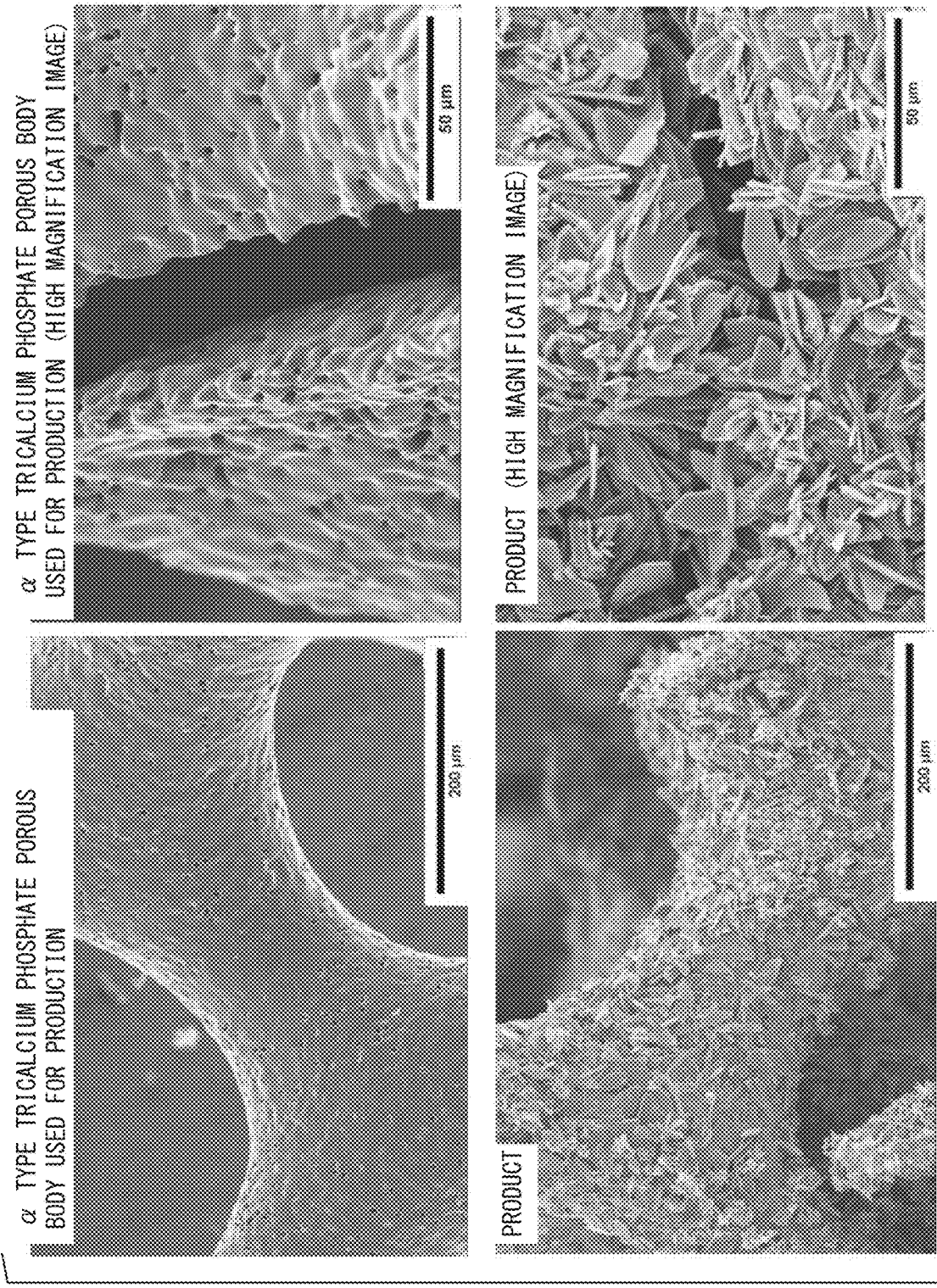
FIG. 31 shows pictures of an α-type tricalcium phosphate porous body used as a raw material in Example 35 (upper portion) and a produced calcium hydrogen phosphate covered α-type tricalcium phosphate porous body (lower portion) under a scanning electron microscope.

The upper portions in FIG. 31 show scanning electron microscopic pictures of the α-type tricalcium phosphate porous body used as a raw material. The lower portions in FIG. 31 show scanning electron microscopic pictures of the calcium hydrogen phosphate covered α-type tricalcium phosphate porous body. Based on such scanning electron microscopic pictures and manipulated electron micrographs of the fractured surface of the product, it was conformed that the product was a material composed of a surface layer portion and a core portion. The core portion was basically dense but some pores were observed. In the surface layer portion, plate-like crystals were aggregated. In addition, the average conversion thickness of the surface layer portion was 20 µm. A coverage rate of the surface layer portion was 100%. As a result of EDAX analysis, it was confirmed that a Ca/P ratio of the core portion was 1.5 and a Ca/P ratio of the surface layer portion was 10. The core portion and the surface layer portion were firmly adhered. In addition, the product exhibited a sufficient mechanical strength for clinical applications as a bone prosthetic material.

Figure 32:
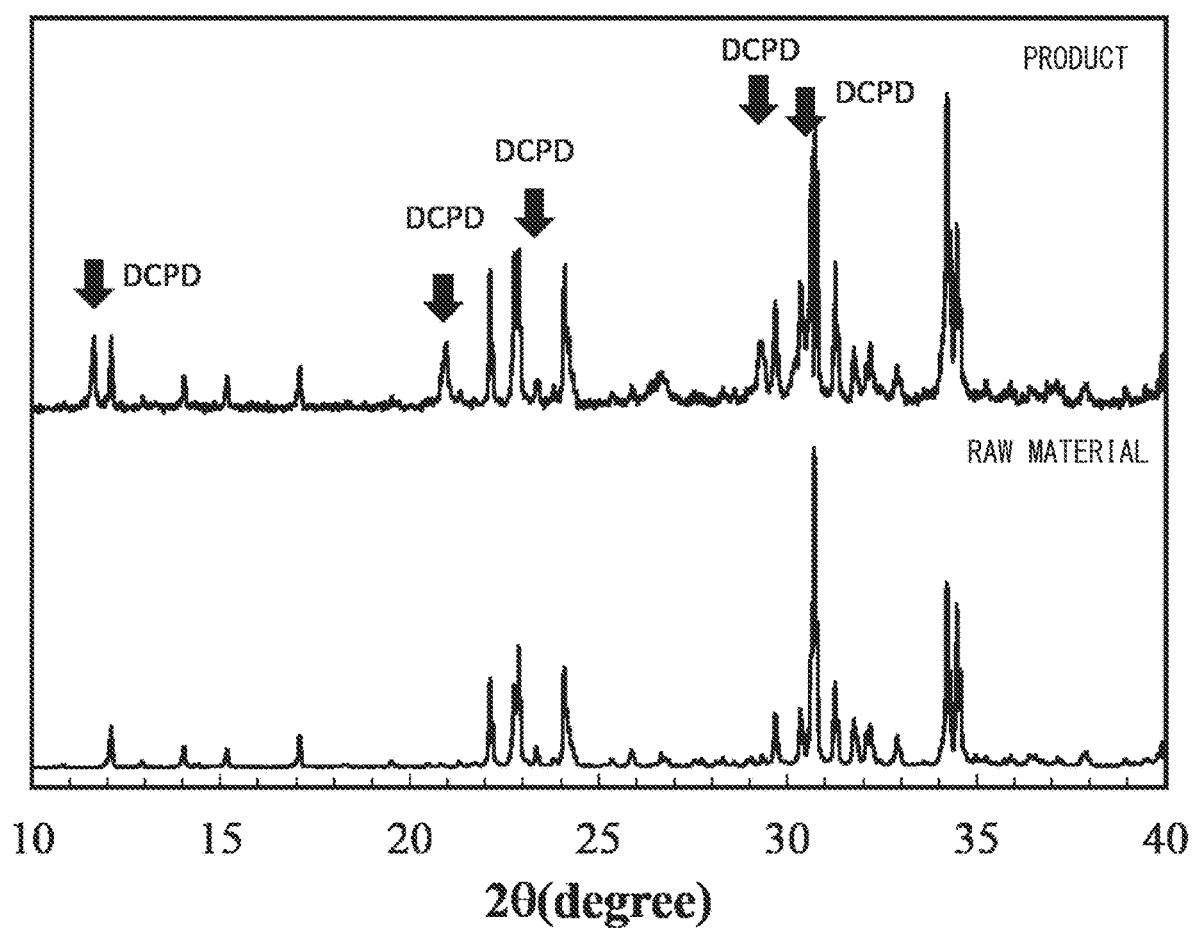
FIG. 32 shows X-ray diffraction patterns of the calcium hydrogen phosphate covered α-type tricalcium phosphate porous body produced in Example 35 (upper portion) and an α-type tricalcium phosphate porous body used as a raw material (lower portion).

The upper portion in FIG. 32 shows a powder X-ray diffraction pattern of the produced calcium hydrogen phosphate covered α-type tricalcium phosphate porous body. The lower portion in FIG. 32 shows a powder X-ray diffraction pattern of the α-type tricalcium phosphate porous body used as a raw material. In the produced porous body material, in addition to peaks derived from α-type tricalcium phosphate, peaks derived from calcium hydrogen phosphate dihydrate were detected.

Based on such results, it was found that a porous body material including the surface layer portion whose composition was calcium hydrogen phosphate and the core portion whose composition was α-type tricalcium phosphate was produced.

A bone defect formed in a rabbit femur with a diameter of 8 mm was reconstructed using the produced calcium hydrogen phosphate covered α-type tricalcium phosphate porous body. It was found that the calcium hydrogen phosphate covered α-type tricalcium phosphate porous body exhibited excellent tissue compatibility through histopathological analysis 4 weeks after implantation. In addition, it was confirmed that osteoconduction occurred on the surface and inside the produced calcium hydrogen phosphate covered α-type tricalcium phosphate porous body.

Comparative Example 7

In order to clarify superiority of the calcium hydrogen phosphate covered α-type tricalcium phosphate porous body in Example 34, a bone defect was reconstructed using the α-type tricalcium phosphate porous body outside the scope of the present invention in the same manner as in Example 34.

Based on the histopathological analysis 4 weeks after implantation, it was found that the α-type tricalcium phosphate porous body exhibited excellent tissue compatibility. In addition, it was confirmed that osteoconduction occurred on the surface and inside the α-type tricalcium phosphate porous body. However, a degree of bone invasion was inferior to that of Example 34.

Based on such results, it was found that the calcium hydrogen phosphate covered α-type tricalcium phosphate porous body in Example 34 was excellent as a hard tissue reconstruction material for medical treatment.

Example 36

Hydroxyapatite granules that passed through a sieve having a mesh opening of 1500 µm but failed to pass through a sieve having a mesh opening of 800 µm were produced.

The hydroxyapatite granules were immersed in the acidic solution described in Example 34 at 25° C. for 15 minutes and calcium hydrogen phosphate covered hydroxyapatite granules were obtained.

Figure 33:
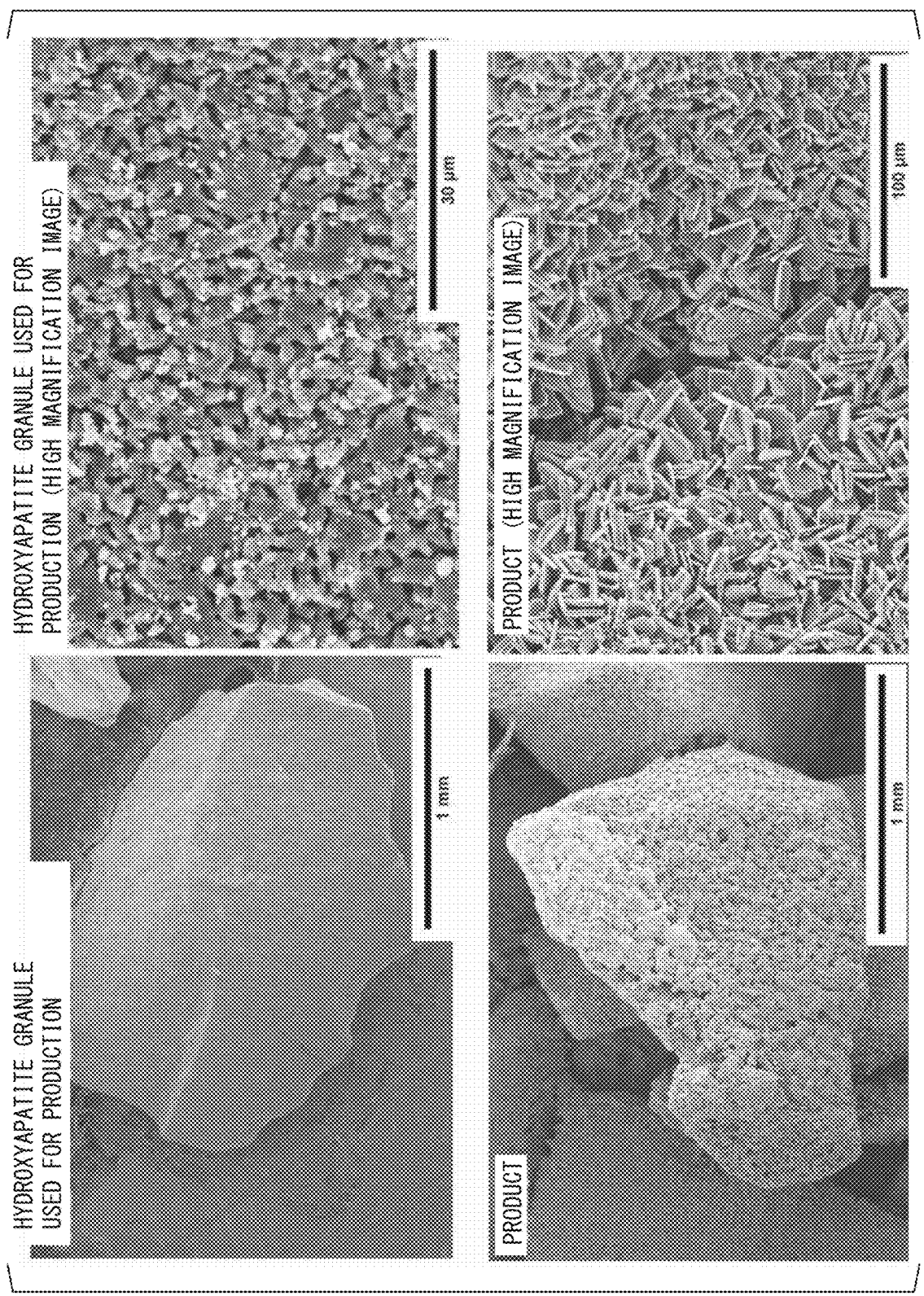
FIG. 33 shows pictures of hydroxyapatite granules used as a raw material in Example 36 (upper portion) and produced calcium hydrogen phosphate covered hydroxyapatite granules (lower portion) under a scanning electron microscope.

The upper portions in FIG. 33 show scanning electron microscopic pictures of the hydroxyapatite granules used as a raw material. The lower portions in FIG. 33 show scanning electron microscopic pictures of the produced calcium hydrogen phosphate covered hydroxyapatite granules. It was confirmed that phases in different forms were formed according to production. Based on the scanning electron microscopic picture of the fractured surface of the produced granules, it was also confirmed that the material was composed of a surface layer portion and a core portion. When an active cross section was observed, the core portion was dense and columnar crystals were aggregated in the surface layer portion. In addition, the average conversion thickness of the surface layer portion was 40 µm. A coverage rate of the surface layer portion was 100%. As a result of EDAX analysis, it was confirmed that a Ca/P ratio of the core portion was 1.67 and a Ca/P ratio of the surface layer portion was 10.

The core portion and the surface layer portion were firmly adhered. In addition, the product exhibited a sufficient mechanical strength for clinical applications as a bone prosthetic material.

Figure 34:
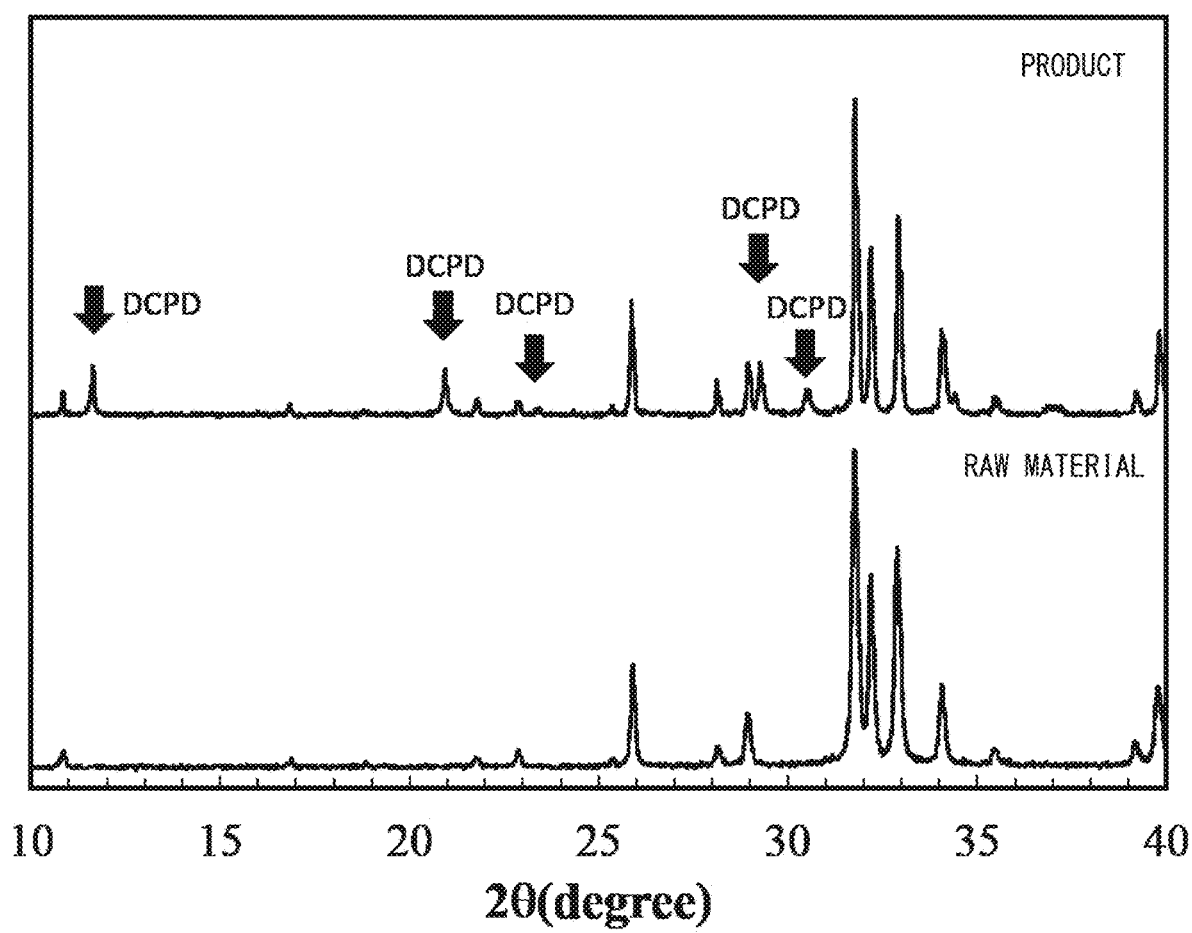
FIG. 34 shows X-ray diffraction patterns of calcium hydrogen phosphate covered hydroxyapatite granules produced in Example 36 (upper portion) and hydroxyapatite granules used as a raw material (lower portion).

The upper portion in FIG. 34 shows a powder X-ray diffraction pattern of the produced calcium hydrogen phosphate covered hydroxyapatite granules. The lower portion in FIG. 34 shows a powder X-ray diffraction pattern of hydroxyapatite granules as a raw material. In the product, in addition to peaks derived from the hydroxyapatite granules, peaks derived from calcium hydrogen phosphate dihydrate were detected.

Based on such results, it was found that a granular material including the surface layer portion whose composition was calcium hydrogen phosphate and the core portion whose composition was hydroxyapatite granules was produced.

A bone defect with a diameter of 4 mm formed in a rat skull was reconstructed using the produced calcium hydrogen phosphate covered hydroxyapatite granules. Excellent tissue compatibility was confirmed from the pathological tissue section 4 weeks after implantation. In addition, it was confirmed that bone grew on surfaces of the produced calcium hydrogen phosphate covered hydroxyapatite granules. An osteogenesis rate was 95%.

Based on the above results, it was found that the produced calcium hydrogen phosphate covered hydroxyapatite granules were a bone prosthetic material having excellent osteoconductivity.

Comparative Example 8

In order to clarify superiority of the calcium hydrogen phosphate covered hydroxyapatite granules in Example 36, a bone defect was reconstructed using hydroxyapatite granules outside the scope of the present invention in the same manner as in Example 36.

When the bone defect was reconstructed using the hydroxyapatite granules, new bone formation was observed from both ends of the bone defect and osteoconduction to the periphery of the hydroxyapatite granules was also observed. However, a bone regeneration rate was 64%.

Based on such results, it was found that the calcium hydrogen phosphate covered hydroxyapatite granules in Example 36 were excellent as a hard tissue reconstruction material for medical treatment.

Example 37

Carbonate apatite granules that passed through a sieve having a mesh opening of 1500 µm but failed to pass through a sieve having a mesh opening of 800 µm were produced.

The carbonate apatite granules were immersed in the acidic solution described in Example 34 at 25° C. for 15 minutes and calcium hydrogen phosphate covered carbonate apatite granules were obtained.

Figure 35:
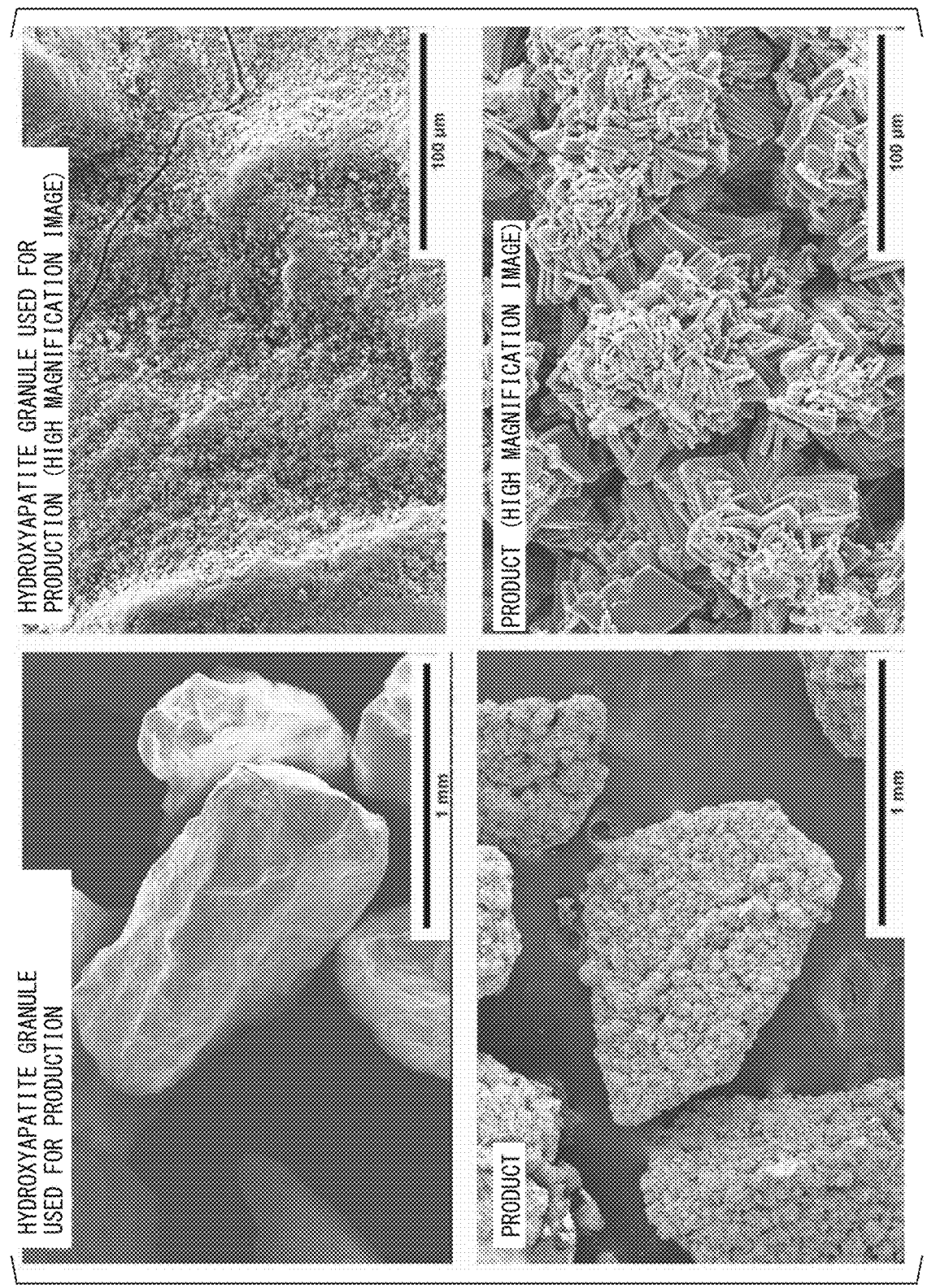
FIG. 35 shows pictures of carbonate apatite granules used as a raw material in Example 37 (upper portion) and produced calcium hydrogen phosphate covered carbonate apatite granules (lower portion) under a scanning electron microscope.

The upper portions in FIG. 35 show scanning electron microscopic pictures of the carbonate apatite granules used as a raw material. The lower portions in FIG. 35 show scanning electron microscopic pictures of the produced calcium hydrogen phosphate covered carbonate apatite granules. It was confirmed that phases in different forms were formed according to production. Based on the scanning electron microscopic pictures of the fractured surface of the produced granules, it was also confirmed that the material was composed of a surface layer portion and a core portion. When an active cross section was observed, the core portion was dense and columnar crystals were aggregated in the surface layer portion. In addition, the average conversion thickness of the surface layer portion was 40 μm. A coverage rate of the surface layer portion was 100%. As a result of EDAX analysis, it was confirmed that a Ca/P ratio of the core portion was 1.9 and a Ca/P ratio of the surface layer portion was 10.

The core portion and the surface layer portion were firmly adhered. In addition, the product exhibited a sufficient mechanical strength for clinical applications as a bone prosthetic material.

Figure 36:
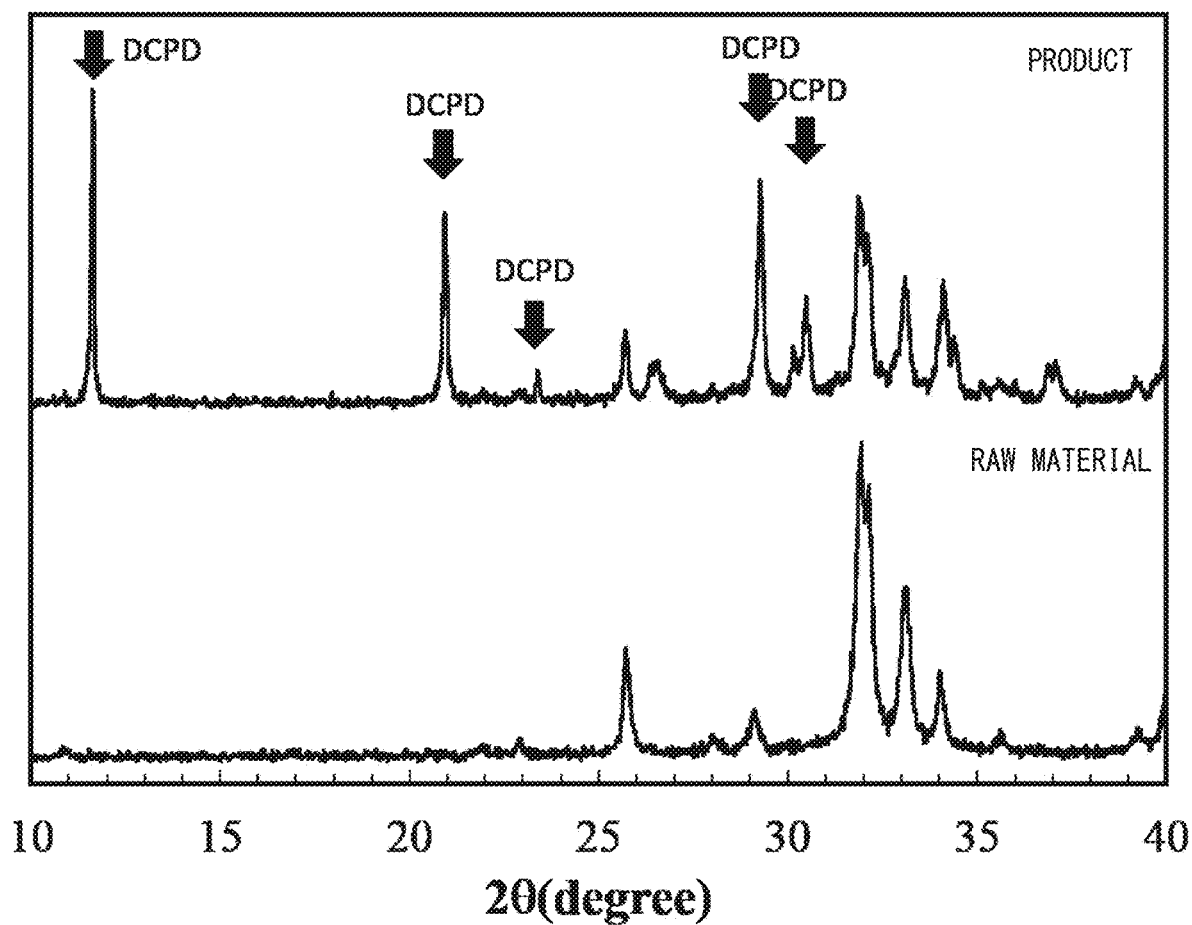
FIG. 36 shows X-ray diffraction patterns of calcium hydrogen phosphate covered carbonate apatite granules produced in Example 37 (upper portion) and carbonate apatite granules used as a raw material (lower portion).

The upper portion in FIG. 36 shows a powder X-ray diffraction pattern of the produced calcium hydrogen phosphate covered carbonate apatite granules. The lower portion in FIG. 36 shows a powder X-ray diffraction pattern of the carbonate apatite granules used as a raw material. In the product, in addition to peaks derived from the carbonate apatite granules, peak derived from calcium hydrogen phosphate dihydrate were detected.

Based on such results, it was found that a granular material including the surface layer portion whose composition was calcium hydrogen phosphate and the core portion whose composition was carbonate apatite granules was produced.

A bone defect with a diameter of 4 mm formed in a rat skull was reconstructed using the produced calcium hydrogen phosphate covered carbonate apatite granules. Excellent tissue compatibility was confirmed from the pathological tissue section 4 weeks after implantation. In addition, it was confirmed that bone grew on surfaces of the produced calcium hydrogen phosphate covered carbonate apatite granules. An osteogenesis rate was 100%.

Based on the above results, it was found that the produced calcium hydrogen phosphate covered carbonate apatite granules were a hard tissue reconstruction material for medical treatment having excellent osteoconductivity and particularly a bone prosthetic material. In addition, since a composition of a core material was the carbonate apatite granules which are a bioabsorbable material, it was found that the material was a bone replacement material.

Comparative Example 9

In order to clarify superiority of the calcium hydrogen phosphate covered carbonate apatite granules in Example 37, a bone defect was reconstructed using the carbonate apatite granules outside the scope of the present invention in the same manner as in Example 37. When the bone defect was reconstructed using the carbonate apatite granules, new bone formation was observed from both ends of the bone defect and osteoconduction to the periphery of the carbonate apatite granules was also observed. However, a bone regeneration rate was 64%.

Based on such results, it was found that the calcium hydrogen phosphate covered carbonate apatite granules in Example 37 were excellent as a hard tissue reconstruction material for medical treatment.

Example 38

Calcium carbonate granules that passed through a sieve having a mesh opening of 500 μm but failed to pass through a sieve having a mesh opening of 800 μm were produced.

The calcium carbonate granules were immersed in the acidic solution described in Example 2 at 25° C. for 15 minutes and calcium hydrogen phosphate covered calcium carbonate granules were obtained.

Figure 37:
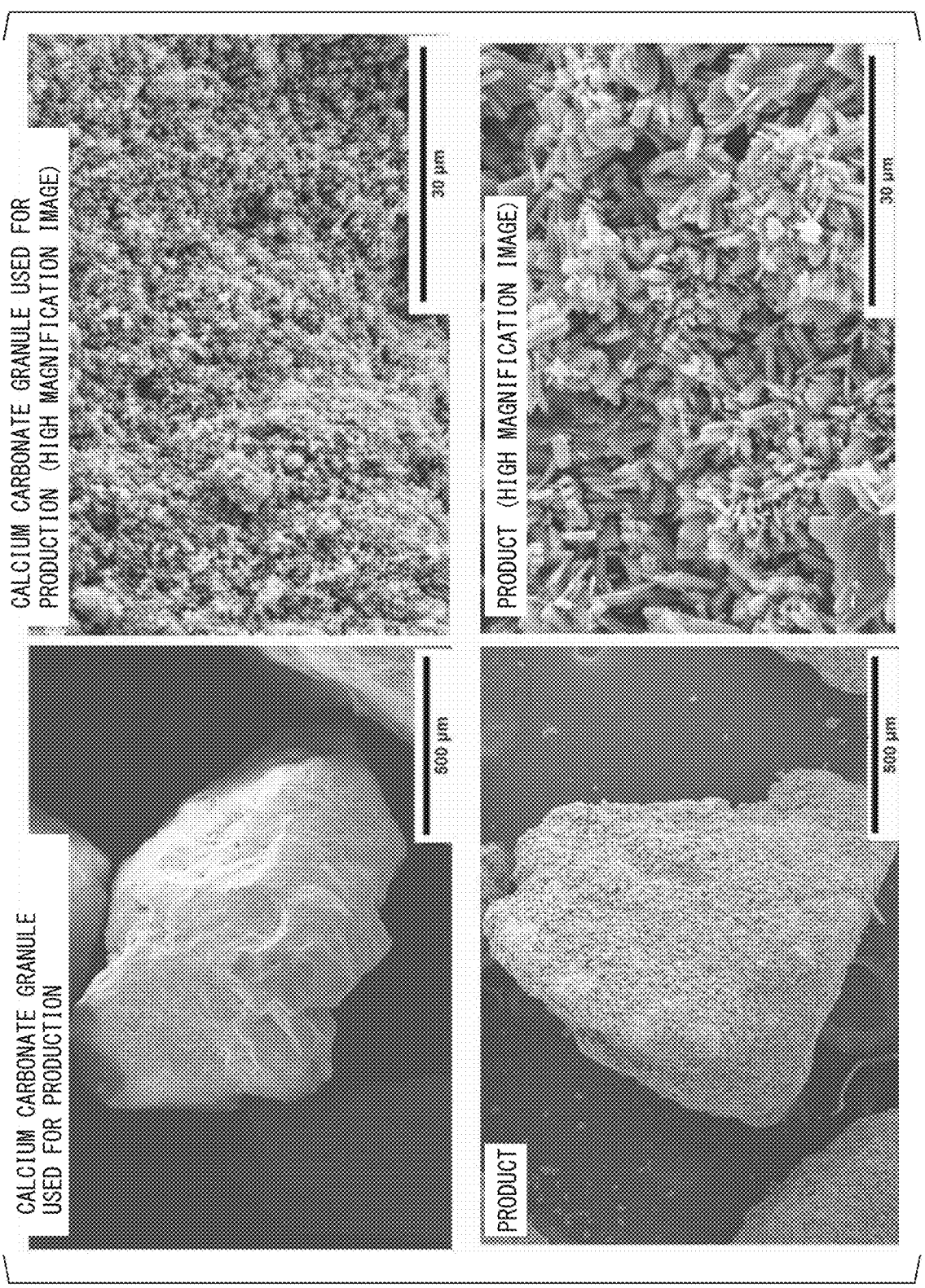
FIG. 37 shows pictures of calcium carbonate granules used as a raw material in Example 38 (upper portion) and produced calcium hydrogen phosphate covered calcium carbonate granules (lower portion) under a scanning electron microscope.

The upper portions in FIG. 37 show scanning electron microscopic pictures of the calcium carbonate granules used as a raw material. The lower portions in FIG. 37 show scanning electron microscopic pictures of the produced calcium hydrogen phosphate covered calcium carbonate granules. It was confirmed that phases in different forms were formed according to production. Based on the scanning electron microscopic pictures of the fractured surface of the produced granules, it was confirmed that the material was composed of a surface layer portion and a core portion. When an active cross section was observed, the core portion was dense and columnar crystals were aggregated in the surface layer portion. In addition, the average conversion thickness of the surface layer portion was 40 μm. A coverage rate of the surface layer portion was 100%. As EDAX analysis results, in the core portion, Ca was detected, but no P was detected. It was confirmed that a Ca/P ratio of the surface layer portion was 10.

The core portion and the surface layer portion were firmly adhered. The product exhibited a sufficient mechanical strength for clinical applications as a bone prosthetic material.

Figure 38:
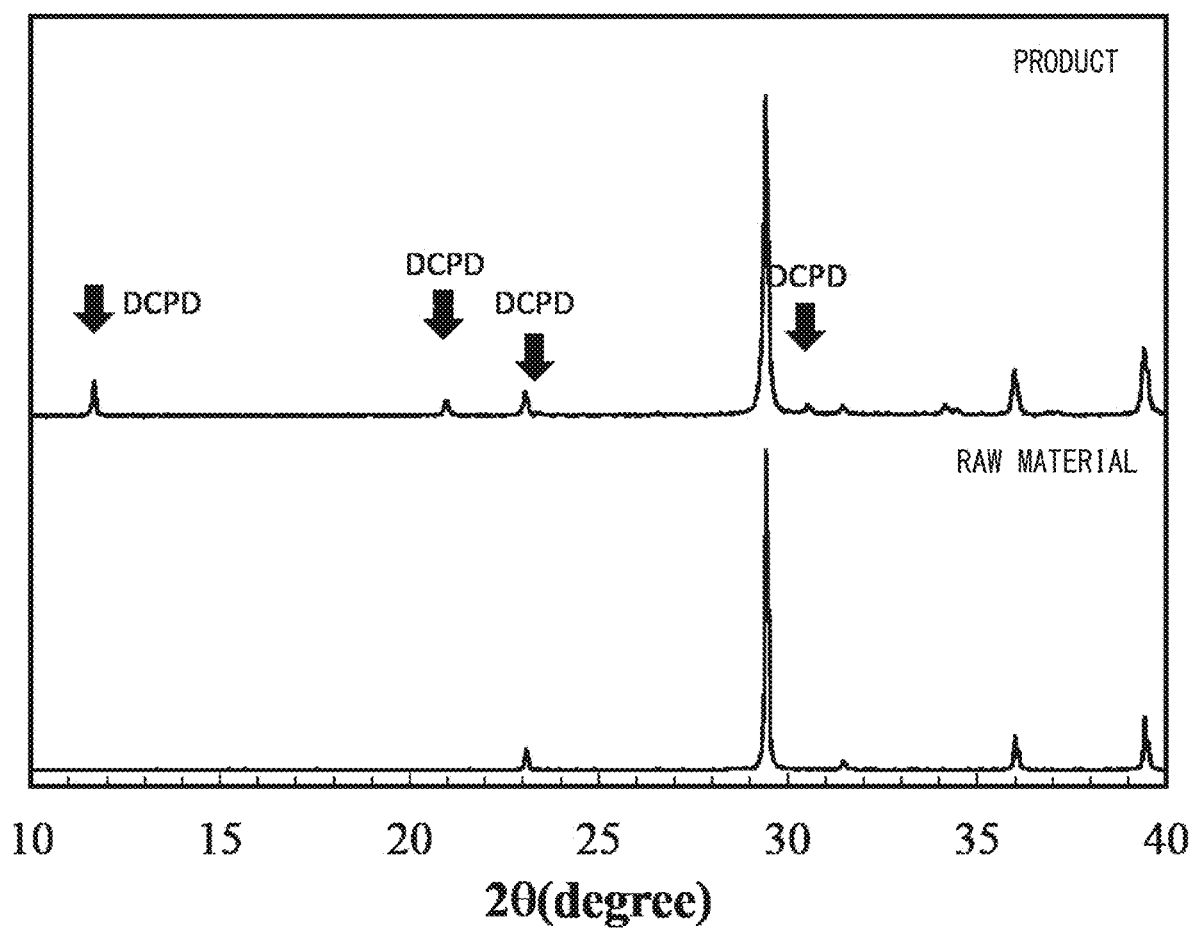
FIG. 38 shows X-ray diffraction patterns of calcium hydrogen phosphate covered calcium carbonate granules produced in Example 38 (upper portion) and calcium carbonate granules used as a raw material (lower portion).

The upper portion in FIG. 38 shows a powder X-ray diffraction pattern of the produced calcium hydrogen phosphate covered calcium carbonate granules. The lower portion in FIG. 38 shows a powder X-ray diffraction pattern of the calcium carbonate granules used as a raw material. In the product, in addition to peaks derived from the calcium carbonate granules, peaks derived from calcium hydrogen phosphate dihydrate were detected.

Based on such results, it was found that a granular material including the surface layer portion whose composition was calcium hydrogen phosphate and the core portion whose composition was calcium carbonate granules was produced.

A bone defect with a diameter of 4 mm formed in a rat skull was reconstructed using the produced calcium hydrogen phosphate covered calcium carbonate granules. Excellent tissue compatibility was confirmed from the pathological tissue section 4 weeks after implantation. In addition, it was confirmed that bone grew on surfaces of the produced calcium hydrogen phosphate covered calcium carbonate granules. An osteogenesis rate was 80%.

Based on the above results, it was found that the produced calcium hydrogen phosphate covered hydroxyapatite granules were a hard tissue reconstruction material for medical treatment having excellent osteoconductivity and particularly a bone prosthetic material. In addition, since a composition of a core material was the calcium carbonate granules which are a bioabsorbable material, it was found that the material was a bone replacement material.

Comparative Example 10

In order to clarify superiority of the calcium hydrogen phosphate covered calcium carbonate granules in Example 38, a bone defect was reconstructed using calcium carbonate granules outside the scope of the present invention in the same manner as in Example 38.

When the bone defect was reconstructed using the calcium carbonate granules, new bone formation was observed from both ends of the bone defect and osteoconduction to the periphery of the calcium carbonate granules was also observed. However, a bone regeneration rate was 46%.

Based on such results, it was found that the calcium hydrogen phosphate covered calcium carbonate granules in Example 38 were excellent as a hard tissue reconstruction material for medical treatment.

Example 39

Calcium-containing glass granules that passed through a sieve having a mesh opening of 1500 μm but failed to pass through a sieve having a mesh opening of 800 μm were produced.

The calcium-containing glass granules were immersed in the acidic solution described in Example 34 at 25° C. for 15 minutes and calcium hydrogen phosphate covered calcium-containing glass granules were obtained.

Figure 39:
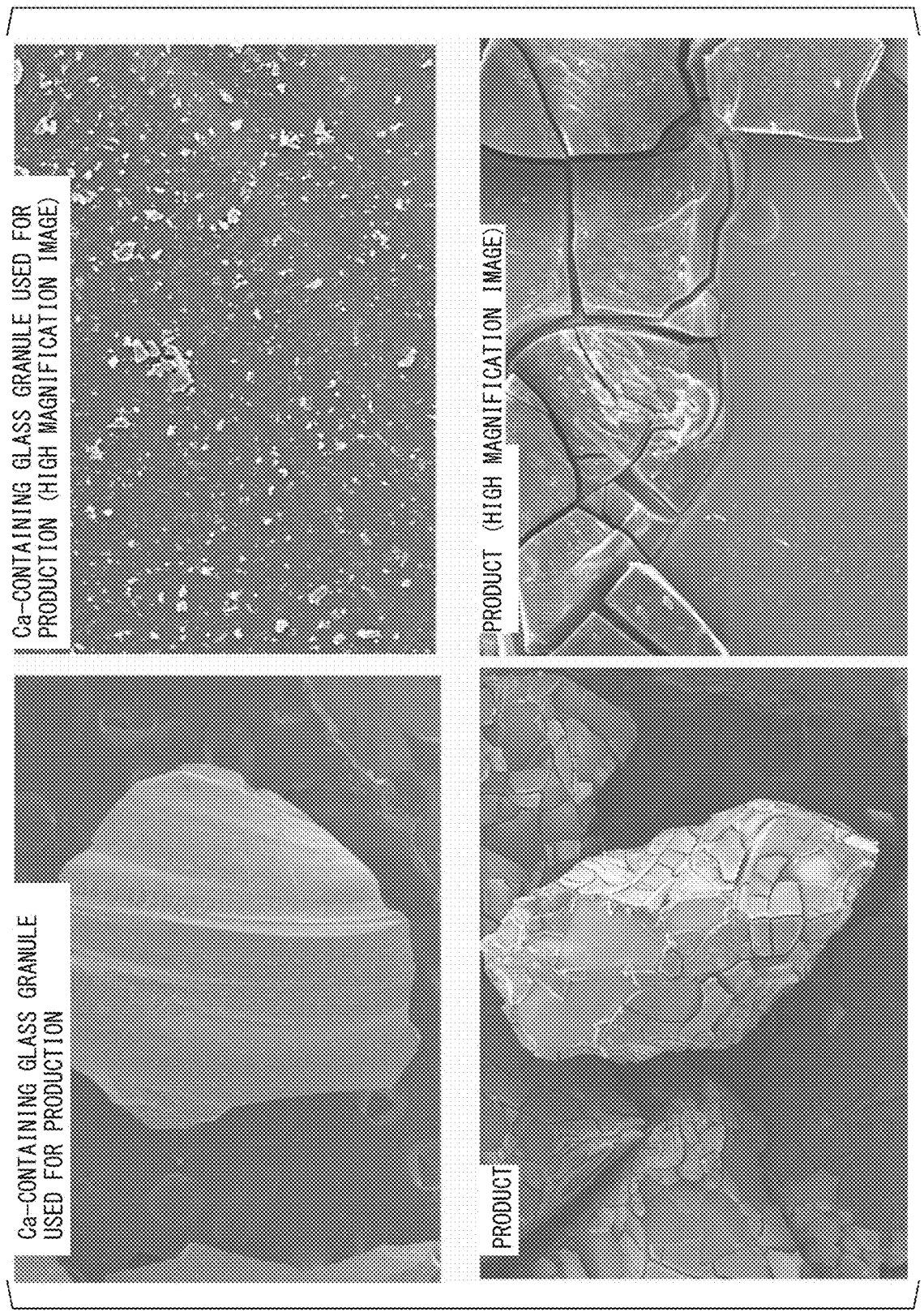
FIG. 39 shows pictures of calcium-containing glass granules used as a raw material in Example 39 (upper portion)

The upper portions in FIG. 39 show scanning electron microscopic pictures of the calcium-containing glass granules used as a raw material. The lower portions in FIG. 39 show scanning electron microscopic pictures of the produced calcium hydrogen phosphate covered calcium-containing glass granules. It was confirmed that phases in different forms were formed according to production. Based on the scanning electron microscopic pictures of the fractured surface of the produced granules, it was confirmed that the material was composed of a surface layer portion and a core portion. In an active cross section, the core portion was dense, and columnar crystals were aggregated in the surface layer portion. In addition, a thickness of the surface layer portion was 20 μm. A coverage rate of the surface layer portion was 100% under an optical microscope and 70% under a scanning electron microscope. As an EDAX analysis result, a Ca/P molar ratio of the core portion was 5.2. In addition, it was confirmed that a Ca/P ratio of the surface layer portion was 10.

The upper portion in FIG. 40 shows a powder X-ray diffraction pattern of the produced calcium hydrogen phosphate covered calcium-containing glass granules. The lower portion in FIG. 40 shows a powder X-ray diffraction pattern of the calcium-containing glass granules used as a raw material. In the product, in addition to characteristic broad peak of glass, peaks derived from calcium hydrogen phosphate dihydrate were detected.

Based on such results, it was found that a material including the surface layer portion whose composition was calcium hydrogen phosphate and the core portion whose composition was calcium-containing glass was produced.

While the core portion and the surface layer portion were adhered, some of the surface layer portion separated during a drying process according to gold coating which was a pretreatment under an electronic microscope. Therefore, it was confirmed that an adherence strength between a surface layer portion and a core portion was lower than those of the products in Examples 34 to 38. However, the product exhibited a sufficient mechanical strength for clinical applications as a bone prosthetic material.

A bone defect with a diameter of 4 mm formed in a rat skull was reconstructed using the produced calcium hydrogen phosphate covered calcium-containing glass granules. Excellent tissue compatibility was confirmed from the pathological tissue section 4 weeks after implantation. In addition, it was confirmed that bone grew on surfaces of the produced calcium hydrogen phosphate covered calcium-containing glass granules. An osteogenesis rate was 95%.

Based on the above results, it was found that the produced calcium hydrogen phosphate covered calcium-containing glass granules were a hard tissue reconstruction material for medical treatment having excellent osteoconductivity, and particularly a bone prosthetic material.

Comparative Example 11

In order to clarify superiority of the calcium hydrogen phosphate covered calcium-containing glass granules in Example 39, a bone defect was reconstructed using calcium-containing glass granules outside the scope of the present invention in place of the calcium hydrogen phosphate covered calcium-containing glass granules which were the material in Example 39, in the same manner as in Example 39.

When a bone defect was reconstructed using calcium carbonate granules, new bone formation was observed from both ends of the bone defect and osteoconduction to the periphery of the calcium-containing glass granules was also observed. A bone regeneration rate was 85%.

Based on such results, it was found that the calcium hydrogen phosphate covered calcium-containing glass granules in Example 39 were excellent as a hard tissue reconstruction material for medical treatment.

Example 40

Calcined bone granules that passed through a sieve having a mesh opening of 1500 μm but failed to pass through a sieve having a mesh opening of 800 μm were produced.

The calcined bone granules were immersed in the acidic solution described in Example 34 at 25° C. for 15 minutes and a calcium hydrogen phosphate covered calcined bone was obtained.

In an active cross section, the core portion had a porous body structure specific to bone, and columnar crystals were aggregated in the surface layer portion. In addition, the average conversion thickness of the surface layer portion was 10 μm. A coverage rate of the surface layer portion was 100%. As an EDAX analysis result, a Ca/P molar ratio of the core portion was 1.8. In addition, it was confirmed that a Ca/P ratio of the surface layer portion was 10.

The upper portion in FIG. 41 shows a powder X-ray diffraction pattern of the produced calcium hydrogen phosphate covered calcined bone. The lower portion in FIG. 41 shows a powder X-ray diffraction pattern of the calcined bone granules used as a raw material. In the product, in addition to characteristic peaks of the calcined bone, peaks derived from calcium hydrogen phosphate dihydrate were detected.

Based on such results, it was found that a material including the surface layer portion whose composition was calcium hydrogen phosphate and the core portion whose composition was a calcined bone was produced.

The core portion and the surface layer portion were firmly bonded. The product exhibited a mechanical strength sufficient for clinical applications.

A bone defect with a diameter of 4 mm formed in a rat skull was reconstructed using the produced calcium hydrogen phosphate covered calcined bone. Excellent tissue compatibility was confirmed from the pathological tissue section 4 weeks after implantation. In addition, it was confirmed that bone grew on surfaces of the produced calcium hydrogen phosphate covered calcined bone granules. An osteogenesis rate was 98%.

Based on the above results, it was found that the produced calcium hydrogen phosphate covered calcined bone granules were a hard tissue reconstruction material for medical treatment having excellent osteoconductivity, and particularly a bone prosthetic material. In addition, since a composition of the core material was the calcined bone granules which are a material exhibiting some degree of bioabsorbability, it was confirmed that the material was a bone replacement material.

Comparative Example 12

In order to clarify superiority of the calcium hydrogen phosphate covered calcined bone in Example 40, a bone defect was reconstructed using calcined bone granules outside the scope of the present invention in the same manner as in Example 40.

When a bone defect was reconstructed using calcined bone granules, new bone formation was observed from both ends of the bone defect and osteoconduction to the periphery of the calcined bone granules was also observed. However, a bone regeneration rate was 80%.

Based on such results, it was found that the calcium hydrogen phosphate covered calcined bone in Example 40 was excellent as a hard tissue reconstruction material for medical treatment.

Example 41

Hydroxyapatite was applied to a titanium rod through plasma spraying and hydroxyapatite covered titanium was produced. Next, the hydroxyapatite covered titanium was immersed in the acidic solution in Example 34 at 25° C. for 15 minutes and a calcium hydrogen phosphate covered implant material for hard tissue reconstruction was obtained.

It was confirmed that phases in different forms were formed according to production. Based on the scanning electron microscopic picture of the fractured surface of the product, it was also confirmed that, in the material, a surface layer portion was observed in addition to a core portion and a support. When an active cross section was observed, the core portion and the support were dense and columnar crystals were aggregated in the surface layer portion. In addition, the average conversion thickness of the surface layer portion was 40 μm and a coverage rate was 100%. As an EDAX analysis result, it was confirmed that a Ca/P molar ratio of the core portion was 1.67 and a Ca/P molar ratio of the surface layer portion was 10.

The core portion and the surface layer portion were firmly adhered. In addition, the product exhibited a sufficient mechanical strength for clinical applications.

Based on the analysis results of powder X-ray diffraction patterns, in the product, in addition to peaks derived from hydroxyapatite of the core portion, peaks derived from calcium hydrogen phosphate dihydrate were detected.

Based on such results, it was found that an implant material for hard tissue reconstruction including the surface layer portion whose composition was calcium hydrogen phosphate, the core portion whose composition was hydroxyapatite, and the support whose composition was titanium was produced.

The produced implant material for hard tissue reconstruction was implanted into a rat tibia.

The produced implant material for hard tissue reconstruction was implanted in a bone defect with a diameter of 2 mm formed in a tibia. Tissue compatibility was confirmed from pathological tissue sections 4 weeks after implantation. In addition, it was confirmed that bone grew on surfaces of the produced calcium hydrogen phosphate covered implant material for hard tissue reconstruction. A bone contact ratio was 95%.

Based on the above results, it was confirmed that the produced calcium hydrogen phosphate covered implant material for hard tissue reconstruction was a hard tissue reconstruction material for medical treatment having excellent osteoconductivity and particularly an implant material for reconstruction.

Comparative Example 13

In order to clarify superiority of the calcium hydrogen phosphate covered implant material for hard tissue reconstruction in Example 41, a bone defect was reconstructed using hydroxyapatite covered titanium outside the scope of the present invention in the same manner as in Example 41.

Tissue compatibility was confirmed from a pathological tissue section 4 weeks after implantation. In addition, it was confirmed that bone grew on surfaces of the apatite covered titanium implant material. A bone contact ratio was 80%. Based on the above results, the produced apatite covered titanium implant material had osteoconductivity. However, it was confirmed that the calcium hydrogen phosphate covered calcium hydrogen phosphate covered implant material for hard tissue reconstruction in Example 41 had a higher bone contact ratio and superiority.

(Evaluation Methods)

Examples 42 to 52 and comparative examples for the Examples were evaluated as follows. That is, the curing reaction was performed under conditions of 37° C. and a relative humidity of 100% similarly to in vivo. Accordingly, when curing was observed in examples and comparative examples, this means that a required condition of the curable inorganic compound: "(1) curing at a body temperature" was satisfied.

After curing was performed under conditions of 37° C. and a relative humidity of 100% for 30 minutes, movement of granules and the like in the cured body was examined. When granules and the like had not moved in a sample, it was determined that this sample satisfied a requirement of "(2) curing within 30 minutes." On the other hand, when granules and the like had moved in a sample, it was determined that this sample failed to satisfy a requirement of "(2) curing within 30 minutes."

In order to determine whether a requirement of "(3) a compressive strength of a cured body is 10 kPa or more" was satisfied, a compressive strength of a sample was measured using a universal testing machine (Autograph AGS-10 kN commercially available from Shimadzu Corporation).

In order to determine whether a requirement of (4) having an interconnected pore proportion of 10 volume % or more" was satisfied, a porosity of the cured body was measured.

In order to determine whether a requirement of "(5) does not exhibit a detrimental effect on tissue" was satisfied, a bone defect was formed in a laboratory animal, and a bone defect was reconstructed using the cured body. Then, the results were visually observed and evaluated through an X-ray micro CT and histopathological observation.

Composition analysis of the cured body was performed using the powder X-ray diffractometer. A D8 ADVANCE type powder X-ray diffractometer commercially available from BRUKER was used. An output was 40 kV and 40 mA. CuKα (λ=0.15418 nm) was used as an X-ray source.

Example 42

A carbonate apatite block was pulverized to produce carbonate apatite granules that passed through a sieve having a mesh opening of 600 μm but failed to pass through a sieve having a mesh opening of 300 The a) of FIG. 42 shows a picture of the produced carbonate apatite granules.

In this example, an aqueous electrolyte solution in which granules serving as a raw material inorganic compound were dispersed when a porous body was produced was referred to as a "mixing solution" and it is similarly referred to in Examples 42 to 52 and Comparative Examples for the Examples.

As a mixing solution, an aqueous solution (hereinafter referred to as a "calcium-phosphoric acid aqueous solution 1" in this example) in which calcium dihydrogen phosphate was dissolved at 25° C. to a 1 molar concentration with respect to 1 molar concentration phosphoric acid was produced. The aqueous solution included calcium at a 1 molar concentration and phosphoric acid at a 3 molar concentration. A pH of the aqueous solution was 1.6.

The carbonate apatite granules were filled into the interior of a plastic cylindrical mold with a diameter of 6 mm and a height of 3 mm placed on a slide glass. 500 μL of the calcium-phosphoric acid aqueous solution 1 was added dropwise to the carbonate apatite granules and the excess calcium-phosphoric acid aqueous solution 1 was removed for reaction. Also, when no load was applied to the granules, a sample was prepared under conditions in which a pressure of 0.5 MPa, 0.9 MPa, or 1.7 MPa was applied to a plastic cylindrical mold. The sample was left in a thermostatic bath at 37° C. and a relative humidity of 100% for 30 minutes. Then, curing was determined according to whether the granules had moved. As a result, it was confirmed that the granules had not moved but had been cured in all cases.

The b) of FIG. 42 shows the results for the cured body produced when a pressure of 0.9 MPa was applied to the plastic cylindrical mold. The c) of FIG. 42 shows a scanning electron microscope image of a surface of the cured body. The d) of FIG. 42 shows a high magnification image showing the bridging between granules in the cured body under a scanning electron microscope. Also, the observation portion in d) of FIG. 42 is indicated by the dashed line in c) of FIG. 42.

As shown in b) of FIG. 42 to d) of FIG. 42, the carbonate apatite granules were cured and formed a porous body. In addition, it was confirmed that a diameter of the interconnected pore was at least 30 μm or more. When light was introduced from below the cured body using a penlight, reflected light was observed from the upper surface of the cured body in all cases, and when distilled water was added dropwise, the water easily passed through the cured body. Therefore, it was confirmed that the cured body was an interconnected porous body. A porosity was about 68%. As shown in c) of FIG. 42 and d) of FIG. 42, the granules were linked by bridging by crystals.

FIG. 43 shows powder X-ray diffraction patterns. The b) of FIG. 43 shows a powder X-ray diffraction pattern of the cured body produced when a pressure of 0.9 MPa was applied to the plastic cylindrical mold. However, when no pressure was applied and when a different pressure was applied, powder X-ray diffraction patterns were almost the same. In b) of FIG. 43 showing a powder X-ray diffraction pattern of the cured body, in addition to a diffraction pattern derived from the carbonate apatite granules shown in a) of FIG. 43, a diffraction pattern derived from dicalcium phosphate dihydrate (DCPD; calcium hydrogen phosphate dihydrate) shown in c) of FIG. 43 was observed. Therefore, it was confirmed that the carbonate apatite granules and the calcium-phosphoric acid aqueous solution 1 had reacted to form calcium hydrogen phosphate.

Based on the scanning electron microscope observation and powder X-ray diffraction results, it was confirmed that, when the carbonate apatite granules and the calcium-phosphoric acid aqueous solution 1 were reacted, calcium hydrogen phosphate dihydrate was formed and the calcium hydrogen phosphate dihydrate bridged the carbonate apatite granules to form the cured body.

When no load was applied to granules, and when a pressure of 0.5 MPa, 0.9 MPa, or 1.7 MPa was applied to the plastic cylindrical mold and stress was applied to the granules, a compressive strength of the cured body was 300 kPa, 600 kPa, 800 kPa, and 100 kPa, respectively.

FIG. 44 shows X-ray micro CT images 1 week after a bone defect with a diameter of 4 mm was formed in a rat skull, carbonate apatite granules were filled into the bone defect, the calcium-phosphoric acid aqueous solution 1 was added dropwise for curing, the excess calcium-phosphoric acid aqueous solution 1 was removed using a gauze, and the defect was blocked.

Curing of the carbonate apatite granules in the bone defect according to the calcium-phosphoric acid aqueous solution 1 was confirmed by the fact that the granules had not moved. In addition, based on the X-ray micro CT image, it was confirmed that the cured body was an interconnected porous body.

FIG. 45 shows a histopathological image of hematoxy-eosin staining 2 weeks after implantation. In the drawing, mother bone is indicated by # and bone defect boundaries are indicated by arrows. G indicates main granules of the cured body of the cured carbonate apatite granules. In the drawing, asterisks indicate new bones. The fact that the cured body of the carbonate apatite granules exhibited excellent tissue compatibility and osteoconductivity was revealed based on the fact that no inflammatory response was caused, new bone was formed from a bone defect boundary, and the new bone was in contact with the cured body of the carbonate apatite granules.

Comparative Example 14

In order to confirm effectiveness of the curable inorganic compound described in Example 42, a curing reaction was examined under the same conditions as in Example 42 except that a mixing solution was distilled water, a sodium hydroxide aqueous solution at a 1 molar concentration, a calcium chloride aqueous solution at a 1 molar concentration, and a disodium hydrogen phosphoric acid aqueous solution at a 0.5 molar concentration. A pH was greater than 5 in all of the aqueous solutions. The carbonate apatite granules were not cured whichever of the aqueous solutions and whatever stress was applied.

Comparative Example 15

In order to confirm effectiveness of the curable inorganic compound described in Example 42, the carbonate apatite powder having a particle size about 2 µm shown in a) of FIG. 46 was mixed in the calcium-phosphoric acid aqueous solution 1.

After mixing, the result was stored and cured in an incubator at 37° C. and a relative humidity of 100%.

The b) of FIG. 46 shows the form of the cured body.

Even when light was introduced from below the cured body using a penlight, no reflected light was observed from the upper surface of the cured body. In addition, when distilled water was added dropwise, since the water did not pass through the cured body, it was confirmed that the cured body was not an interconnected porous body. The c) of FIG. 46 shows a scanning electron microscope image of the cured body. No interconnected pores of 30 µm or more were observed in the cured body.

Example 43

A hydroxyapatite block was pulverized to produce hydroxyapatite granules that passed through a sieve having a mesh opening of 2 mm but failed to pass through a sieve having a mesh opening of 500 µm. The a) of FIG. 47 shows a scanning electron microscopic picture of the produced hydroxyapatite granules. The b) of FIG. 47 shows a high magnification image thereof.

The calcium-phosphoric acid aqueous solution 1 was used as a mixing solution.

The hydroxyapatite granules were filled into the interior of a plastic cylindrical mold with a diameter of 6 mm and a height of 3 mm placed on a slide glass. 500 µL of the prepared calcium-phosphoric acid aqueous solution 1 was added dropwise to the hydroxyapatite granules, and the excess calcium-phosphoric acid aqueous solution 1 was removed for reaction. Also, a reaction was caused under conditions in which no load was applied to the granules. The sample was left in a thermostatic bath at 37° C. and a relative humidity of 100% for 30 minutes. Then, curing was determined according to whether the granules had moved. As a result, it was confirmed that the granules had not moved but had been cured.

The c) of FIG. 47 shows a scanning electron microscope image of the cured body. The d) of FIG. 47 shows a high magnification image showing the bridging between granules in the cured body under a scanning electron microscope.

As shown in c) of FIG. 47 to d) of FIG. 47, it was confirmed that the hydroxyapatite granules were cured, crystals were precipitated in the hydroxyapatite granules, and the precipitated crystals bridged the hydroxyapatite granules for curing.

When light was introduced from below the cured body using a penlight, reflected light was observed from the upper surface of the cured body and when distilled water was added dropwise, the water easily passed through the cured body. Therefore, it was confirmed that the cured body was an interconnected porous body. In addition, based on observation under a scanning electron microscope, it was confirmed that a diameter of the interconnected pore was at least 30 µm or more. A porosity was about 65%.

FIG. 48 shows powder X-ray diffraction patterns. In b) of FIG. 48 showing a powder X-ray diffraction pattern of the cured body, in addition to a diffraction pattern derived from the hydroxyapatite granules shown in c) of FIG. 48, a diffraction pattern derived from dicalcium phosphate dihydrate (DCPD) shown in a) of FIG. 48 was observed. Therefore, it was confirmed that the hydroxyapatite granules and the calcium-phosphoric acid aqueous solution 1 had reacted to form calcium hydrogen phosphate.

Based on the scanning electron microscope observation and powder X-ray diffraction results, it was confirmed that, when the hydroxyapatite granules and the calcium-phosphoric acid aqueous solution 1 having a pH of 4 or less were reacted, calcium hydrogen phosphate dihydrate was formed and the cured body was formed by bridging by the calcium hydrogen phosphate dihydrate.

A compressive strength of the cured body was 160 kPa.

A bone defect with a diameter of 4 mm was formed in a rat skull, hydroxyapatite granules were filled into the bone defect, the calcium-phosphoric acid aqueous solution 1 was added dropwise for curing, the excess calcium-phosphoric acid aqueous solution 1 was removed using a gauze, curing of the hydroxyapatite granules inside the bone defect was confirmed and the defect was then sealed.

When a bone defect repairing operation was performed and the result was histopathologically evaluated after 2 weeks, it was revealed that the cured body of the hydroxyapatite granules exhibited excellent tissue compatibility and osteoconductivity.

Comparative Example 16

In order to confirm effectiveness of the curable inorganic compound described in Example 43, a curing reaction was examined under the same conditions as in Example 43 except that a mixing solution was distilled water, a sodium hydroxide aqueous solution at a 1 molar concentration, a calcium chloride aqueous solution at a 1 molar concentration, and a disodium hydrogen phosphoric acid aqueous solution at a 0.5 molar concentration.

The hydroxyapatite granules were not cured when any of the aqueous solutions was used.

Comparative Example 17

In order to confirm effectiveness of the curable inorganic compound described in Example 2, a hydroxyapatite powder having a particle size of about 3 µm shown in a) of FIG. 49 was mixed in the calcium-phosphoric acid aqueous solution 1.

After mixing, the result was stored and cured in an incubator at 37° C. and a relative humidity of 100%.

The b) of FIG. 49 shows the form of the cured body.

When light was introduced from below the cured body using a penlight, no reflected light was observed from the upper surface of the cured body. In addition, when distilled water was added dropwise, since the water did not pass through the cured body, it was confirmed that the cured body was not an interconnected porous body. The c) of FIG. 49 shows a scanning electron microscope image of the cured body. No interconnected pores of 30 µm or more were observed in the cured body.

Example 44

A β-type tricalcium phosphate block was pulverized to prepare β-type tricalcium phosphate granules that passed through a sieve having a mesh opening of 600 µm but failed to pass through a sieve having a mesh opening of 300 μm. The a) of FIG. 50 shows a picture of the granules.

As a mixing solution, the calcium-phosphoric acid aqueous solution 1, phosphoric acid at a 1 molar concentration with a pH of 0.1, or hydrochloric acid at a 3 molar concentration with a pH of 0.9 was used.

The β-type tricalcium phosphate granules were filled in a stainless steel mold with a diameter of 6 mm and a height of 3 mm placed on a slide glass. The calcium-phosphoric acid aqueous solution 1, phosphoric acid at a 1 molar concentration or hydrochloric acid at a 3 molar concentration was added dropwise to the β-type tricalcium phosphate granules. The excess calcium-phosphoric acid aqueous solution 1 was removed using a gauze. Then, the sample was left in a thermostatic bath at 37° C. and a relative humidity of 100% for 30 minutes, and curing was then determined according to whether the granules had moved. As a result, it was confirmed that the granules had not moved but had been cured in all cases.

The b) of FIG. 50, c) of FIG. 50, and d) of FIG. 50 show the results for the cured body. The b) of FIG. 50 shows a picture of the cured body when the calcium-phosphoric acid aqueous solution 1 was used. The c) of FIG. 50 shows a picture of the cured body when phosphoric acid at a 1 molar concentration was used. The d) of FIG. 50 shows a picture of the cured body when hydrochloric acid at a 3 molar concentration was used. In any case, the β-type tricalcium phosphate granules were cured to form a porous body. When light was introduced from below the porous body using a penlight, reflected light was observed from the upper surface of the porous body and when distilled water was added dropwise, the water easily passed through the cured body. Therefore, it was confirmed that the interconnected porous body was formed. In the porous bodies obtained by curing the β-type tricalcium phosphate granules in the calcium-phosphoric acid aqueous solution 1, phosphoric acid at a 1 molar concentration, and hydrochloric acid at a 3 molar concentration, a porosity was 67%, 63%, and 63%.

FIG. 51 shows powder X-ray diffraction patterns. Also, the b) of FIG. 51 shows a powder X-ray diffraction pattern of the cured body when the calcium-phosphoric acid aqueous solution 1 was used. The c) of FIG. 51 shows a powder X-ray diffraction pattern of the cured body when phosphoric acid at a 1 molar concentration was used. The d) of FIG. 51 shows a powder X-ray diffraction pattern of the cured body when hydrochloric acid at a 3 molar concentration was used.

In b) of FIG. 51 to d) of FIG. 51 showing powder X-ray diffraction patterns of the cured body, in addition to a diffraction pattern derived from β-type tricalcium phosphate granules shown in a) of FIG. 51, a diffraction pattern derived from calcium hydrogen phosphate dihydrate (DCPD) shown in e) of FIG. 51 was observed. Therefore, it was confirmed that the β-type tricalcium phosphate granules were reacted with the calcium-phosphoric acid aqueous solution 1, phosphoric acid at a 1 molar concentration or hydrochloric acid at a 3 molar concentration to form calcium hydrogen phosphate dihydrate.

FIG. 52 shows a scanning electron microscope image. The a) of FIG. 52 shows β-type tricalcium phosphate granules. The b) of FIG. 52 to g) of FIG. 52 show scanning electron microscope images of the cured body. The b) of FIG. 52 and c) of FIG. 52 show images obtained when the calcium-phosphoric acid aqueous solution 1 was used as a mixing solution. The d) of FIG. 52 and e) of FIG. 52 show images obtained when phosphoric acid at a 1 molar concentration was used as a mixing solution. The f) of FIG. 52 and g) of FIG. 52 show images obtained when hydrochloric acid at a 3 molar concentration was used as a mixing solution. The b) of FIG. 52, d) of FIG. 52 and f) of FIG. 52 show low magnification images. The c) of FIG. 52, e) of FIG. 52, and g) of FIG. 52 show high magnification images. In any case, a precipitate that was not observed in β-type tricalcium phosphate granules was observed on surfaces of the β-type tricalcium phosphate granules and between the β-type tricalcium phosphate granules in all of the cured bodies. Also, when the calcium-phosphoric acid aqueous solution 1 was used, more crystals were observed than when another mixing solution was used. In addition, in all cured bodies, it was confirmed that a diameter of the interconnected pore was at least 30 μm or more.

Based on the scanning electron microscope observation and powder X-ray diffraction results, it was confirmed that, when the β-type tricalcium phosphate granules were reacted with the calcium-phosphoric acid aqueous solution 1, phosphoric acid at a 1 molar concentration, or hydrochloric acid at a 3 molar concentration, dicalcium phosphate dihydrate was formed, and the calcium hydrogen phosphate dihydrate bridged the β-type tricalcium phosphate granules to form the cured body.

A compressive strength of the cured body was 180 kPa, 110 kPa, or 70 kPa when the calcium-phosphoric acid aqueous solution 1, phosphoric acid at a 1 molar concentration or hydrochloric acid at a 3 molar concentration was used, respectively.

FIG. 53 shows a histopathological image after 2 weeks when a bone defect with a diameter of 4 mm was formed in a rat skull, the β-type tricalcium phosphate granules were filled into the bone defect, the calcium-phosphoric acid aqueous solution 1 was added dropwise, and the β-type tricalcium phosphate granules were cured. An inflammatory response due to a material was not observed before a specimen was prepared. In addition, it was confirmed that the cured state of the β-type tricalcium phosphate granules had been preserved when the sample was excised. In FIG. 53, G indicates β-type tricalcium phosphate granules and no inflammatory cells were observed therearound. In addition, it was confirmed that a bone grew inside the bone defect which was reconstructed using the cured body of the β-type tricalcium phosphate granules from a boundary of the bone defect. When phosphoric acid at a 1 molar concentration and hydrochloric acid at a 3 molar concentration were used for curing, similar results were obtained.

Example 45

A β-type tricalcium phosphate block was pulverized to prepare β-type tricalcium phosphate granules that passed through a sieve having a mesh opening of 1000 μm but failed to pass through a sieve having a mesh opening of 600 μm. The a) of FIG. 54 shows the form thereof.

MCPM was suspended in methanol, and β-type tricalcium phosphate granules were immersed in the suspension, removed from the suspension, and dried to produce β-type tricalcium phosphate granules to which MCPM was adhered (hereinafter referred to as MCPM-adhered βTCP granules). The b) of FIG. 54 shows a scanning electron microscopic picture of the obtained MCPM adhered βTCP granule.

Distilled water was used as a mixing solution.

The MCPM adhered βTCP granules were mixed with distilled water and put into a 1 mL plastic centrifugal tube. The adhered MCPM was dissolved in contact with distilled water. Therefore, the βTCP granules substantially reacted with an acidic calcium phosphoric acid aqueous solution having a pH of 5 or less.

The sample was left in a thermostatic bath at 37° C. and a relative humidity of 100% for 6 hours. Then, curing was determined according to whether the granules had moved. As a result, it was confirmed that the granules had not moved but had been cured as shown in c) of FIG. 54.

FIG. 55 shows powder X-ray diffraction patterns. The a) of FIG. 55 shows a powder X-ray diffraction pattern of the produced MCPM adhered βTCP granules. In the case of the cured body, as shown in b) of FIG. 55, a diffraction pattern derived from calcium hydrogen phosphate dihydrate (DCPD) shown in c) of FIG. 55 was observed. Therefore, it is thought that MCPM adhered to β-type tricalcium phosphate dissolved in distilled water and reacted with β-type tricalcium phosphate to form calcium hydrogen phosphate dihydrate (DCPD).

FIG. 56 shows scanning electron microscope images of the cured body. As shown in a) of FIG. 56, it was confirmed that crystals were precipitated on the surface of β-type tricalcium phosphate, and the precipitated crystals bridged and cured the β-type tricalcium phosphate granules. In addition, it was confirmed that a diameter of the interconnected pore was at least 30 μm or more.

When light was introduced from below the cured body using a penlight, reflected light was observed from the upper surface of the cured body and when distilled water was added dropwise, the water easily passed through the cured body. Therefore, it was confirmed that the cured body was an interconnected porous body. A porosity was about 68% and a compressive strength was 50 kPa.

Comparative Example 18

In order to confirm effectiveness of the curable inorganic compound described in Example 45, a curing reaction was examined under the same conditions as in Example 45 except that a mixing solution was distilled water, a sodium hydroxide aqueous solution at a 1 molar concentration, a calcium chloride aqueous solution at a 1 molar concentration, and a disodium hydrogen phosphoric acid aqueous solution at a 0.5 molar concentration. A pH was greater than 5 in all of the aqueous solutions. When any aqueous solution was used, the β-type tricalcium phosphate granules were not cured.

Comparative Example 19

In order to confirm effectiveness of the curable inorganic compound described in Example 45, a β-type tricalcium phosphate powder having a particle size of about 3 was mixed in the calcium-phosphoric acid aqueous solution 1, phosphoric acid at a 1 molar concentration, or hydrochloric acid at a 3 molar concentration.

After mixing, the result was stored and cured in an incubator at 37° C. and a relative humidity of 100%.

The a) of FIG. 57 shows the form of the cured body when mixed in the calcium-phosphoric acid aqueous solution 1.

Even when light was introduced from below the cured body using a penlight, no reflected light was observed from the upper surface of the cured body. In addition, when distilled water was added dropwise, since the water did not pass through the cured body, it was confirmed that the cured body was not an interconnected porous body. The b) of FIG. 57 shows a scanning electron microscope image of the cured body. No interconnected pores of 30 μm or more were observed in the cured body.

Similar results were obtained when mixing was performed using phosphoric acid at a 1 molar concentration and hydrochloric acid at a 3 molar concentration.

Example 46

A polyurethane foam was immersed in a tricalcium phosphate suspension and calcined at 1500° C. to produce an α-type calcium phosphate foam. The produced α-type tricalcium phosphate foam was pulverized to produce α-type calcium phosphate foam granules that passed through a sieve having a mesh opening of 10 mm but failed to pass through a sieve of 0.3 mm. The a) of FIG. 58 shows a picture of the form of the α-type calcium phosphate foam granules and b) of FIG. 58 shows a scanning electron microscope image thereof.

α-type tricalcium phosphate foam granules were filled in a stainless steel split mold (for preparing a sample with a diameter of 6 mmφ and a height of 3 mm) placed on a glass plate. From the side above the stainless steel split mold, the calcium-phosphoric acid aqueous solution produced in Example 42 was added in the same amount as the weight of granules and reaction was performed in a thermostatic bath at 37° C. and a relative humidity of 100% for 30 minutes. Then, curing was determined according to whether the granules had moved. As a result, it was confirmed that the granules had not moved but had been cured. The c) of FIG. 58 shows a picture of the cured body. When light was introduced from below the porous body using a penlight, reflected light was observed from the upper surface of the cured body and when distilled water was added dropwise, the distilled water easily passed therethrough. Therefore, it was confirmed that the interconnected porous body was formed. A porosity of the cured body was 60%. A compressive strength was 280 kPa.

The b) of FIG. 58 shows the α-type tricalcium phosphate foam granules used. The d) of FIG. 58 shows a scanning electron microscopic picture of the cured body. A precipitate was not observed on surfaces of the α-type tricalcium phosphate foam of granules in b) of FIG. 58 but was observed on the surface of the cured body in d) of FIG. 58. In addition, it was confirmed that precipitates entangle among the granules in the cured body and curing occurred due to bridging by entangling of the precipitates.

Example 47

An α-type tricalcium phosphate powder (commercially available from Taihei Chemical Industrial Co., Ltd.) was uniaxially compacted at 28 MPa to prepare an α-type tricalcium phosphate powder compacted body with a diameter of 3 mm and a height of 3 mm. The body was calcined at 1000° C. for 5 hours and polished to produce a spherical body with a diameter of 1.4 mm. The spherical body was calcined at 1400° C. for 5 hours to produce an α-type tricalcium phosphate sphere with a diameter of 1.3 mm.

As a mixing solution, a calcium dihydrogen phosphate-phosphoric acid aqueous solution (hereinafter, the solution will be referred to as a "calcium-phosphoric acid aqueous solution 6" in this example) in which calcium dihydrogen phosphate was dissolved at 25° C. to a concentration of 0.2 mol with respect to phosphoric acid at a 0.1 molar concentration was produced. The calcium-phosphoric acid aqueous solution 6 included calcium at a 0.2 molar concentration and phosphoric acid at a 0.5 molar concentration. A pH of the calcium-phosphoric acid aqueous solution 6 was 2.

α-type tricalcium phosphate spheres were filled in a stainless steel split mold (for preparing a sample with a diameter of 6 mmφ and a height of 6 mm) placed on a glass plate. From the side above the stainless steel split mold, 0.18 mL of the calcium-phosphoric acid aqueous solution 6 having a pH of 2 was added. The sample was reacted in a thermostatic bath at 37° C. and a relative humidity of 100% for 30 minutes. Then, curing was determined according to whether the granules had moved. As a result, it was confirmed that the granules had not moved but had been cured.

In addition, when light was introduced from below the porous body using a penlight, reflected light was observed from the upper surface of the porous body and when distilled water was added dropwise, the water easily passed through the cured body. Therefore, it was confirmed that the interconnected porous body was formed.

The a) of FIG. 60 shows a picture of the α-type tricalcium phosphate spheres used. The b) of FIG. 60 shows a picture of the cured body of the α-type tricalcium phosphate spheres. The c) of FIG. 60 shows a micro CT image of the cured body of the α-type tricalcium phosphate spheres. The d) of FIG. 60 shows a cross-sectional micro CT image of the cured body of the α-type tricalcium phosphate spheres. It was confirmed that the interconnected porous body was formed based on the micro CT image.

The b) of FIG. 61 shows thin-film powder X-ray diffraction patterns of the cured body of the α-type tricalcium phosphate spheres. Patterns that were not observed in thin-film powder X-ray diffraction patterns of the α-type tricalcium phosphate spheres shown in a) of FIG. 61 and that were derived from calcium hydrogen phosphate dihydrate (DCPD) shown in c) of FIG. 61 were observed. Therefore, it was confirmed that the α-type tricalcium phosphate spheres and the calcium-phosphoric acid aqueous solution 6 had reacted to form calcium hydrogen phosphate dihydrate.

The a) of FIG. 62 shows the α-type tricalcium phosphate spheres. The b) of FIG. 62 shows a scanning electron microscopic picture between α-type tricalcium phosphate spheres. The precipitate that was not observed on the surface of the α-type tricalcium phosphate sphere was observed in the cured body. In addition, it was confirmed that precipitates entangle the spheres in the cured body and the precipitate bridged the α-type tricalcium phosphate spheres and cured the α-type tricalcium phosphate spheres.

A porosity of the cured body was 50%. A compressive strength was 30 kPa.

Comparative Example 20

In order to confirm effectiveness of the curable inorganic compounds described in Examples 46 and 47, a curing reaction was examined under the same conditions as in Examples 46 and 47 except that a mixing solution was distilled water, a sodium hydroxide aqueous solution at a 1 molar concentration, a calcium chloride aqueous solution at a 1 molar concentration, and a disodium hydrogen phosphoric acid aqueous solution at a 0.5 molar concentration. A pH was greater than 5 in all of the aqueous solutions.

The α-type tricalcium phosphate foam granules and the α-type tricalcium phosphate sphere were not cured when any of the aqueous solutions was used.

Comparative Example 21

In order to confirm effectiveness of the curable inorganic compounds described in Examples 46 and 47, the α-type tricalcium phosphate powder having a particle size of about 6 μm shown in a) of FIG. 63 was mixed in the calcium-phosphoric acid aqueous solution 1, phosphoric acid at a 1 molar concentration, or hydrochloric acid at a 3 molar concentration.

After mixing, the result was stored and cured in an incubator at 37° C. and a relative humidity of 100%.

The b) of FIG. 63 shows the form of the cured body when mixed in the calcium-phosphoric acid aqueous solution 1.

Even when light was introduced from below the cured body using a penlight, no reflected light was observed from the upper surface of the cured body. In addition, when distilled water was added dropwise, since the water did not pass through the cured body, it was confirmed that the cured body was not an interconnected porous body. The c) of FIG. 63 shows a scanning electron microscope image of the cured body. No interconnected pores of 30 μm or more were observed in the cured body.

Similar results were obtained when mixing was performed using phosphoric acid with a 1 molar concentration and hydrochloric acid with a 3 molar concentration.

Example 48

A rat femur and tibia were calcined at 1000° C. for 5 hours. A cancellous bone portion was selected to produce cancellous bone granules that passed through a sieve having a mesh opening of 2 mm but failed to pass through a sieve having a mesh opening of 500 μm. The a) of FIG. 64 and c) of FIG. 64 show a picture of the produced cancellous bone granules and a scanning electron microscopic picture. Based on the scanning electron microscopic picture shown in c) of FIG. 64, it was confirmed that the cancellous bone granule was an interconnected porous body.

The calcium-phosphoric acid aqueous solution 1 was used as a mixing solution. 500 mg of the cancellous bone apatite granules were filled in a centrifugal tube and 500 μL of the calcium-phosphoric acid aqueous solution 1 was added dropwise. The sample was left in a thermostatic bath at 37° C. and a relative humidity of 100% for 30 minutes. Then, curing was determined according to whether the granules had moved. As a result, it was confirmed that the granules had not moved but had been cured.

The b) of FIG. 64 shows a picture of the cured body. The d) of FIG. 64 shows a scanning electron microscope image.

As shown in d) of FIG. 64, when cancellous bone granules were reacted with a mixing solution, crystals were precipitated and the precipitated crystals bridged the cancellous bone granules to form the cured body.

When light was introduced from below the cured body using a penlight, reflected light was observed from the upper surface of the cured body and when distilled water was added dropwise, the water easily passed through the cured body. Therefore, it was confirmed that the cured body was an interconnected porous body. In addition, based on observation under a scanning electron microscope, it was confirmed that a diameter of the interconnected pore was at least 30 μm or more. A porosity was about 75%.

FIG. 65 shows powder X-ray diffraction patterns. In b) of FIG. 65 showing a powder X-ray diffraction pattern of the cured body, in addition to a diffraction pattern derived from the cancellous bone shown in a) of FIG. 65, a diffraction pattern derived from dicalcium phosphate dihydrate (DCPD) shown in c) of FIG. 65 was observed. Therefore, it was confirmed that the cancellous bone granules and the calcium-phosphoric acid aqueous solution 1 had reacted to form calcium hydrogen phosphate dihydrate.

A compressive strength of the cured body was 170 kPa.

A bone defect with a diameter of 4 mm was formed in a rat skull, cancellous bone granules were filled into the bone defect, the calcium-phosphoric acid aqueous solution 1 was added dropwise for curing, the excess calcium-phosphoric acid aqueous solution 1 was removed using a gauze, curing of the cancellous bone granules inside the bone defect was confirmed and the defect was then sealed.

When a bone defect repairing operation was performed and the result was histopathologically evaluated after 2 weeks, it was revealed that the cured body of the cancellous bone granules exhibited excellent tissue compatibility and osteoconductivity.

Example 49

Bioglass (bioglass 45S5TM) produced from $SiO_2$, CaO, $Na_2O$, and $P_2O_5$ was used as calcium-containing glass.

A calcium-containing glass block was pulverized to produce calcium-containing glass granules that passed through a sieve having a mesh opening of 2 mm but failed to pass through a sieve having a mesh opening of 500 μm. The a) of FIG. 66 shows a picture of the produced calcium-containing glass granules.

The calcium-phosphoric acid aqueous solution 1 was used as a mixing solution.

The calcium-containing glass granules were filled in a stainless steel split mold for preparing a sample with a diameter of 6 mm and a height of 3 mm placed on a slide glass. The calcium-phosphoric acid aqueous solution 1 was added dropwise to the calcium-containing glass granules. The excess calcium-phosphoric acid aqueous solution 1 was removed for reaction. The sample was left in a thermostatic bath at 37° C. and a relative humidity of 100% for 30 minutes and curing was then determined according to whether the granules had moved. As a result, it was confirmed that the granules had not moved but had been cured in all cases.

The b) of FIG. 66 shows a picture of the cured body. As shown in b) of FIG. 66, the calcium-containing glass granules were cured and the interconnected porous body was formed. In addition, it was confirmed that a diameter of the interconnected pore was at least 30 μm or more. When light was introduced from below the cured body using a penlight, reflected light was observed from the upper surface of the cured body in all cases, and when distilled water was added dropwise, the water easily passed through the cured body. Therefore, it was confirmed that the cured body was an interconnected porous body. A porosity was about 54%.

In addition, the a) of FIG. 67 shows a scanning electron microscope image of the calcium-containing glass granules. The b) of FIG. 67 shows a scanning electron microscope image of the cured body. The c) of FIG. 67 shows a high magnification image of the cured body under a scanning electron microscope. As shown in b) of FIG. 67 and c) of FIG. 67, on the surface of the cured body, crystals that were not observed in the calcium-containing glass granules were precipitated, the granules being linked by bridging by crystals.

FIG. 68 shows powder X-ray diffraction patterns. In b) of FIG. 68 showing a powder X-ray diffraction pattern of the cured body, in addition to a diffraction pattern derived from calcium-containing glass granules shown in a) of FIG. 68, a diffraction pattern derived from dicalcium phosphate dihydrate (DCPD) shown in c) of FIG. 68 was observed. Therefore, it was confirmed that the calcium-containing glass granules and the calcium-phosphoric acid aqueous solution 1 having a pH of 1.2 had reacted to form calcium hydrogen phosphate.

Based on the scanning electron microscope observation and powder X-ray diffraction results, it was confirmed that, when the calcium-containing glass granules and the calcium-phosphoric acid aqueous solution 1 having a pH of 1.2 were reacted, calcium hydrogen phosphate dihydrate was formed and the calcium hydrogen phosphate dihydrate bridged the calcium-containing glass granules to form the cured body.

A compressive strength of the cured body was 100 kPa.

Example 50

A calcium hydroxide powder (commercially available from Nacalai Tesque, Inc.) was isostatically compacted at 100 MPa, and carbonated in a 10 L desiccator at 25° C. and a humidity of 100% in which carbon dioxide was supplied at 100 mL per minute for 48 hours to prepare a cured body. The cured body was pulverized and then sieved separately. Granules that passed through a sieve having a mesh opening of 1000 μm but failed to pass through a sieve having a mesh opening of 600 μm were additionally carbonated under the same conditions for 7 days. Calcium carbonate granules shown in the scanning electron microscope image of FIG. 69a were produced.

As a mixing solution, a calcium-phosphoric acid aqueous solution (hereinafter referred to as a "calcium-phosphoric acid aqueous solution 9" in this example) in which calcium dihydrogen phosphate was dissolved at 25° C. to a concentration of 1.2 mol with respect to phosphoric acid at a 0.6 molar concentration was produced. The calcium-phosphoric acid aqueous solution 9 included calcium at a 1.2 molar concentration and phosphoric acid at a 3 molar concentration. A pH of the calcium-phosphoric acid aqueous solution 9 was 1.2.

The calcium carbonate granules were filled in an acrylic pipe with an inner diameter of 6 mm and the acrylic pipe was fixed to an acrylic plate. Also, air or a liquid passes between the acrylic pipe and the acrylic plate. From the side above the acrylic pipe, 0.34 mL of the mixing solution was added and stress was applied from the upper surface so that a pressure of 7.1 MPa was applied using a stainless steel push rod. The sample was reacted in a thermostatic bath at 37° C. and a relative humidity of 100% for 30 minutes. Then, curing was determined according to whether the granules had moved. As a result, it was confirmed that the granules had not moved but had been cured.

The b) of FIG. 69 shows a scanning electron microscope image of the surface of the cured body. A precipitate was formed on surfaces of calcium carbonate granules and the formed precipitate bridged the calcium carbonate granules. Therefore, it was confirmed that the calcium carbonate granules were cured.

When light was introduced from below the cured body using a penlight, reflected light was observed from the upper surface of the porous body and when distilled water was added dropwise, the water easily passed therethrough. Therefore, it was confirmed that the interconnected porous body was formed. The c) of FIG. 69 shows a micro CT image of the cured body. Based on such results, it was confirmed that the interconnected porous body was formed according to the curing of the calcium carbonate granules.

The b) of FIG. 70 shows powder X-ray diffraction patterns of the cured body. In addition to diffraction patterns derived from calcium carbonate granules shown in a) of FIG. 70, diffraction patterns derived from calcium hydrogen phosphate dihydrate shown in c) of FIG. 70 were detected. Therefore, it was confirmed that the formed precipitate was calcium hydrogen phosphate dihydrate.

A porosity of the cured body was 52%. A compressive strength was 15000 kPa (15 MPa).

The obtained cured body of the calcium carbonate granules was implanted in a white rabbit femoral defect. Based on the histopathological image after 2 weeks, it was confirmed that no inflammatory response was caused, excellent tissue compatibility was exhibited, and a bone invaded into the pore.

Example 51

A carbonate apatite block was pulverized to produce carbonate apatite granules that passed through a sieve having a mesh opening of 200 μm but failed to pass through a sieve having a mesh opening of 100

As a mixing solution, the following three solutions were produced.

An aqueous solution (hereinafter referred to as a "0.5 M calcium-phosphoric acid aqueous solution" in this example) in which calcium dihydrogen phosphate was dissolved at 25° C. to a concentration of 0.5 mol with respect to phosphoric acid at a 0.2 molar concentration was produced. The 0.5 M calcium-phosphoric acid aqueous solution included calcium at a 0.5 molar concentration and phosphoric acid at a 1.2 molar concentration. A pH of the 0.5 M calcium-phosphoric acid aqueous solution was 2.0.

An aqueous solution (hereinafter referred to as a "0.8 M calcium-phosphoric acid aqueous solution" in this example) in which calcium dihydrogen phosphate was dissolved at 25° C. to a concentration of 0.8 mol with respect to phosphoric acid at a 0.4 molar concentration was produced. The 0.8 M calcium-phosphoric acid aqueous solution included calcium at a 0.8 molar concentration and phosphoric acid at a 2 molar concentration. A pH of the 0.8 M calcium-phosphoric acid aqueous solution was 1.8.

An aqueous solution (hereinafter referred to as a "1 M calcium-phosphoric acid aqueous solution" in this example) in which calcium dihydrogen phosphate at a 1 molar concentration was dissolved at 25° C. with respect to phosphoric acid at a 0.6 molar concentration was produced. The 1 M calcium-phosphoric acid aqueous solution included calcium at a 1 molar concentration and phosphoric acid at a 2.6 molar concentration. A pH of the 1 M calcium-phosphoric acid aqueous solution was 1.6.

0.1 g of the carbonate apatite granules were introduced into an injection syringe with an inner diameter of 6 mmφ and a mixing solution of 0.5 mL was introduced thereinto. Then, a push rod of the syringe was introduced and an excess mixing solution was removed by air. A stress of 1.4 MPa was applied to the push rod and the carbonate apatite granules were cured under pressure at 25° C. for 30 minutes.

The a) of FIG. 71 to f) of FIG. 71 show scanning electron microscope images of the cured bodies that were cured in a 0.5 M calcium-phosphoric acid aqueous solution, a 0.8 M calcium-phosphoric acid aqueous solution, and a 1.0 M calcium-phosphoric acid aqueous solution. In any case, it was confirmed that crystals were precipitated on surfaces of the carbonate apatite granules and between the carbonate apatite granules, and the carbonate apatite granules were bridged by the precipitated crystals to cure a carbonate apatite.

A compressive strength of the cured body was 1.3 MPa, 1.8 MPa, or 3.2 MPa, respectively.

FIG. 72 shows powder X-ray diffraction patterns. It was confirmed that the precipitate was calcium hydrogen phosphate dihydrate similarly to Example 1.

Next, the carbonate apatite granules cured by bridging by the calcium hydrogen phosphate dihydrate were immersed in a sodium hydrogen carbonate aqueous solution at a 1 molar concentration at 60° C. for 3 hours. A pH of the sodium hydrogen carbonate aqueous solution at a 1 molar concentration was 8.4.

The d) of FIG. 71, e) of FIG. 71, and f) of FIG. 71 show scanning electron microscope images of the cured bodies cured in a 0.5 M calcium-phosphoric acid aqueous solution, a 0.8 M calcium-phosphoric acid aqueous solution, and a 1.0 M calcium-phosphoric acid aqueous solution. While the form of the crystals on the surface was changed due to the sodium hydrogen carbonate aqueous solution treatment, no change was observed in the macro form, and an interconnected porous body structure was confirmed. In addition, it was confirmed that a diameter of the interconnected pore was at least 30 μm or more.

Based on powder X-ray diffraction patterns in FIG. 72, it was confirmed that the calcium hydrogen phosphate dihydrate formed in a calcium-phosphoric acid aqueous solution of carbonate apatite granules was compositionally converted into a carbonate apatite due to the sodium hydrogen carbonate aqueous solution treatment.

A compressive strength of the interconnected porous body obtained after the sodium hydrogen carbonate aqueous solution treatment was 0.6 MPa, 1.1 MPa, or 1.4 MPa, respectively when an interconnected porous body prepared using a 0.5 M calcium-phosphoric acid aqueous solution, a 0.8 M calcium-phosphoric acid aqueous solution, or a 1.0 M calcium-phosphoric acid aqueous solution was treated with sodium hydrogen carbonate. In addition, a porosity was 68%, 63%, and 62%.

Next, in order to examine tissue compatibility of the obtained interconnected porous body, a bone defect with a diameter of 6 mm was formed in the tibia of a Japanese white house rabbit having a body weight of about 3.5 kg, and the bone defect was reconstructed using the produced interconnected porous body.

FIG. 73 shows X-ray micro CT images one month after implantation. In the a) of FIG. 73 and b) of FIG. 73, the upper portions show ankle sides and the lower portions show knee joint sides.

The a) of FIG. 73 shows an X-ray micro CT image obtained when a bone defect was reconstructed using an interconnected porous body obtained by curing carbonate apatite granules in a 1.0 M calcium-phosphoric acid aqueous solution. The c) of FIG. 73 shows an image when the sample was observed in a perpendicular direction with respect to a bone axis. In addition, the b) of FIG. 73 shows an X-ray micro CT image obtained when a bone defect was reconstructed using an interconnected porous body in which calcium hydrogen phosphate dihydrate bridging carbonate apatite granules were additionally changed to a carbonate apatite due to sodium hydrogen carbonate. The d) of FIG. 73 shows an image when the sample was observed in a perpendicular direction with respect to a bone axis.

It was confirmed that no inflammatory response was observed in any cases and excellent tissue compatibility was exhibited. In addition, it was confirmed that the interconnected porous body and a bone were linked and osteoconductivity was exhibited.

Example 52

α-type tricalcium phosphate spheres with a diameter of about 100 μm were formed into granules. The a) of FIG. 74 and b) of FIG. 74b show scanning electron microscope images of the α-type tricalcium phosphate spheres.

As a mixing solution, an aqueous solution (hereinafter referred to as a "calcium-phosphoric acid aqueous solution 11" in this example) in which calcium dihydrogen phosphate was dissolved at 25° C. to a concentration of 0.08 mol with respect to phosphoric acid at a 0.05 molar concentration was produced. The calcium-phosphoric acid aqueous solution 11 was a solution including calcium at a 0.08 molar concentration and phosphoric acid at a 0.21 molar concentration. A pH of the calcium-phosphoric acid aqueous solution 11 was 2.0.

The α-type tricalcium phosphate spheres were introduced into an injection syringe with an inner diameter of 6 tramp and a mixing solution of 0.5 mL was introduced thereinto. Then, a push rod of the syringe was introduced and an excess mixing solution was removed by air. No load was applied to the push rod, and the α-type tricalcium phosphate spheres were cured at 25° C. for 30 minutes under no pressure.

The c) of FIG. 74 shows a scanning electron microscope image of the interconnected porous body cured when the α-type tricalcium phosphate spheres and a calcium-phosphoric acid aqueous solution were reacted. It was confirmed that crystal precipitation was observed on surfaces of the α-type tricalcium phosphate spheres and between the α-type tricalcium phosphate spheres and the α-type tricalcium phosphate spheres were cured by bridging by the precipitated crystals.

Next, the produced interconnected porous body was calcined at 1500° C. for 6 hours. The d) of FIG. 74 shows a scanning electron microscope image of the calcined interconnected porous body. It was confirmed that the α-type tricalcium phosphate spheres were sintered. It was confirmed that a compressive strength of the sintered interconnected porous body was 7 MPa and a mechanical strength of an α-type tricalcium phosphate interconnected porous body was significantly improved due to the sintering operation.

The b) of FIG. 75 shows an α-type tricalcium phosphate interconnected porous body solid before sintering. The c) of FIG. 75 shows powder X-ray diffraction patterns of the sintered α-type tricalcium phosphate interconnected porous body.

In the α-type tricalcium phosphate interconnected porous body before sintering, in addition to a diffraction pattern derived from the α-type tricalcium phosphate spheres shown in a) of FIG. 75, a diffraction pattern derived from calcium hydrogen phosphate dihydrate (DCPD) shown in d) of FIG. 75 was observed. Therefore, it was confirmed that the crystals obtained when the α-type tricalcium phosphate spheres and the calcium-phosphate mixing solution were reacted was calcium hydrogen phosphate.

The c) of FIG. 75 shows powder X-ray diffraction patterns of an interconnected porous body obtained after the interconnected porous body was calcined. It was confirmed that diffraction patterns derived from calcium hydrogen phosphate dihydrate (DCPD) disappeared due to the calcination operation. This can be understood to be because, since diffusion occurred due to the calcination operation and there was a very small amount of calcium hydrogen phosphate, this was highly likely to have diffused into the α-type tricalcium phosphate spheres.

Next, a bone defect with a diameter of 6 mm was formed in the tibia of a Japanese white house rabbit and the bone defect was reconstructed using the produced interconnected porous body.

It was found that no inflammatory response was caused in both interconnected porous bodies before sintering and after sintering and excellent tissue compatibility was exhibited. In addition, in all cases, it was confirmed that the interconnected porous body and a bone were linked and osteoconductivity was exhibited.

Comparative Example 22

In order to verify usefulness of Example 52, the same α-type tricalcium phosphate spheres as in Example 52 were filled in a paper container and heated in an electric furnace at 1500° C. for 6 hours. In this system, no calcium hydrogen phosphate was formed.

Even with heat treatment, the α-type tricalcium phosphate spheres were not linked but disaggregated. Accordingly, it was found that, when the α-type tricalcium phosphate spheres were used to produce an α-type tricalcium phosphate interconnected porous body, it was necessary to fix the α-type tricalcium phosphate spheres.

Example 53

Hydroxyapatite granules (a raw material inorganic compound 9) were used. The a) of FIG. 76 shows a picture of the produced hydroxyapatite granules.

A sodium hydrogen sulfate aqueous solution at a 2 molar concentration was used as a mixing solution.

The hydroxyapatite granules were filled into the interior of a plastic cylindrical mold with a diameter of 6 mm and a height of 3 mm placed on a slide glass. A sodium hydrogen sulfate aqueous solution (500 μL) at a 2 molar concentration was added dropwise to the hydroxyapatite granules. The excess sodium hydrogen sulfate aqueous solution was removed for reaction.

The sample was left in a thermostatic bath at 37° C. and a relative humidity of 100% for 30 minutes. Then, curing was determined according to whether the granules had moved. As a result, it was confirmed that the granules had not moved but had been cured.

The b) of FIG. 76 shows the results for the produced cured body. The c) of FIG. 76 shows a scanning electron microscope image of the surface of the cured body. The d) of FIG. 76 shows a high magnification image showing the bridging between granules in the cured body under a scanning electron microscope.

As shown in b) of FIG. 76 to d) of FIG. 76, the hydroxyapatite granules were cured and a porous body was formed. In addition, it was confirmed that a diameter of the interconnected pore was at least 30 μm or more. When light was introduced from below the cured body using a penlight, reflected light was observed from the upper surface of the cured body in all cases, and when distilled water was added dropwise, the water easily passed through the cured body. Therefore, it was confirmed that the cured body was an interconnected porous body. A porosity was about 68%. As shown in the c) of FIG. 76 and d) of FIG. 76, the granules were linked by bridging by crystals.

The a) of FIG. 77 to b) of FIG. 77 show powder X-ray diffraction patterns according to this example. The b) of FIG. 77 shows powder X-ray diffraction patterns of the cured body. In the b) of FIG. 77 showing powder X-ray diffraction patterns of the cured body, in addition to a diffraction pattern derived from the hydroxyapatite granules shown in a) of FIG. 77, a diffraction pattern derived from calcium sulfate dihydrate (CSD) shown in j) of FIG. 77 was observed. Therefore, it was confirmed that the hydroxyapatite granules and the sodium hydrogen sulfate aqueous solution had reacted to form calcium sulfate dihydrate.

Based on the scanning electron microscope observation and powder X-ray diffraction results, it was confirmed that, when the hydroxyapatite granules and the sodium hydrogen sulfate aqueous solution were reacted, calcium sulfate dihydrate was formed and the calcium sulfate dihydrate bridged the hydroxyapatite granules to form the cured body.

A compressive strength of the cured body was 2.5 MPa.

Example 54

The hydroxyapatite granules (the raw material inorganic compound 9) in Example 53 were immersed in a sodium hydrogen sulfate aqueous solution at a 2 molar concentration while being stirred. Due to the stirring, curing of the hydroxyapatite granules was suppressed and calcium sulfate dihydrate covered hydroxyapatite granules were produced. The covered granules were heated at 100° C. for 6 hours. Based on c) of FIG. 77 showing powder X-ray diffraction patterns of the obtained granules, it was confirmed that calcium sulfate dihydrate was dehydrated to calcium sulfate hemihydrate and calcium sulfate hemihydrate covered hydroxyapatite granules were formed as a result. The a) of FIG. 78 shows a scanning electron microscope image of the produced calcium sulfate hemihydrate covered hydroxyapatite granules.

The granules were mixed with water and filled into the interior of a plastic cylindrical mold with a diameter of 6 mm and a height of 3 mm. The sample was left in a thermostatic bath at 37° C. and a relative humidity of 100% for 60 minutes. Then, curing was determined according to whether the granules had moved. As a result, it was confirmed that the granules had not moved but had been cured. The b) of FIG. 78 shows a picture of the cured body. In addition, c) of FIG. 78 shows a scanning electron microscope image of the surface of the cured body. The d) of FIG. 78 shows a high magnification image showing the bridging between granules in the cured body under a scanning electron microscope.

As shown in b) of FIG. 78 to d) of FIG. 78, the calcium sulfate covered hydroxyapatite granules were cured to form a porous body. A compressive strength was 95 kPa. In addition, it was confirmed that a diameter of the interconnected pore was at least 50 μm or more. When light was introduced from below the cured body using a penlight, reflected light was observed from the upper surface of the cured body in all cases, and when distilled water was added dropwise, the water easily passed through the cured body. Therefore, it was confirmed that the cured body was an interconnected porous body. A porosity was about 68%. As shown in the c) of FIG. 78 and d) of FIG. 78, the granules were linked by bridging by crystals. In addition, when the mixing solution was changed to a sodium chloride aqueous solution at a 0.1 molar concentration from water, curing occurred within 10 minutes. It was also confirmed that curing occurred within 10 minutes when a calcium chloride aqueous solution at a 0.1 molar concentration was used as the mixing solution.

Example 55

β-type tricalcium phosphate granules (a raw material inorganic compound 4) were used. The a) of FIG. 79 shows a picture of the β-type tricalcium phosphate granules.

A sodium hydrogen sulfate aqueous solution at a 2 molar concentration was used as a mixing solution.

The β-type tricalcium phosphate granules were filled into the interior of a plastic cylindrical mold with a diameter of 6 mm and a height of 3 mm placed on a slide glass. A sodium hydrogen sulfate aqueous solution (500 μL) at a 2 molar concentration was added dropwise to the β-type tricalcium phosphate granules and the excess sodium hydrogen sulfate aqueous solution was removed for reaction.

The sample was left in a thermostatic bath at 37° C. and a relative humidity of 100% for 30 minutes. Then, curing was determined according to whether the granules had moved. As a result, it was confirmed that the granules had not moved but had been cured.

The b) of FIG. 79 shows the results for the produced cured body. The c) of FIG. 79 shows a scanning electron microscope image of the surface of the cured body. The d) of FIG. 79 shows a high magnification image showing the bridging between granules in the cured body under a scanning electron microscope.

As shown in the b) of FIG. 79 to d) of FIG. 79, the β-type tricalcium phosphate granules were cured to form a porous body. In addition, it was confirmed that a diameter of the interconnected pore was at least 30 μm or more. When light was introduced from below the cured body using a penlight, reflected light was observed from the upper surface of the cured body in all cases, and when distilled water was added dropwise, the water easily passed through the cured body. Therefore, it was confirmed that the cured body was an interconnected porous body. A porosity was about 68%. As shown in the c) of FIG. 79 and d) of FIG. 79, the granules were linked by bridging by crystals.

The d) of FIG. 77 to e) of FIG. 77 shows powder X-ray diffraction patterns according to this example. The e) of FIG. 77 shows powder X-ray diffraction patterns of the cured body. In 3) of FIG. 77 showing powder X-ray diffraction patterns of the cured body, in addition to a diffraction pattern derived from the β-type tricalcium phosphate granules shown in d) of FIG. 77, a diffraction pattern derived from calcium sulfate dihydrate (CSD) shown in j) of FIG. 77 was observed. Therefore, it was confirmed that the β-type tricalcium phosphate granules and the sodium hydrogen sulfate aqueous solution had reacted to form calcium sulfate dihydrate.

Based on the scanning electron microscope observation and powder X-ray diffraction results, it was confirmed that, when the β-type tricalcium phosphate granules and the sodium hydrogen sulfate aqueous solution were reacted, calcium sulfate dihydrate was formed and the calcium sulfate dihydrate bridged the β-type tricalcium phosphate granules to form the cured body.

A compressive strength of the cured body was 3.2 MPa.

Example 56

The β-type tricalcium phosphate granules (the raw material inorganic compound 4) in Example 55 were immersed in a sodium hydrogen sulfate aqueous solution at a 2 molar concentration while being stirred. Due to the stirring, curing of the β-type tricalcium phosphate granules was suppressed and calcium sulfate dihydrate covered β-type tricalcium phosphate granules were produced. The covered granules were heated at 100° C. for 6 hours. Based on the f) of FIG. 77 showing powder X-ray diffraction patterns of the obtained granules, it was confirmed that calcium sulfate dihydrate was dehydrated to calcium sulfate hemihydrate and calcium sulfate hemihydrate covered β-type tricalcium phosphate granules were formed as a result. The a) of FIG. 80 shows a scanning electron microscope image of the produced calcium sulfate hemihydrate covered β-type tricalcium phosphate granules.

The granules were mixed with water and filled into the interior of a plastic cylindrical mold with a diameter of 6 mm and a height of 3 mm. The sample was left in a thermostatic bath at 37° C. and a relative humidity of 100% for 60 minutes. Then, curing was determined according to whether the granules had moved. As a result, it was confirmed that the granules had not moved but had been cured. A compressive strength of the cured body was 105 kPa. The b) of FIG. 80 shows a picture of the cured body. In addition, c) of FIG. 80 shows a scanning electron microscope image of the surface of the cured body. The d) of FIG. 80 shows a high magnification image showing the bridging between granules in the cured body under a scanning electron microscope.

As shown in the b) of FIG. 80 to d) of FIG. 80, the calcium sulfate covered β-type tricalcium phosphate granules were cured to form a porous body. In addition, it was confirmed that a diameter of the interconnected pore was at least 50 μm or more. When light was introduced from below the cured body using a penlight, reflected light was observed from the upper surface of the cured body in all cases, and when distilled water was added dropwise, the water easily passed through the cured body. Therefore, it was confirmed that the cured body was an interconnected porous body. A porosity was about 68%. As shown in the c) of FIG. 80 and d) of FIG. 80, the granules were linked by bridging by crystals. In addition, when the mixing solution was changed to a sodium chloride aqueous solution at a 0.1 molar concentration from water, curing occurred within 10 minutes. It was also confirmed that curing occurred within 10 minutes when a calcium chloride aqueous solution at a 0.1 molar concentration was used as the mixing solution.

Example 57

Carbonate apatite granules (a raw material inorganic compound 8) were used. The a) of FIG. 81 shows a picture of the produced carbonate apatite granules.

A sodium hydrogen sulfate aqueous solution at a 2 molar concentration was used as a mixing solution.

The carbonate apatite granules were filled into the interior of a plastic cylindrical mold with a diameter of 6 mm and a height of 3 mm placed on a slide glass. A sodium hydrogen sulfate aqueous solution (500 μL) at a 2 molar concentration was added dropwise to the carbonate apatite granules and the excess sodium hydrogen sulfate aqueous solution was removed for reaction.

The sample was left in a thermostatic bath at 37° C. and a relative humidity of 100% for 30 minutes. Then, curing was determined according to whether the granules had moved. As a result, it was confirmed that the granules had not moved but had been cured.

The b) of FIG. 81 shows the results for the produced cured body. The c) of FIG. 81 shows a scanning electron microscope image of the surface of the cured body. The d) of FIG. 81 shows a high magnification image showing the bridging between granules in the cured body under a scanning electron microscope.

As shown in b) of FIG. 81 to d) of FIG. 81, the carbonate apatite granules were cured to form a porous body. In addition, it was confirmed that a diameter of the interconnected pore was at least 30 μm or more. When light was introduced from below the cured body using a penlight, reflected light was observed from the upper surface of the cured body in all cases, and when distilled water was added dropwise, the water easily passed through the cured body. Therefore, it was confirmed that the cured body was an interconnected porous body. A porosity was about 52%. As shown in c) of FIG. 81 and d) of FIG. 81, the granules were linked by bridging by crystals.

The g) of FIG. 77 to the h) of FIG. 77 shows powder X-ray diffraction patterns according to this example. The h) of FIG. 77 shows powder X-ray diffraction patterns of the cured body. In h) of FIG. 77 showing powder X-ray diffraction patterns of the cured body, in addition to a diffraction pattern derived from the carbonate apatite granules shown in g) of FIG. 77, a diffraction pattern derived from calcium sulfate dihydrate (CSD) shown in j) of FIG. 77 was observed. Therefore, it was confirmed that the hydroxyapatite granules and the sodium hydrogen sulfate aqueous solution had reacted to form calcium sulfate dihydrate.

Based on the scanning electron microscope observation and powder X-ray diffraction results, it was confirmed that, when the carbonate apatite granules and the sodium hydrogen sulfate aqueous solution were reacted, calcium sulfate dihydrate was formed and the calcium sulfate dihydrate bridged the carbonate apatite granules to form the cured body.

A compressive strength of the cured body was 2.5 MPa.

Example 58

The carbonate apatite granules (the raw material inorganic compound 9) in Example 57 were immersed in a sodium hydrogen sulfate aqueous solution at a 2 molar concentration while being stirred. Due to the stirring, curing of the carbonate apatite granules was suppressed and calcium sulfate dihydrate covered carbonate apatite granules were produced. The covered granules were heated at 100° C. for 6 hours. Based on i) of FIG. 77 showing powder X-ray diffraction patterns of the obtained granules, it was confirmed that calcium sulfate dihydrate was dehydrated to calcium sulfate hemihydrate and calcium sulfate hemihydrate covered carbonate apatite granules were formed as a result. The a) of FIG. 82 shows a scanning electron microscope image of the produced calcium sulfate hemihydrate covered hydroxyapatite granules.

The granules were mixed with water and filled into the interior of a plastic cylindrical mold with a diameter of 6 mm and a height of 3 mm. The sample was left in a thermostatic bath at 37° C. and a relative humidity of 100% for 60 minutes. Then, curing was determined according to whether the granules had moved. As a result, it was confirmed that the granules had not moved but had been cured. A compressive strength was 85 kPa. The b) of FIG. 82 shows a picture of the cured body. In addition, the c) of FIG. 82 shows a scanning electron microscope image of the surface of the cured body. The d) of FIG. 82 shows a high magnification image showing the bridging between granules in the cured body under a scanning electron microscope.

As shown in b) of FIG. 82 to d) of FIG. 82, the calcium sulfate covered carbonate apatite granules were cured to form a porous body. In addition, it was confirmed that a diameter of the interconnected pore was at least 50 μm or more. When light was introduced from below the cured body using a penlight, reflected light was observed from the upper surface of the cured body in all cases, and when distilled water was added dropwise, the water easily passed through the cured body. Therefore, it was confirmed that the cured body was an interconnected porous body. A porosity was about 57%. As shown in c) of FIG. 82 and d) of FIG. 82, the granules were linked by bridging by crystals. In addition, when the mixing solution was changed to a sodium chloride aqueous solution at a 0.1 molar concentration from water, curing occurred within 10 minutes. It was also confirmed that curing occurred within 10 minutes when a calcium chloride aqueous solution at a 0.1 molar concentration was used as the mixing solution.

INDUSTRIAL APPLICABILITY

According to the present invention, it is possible to produce inorganic compound blocks and granules as the product inorganic compound without sintering causing high energy consumption. In addition, it is possible to produce highly active inorganic compound blocks and granules as the product inorganic compound.

In particular, when calcium sulfate is used as a raw material inorganic compound having a solubility of 5 or less, formation is easy since calcium sulfate has a characteristic form exhibiting self-curability. In addition, since calcium sulfate has a melting point of 1460° C., it is possible to easily produce a porous body inorganic substance using a method of introducing and incinerating an organic substance.

The invention claimed is:

1. A method of producing a product inorganic compound, the method comprising the following steps:
    (A) immersing a raw material inorganic compound in an electrolyte aqueous solution;
    (B) forming a precipitated inorganic compound layer on unreacted raw material inorganic compound, comprising:
        (B1) exchanging anions in the raw material inorganic compound with anions in the electrolyte aqueous solution, wherein the anions in the electrolyte aqueous solution consist of at least one selected from the group consisting of carbonate ions, bicarbonate ions, sulfate ions, and hydrogen sulfate ions, or
        (B2) exchanging cations in the raw material inorganic compound with cations in the electrolyte aqueous solution; and
    (C) obtaining a product inorganic compound from the raw material inorganic compound,
    wherein:
    the raw material inorganic compound:
        is an artificial material comprising at least one of calcium carbonate and calcium phosphate,
        is an interconnected porous body,
        has a volume of $10^{-13}$ m$^3$ or more, and
        has a solubility that is greater than 0 and 5 or less with respect to distilled water or the electrolyte aqueous solution at 20° C.; and
    the product inorganic compound:
        has a volume of $10^{-13}$ m$^3$ or more, and
        comprises:
            a core portion comprising the unreacted raw material inorganic compound, and
            a surface layer portion comprising the precipitated inorganic layer covering the core portion.

2. The method of producing a product inorganic compound according to claim 1, wherein:
    the product inorganic compound is a porous body including pores having an aspect ratio of at least 2 or more, and
    a porosity of the raw material inorganic compound is 30% or more.

3. The method of producing a product inorganic compound according to claim 1, wherein the surface layer portion comprises at least one selected from the group consisting of calcium hydrogen phosphate, calcium carbonate, and apatite.

4. The method of producing a product inorganic compound according to claim 1, wherein step (C) comprises curing the precipitated inorganic compound layer formed in step (B), thereby bridging a plurality of the raw material inorganic compound to form the product inorganic compound having an interconnected porous body.

5. The method of producing a product inorganic compound according to claim 1, wherein the core portion further comprises a support.

6. The method of producing a product inorganic compound according to claim 5, wherein the support comprises at least one selected from the group consisting of a metal, a polymer, and a ceramic.

7. The method of producing a product inorganic compound according to claim 1, wherein a temperature at which the raw material inorganic compound is immersed in the electrolyte aqueous solution or the electrolyte suspension is 10° C. or less.

8. The method of producing a product inorganic compound according to claim 1, wherein the electrolyte aqueous solution includes carbonate ions.

9. The method of producing a product inorganic compound according to claim 1, wherein the electrolyte aqueous solution includes bicarbonate ions.

10. The method of producing a product inorganic compound according to claim 1, wherein the electrolyte aqueous solution includes sulfate ions.

11. The method of producing a product inorganic compound according to claim 1, wherein the electrolyte aqueous solution includes hydrogen sulfate ions.

* * * * *